(12) United States Patent
Rudnicki et al.

(10) Patent No.: US 9,732,130 B2
(45) Date of Patent: Aug. 15, 2017

(54) WNT7A COMPOSITIONS AND METHOD OF USING THE SAME

(75) Inventors: Michael A. Rudnicki, Ottawa (CA); Conrad Florian Bentzinger, Ottawa (CA); Radoslav Zinoviev, New Haven, CT (US)

(73) Assignee: Ottawa Hospital Research Institute, Ottawa (CA)

( * ) Notice: Subject to any disclaimer, the term of this patent is extended or adjusted under 35 U.S.C. 154(b) by 417 days.

(21) Appl. No.: 14/344,309

(22) PCT Filed: Sep. 14, 2012

(86) PCT No.: PCT/US2012/055396
§ 371 (c)(1),
(2), (4) Date: Jan. 13, 2015

(87) PCT Pub. No.: WO2013/040341
PCT Pub. Date: Mar. 21, 2013

(65) Prior Publication Data
US 2015/0111822 A1     Apr. 23, 2015

Related U.S. Application Data

(60) Provisional application No. 61/535,915, filed on Sep. 16, 2011.

(51) Int. Cl.
| | |
|---|---|
| *C07K 14/47* | (2006.01) |
| *A61K 38/17* | (2006.01) |
| *A61K 38/00* | (2006.01) |
| *C12N 5/077* | (2010.01) |
| *A61K 45/06* | (2006.01) |
| *C12N 7/00* | (2006.01) |
| *A61K 48/00* | (2006.01) |

(52) U.S. Cl.
CPC ...... *C07K 14/4705* (2013.01); *A61K 38/1709* (2013.01); *A61K 45/06* (2013.01); *C07K 14/4702* (2013.01); *C07K 14/4707* (2013.01); *C07K 14/4708* (2013.01); *C12N 5/0659* (2013.01); *C12N 7/00* (2013.01); *A61K 38/00* (2013.01); *A61K 48/00* (2013.01); *C12N 2501/415* (2013.01); *C12N 2533/52* (2013.01); *C12N 2710/10042* (2013.01); *C12N 2740/10042* (2013.01); *C12N 2740/15042* (2013.01)

(58) Field of Classification Search
CPC ............ C07K 14/4705; C07K 14/4708; C07K 14/4707; A61K 38/1709; A61K 38/00; C12N 5/0659
See application file for complete search history.

(56) References Cited

U.S. PATENT DOCUMENTS

| | | | |
|---|---|---|---|
| 4,544,752 A | 10/1985 | Beck et al. | |
| 4,751,180 A | 6/1988 | Cousens et al. | |
| 4,935,233 A | 6/1990 | Bell et al. | |
| 5,679,647 A | 10/1997 | Carson et al. | |
| 5,739,118 A | 4/1998 | Carrano et al. | |
| 5,837,533 A | 11/1998 | Boutin | |
| 6,297,030 B1 * | 10/2001 | Barnes | C07K 14/475 |
| | | | 435/252.3 |
| 6,337,184 B1 | 1/2002 | Miller | |
| 6,590,075 B2 | 7/2003 | Ruben et al. | |
| 7,153,832 B2 | 12/2006 | Nusse et al. | |
| 7,335,643 B2 | 2/2008 | Nusse et al. | |
| 7,541,183 B2 * | 6/2009 | Rudnicki | A61K 35/34 |
| | | | 435/354 |
| 2004/0005579 A1 | 1/2004 | Birse et al. | |
| 2005/0130181 A1 | 6/2005 | McSwiggen | |
| 2006/0171931 A1 | 8/2006 | Rudnicki et al. | |
| 2008/0226707 A1 | 9/2008 | Helms et al. | |
| 2008/0299135 A1 | 12/2008 | Zou | |
| 2009/0074777 A1 | 3/2009 | Wands et al. | |
| 2011/0319337 A1 | 12/2011 | Bravo et al. | |
| 2012/0213744 A1 | 8/2012 | Rudnicki et al. | |
| 2014/0142046 A1 | 5/2014 | Lee et al. | |
| 2014/0200179 A1 | 7/2014 | Garcia et al. | |
| 2015/0099708 A1 | 4/2015 | Lee et al. | |

FOREIGN PATENT DOCUMENTS

| | | |
|---|---|---|
| JP | 2010-520286 A | 6/2010 |
| JP | 2014-506568 A | 3/2014 |
| WO | WO 92/06180 A1 | 4/1992 |
| WO | WO 92/22635 A1 | 12/1992 |
| WO | WO 93/14188 A1 | 7/1993 |
| WO | WO 93/20221 A1 | 10/1993 |
| WO | WO 2004/029229 A2 | 4/2004 |
| WO | WO 2006/026652 A2 | 3/2006 |
| WO | WO 2006/072016 A2 | 7/2006 |
| WO | WO 2007/059612 A1 | 5/2007 |

(Continued)

OTHER PUBLICATIONS

Alland, L. et al. "Dual myristylation and palmitylation of Src family member p59fyn affects subcellular localization", Journal of Biological Chemistry, 269:16701-16705 (1994).

Altschul et al., "Gapped BLAST and PSI-BLAST: a new generation of protein database search programs", Nucleic Acids Research, 25(17): 3389-402 (1997).

Amerongen, "Alternative Wnt Pathways and Receptors", Cold Spring Harbor Perspectives in Biology, 4(10): a007914, 18 pages (2012).

(Continued)

*Primary Examiner* — Daniel C Gamett
(74) *Attorney, Agent, or Firm* — Rothwell, Figg, Ernt & Manbeck, P.C.

(57) ABSTRACT

There are provided compositions and methods for modulating stem cell division, in particular, division symmetry. It has been demonstrated that Wnt7a polypeptide fragments promoting symmetrical expansion of stem cells. The compositions and methods of the invention are useful, for example, in modulating stem cell division symmetry in vitro, ex vivo, and in vivo, in replenishing and expanding the stem cell pool, and in promoting the formation, maintenance, repair and regeneration of tissue.

26 Claims, 48 Drawing Sheets

(56) References Cited

FOREIGN PATENT DOCUMENTS

| WO | WO 2008/109119 A2 | 9/2008 |
|---|---|---|
| WO | WO 2010/014948 A1 | 2/2010 |
| WO | WO 2010/124365 A1 | 4/2010 |
| WO | WO 2010/078458 A1 | 7/2010 |
| WO | WO 2011/088127 A1 | 7/2011 |
| WO | WO 2012/097093 A2 | 7/2012 |
| WO | WO 2012/103360 A2 | 8/2012 |
| WO | WO 2013/040309 A2 | 3/2013 |
| WO | WO 2013/040341 A2 | 3/2013 |
| WO | WO 2004/113513 A2 | 12/2014 |

OTHER PUBLICATIONS

Anakwe et al., "Wnt signalling regulates myogenic differentiation in the developing avian wing," Development 130:3503-3514, 2003.
Anastas, et al., "WNT signalling pathways as therapeutic targets in cancer," Nature Reviews Cancer, 13(1):11-26 (2012).
Bae et al., "Regulation of myoblast motility and fusion by the CXCR4-associated sialomucin, CD164," J Biol Chem, 283(13):8301-8309 (2008).
Bass et al., "Syndecan-4-dependent Rac1 regulation determines directional migration in response to the extracellular matrix", The Journal of Cell Biology, 177(3): 527-538 (2007).
Bazan, et al., "Structural architecture and functional evolution of Wnts," Dev Cell., 23(2): 227-232 (2012).
Bentzinger et al., "Extrinsic regulation of satellite cell specification", Stem Cell Res Ther, 1(3): 27 (2010).
Bhanot, et al., "A new member of the frizzled family from Drosophila functions as a Wingless receptor," Nature, 382(6588):225-230 (1996).
Bird et al.,"Single-chain antigen-binding proteins", Science, 242: 423-426 (1988).
Bodine et al., "Akt/mTOR pathway is a crucial regulator of skeletal muscle hypertrophy and can prevent muscle atrophy in vivo", Nature Cell Biology, 3: 1014-1019 (2001).
Bönnemann, "Beyond dystrophin: current progress in the muscular dystrophies", C. G. et al., Curr. Opin. Ped., 8(6): 569-582 (1996).
Bosnakovski et al., "Prospective isolation of skeletal muscle stem cells with a Pax7 reporter", Stem Cells, 26(12): 3194-3204 (2008). Epub Sep. 18, 2008.
Borello et al., "The Wnt/β-catenin pathway regulates Gli-mediated Myf5 expression during somitogenesis", Development, 133: 3723-3732 (2006).
Brack et al., "A Temporal Switch from Notch to Wnt Signaling in Muscle Stem Cells Is Necessary for Normal Adult Myogenesis", Cell Stem Cell, 2: 50-59 (2008).
Bradley, et al., "A soluble form of Wnt-1 protein with mitogenic activity on mammary epithelial cells," Mol Cell Biol, 15(8):4616-4622 (1995).
Brown, R.H., Jr., "Dystrophin-associated proteins and the muscular dystrophies", Annu. Rev. Med., 48: 457-466 (1997).
Burrus et al., "Biochemical analysis of murine Wnt proteins reveals both shared and distinct properties", Exp Cell Res., 220(2): 363-373 (1995).
Cerletti et al., "Highly efficient, functional engraftment of skeletal muscle stem cells in dystrophic muscles," Cell, 134:37-47 (2008).
Chargé and Rudnicki, "Cellular and molecular regulation of muscle regeneration", Physiol Rev., 84(1): 209-238 (2004).
Chargé et al., "Aging-related satellite cell differentiation defect occurs prematurely after Ski-induced muscle hypertrophy", Am J Physiol Cell Physiol, 283:C1228-1241 (2002).
Chaudhary et al., "A rapid method of cloning functional variable-region antibody genes in Escherichia coli as single-chain immunotoxins", Proc. Natl. Acad. Sci. U.S.A., 87: 1066-1070 (1990).
Chen et al., "Protein kinase A signalling via CREB controls myogenesis induced by Wnt proteins", Nature, 433: 317-322 (2005).

Ching et al. "Lipid-independent Secretion of a Drosophila Wnt Protein", Journal of Biological Chemistry, 283(25): 17092-17098 (2008).
Ciciliot and Schiaffino, "Regeneration of mammalian skeletal muscle. Basic mechanisms and clinical implications", Current Pharmaceutical Design,16(8): 906-914 (2010).
Ciruna et al., "Planar cell polarity signalling couples cell division and morphogenesis during neurulation," Nature 439:220-224. 2006.
Clevers, "Wnt/β-Catenin Signaling in Development and Disease," Cell 127:469-480 (2006).
Collins et al., "Stem Cell Function, Self-Renewal, and Behavioral Heterogeneity of Cells from the Adult Muscle Satellite Cell Niche," Cell 122, 289-301 (2005).
Cooper, "Advances in membrane receptor screening and analysis," Journal of Molecular Recognition, 17(4):286-315 (2004).
Cornelison et al., "Essential and separable roles for Syndecan-3 and Syndecan-4 in skeletal muscle development and regeneration," Genes & Development,18:2231-2236, 2004.
Cornelison et al., "Syndecan-3 and Syndecan-4 Specifically Mark Skeletal Muscle Satellite Cells and are Implicated in Satellite Cell Maintenance and Muscle Regeneration," Dev Biol, 239:79-94 (2001).
Cosgrove et al., "A home away from home: challenges and opportunities in engineering in vitro muscle satellite cell niches", Differentiation, 78(2-3): 185-194 (2009).
Cossu et al., "Wnt signaling and the activation of myogenesis in mammals," EMBO J ,18, 6867-6872, 1999.
Couso, et al., "Notch is Required for wingless Signaling in the Epidermis of Drosophila," Cell, 79(2): 259-272 (1994).
Crise et al., "Identification of palmitoylation sites on CDR, the Human Immunodeficiency Virus receptor", Journal of Biological Chemistry 267: 13593-13597 (1992).
Daley et al., "Identification of a mechanochemical checkpoint and negative feedback loop regulating branching morphogenesis", Developmental Biology, 336(2):169-182 (2009). Epub Oct. 3, 2009.
Daley et al., "A focal adhesion protein-based mechanochemical checkpoint regulates cleft progression during branching morphogenesis", Dev Dyn., 240(9): 2069-2083 (2011).
Dann et al., "Insights into Wnt binding and signalling from the structures of two Frizzled cysteine-rich domains," Nature, 412:86-90, 2001.
Database EMBL [Online] "Rattus norvegicus (Norway rat) rCG56255", Aug. 9, 2005 (Sep. 8, 2005), NPL reference No. XP002734433: obtained on NCBI, NCBI Accession No. EDL91364.
De Vos et al., "Human growth hormone and extracellular domain of its receptor: crystal structure of the complex", Science, 255:306-312 (1992).
Del Alamo and Miodzik, "Frizzled/PCP-Dependent Asymmetric Neuralized Expression Determines R3/R4 Fates in the Drosophilia Eye," Developmental Cell, 11:887-894 (2006).
Diatchenko et al., "Suppression subtractive hybridization: a method for generating differentially regulated or tissue-specific cDNA probes and libraries," Proc Natl Acad Sci U S A, 93:6025-6030 (1997).
Dierick and Bejsovec, "Cellular Mechanisms of Wingless/Wnt Signal Transduction", Current Topics in Developmental Biology, 43: 153-178 (1999).
Doubravska et al. "Fatty acid modification of Wnt1 and Wnt3a at serine is prerequisite for lipidation at cysteine and is essential for Wnt signalling", Cellular Signalling, 23(5): 837-848 (2011).
Egger-Adam et al., "Trimeric G protein-dependent signaling by Frizzled receptors in animal development," Front Biosci, 13:4740-4755 (2008).
EMBL Accession No. EDL91364, Aug. 9, 2005, XP-002934433, 1 page.
European Application No. 10769170.1, (Corrected) European Search Report dated May 27, 2013.
European Application No. 10769170.1, European Search Report dated Apr. 24, 2013.
European Application No. 12734079.2, Extended European Search Report dated Apr. 2, 2015.

(56) References Cited

OTHER PUBLICATIONS

European Application No. 12734079.2, Partial European Search Report Dec. 4, 2014.
European Application No. 12738949.2, Extended European Search Report dated Jul. 4, 2014.
European Application No. 12831452.3, Extended European Search Report dated Dec. 23, 2014.
European Application No. 12831715.3, Extended European Search Report dated Feb. 9, 2015.
Fisher and Upadhyaya, "Molecular genetics of facioscapulohumeral muscular dystrophy (FSHD)", Neuromuscular Disorders, 7(1): 55-62 (1997).
Franch-Marro et al., "Wingless secretion requires endosome-to-Golgi retrieval of Wntless/Evi/Sprinter by the retromer complex", Nature Cell Biology, 10(2): 170-177 (2008). Published online: Jan. 13, 2008.
Fredriksson et al., "Protein detection using proximity-dependent DNA ligation assays", Nature Biotechnology, 20: 473 -477 (2002).
Funakoshi et al., "Emerin and cardiomyopathy in Emery-Dreifuss muscular dystrophy", Neuromuscular Disorders, 9(2): 108-114 (1999).
Galli and Burrus, "Differential Palmit(e)oylation of Wnt1 on C93 and S224 Residues Has Overlapping and Distinct Consequences", PLoS One, 6(10): e26636, pp. 1-17 (2011).
GenBank Accession No. G36470, "Wnt-7a protein—mouse". Downloaded Apr. 30, 2013. http://www.ncbi.nlm.nih.gov/protein/G36470?report=genpept.
GenBank Accession No. H36470, "Wnt-7b protein—mouse". Downloaded Apr. 30, 2013. http://www.ncbi.nlm.nih.gov/protein/H36470?report=genpept.
GenBank Accession No. M89801, "Mouse Wnt-7a mRNA, complete cds." Downloaded Apr. 30, 2013. http://www.ncbi.nlm.nih.gov/nuccore/M89801.
GenBank Accession No. NM_004625, "*Homo sapiens* wingless-type MMTV integration site family, member 7A (WNT7A), mRNA." Downloaded Apr. 30, 2013. http://www.ncbi.nlm.nih.gov/nuccore/NM_004625.
GenBank Accession No. NP_004616, "protein Wnt-7a precursor [*Homo sapiens*]." Downloaded Apr. 30, 2013. http://www.ncbi.nlm.nih.gov/protein/NP_004616.
GenBank Accession No. O00755, RecName: Full=Protein Wnt-7a; Flags: Precursor. Downloaded Apr. 30, 2013. http://www.ncbi.nlm.nih.gov/protein/O00755.
GenBank Accession No. P24383, RecName: Full=Protein Wnt-7a; Flags: Precursor. Downloaded Apr. 30, 2013. http://www.ncbi.nlm.nih.gov/protein/P24383.
GenBank Accession No. P28047, RecName: Full=Protein Wnt-7b; Flags: Precursor. Downloaded Apr. 30, 2013. http://www.ncbi.nlm.nih.gov/protein/P28047.
GenBank Accession No. PF6706, Uncultured bacterium clone PF6706 16S ribosomal RNA gene, partial sequence. Downloaded Apr. 30, 2013. http://www.ncbi.nlm.nih.gov/nuccore/290611196.
Giles, et al., "Caught up in a Wnt storm: Wnt signaling in cancer," Biochim Biophys Acta, 1653(1):1-24 (2003).
Glass et al., "Signalling pathways that mediate skeletal muscle hypertrophy and atrophy", Nature Cell Biology, 5: 87-90 (2003).
Goto et al., "Planar Cell Polarity Genes Regulate Polarized Extracellular Matrix Deposition During Frog Gastrulation," Curr Biol, 15:787-793 (2005).
Green et al., "Opposing Wnt pathways orient cell polarity during organogenesis," Nature, 134:646-656 (2008).
Gros et al., "WNT11 acts as a directional cue to organize the elongation of early muscle fibres", Nature, 457: 589-593 (2009).
Hall et al., "Axonal Remodeling and Synaptic Differentiation in the Cerebellum Is Regulated by WNT-7a Signaling," Cell, 100:525-535 (2000).
Hayman and Ruoslahti, "Distribution of fetal bovine serum fibronectin and endogenous rat cell fibronectin in extracellular matrix", The Journal of Cell Biology, 83(1): 255-259 (1979).

Henikoff and Henikoff, "Amino acid substitution matrices from protein blocks", Proc Natl Acad Sci U S A., 89(22): 10915-10919 (1992).
Hirabayashi et al., "The Wnt/β-catenin pathway directs neuronal differentiation of cortical neural precursor cells," Development 131:2791-2801, 2004.
Hoffman et al., "Characterization of dystrophin in muscle-biopsy specimens from patients with Duchenne's or Becker's muscular dystrophy", N. Engl. J. Med., 318(21): 1363-1368 (1988).
Hoppler, et al., "Expression of a dominant-negative Wnt blocks induction of MyoD in Xenopus embryos," Genes & Development, 10(21):2805-2817 (1996).
Hruby, "Designing peptide receptor agonists and antagonists," Nature Reviews Drug Discovery, 1(11):847-858 (2002).
Hsieh, et al., "Biochemical characterization of Wnt-Frizzled interactions using a soluble, biologically active vertebrate Wnt protein," Proceedings of the National Academy of Sciences, 96(7):3546-3551 (1999).
Huang et al., "Interference of tenascin-C with syndecan-4 binding to fibronectin blocks cell adhesion and stimulates tumor cell proliferation", Cancer Research, 61(23): 8586-8594 (2001).
Huston et al., "Protein engineering of antibody binding sites: recovery of specific activity in an anti-digoxin single-chain Fv analogue produced in *Escherichia coli*", Proc. Natl. Acad. Sci. U.S.A., 85: 5879-5883 (1988).
Hynes and Yamada, "Fibronectins: Multifunctional Modular Glycoproteins", The Journal of Cell Biology, 95: 369-377 (1982).
Ingham, "Has the quest for a Wnt receptor finally frizzled out?," Trends Genet., 12(10)382-384 (1996).
Ishibashi et al, "MyoD induces myogenic differentiation through cooperation of its NH2- and COOH-terminal regions," J Cell Biol, 171, 471-482 (2005).
Ishikawa et al., Seibutsugaku Jiten [Biology Dictionary], first print, Tokyo Kagaku Dojin K.K., (2010); Housekeeping gene (plants) (genes); A gene encoding a protein required for general functions of a cell, which is constitutively expressed (constitutive gene). (Japanese dictionary reference with English summary of relevant portion.).
Janda, et al., "Structural basis of Wnt Recognition by Frizzled," Science, 337(6090):59-64, (2012).
Kadowaki et al., "The segment polarity gene porcupine encodes a putative multitransmembrane protein involved in Wingless processing", Genes Development, 10: 3116-3128 (1996).
Kengaku et al., "Distinct WNT Pathways Regulating AER Formation and Dorsoventral Polarity in the Chick Limb Bud," Science 280:1274-1277, 1998.
Kikuchi, et al., "Multiplicity of the interactions of Wnt proteins and their receptors," Cell Signal, 19(4):659-671 (2007).
Klaus, et al., "Wnt signalling and its impact on development and cancer," Nature Reviews Cancer, 8(5):387-398 (2008).
Koller and Smithies, "Inactivating the β₂-microglobulin locus in mouse embryonic stem cells by homologous recombination", Proc. Natl. Acad. Sci. USA, 86: 8932-8935 (1989).
Komekado, H. et al. "Glycosylation and palmitoylation of Wnt-3a are coupled to produce an active form of Wnt-3a", Genes to Cells, 12(4): 521-534 (2007).
Kuang et al., "Asymmetric self-renewal and commitment of satellite stem cells in muscle," Cell, 129(5):999-1010 (2007).
Kuang et al., "Distinct roles for Pax7 and Pax3 in adult regenerative myogenesis," J Cell Biol,172:103-113 (2006).
Kuang et al., Niche Regulation of Muscle Satellite Cell Self-Renewal and Differentiation, Cell Stem Cell, 2:22-31 (2008).
Kurayoshi et al. "Post-translational palmitoylation and glycosylation of Wnt-5a are necessary for its signalling", Biochem J., 402(3): 515-523 (2007).
Le Grand et al., "Wnt7a activates the planar cell polarity pathway to drive the symmetric expansion of satellite stem cells", Cell Stem Cell, 4: 535-547 (2009).
Lim et al. "Direct Binding of Syndecan-4 Cytoplasmic Domain to the Catalytic Domain of Protein Kinase C (PKCα) Increases Focal Adhesion Localization of PKCα", The Journal of Biological Chemistry, 278(16): 13795-13802 (2003).

(56) References Cited

OTHER PUBLICATIONS

Lim and Campbell, "The sarcoglycan complex in limb-girdle muscular dystrophy," Curr. Opin. Neurol., 11(5):443-452, 1998.
Logan, et al., "The Wnt Signaling Pathway in Development and Disease," (2004) Annu Rev Cell Dev Biol 20:781-810 (2004).
Lyon et al., "Elucidation of the structural features of heparan sulfate important for interaction with the Hep-2 domain of fibronectin", The Journal of Biological Chemistry, 275(7): 4599-4606 (2000).
Lyu and Joo, "Wnt-7a Up-regulates Matrix Metalloproteinase-12 Expression and Promotes Cell Prliferation in Corneal Epithelial Cells during Sound Healing," The Journal of Biological Chemistry, 280(22):21653-21660, 2005.
Maltzahn et al., "A truncated Wnt7a retains full biological activity in skeletal muscle", Nature Communications, 4: 2869, 9 pages (2013).
Maratea et al., "Deletion and fusion analysis of the phage phi X174 lysis gene E", Gene, 40: 39-46 (1985).
Massie et al., "New adenovirus vectors for protein production and gene transfer", Cytotechnology, 28(1-3): 53-64 (1998).
Mason et al., "Mutational analysis of mouse Wnt-1 identifies two temperature-sensitive alleles and attributes of Wnt-1 protein essential for transformation of a mammary cell line", Mol. Biol. Cell, 3: 521-533 (1992).
Matthews et al., "Directional migration of neural crest cells in vivo is regulated by Syndecan-4/Rac1 and non-canonical Wnt signaling/RhoA," Development, 135:1771-1780 (2008).
McKinnell et al., "Pax7 activates myogenic genes by recruitment of a histone methyltransferase complex," Nat Cell Biol,,10:77-84, 2008.
McMahon, "The Wnt family of developmental regulators," Trends Genet., 8(7):236-242 (1992).
Miller, "The Wnts," Genome Biol., 3(1)reviews3001.1-3001.15 (2001).
Miller and Sassoon, "Wnt-7a maintains appropriate uterine patterning during the development of the mouse female reproductive tract," Development, 125:3201-3211 (1998).
Montarras et al., "Direct Isolation of Satellite Cells for Skeletal Muscle Regeneration," Science, 309:2064-2067 (2005).
Montcouquiol et al., "Asymmetric localization of Vangl2 and Fz3 indicate novel mechanisms for planar cell polarity in mammals," J Neurosci, 26:5265-5275 (2006).
Montcouquiol et al., "Identification of Vangl2 and Scrb1 as planar polarity genes in mammals," Nature, 423:173-177 (2003).
Morrell, et al., "Liposomal Packaging Generates Wnt Protein with In Vivo Biological Activity," PLoS One, 3(8):e2930 (2008).
Munoz et al., "Syndecan-4 regulates non-canonical Wnt signalling and is essential for convergent and extension movements in Xenopus embryos," Nat Cell Biol, 8:492-500 (2006).
Murakami et al., "Non-canonical fibroblast growth factor signalling in angiogenesis", Cardiovascular Research, 78: 223-231 (2008).
Murphy et al., "Genetic construction, expression, and melanoma-selective cytotoxicity of a diphtheria toxin-related alpha-melanocyte-stimulating hormone fusion protein", Proc. Natl. Acad. Sci. USA, 83: 8258-8262 (1986).
Nagaoka et al., "Cripto-1 enhances the canonical Wnt/β-catenin signaling pathway by binding to LRP5 and LRP6 co-receptors", Cell Signal, 25(1): 178-189 (2013). Published online Sep. 27, 2012. doi: 10.1016/j.cellsig.2012.09.024.
Nusse, "Wnt signaling in disease and in development," Cell Research, 15(1):28-32 (2005).
Nusse, et al., "Many Tumors Induced by the Mouse Mammary Tumor Virus Contain a Provirus Integrated in the Same Region of the Host Genome," Cell, 31(1):99-109 (1982).
Nusse, R., "Wnts and Hedgehogs: lipid-modified proteins and similarities in signaling mechanisms at the cell surface", Development, 130: 5297-5305 (2003).
O'Dowd et al., "Palmitoylation of the human beta 2 adrenergic receptor" Journal of Biological Chemistry 269: 7564-7569 (1989).

Oustanina et al., "Pax7 directs postnatal renewal and propagation of myogenic satellite cells but not their specification," The EMBO Journal, 23:3430-3439, 2004.
Papkoff, et al., "Wnt-1 Regulates Free Pools of Catenins and Stabilizes APC-Catenin Complexes," Mol. Cell Biol., 16(5):2128-2134 (1996).
Park and Moon, "The planar cell-polarity gene stbm regulates cell behaviour and cell fate in vertebrate embryos," Nat Cell Biol, 4:20-25, 2002.
PCT Application No. International PCT/CA2010/000601, International Search Report mailed Jul. 22, 2010, 7 pages.
PCT Application No. PCT/CA2010/000601, Written Opinion mailed Jul. 22, 2010, 9 pages.
PCT Application No. PCT/CA2010/000601, International Preliminary Report on Patentability mailed Nov. 1, 2011, 10 pages.
PCT Application No. PCT/US2012/020984, International Search Report and Written Opinion, mailed Jul. 30, 2012, 14 pages.
PCT Application No. PCT/US2012/020984, International Preliminary Report on Patentability, dated Jul. 16, 2013, 7 pages.
PCT Application No. PCT/US2012/022761, International Search Report and Written Opinion dated Aug. 10, 2012, 10 pages.
PCT Application No. PCT/US2012/022761, International Preliminary Report on Patentability dated Aug. 10, 2012, 6 pages.
PCT Application No. PCT/US2012/055336, International Search Report and Written Opinion dated Feb. 25, 2013, 11 pages.
PCT Application No. PCT/US2012/055336, International Reliminary Report on Patentability dated Mar. 18, 2014, 7 pages.
PCT Application No. PCT/US2012/055396, International Search Report and Written Opinion dated Feb. 26, 2013, 14 pages.
PCT Application No. PCT/US2012/055396, International Reliminary Report on Patentability dated Feb. 26, 2013, 14 pages.
Peifer et al., "wingless signal and Zeste-white 3 kinase trigger opposing changes in the intracellular distribution of Armadillo," Development, 120(2):369-380 (1994).
Peters et al., "Fibronectin isoform distribution in the mouse. II. Differential distribution of the alternatively spliced EIIIB, EIIIA, and V segments in the adult mouse", Cell Adhesion and Communication, 4(2):127-48 (1996).
Pisconti et al., "Syndecan-3 and Notch cooperate in regulating adult myogenesis", J Cell Biol., 190(3): 427-441 (2010).
Polesskaya et al, "Wnt signaling induces the myogenic specification of resident CD45+ adult stem cells during muscle regeneration", Cell, 113(7): 841-52 (2003).
Resh, M.A. "Fatty acylation of proteins: new insights into membrane targeting of myristoylated and palmitoylated proteins" Biochimica et Biophysica Acta 1451:1-16 (1999).
Rochat et al., "Insulin and Wnt1 Pathways Cooperate to Induce Reserve Cell Activation in Differentiation and Myotube Hypertrophy", Molecular Biology of the Cell, 15: 4544-4555 (2004).
Sacco et al., "Self-renewal and expansion of single transplanted muscle stem cells," Nature, 56:502-506 (2008).
Seale et al., "Pax7 Is Required for the Specification of Myogenic Satellite Cells," Cell, 102(6):777-786 (2000).
Seifert et al., "Frizzled/PCP signalling: a conserved mechanism regulating cell polarity and directed motility," Nat Rev Genet, 8(2):126-138 (2007).
Singh et al., "Assembly of fibronectin extracellular matrix", Annual Review of Cell and Developmental Biology, 26: 397-419 (2010).
Smith et al., "Human interleukin 4. The solution structure of a four-helix bundle protein", J. Mol. Biol., 224: 899-904 (1992).
Smolich et al., "Wnt family proteins are secreted and associated with the cell surface", Molecular Biology of the Cell, 4(12): 1267-1275 (1993).
Srinivas et al., "Cre reporter strains produced by targeted insertion of EYFP and ECFP into the R0SA26 locus," BMC Dev Biol, 1:4 (2001).
Struewing, et al., "Mitochondrial and Nuclear Forms of Wnt13 Are Generated via Alternative Promoters, Alternative RNA Splicing, and Alternative Translation Start Sites," Journal of Biological Chemistry, 281(11):7282-7293 (2006).

(56) References Cited

OTHER PUBLICATIONS

Tajbakhsh et al., "Differential activation of Myf5 and MyoD by different Wnts in explants of mouse paraxial mesoderm and the later activation of myogenesis in the absence of Myf5", Development, 125: 4155-4162 (1998).
Takada et al. "Monounsaturated Fatty Acid Modification of Wnt Protein: Its Role in Wnt Secretion", Developmental Cell, 11(6): 791-801 (2006).
Tallquist et al., "Early myotome specification regulates PDGFA expression and axial skeleton development," Development 127:5059-5070 (2000).
Tanaka et al. "*Drosophila* segment polarity gene product porcupine stimulates the posttranslational N-glycosylation of wingless in the endoplasmic reticulum", J. Biol. Chem., 277: 12816-12823 (2002).
Torban et al., "Genetic interaction between members of the Vangl family causes neural tube defects in mice," Proc Natl Acad Sci U S A,105:3449-3454, 2008.
Torban et al., "Van Gogh-like2 (Strabismus) and its role in planar cell polarity and convergent extension in vertebrates," Trends Genet, 20(11):570-577, 2004.
Torrente et al., "Human circulating AC133+ stem cells restore dystrophin expression and ameliorate function in dystrophic skeletal muscle", The Journal of Clinical Investigation, 114(2): 182-195 (2004).
U.S. Appl. No. 13/266,428, Advisory Action mailed Dec. 5, 2014.
U.S. Appl. No. 13/266,428, Office Action mailed Jun. 30, 2014.
U.S. Appl. No. 13/266,428, Office Action mailed Jun. 9, 2015.
U.S. Appl. No. 13/266,428, Office Action mailed Nov. 12, 2015.
U.S. Appl. No. 13/266,428, Office Action mailed Oct. 15, 2013.
U.S. Appl. No. 13/266,428, Office Action mailed Apr. 19, 2016.
U.S. Appl. No. 13/979,368, Office Action mailed Oct. 6, 2015.
U.S. Appl. No. 13/982,184, Office Action mailed Jun. 11, 2015.
U.S. Appl. No. 13/982,184, Office Action mailed Jan. 4, 2016.
U.S. Appl. No. 14/344,310, Office Action mailed Dec. 30, 2015.
Uhlman and Peyman, "Antisense Oligonucleotides: A New Therapeutic Principle", Chemical Reviews, 90(4): 544-584 (1990).
Van Den Heuvel et al., "Mutations in the segment polarity genes wingless and porcupine impair secretion of the wingless protein", 12(13): 5293-5302 (1993).
Van Leeuwen, et al., "Biological activity of soluble wingless protein in cultured *Drosophila* imaginal disc cells," Nature, 368(6469):342-344 (1994).
Veeman, et al., "A Second Canon: Functions and Mechanisms of Beta-Catenin-Independent Wnt Signaling," Dev. Cell 5(3):367-377 (2003).
Voit, T., "Congenital muscular dystrophies: 1997 update", Brain Development, 20(2): 65-74 (1998).
Von Maltzahn et al, "Wnt7a-Fzd7 signalling directly activates the Akt/mTOR anabolic growth pathway in skeletal muscle", Nature Cell Biology, 14(2): 186-191 (2012).
Wang, et al., "Wnt7b Activates Canonical Signaling in Epithelial and Vascular Smooth Muscle Cells through Interactions with Fzd1, Fzd10, and LRP5," Mol Cell Biol., 25(12): 5022-5030 (2005).
Willert et al., "Wnt Proteins are lipid-modified and can act as stem cell growth factors", Nature, 423(6938): 448-452 (2003).
Wodarz and Nusse, "Mechanisms of Wnt signaling in development", Annu. Rev. Cell. Dev. Biol., 14: 59-88 (1998).
Worton, R., "Muscular dystrophies: diseases of the dystrophin-glycoprotein complex", Science, 270: 755-756 (1995).
Woods et al., "Syndecan-4 binding to the high affinity heparin-binding domain of fibronectin drives focal adhesion formation in fibroblasts", Archives of Biochemistry and Biophysics, 374(1):66-72 (2000).
Xian et al. "Syndecans as receptors and organizers of the extracellular matrix", Cell and Tissue Research, 339(1): 31-46 (2010).
Yamanaka et al., "Wnt11 stimulation induces polarized accumulation of dishevelled at apical adherens junctions through Frizzled 7," Genes to Cells Devoted to Molecular & Cellular Mechanisms, 12:961-967 (2007).
Yang-Snyder, et al., "A frizzled homolog functions in a vertebrate Wnt signaling pathway," Curr Biol., 6(10):1302-1306 (1996).
Zallen, "Planar Polarity and Tissue Morphogenesis," Cell,129(6):1051-1063 (2007).
Zhai et al., "*Drosophila* Wnt-1 Undergoes a Hydrophobic Modification and Is Targeted to Lipid Rafts, a Process That Requires Porcupine", The Journal of Biological Chemistry, 279(32): 33220-33227 (2004).
Zhao, et al., "Controlling the In Vivo Activity of Wnt Liposomes," Methods Enzymol, 465:331-347 (2009).
Zijlstra et al., "Germ-line transmission of a disrupted $\beta_2$-microglobulin gene produced by homologous recombination in embryonic stem cells", Nature, 342: 435-438 (1989).
Zusinaite et al., "Mutations at the palmitoylation site of non-structural protein nsP1 of Semliki Forest virus attenuate virus replication and cause accumulation of compensatory mutations" Journal of General Virology 88: 1977-1985 (2007).

\* cited by examiner

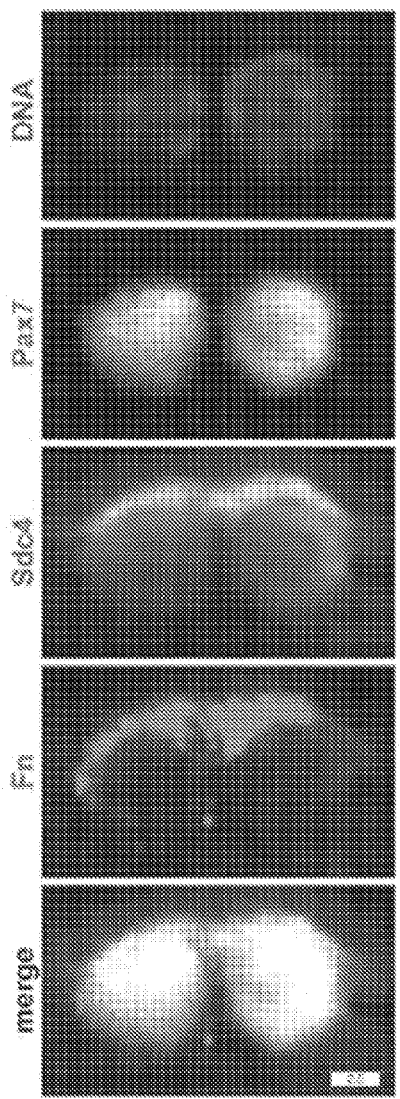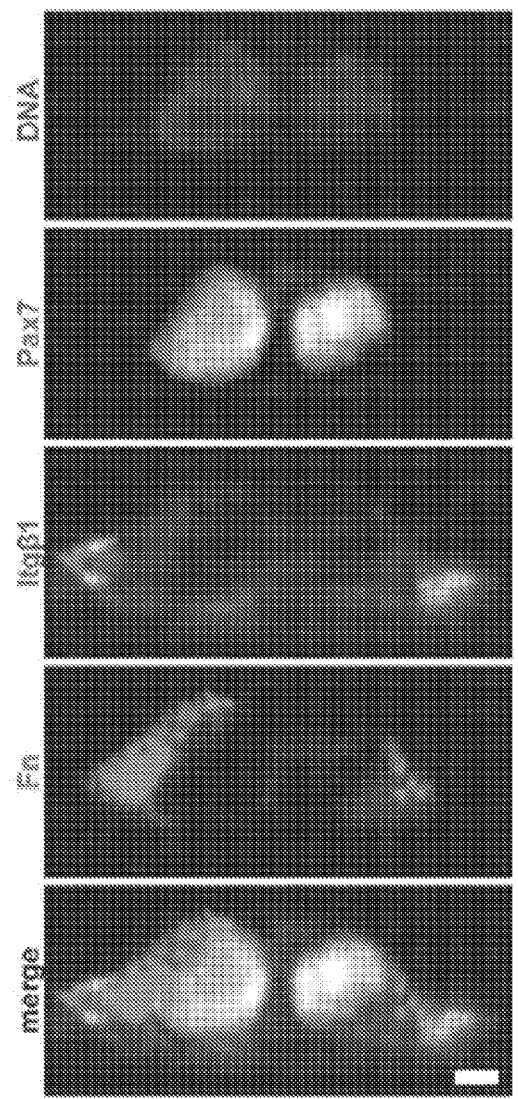

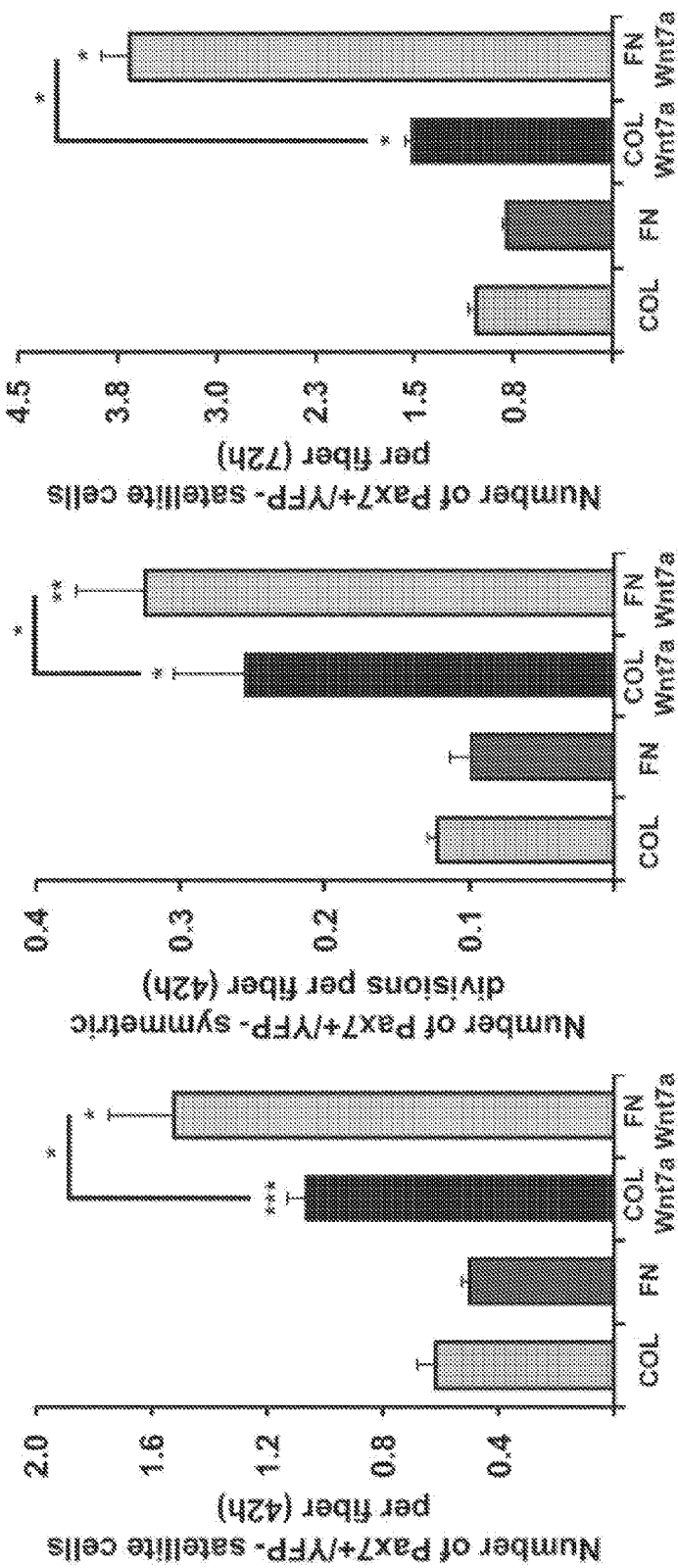

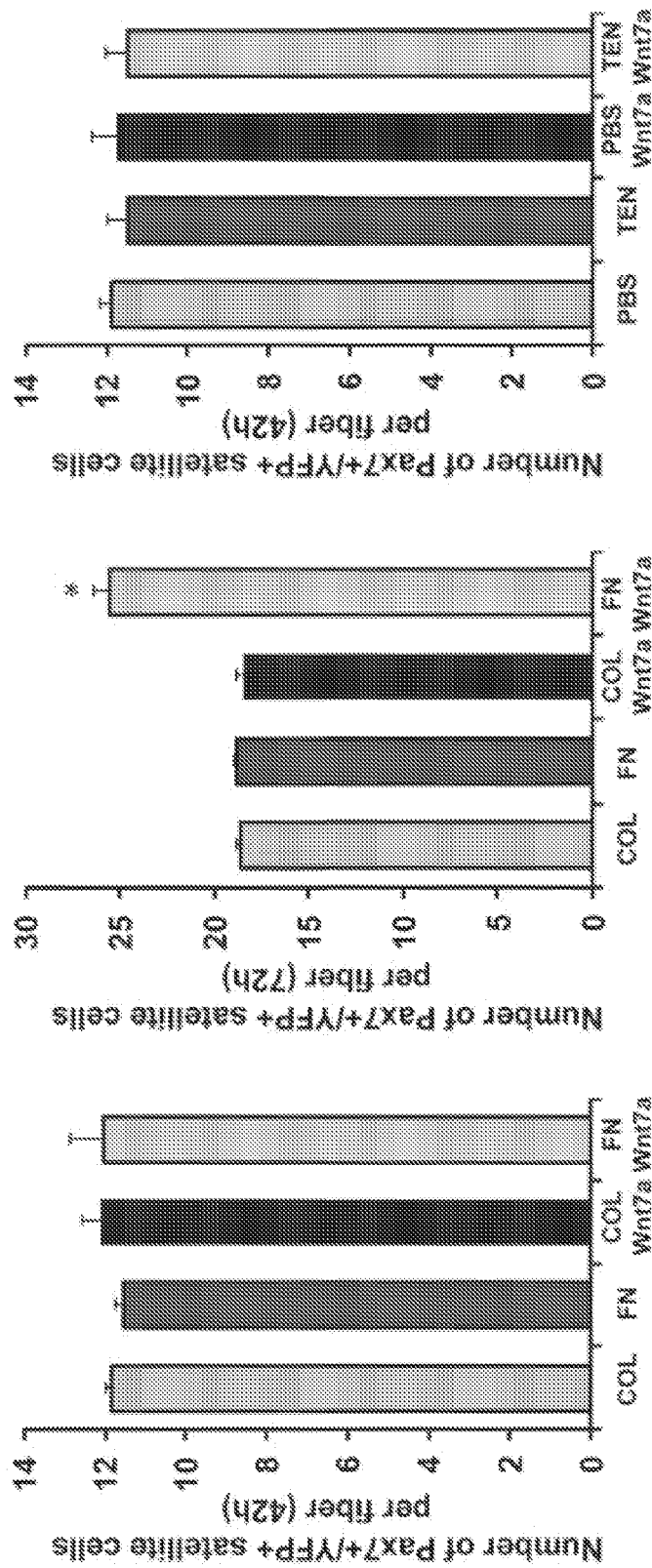

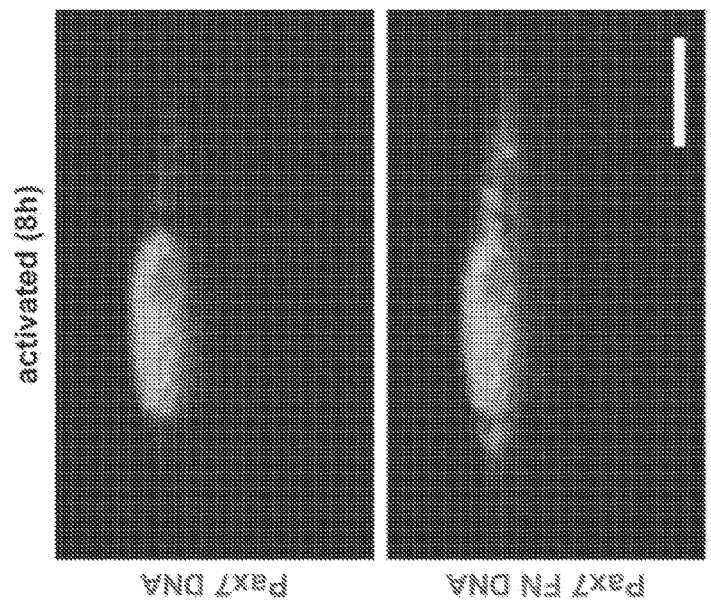
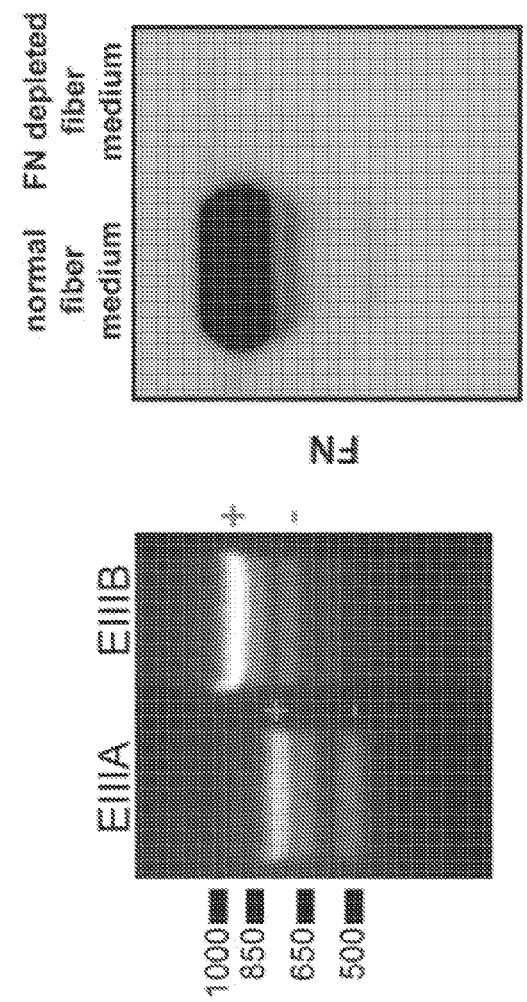
FIG. 22D
FIG. 22E
FIG. 22F

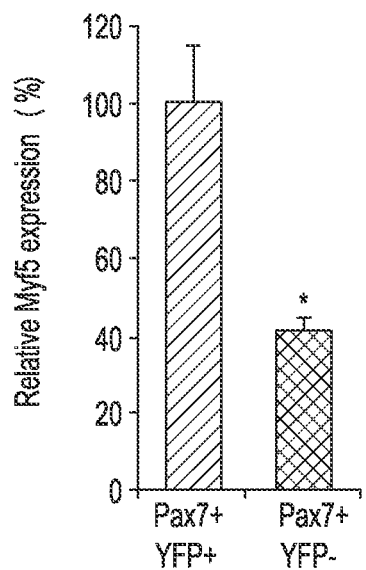
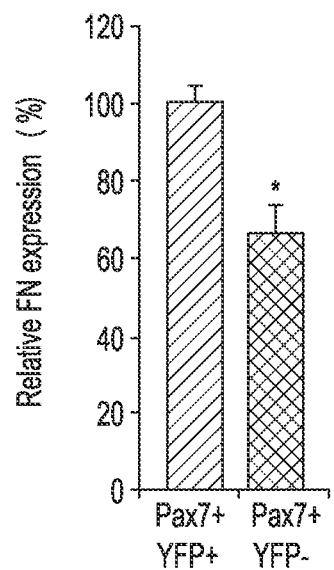
*FIG. 24B*  *FIG. 24C*
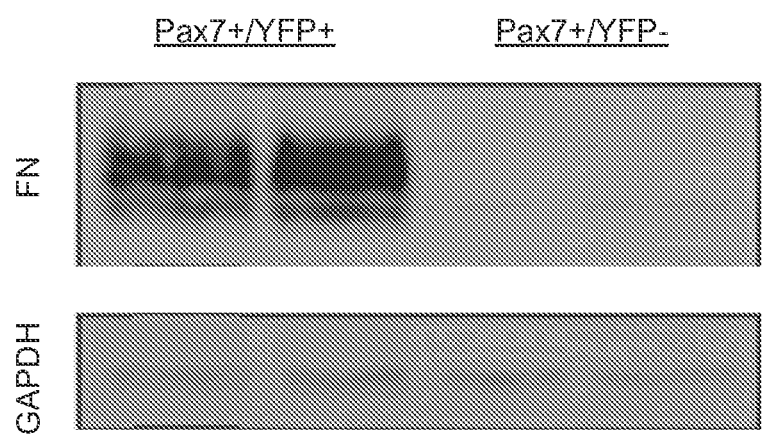
*FIG. 24D*

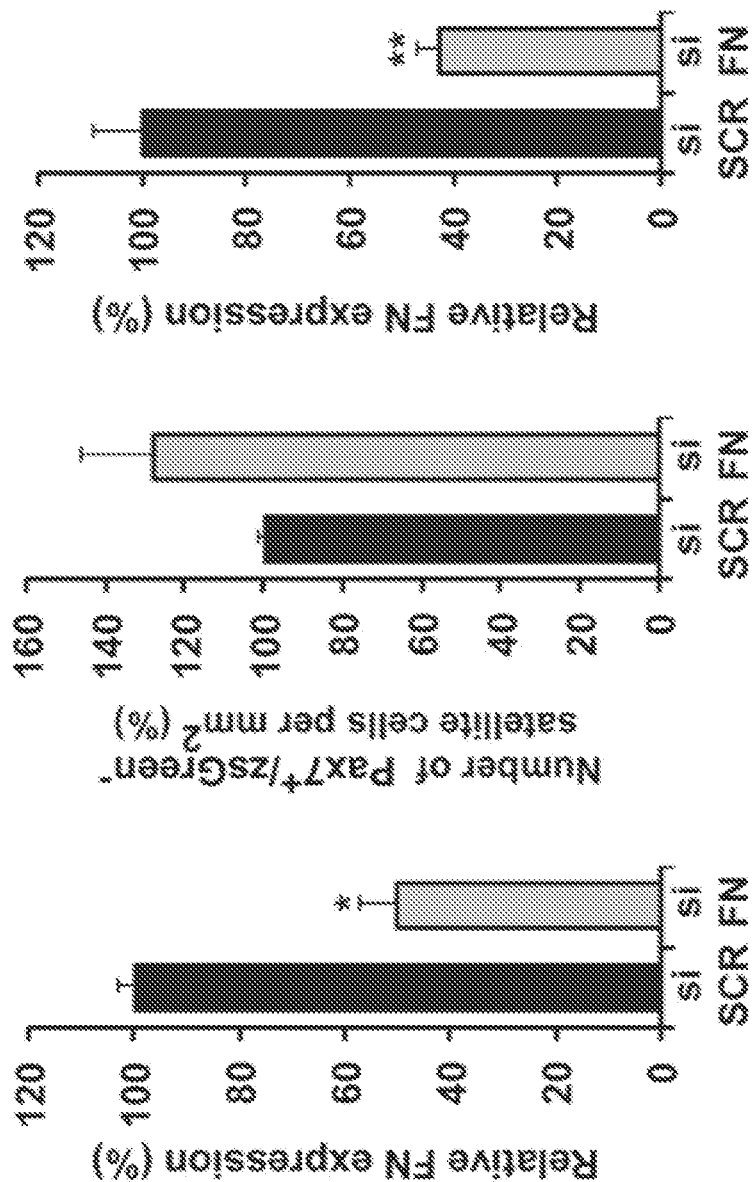

SEQUENCE LISTING

```
<160> NUMBER OF SEQ ID NOS: 50

<210> SEQ ID NO 1
<211> LENGTH: 1732
<212> TYPE: DNA
<213> ORGANISM: Homo sapiens

<400> SEQUENCE: 1
gaggggcggg ggctggaggc agcagcgccc ccgcactccc cgcgtctcgc acacttgcac      60
cggtcgctcg cgcgcagccc ggcgtcgccc cacgccgcgc tcgctcctcc ctccctcctc     120
ccgctccgtg gctcccgtgc tcctggcgag gctcaggcgc ggagcgcgcg gacgggcgca     180
ccgacagacg gccccgggga cgcctcggct cgcgcctccc gggcgggcta tgttgattgc     240
cccgccgggg ccggccgcg ggatcagcac agcccggccc gcggccccgg cggccaatcg     300
ggactatgaa ccggaaagcg cggcgctgcc tgggccacct cttctcagc ctgggcatgg     360
```

```
tctacctccg atcggtggc ttctcctcag tggtagctct gggcgcaagc atcatctgta    420
acaagatccc aggcctggct cccagacagc gggcgatctg ccagagccgg cccgacgcca    480
tcatcgtcat aggagaaggc tcacaaatgg gcctggacga gtgtcagttt cagttccgca    540
atggccgctg gaactgctct gcactgggag agcgcaccgt cttcgggaag gagctcaaag    600
tggggagccg ggaggctgcg ttcacctacg ccatcattgc cgccggcgtg gcccacgcca    660
tcacagctgc ctgtacccag gcaacctga gcgactgtgg ctgcgacaaa gagaagcaag    720
gccagtacca ccgggacgag ggctggaagt ggggtggctg ctctgccgac atccgctacg    780
gcatcggctt cgccaaggtc tttgtggatg cccgggagat caagcagaat gcccggactc    840
tcatgaactt gcacaacaac gaggcaggcc gaaagatcct ggaggagaac atgaagctgg    900
aatgtaagtg ccacggcgtg tcaggctcgt gcaccaccaa gacgtgctgg accacactgc    960
cacagtttcg ggagctgggc tacgtgctca aggacaagta caacgaggcc gttcacgtgg   1020
agcctgtgcg tgccagccgc aacaagcggc ccaccttcct gaagatcaag aagccactgt   1080
cgtaccgcaa gcccatggac acggacctgg tgtacatcga gaagtcgccc aactactgcg   1140
aggaggaccc ggtgaccggc agtgtgggca cccagggccg cgcctgcaac aagacggctc   1200
cccaggccag cggctgtgac ctcatgtgct gtgggcgtgg ctacaacacc accagtacg   1260
cccgcgtgtg gcagtgcaac tgtaagttcc actggtgctg ctatgtcaag tgcaacacgt   1320
gcagcgagcg cacggagatg tacacgtgca agtgagcccc gtgtgcacac caccctcccg   1380
ctgcaagtca gattgctggg aggactggac cgtttccaag ctgcgggctc cctggcagga   1440
tgctgagctt gtcttttctg ctgaggaggg tactttttcct gggtttcctg caggcatccg   1500
tgggggaaaa aaaatctctc agagccctca actattctgt tccacaccca atgctgctcc   1560
accctccccc agacacagcc caggtccctc cgcggctgga gcgaagcctt ctgcagcagg   1620
aactctggac ccctgggcct catcacagca atatttaaca atttattctg ataaaaataa   1680
tattaattta tttaattaaa aagaattctt ccacaaaaaa aaaaaaaaa aa           1732
```

<210> SEQ ID NO 2
<211> LENGTH: 349
<212> TYPE: PRT
<213> ORGANISM: Mus musculus

<400> SEQUENCE: 2

```
Met Thr Arg Lys Ala Arg Arg Cys Leu Gly His Leu Phe Leu Ser Leu
1               5                   10                  15

Gly Ile Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
```

```
            130                 135                 140
Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
            195                 200                 205

Cys Thr Thr Lys Thr Cys Trp Thr Thr Leu Pro Gln Phe Arg Glu Leu
210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
                260                 265                 270

Lys Ser Pro Asn Tyr Cys Glu Glu Asp Pro Val Thr Gly Ser Val Gly
            275                 280                 285

Thr Gln Gly Arg Ala Cys Asn Lys Thr Ala Pro Gln Ala Ser Gly Cys
        290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 3
<211> LENGTH: 349
<212> TYPE: PRT
<213> ORGANISM: Homo sapiens

<400> SEQUENCE: 3

Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160
```

```
Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Gln Phe Arg Glu Leu
    210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 4
<211> LENGTH: 181
<212> TYPE: PRT
<213> ORGANISM: Homo sapiens

<400> SEQUENCE: 4

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
                20                  25                  30

Glu Gly Ser Gln Met Gly Leu Asp Glu Cys Gln Phe Gln Phe Arg Asn
            35                  40                  45

Gly Arg Trp Asn Cys Ser Ala Leu Gly Glu Arg Thr Val Phe Gly Lys
        50                  55                  60

Glu Leu Lys Val Gly Ser Arg Glu Ala Ala Phe Thr Tyr Ala Ile Ile
65                  70                  75                  80

Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys
            180
```

<210> SEQ ID NO 5
<211> LENGTH: 137
<212> TYPE: PRT
<213> ORGANISM: Homo sapiens

<400> SEQUENCE: 5

Thr Cys Trp Thr Thr Leu Pro Gln Phe Arg Glu Leu Gly Tyr Val Leu
1               5                   10                  15

Lys Asp Lys Tyr Asn Glu Ala Val His Val Glu Pro Val Arg Ala Ser
            20                  25                  30

Arg Asn Lys Arg Pro Thr Phe Leu Lys Ile Lys Lys Pro Leu Ser Tyr
        35                  40                  45

Arg Lys Pro Met Asp Thr Asp Leu Val Tyr Ile Glu Lys Ser Pro Asn
    50                  55                  60

Tyr Cys Glu Glu Asp Pro Val Thr Gly Ser Val Gly Thr Gln Gly Arg
65                  70                  75                  80

Ala Cys Asn Lys Thr Ala Pro Gln Ala Ser Gly Cys Asp Leu Met Cys
                85                  90                  95

Cys Gly Arg Gly Tyr Asn Thr His Gln Tyr Ala Arg Val Trp Gln Cys
            100                 105                 110

Asn Cys Lys Phe His Trp Cys Cys Tyr Val Lys Cys Asn Thr Cys Ser
        115                 120                 125

Glu Arg Thr Glu Met Tyr Thr Cys Lys
    130                 135

<210> SEQ ID NO 6
<211> LENGTH: 349
<212> TYPE: PRT
<213> ORGANISM: Rattus norvegicus

<400> SEQUENCE: 6

Met Thr Arg Lys Ala Arg Arg Cys Leu Gly His Leu Phe Leu Ser Leu
1               5                   10                  15

Gly Ile Val Tyr Leu Arg Ile Gly Asp Phe Ser Ser Val Val Ala Leu
            20                  25                  30

Gly Ala Ser Ile Ile Cys Asn Lys Ile Pro Gly Leu Ala Pro Arg Gln
        35                  40                  45

Arg Ala Ile Cys Gln Ser Arg Pro Asp Ala Ile Val Ile Gly Glu
    50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

```
Glu Glu Asn Met Lys Leu Glu Cys Lys Cys His Gly Val Ser Gly Ser
            195                 200                 205

Cys Thr Thr Lys Thr Cys Trp Thr Thr Leu Pro Gln Phe Arg Glu Leu
210                 215                 220

Gly Tyr Val Leu Lys Asp Lys Tyr Asn Glu Ala Val His Val Glu Pro
225                 230                 235                 240

Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
                260                 265                 270

Lys Ser Pro Asn Tyr Cys Glu Glu Asp Pro Val Thr Gly Ser Val Gly
            275                 280                 285

Thr Gln Gly Arg Ala Cys Asn Lys Thr Ala Pro Gln Ala Ser Gly Cys
        290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Met Tyr Thr Cys Lys
            340                 345

<210> SEQ ID NO 7
<211> LENGTH: 349
<212> TYPE: PRT
<213> ORGANISM: Bos taurus

<400> SEQUENCE: 7

Met Asn Arg Lys Ala Arg Arg Cys Leu Gly His Leu Phe Leu Ser Leu
1               5                   10                  15

Gly Met Val Tyr Leu Arg Ile Gly Gly Phe Ser Ser Val Val Ala Leu
                20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
        50                  55                  60

Gly Ser Gln Met Gly Leu Asp Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Arg Asp
130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
            195                 200                 205

Cys Thr Thr Lys Thr Cys Trp Thr Thr Leu Pro Gln Phe Arg Glu Leu
```

Gly Tyr Val Leu Lys Asp Lys Tyr Asn Glu Ala Val His Val Glu Pro
225                 230                 235                 240

Val Arg Ala Ser Arg Asn Lys Arg Pro Ala Phe Leu Lys Ile Lys Lys
            245                 250                 255

Pro Leu Ser Tyr Arg Lys Pro Met Asp Thr Glu Leu Val Tyr Ile Glu
                260                 265                 270

Lys Ser Pro Ser Tyr Cys Glu Glu Asp Pro Ala Thr Gly Ser Val Gly
            275                 280                 285

Thr Gln Gly Arg Ala Cys Asn Lys Thr Ala Pro Gln Ala Ser Gly Cys
    290                 295                 300

Asp Leu Met Cys Cys Gly Arg Gly Tyr Asn Thr His Gln Tyr Ala Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Val Tyr Thr Cys Lys
            340                 345

<210> SEQ ID NO 8
<211> LENGTH: 349
<212> TYPE: PRT
<213> ORGANISM: Gallus gallus

<400> SEQUENCE: 8

Met Asn Arg Lys Thr Arg Arg Trp Ile Phe His Ile Phe Leu Ser Leu
1               5                   10                  15

Gly Ile Val Tyr Ile Lys Ile Gly Gly Phe Ser Ser Val Val Ala Leu
                20                  25                  30

Gly Ala Ser Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
        50                  55                  60

Gly Ser Gln Met Gly Ile Asn Glu Cys Gln Phe Gln Phe Arg Asn Gly
65                  70                  75                  80

Arg Trp Asn Cys Ser Ala Leu Gly Glu Arg Thr Val Phe Gly Lys Glu
                85                  90                  95

Leu Lys Val Gly Ser Arg Glu Ala Ala Phe Thr Tyr Ala Ile Ile Ala
            100                 105                 110

Ala Gly Val Ala His Ala Ile Thr Ala Ala Cys Thr Gln Gly Asn Leu
        115                 120                 125

Ser Asp Cys Gly Cys Asp Lys Glu Lys Gln Gly Gln Tyr His Lys Glu
    130                 135                 140

Glu Gly Trp Lys Trp Gly Gly Cys Ser Ala Asp Ile Arg Tyr Gly Ile
145                 150                 155                 160

Gly Phe Ala Lys Val Phe Val Asp Ala Arg Glu Ile Lys Gln Asn Ala
                165                 170                 175

Arg Thr Leu Met Asn Leu His Asn Asn Glu Ala Gly Arg Lys Ile Leu
            180                 185                 190

Glu Glu Asn Met Lys Leu Glu Cys Lys Cys His Gly Val Ser Gly Ser
        195                 200                 205

Cys Thr Thr Lys Thr Cys Trp Thr Thr Leu Pro Lys Phe Arg Glu Leu
    210                 215                 220

Gly Tyr Ile Leu Lys Asp Lys Tyr Asn Glu Ala Val Gln Val Glu Pro
225                 230                 235                 240

-continued

```
Val Arg Ala Ser Arg Asn Lys Arg Pro Thr Phe Leu Lys Ile Lys Lys
                245                 250                 255

Pro Leu Ser Tyr Arg Lys Pro Met Asp Thr Asp Leu Val Tyr Ile Glu
            260                 265                 270

Lys Ser Pro Asn Tyr Cys Glu Glu Asp Pro Val Thr Gly Ser Val Gly
        275                 280                 285

Thr Gln Gly Arg Met Cys Asn Lys Thr Ala Gln Gln Ser Asn Gly Cys
    290                 295                 300

Asp Leu Met Cys Cys Gly Arg Gly Tyr Asn Thr His Gln Tyr Ser Arg
305                 310                 315                 320

Val Trp Gln Cys Asn Cys Lys Phe His Trp Cys Cys Tyr Val Lys Cys
                325                 330                 335

Asn Thr Cys Ser Glu Arg Thr Glu Val Tyr Thr Cys Lys
                340                 345

<210> SEQ ID NO 9
<211> LENGTH: 26
<212> TYPE: DNA
<213> ORGANISM: Homo sapiens

<400> SEQUENCE: 9
atataagctt atgaaccgga aagcgc                                          26

<210> SEQ ID NO 10
<211> LENGTH: 26
<212> TYPE: DNA
<213> ORGANISM: Homo sapiens

<400> SEQUENCE: 10
atatggatcc agctaccact gaggag                                          26

<210> SEQ ID NO 11
<211> LENGTH: 26
<212> TYPE: DNA
<213> ORGANISM: Homo sapiens

<400> SEQUENCE: 11
atatggatcc ctgggcgcaa gcatca                                          26

<210> SEQ ID NO 12
<211> LENGTH: 56
<212> TYPE: DNA
<213> ORGANISM: Homo sapiens

<400> SEQUENCE: 12
atatctcgag tcaggcgtag tcaggcacgt cgtatggata cttggtggtg cacgag         56

<210> SEQ ID NO 13
<211> LENGTH: 30
<212> TYPE: DNA
<213> ORGANISM: Homo sapiens

<400> SEQUENCE: 13
atatggatcc acgtgctgga ccacactgcc                                      30

<210> SEQ ID NO 14
<211> LENGTH: 56
<212> TYPE: DNA
<213> ORGANISM: Homo sapiens

<400> SEQUENCE: 14
```
atatctcgag tcaggcgtag tcaggcacgt cgtatggata cttgcacgtg tacatc       56

<210> SEQ ID NO 15
<211> LENGTH: 26
<212> TYPE: DNA
<213> ORGANISM: Homo sapiens

<400> SEQUENCE: 15
atatggatcc ctgggcgcaa gcatca                                        26

<210> SEQ ID NO 16
<211> LENGTH: 56
<212> TYPE: DNA
<213> ORGANISM: Homo sapiens

<400> SEQUENCE: 16
atatctcgag tcaggcgtag tcaggcacgt cgtatggata cttgcacgtg tacatc       56

<210> SEQ ID NO 17
<211> LENGTH: 20
<212> TYPE: DNA
<213> ORGANISM: Homo sapiens

<400> SEQUENCE: 17
tcttactgcc cacccaccta                                               20

<210> SEQ ID NO 18
<211> LENGTH: 20
<212> TYPE: DNA
<213> ORGANISM: Homo sapiens

<400> SEQUENCE: 18
cacgtttttg gccaggtaat                                               20

<210> SEQ ID NO 19
<211> LENGTH: 20
<212> TYPE: DNA
<213> ORGANISM: Homo sapiens

<400> SEQUENCE: 19
ggccacacct acaaccagta                                               20

<210> SEQ ID NO 20
<211> LENGTH: 20
<212> TYPE: DNA
<213> ORGANISM: Homo sapiens

<400> SEQUENCE: 20
tcgtctctgt cagcttgcac                                               20

<210> SEQ ID NO 21
<211> LENGTH: 20
<212> TYPE: DNA
<213> ORGANISM: Homo sapiens

<400> SEQUENCE: 21
aatcctcaag accagcctca                                               20

<210> SEQ ID NO 22
<211> LENGTH: 20
<212> TYPE: DNA
<213> ORGANISM: Homo sapiens

<400> SEQUENCE: 22
tagaggagct gttggccttc                                            20

<210> SEQ ID NO 23
<211> LENGTH: 20
<212> TYPE: DNA
<213> ORGANISM: Homo sapiens

<400> SEQUENCE: 23
tgagggaaca ggtggagaac                                            20

<210> SEQ ID NO 24
<211> LENGTH: 20
<212> TYPE: DNA
<213> ORGANISM: Homo sapiens

<400> SEQUENCE: 24
ctgttctttc gggaccagac                                            20

<210> SEQ ID NO 25
<211> LENGTH: 20
<212> TYPE: DNA
<213> ORGANISM: Homo sapiens

<400> SEQUENCE: 25
ggctacgaca ccgcctacta                                            20

<210> SEQ ID NO 26
<211> LENGTH: 20
<212> TYPE: DNA
<213> ORGANISM: Homo sapiens

<400> SEQUENCE: 26
gtggagatgc gctccactat                                            20

<210> SEQ ID NO 27
<211> LENGTH: 20
<212> TYPE: DNA
<213> ORGANISM: Homo sapiens

<400> SEQUENCE: 27
aaccacatcc ctgagaatgc                                            20

<210> SEQ ID NO 28
<211> LENGTH: 20
<212> TYPE: DNA
<213> ORGANISM: Homo sapiens

<400> SEQUENCE: 28
aggaaaacgg caaagaggat                                            20

<210> SEQ ID NO 29
<211> LENGTH: 20
<212> TYPE: DNA
<213> ORGANISM: Homo sapiens

<400> SEQUENCE: 29
cagcttcttt gcagctcctt                                            20

<210> SEQ ID NO 30
<211> LENGTH: 19
<212> TYPE: DNA
<213> ORGANISM: Homo sapiens

```
<400> SEQUENCE: 30
gcagcgatat cgtcatcca                                              19

<210> SEQ ID NO 31
<211> LENGTH: 19
<212> TYPE: DNA
<213> ORGANISM: Homo sapiens

<400> SEQUENCE: 31
acccagaaga ctgtggatg                                              19

<210> SEQ ID NO 32
<211> LENGTH: 20
<212> TYPE: DNA
<213> ORGANISM: Homo sapiens

<400> SEQUENCE: 32
acacattggg ggtaggaaca                                             20

<210> SEQ ID NO 33
<211> LENGTH: 18
<212> TYPE: DNA
<213> ORGANISM: Homo sapiens

<400> SEQUENCE: 33
cgagatggcc aggagaga                                               18

<210> SEQ ID NO 34
<211> LENGTH: 20
<212> TYPE: DNA
<213> ORGANISM: Homo sapiens

<400> SEQUENCE: 34
aaggttggtg agggtgatgg                                             20

<210> SEQ ID NO 35
<211> LENGTH: 20
<212> TYPE: DNA
<213> ORGANISM: Homo sapiens

<400> SEQUENCE: 35
aaggttggtg agggtgatgg                                             20

<210> SEQ ID NO 36
<211> LENGTH: 27
<212> TYPE: DNA
<213> ORGANISM: Homo sapiens

<400> SEQUENCE: 36
ccagtttcca tcaattataa aacagaa                                     27

<210> SEQ ID NO 37
<211> LENGTH: 22
<212> TYPE: DNA
<213> ORGANISM: Homo sapiens

<400> SEQUENCE: 37
ccctgaagaa caatcagaag ag                                          22

<210> SEQ ID NO 38
<211> LENGTH: 20
<212> TYPE: DNA
<213> ORGANISM: Homo sapiens
```

<400> SEQUENCE: 38
tgaaatgacc actgccaaag					20

<210> SEQ ID NO 39
<211> LENGTH: 8815
<212> TYPE: DNA
<213> ORGANISM: Homo sapiens

<400> SEQUENCE: 39

| | | | | | |
|---|---|---|---|---|---|
| gcccgcgccg | gctgtgctgc | acaggggag | gagagggaac | cccaggcgcg | agcgggaaga | 60 |
| ggggacctgc | agccacaact | tctctggtcc | tctgcatccc | ttctgtccct | ccacccgtcc | 120 |
| ccttccccac | cctctggccc | ccaccttctt | ggaggcgaca | accccgggga | ggcattagaa | 180 |
| gggatttttc | ccgcaggttg | cgaagggaag | caaacttggt | ggcaacttgc | ctcccggtgc | 240 |
| gggcgtctct | cccccaccgt | ctcaacatgc | ttaggggtcc | ggggcccggg | ctgctgctgc | 300 |
| tggccgtcca | gtgcctgggg | acagcggtgc | cctccacggg | agcctcgaag | agcaagaggc | 360 |
| aggctcagca | aatggttcag | ccccagtccc | cggtggctgt | cagtcaaagc | aagcccggtt | 420 |
| gttatgacaa | tggaaaacac | tatcagataa | atcaacagtg | ggagcggacc | tacctaggca | 480 |
| atgcgttggt | ttgtacttgt | tatggaggaa | gccgaggttt | taactgcgag | agtaaacctg | 540 |
| aagctgaaga | gacttgcttt | gacaagtaca | ctgggaacac | ttaccgagtg | ggtgacactt | 600 |
| atgagcgtcc | taaagactcc | atgatctggg | actgtacctg | catcgggct | gggcgaggga | 660 |
| gaataagctg | taccatcgca | aaccgctgcc | atgaaggggg | tcagtcctac | aagattggtg | 720 |
| acacctggag | gagaccacat | gagactggtg | gttacatgtt | agagtgtgtg | tgtcttggta | 780 |
| atggaaaagg | agaatggacc | tgcaagccca | tagctgagaa | gtgttttgat | catgctgctg | 840 |
| ggacttccta | tgtggtcgga | gaaacgtggg | agaagcccta | ccaaggctgg | atgatggtag | 900 |
| attgtacttg | cctgggagaa | ggcagcgac | gcatcacttg | cacttctaga | aatagatgca | 960 |
| acgatcagga | cacaaggaca | tcctatagaa | ttggagacac | ctggagcaag | aaggataatc | 1020 |
| gaggaaacct | gctccagtgc | atctgcacag | gcaacggccg | aggagagtgg | aagtgtgaga | 1080 |
| ggcacaccct | ctgtgcagacc | acatcgagcg | gatctggccc | cttcaccgat | gttcgtgcag | 1140 |
| ctgtttacca | accgcagcct | cacccccagc | ctcctcccta | tggccactgt | gtcacagaca | 1200 |
| gtggtgtggt | ctactctgtg | gggatgcagt | ggctgaagac | acaaggaaat | aagcaaatgc | 1260 |
| tttgcacgtg | cctgggcaac | ggagtcagct | gccaagagac | agctgtaacc | cagacttacg | 1320 |
| gtggcaactc | aaatgggagag | ccatgtgtct | taccattcac | ctacaatggc | aggacgttct | 1380 |
| actcctgcac | cacagaaggg | cgacaggacg | gacatctttg | gtgcagcaca | acttcgaatt | 1440 |
| atgagcagga | ccagaaatac | tctttctgca | cagaccacac | tgtttggtt | cagactcgag | 1500 |
| gaggaaattc | caatggtgcc | ttgtgccact | tcccttcct | atacaacaac | cacaattaca | 1560 |
| ctgattgcac | ttctgagggc | agaagagaca | acatgaagtg | gtgtgggacc | acacagaact | 1620 |
| atgatgccga | ccagaagttt | gggttctgcc | ccatggctgc | ccacgaggaa | atctgcacaa | 1680 |
| ccaatgaagg | ggtcatgtac | cgcattggag | atcagtggga | taagcagcat | gacatgggtc | 1740 |
| acatgatgag | gtgcacgtgt | gttgggaatg | gtcgtgggga | atggacatgc | attgcctact | 1800 |
| cgcagcttcg | agatcagtgc | attgttgatg | acatcactta | caatgtgaac | gacacattcc | 1860 |
| acaagcgtca | tgaagagggg | cacatgctga | actgtacatg | cttcggtcag | ggtcgggca | 1920 |
| ggtggaagtg | tgatcccgtc | gaccaatgcc | aggattcaga | gactgggacg | ttttatcaaa | 1980 |

| | |
|---|---|
| ttggagattc atgggagaag tatgtgcatg gtgtcagata ccagtgctac tgctatggcc | 2040 |
| gtggcattgg ggagtggcat tgccaacctt tacagaccta tccaagctca agtggtcctg | 2100 |
| tcgaagtatt tatcactgag actccgagtc agcccaactc ccaccccatc cagtggaatg | 2160 |
| caccacagcc atctcacatt tccaagtaca ttctcaggtg gagacctaaa aattctgtag | 2220 |
| gccgttggaa ggaagctacc ataccaggcc acttaaactc ctacaccatc aaaggcctga | 2280 |
| agcctggtgt ggtatacgag ggccagctca tcagcatcca gcagtacggc caccaagaag | 2340 |
| tgactcgctt tgacttcacc accaccagca ccagcacacc tgtgaccagc aacaccgtga | 2400 |
| caggagagac gactcccttt tctcctcttg tggccacttc tgaatctgtg accgaaatca | 2460 |
| cagccagtag ctttgtggtc tcctgggtct cagcttccga caccgtgtcg ggattccggg | 2520 |
| tggaatatga gctgagtgag gagggagatg agccacagta cctggatctt ccaagcacag | 2580 |
| ccacttctgt gaacatccct gacctgcttc ctggccgaaa atacattgta aatgtctatc | 2640 |
| agatatctga ggatgggag cagagtttga tcctgtctac ttcacaaaca acagcgcctg | 2700 |
| atgcccctcc tgacccgact gtggaccaag ttgatgacac ctcaattgtt gttcgctgga | 2760 |
| gcagaccca ggctcccatc acagggtaca gaatagtcta ttcgccatca gtagaaggta | 2820 |
| gcagcacaga actcaacctt cctgaaactg caaactccgt caccctcagt gacttgcaac | 2880 |
| ctggtgttca gtataacatc actatctatg ctgtggaaga aaatcaagaa agtacacctg | 2940 |
| ttgtcattca acaagaaacc actggcaccc cacgctcaga tacagtgccc tctcccaggg | 3000 |
| acctgcagtt tgtggaagtg acagacgtga aggtcaccat catgtggaca ccgcctgaga | 3060 |
| gtgcagtgac cggctaccgt gtggatgtga tccccgtcaa cctgcctggc gagcacgggc | 3120 |
| agaggctgcc catcagcagg aacacctttg cagaagtcac cgggctgtcc cctggggtca | 3180 |
| cctattactt caaagtcttt gcagtgagcc atgggaggga gcagcagcct ctgactgctc | 3240 |
| aacagacaac caaactggat gctcccacta acctccagtt tgtcaatgaa actgattcta | 3300 |
| ctgtcctggt gagatggact ccacctcggg cccagataac aggatacaga ctgaccgtgg | 3360 |
| gccttacccg aagaggacag cccaggcagt acaatgtggg tccctctgtc tccaagtacc | 3420 |
| cactgaggaa tctgcagcct gcatctgagt acaccgtatc cctcgtggcc ataaagggca | 3480 |
| accaagagag ccccaaagcc actggagtct ttaccacact gcagcctggg agctctattc | 3540 |
| caccttacaa caccgaggtg actgagacca ccattgtgat cacatggacg cctgctccaa | 3600 |
| gaattggttt taagctgggt gtacgaccaa gccagggagg agaggcacca cgagaagtga | 3660 |
| cttcagactc aggaagcatc gttgtgtccg gcttgactcc aggagtagaa tacgtctaca | 3720 |
| ccatccaagt cctgagagat ggacaggaaa gagatgcgcc aattgtaaac aaagtggtga | 3780 |
| caccattgtc tccaccaaca aacttgcatc tggaggcaaa ccctgacact ggagtgctca | 3840 |
| cagtctcctg ggagaggagc accaccccag acattactgg ttatagaatt accacaaccc | 3900 |
| ctacaaacgg ccagcaggga aattctttgg aagaagtggt ccatgctgat cagagctcct | 3960 |
| gcactttga taacctgagt cccggcctgg agtacaatgt cagtgtttac actgtcaagg | 4020 |
| atgacaagga aagtgtccct atctctgata ccatcatccc agaggtgccc caactcactg | 4080 |
| acctaagctt tgttgatata accgattcaa gcatcggcct gaggtggacc ccgctaaact | 4140 |
| cttccaccat tattgggtac cgcatcacag tagttgcggc aggagaaggt atccctattt | 4200 |
| ttgaagattt tgtggactcc tcagtaggat actacacagt cacagggctg agccgggca | 4260 |
| ttgactatga tatcagcgtt atcactctca ttaatggcgg cgagagtgcc cctactacac | 4320 |
| tgacacaaca aacggctgtt cctcctccca ctgacctgcg attcaccaac attggtccag | 4380 |

```
acaccatgcg tgtcacctgg gctccacccc catccattga tttaaccaac ttcctggtgc   4440
gttactcacc tgtgaaaaat gaggaagatg ttgcagagtt gtcaatttct ccttcagaca   4500
atgcagtggt cttaacaaat ctcctgcctg gtacagaata tgtagtgagt gtctccagtg   4560
tctacgaaca acatgagagc acacctctta gaggaagaca gaaaacaggt cttgattccc   4620
caactggcat tgacttttct gatattactg ccaactcttt tactgtgcac tggattgctc   4680
ctcgagccac catcactggc tacaggatcc gccatcatcc cgagcacttc agtgggagac   4740
ctcgagaaga tcgggtgccc cactctcgga attccatcac cctcaccaac ctcactccag   4800
gcacagagta tgtggtcagc atcgttgctc ttaatggcag agaggaaagt cccttattga   4860
ttggccaaca atcaacagtt tctgatgttc cgagggacct ggaagttgtt gctgcgaccc   4920
ccaccagcct actgatcagc tgggatgctc ctgctgtcac agtgagatat tacaggatca   4980
cttacggaga gacaggagga aatagccctg tccaggagtt cactgtgcct gggagcaagt   5040
ctacagctac catcagcggc cttaaacctg gagttgatta taccatcact gtgtatgctg   5100
tcactggccg tggagacagc cccgcaagca gcaagccaat ttccattaat taccgaacag   5160
aaattgacaa accatcccag atgcaagtga ccgatgttca ggacaacagc attagtgtca   5220
agtggctgcc ttcaagttcc cctgttactg gttacagagt aaccaccact cccaaaaatg   5280
gaccaggacc aacaaaaact aaaactgcag gtccagatca aacagaaatg actattgaag   5340
gcttgcagcc cacagtggag tatgtggtta gtgtctatgc tcagaatcca agcggagaga   5400
gtcagcctct ggttcagact gcagtaacca acattgatcg ccctaaagga ctggcattca   5460
ctgatgtgga tgtcgattcc atcaaaattg cttgggaaag cccacagggg caagtttcca   5520
ggtacagggt gacctactcg agccctgagg atggaatcca tgagctattc cctgcacctg   5580
atggtgaaga agacactgca gagctgcaag gcctcagacc gggttctgag tacacagtca   5640
gtgtggttgc cttgcacgat gatatggaga gccagcccct gattggaacc cagtccacag   5700
ctattcctgc accaactgac ctgaagttca ctcaggtcac acccacaagc ctgagcgccc   5760
agtggacacc acccaatgtt cagctcactg gatatcgagt gcgggtgacc cccaaggaga   5820
agaccggacc aatgaaagaa atcaaccttg ctcctgacag ctcatccgtg gttgtatcag   5880
gacttatggt ggccaccaaa tatgaagtga gtgtctatgc tcttaaggac actttgacaa   5940
gcagaccagc tcagggagtt gtcaccactc tggagaatgt cagcccacca agaagggctc   6000
gtgtgacaga tgctactgag accaccatca ccattagctg gagaaccaag actgagacga   6060
tcactggctt ccaagttgat gccgttccag ccaatggcca gactccaatc cagagaacca   6120
tcaagccaga tgtcagaagc tacaccatca caggtttaca accaggcact gactacaaga   6180
tctacctgta cacttgaat gacaatgctc ggagctcccc tgtggtcatc gacgcctcca   6240
ctgccattga tgcaccatcc aacctgcgtt tcctggccac cacacccaat tccttgctgg   6300
tatcatggca gccgccacgt gccaggatta ccggctacat catcaagtat gagaagcctg   6360 gtctcctcc cagagaagtg gtccctcggc cccgccctgg tgtcacagag gctactatta   6420
ctggcctgga accgggaacc gaatatacaa tttatgtcat tgccctgaag aataatcaga   6480
agagcgagcc cctgattgga aggaaaaaga cagacgagct tccccaactg gtaacccttc   6540
cacaccccaa tcttcatgga ccagagatct tggatgttcc ttccacagtt caaaagaccc   6600
ctttcgtcac ccaccctggg tatgacactg gaaatggtat tcagcttcct ggcacttctg   6660
gtcagcaacc cagtgttggg caacaaatga tctttgagga acatggtttt aggcggacca   6720
```

| | |
|---|---|
| caccgcccac aacggccacc cccataaggc ataggccaag accatacccg ccgaatgtag | 6780 |
| gtgaggaaat ccaaattggt cacatcccca gggaagatgt agactatcac ctgtacccac | 6840 |
| acggtccggg actcaatcca aatgcctcta caggacaaga agctctctct cagacaacca | 6900 |
| tctcatgggc cccattccag gacacttctg agtacatcat ttcatgtcat cctgttggca | 6960 |
| ctgatgaaga acccttacag ttcagggttc ctggaacttc taccagtgcc actctgacag | 7020 |
| gcctcaccag aggtgccacc tacaacatca tagtggaggc actgaaagac cagcagaggc | 7080 |
| ataaggttcg ggaagaggtt gttaccgtgg gcaactctgt caacgaaggc ttgaaccaac | 7140 |
| ctacggatga ctcgtgcttt gaccoctaca cagtttccca ttatgccgtt ggagatgagt | 7200 |
| gggaacgaat gtctgaatca ggctttaaac tgttgtgcca gtgcttaggc tttggaagtg | 7260 |
| gtcatttcag atgtgattca tctagatggt gccatgacaa tggtgtgaac tacaagattg | 7320 |
| gagagaagtg ggaccgtcag ggagaaaatg gccagatgat gagctgcaca tgtcttggga | 7380 |
| acggaaaagg agaattcaag tgtgaccctc atgaggcaac gtgttatgat gatgggaaga | 7440 |
| cataccacgt aggagaacag tggcagaagg aatatctcgg tgccatttgc tcctgcacat | 7500 |
| gctttggagg ccagcgggc tggcgctgtg acaactgccg cagacctggg ggtgaaccca | 7560 |
| gtcccgaagg cactactggc cagtcctaca accagtattc tcagagatac catcagaaa | 7620 |
| caaacactaa tgttaattgc ccaattgagt gcttcatgcc tttagatgta caggctgaca | 7680 |
| gagaagattc ccgagagtaa atcatctttc caatccagag aacaagcat gtctctctgc | 7740 |
| caagatccat ctaaactgga gtgatgttag cagacccagc ttagagttct tctttctttc | 7800 |
| ttaagcccct tgctctggag gaagttctcc agcttcagct caactcacag cttctccaag | 7860 |
| catcaccctg ggagtttcct gagggttttc tcataaatga gggctgcaca ttgcctgttc | 7920 |
| tgcttcgaag tattcaatac cgctcagtat tttaaatgaa gtgattctaa gatttggttt | 7980 |
| gggatcaata ggaaagcata tgcagccaac caagatgcaa atgttttgaa atgatatgac | 8040 |
| caaaatttta agtaggaaag tcacccaaac acttctgctt tcacttaagt gtctggcccg | 8100 |
| caatactgta ggaacaagca tgatcttgtt actgtgatat tttaaatatc cacagtactc | 8160 |
| acttttccca aatgatccta gtaattgcct agaaatatct ttctcttacc tgttatttat | 8220 |
| caattttcc cagtattttt atacggaaaa aattgtattg aaaacactta gtatgcagtt | 8280 |
| gataagagga atttggtata attatggtgg gtgattattt tttatactgt atgtgccaaa | 8340 |
| gctttactac tgtggaaaga caactgtttt aataaaagat ttacattcca caacttgaag | 8400 |
| ttcatctatt tgatataaga caccttcggg ggaaataatt cctgtgaata ttcttttca | 8460 |
| attcagcaaa catttgaaaa tctatgatgt gcaagtctaa ttgttgattt cagtacaaga | 8520 |
| ttttctaaat cagttgctac aaaaactgat tggtttttgt cacttcatct cttcactaat | 8580 |
| ggagatagct ttacactttc tgctttaata gatttaagtg daccccaata tttattaaaa | 8640 |
| ttgctagttt accgttcaga agtataatag aaataatctt tagttgctct tttctaacca | 8700 |
| ttgtaattct tcccttcttc cctccacctt tccttcattg aataaacctc tgttcaaaga | 8760 |
| gattgcctgc aagggaaata aaaatgacta agatattaaa aaaaaaaaa aaaaa | 8815 |

<210> SEQ ID NO 40
<211> LENGTH: 2477
<212> TYPE: PRT
<213> ORGANISM: Homo sapiens

<400> SEQUENCE: 40

Met Leu Arg Gly Pro Gly Pro Gly Leu Leu Leu Leu Ala Val Gln Cys

-continued

```
1               5                   10                  15
Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
                35                  40                  45

Lys Pro Gly Cys Tyr Asp Asn Gly Lys His Tyr Gln Ile Asn Gln Gln
            50                  55                  60

Trp Glu Arg Thr Tyr Leu Gly Asn Ala Leu Val Cys Thr Cys Tyr Gly
 65                 70                  75                  80

Gly Ser Arg Gly Phe Asn Cys Glu Ser Lys Pro Glu Ala Glu Glu Thr
                    85                  90                  95

Cys Phe Asp Lys Tyr Thr Gly Asn Thr Tyr Arg Val Gly Asp Thr Tyr
                100                 105                 110

Glu Arg Pro Lys Asp Ser Met Ile Trp Asp Cys Thr Cys Ile Gly Ala
                115                 120                 125

Gly Arg Gly Arg Ile Ser Cys Thr Ile Ala Asn Arg Cys His Glu Gly
            130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                    165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
            210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                    245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
            275                 280                 285

Val Arg Ala Ala Val Tyr Gln Pro Gln Pro His Pro Gln Pro Pro Pro
            290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                    325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
            370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                    405                 410                 415

Gly Ala Leu Cys His Phe Pro Phe Leu Tyr Asn Asn His Asn Tyr Thr
                420                 425                 430
```

```
Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
        500                 505                 510

Gln Leu Arg Asp Gln Cys Ile Val Asp Asp Ile Thr Tyr Asn Val Asn
            515                 520                 525

Asp Thr Phe His Lys Arg His Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
        580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
        660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
        690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
        740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
        820                 825                 830

Arg Pro Gln Ala Pro Ile Thr Gly Tyr Arg Ile Val Tyr Ser Pro Ser
    835                 840                 845
```

-continued

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                    885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Pro Arg Ala Gln
    1010            1015            1020

Ile Thr Gly Tyr Arg Leu Thr Val Gly Leu Thr Arg Arg Gly Gln
    1025            1030            1035

Pro Arg Gln Tyr Asn Val Gly Pro Ser Val Ser Lys Tyr Pro Leu
    1040            1045            1050

Arg Asn Leu Gln Pro Ala Ser Glu Tyr Thr Val Ser Leu Val Ala
    1055            1060            1065

Ile Lys Gly Asn Gln Glu Ser Pro Lys Ala Thr Gly Val Phe Thr
    1070            1075            1080

Thr Leu Gln Pro Gly Ser Ser Ile Pro Pro Tyr Asn Thr Glu Val
    1085            1090            1095

Thr Glu Thr Thr Ile Val Ile Thr Trp Thr Pro Ala Pro Arg Ile
    1100            1105            1110

Gly Phe Lys Leu Gly Val Arg Pro Ser Gln Gly Gly Glu Ala Pro
    1115            1120            1125

Arg Glu Val Thr Ser Asp Ser Gly Ser Ile Val Val Ser Gly Leu
    1130            1135            1140

Thr Pro Gly Val Glu Tyr Val Tyr Thr Ile Gln Val Leu Arg Asp
    1145            1150            1155

Gly Gln Glu Arg Asp Ala Pro Ile Val Asn Lys Val Val Thr Pro
    1160            1165            1170

Leu Ser Pro Pro Thr Asn Leu His Leu Glu Ala Asn Pro Asp Thr
    1175            1180            1185

Gly Val Leu Thr Val Ser Trp Glu Arg Ser Thr Thr Pro Asp Ile
    1190            1195            1200

Thr Gly Tyr Arg Ile Thr Thr Thr Pro Thr Asn Gly Gln Gln Gly
    1205            1210            1215

Asn Ser Leu Glu Glu Val Val His Ala Asp Gln Ser Ser Cys Thr
    1220            1225            1230

Phe Asp Asn Leu Ser Pro Gly Leu Glu Tyr Asn Val Ser Val Tyr
    1235            1240            1245

Thr Val Lys Asp Asp Lys Glu Ser Val Pro Ile Ser Asp Thr Ile

```
            1250                1255                1260

Ile Pro Glu Val Pro Gln Leu Thr Asp Leu Ser Phe Val Asp Ile
        1265                1270                1275

Thr Asp Ser Ser Ile Gly Leu Arg Trp Thr Pro Leu Asn Ser Ser
        1280                1285                1290

Thr Ile Ile Gly Tyr Arg Ile Thr Val Val Ala Ala Gly Glu Gly
        1295                1300                1305

Ile Pro Ile Phe Glu Asp Phe Val Asp Ser Ser Val Gly Tyr Tyr
        1310                1315                1320

Thr Val Thr Gly Leu Glu Pro Gly Ile Asp Tyr Asp Ile Ser Val
        1325                1330                1335

Ile Thr Leu Ile Asn Gly Gly Glu Ser Ala Pro Thr Thr Leu Thr
        1340                1345                1350

Gln Gln Thr Ala Val Pro Pro Pro Thr Asp Leu Arg Phe Thr Asn
        1355                1360                1365

Ile Gly Pro Asp Thr Met Arg Val Thr Trp Ala Pro Pro Pro Ser
        1370                1375                1380

Ile Asp Leu Thr Asn Phe Leu Val Arg Tyr Ser Pro Val Lys Asn
        1385                1390                1395

Glu Glu Asp Val Ala Glu Leu Ser Ile Ser Pro Ser Asp Asn Ala
        1400                1405                1410

Val Val Leu Thr Asn Leu Leu Pro Gly Thr Glu Tyr Val Val Ser
        1415                1420                1425

Val Ser Ser Val Tyr Glu Gln His Glu Ser Thr Pro Leu Arg Gly
        1430                1435                1440

Arg Gln Lys Thr Gly Leu Asp Ser Pro Thr Gly Ile Asp Phe Ser
        1445                1450                1455

Asp Ile Thr Ala Asn Ser Phe Thr Val His Trp Ile Ala Pro Arg
        1460                1465                1470

Ala Thr Ile Thr Gly Tyr Arg Ile Arg His His Pro Glu His Phe
        1475                1480                1485

Ser Gly Arg Pro Arg Glu Asp Arg Val Pro His Ser Arg Asn Ser
        1490                1495                1500

Ile Thr Leu Thr Asn Leu Thr Pro Gly Thr Glu Tyr Val Val Ser
        1505                1510                1515

Ile Val Ala Leu Asn Gly Arg Glu Glu Ser Pro Leu Leu Ile Gly
        1520                1525                1530

Gln Gln Ser Thr Val Ser Asp Val Pro Arg Asp Leu Glu Val Val
        1535                1540                1545

Ala Ala Thr Pro Thr Ser Leu Leu Ile Ser Trp Asp Ala Pro Ala
        1550                1555                1560

Val Thr Val Arg Tyr Tyr Arg Ile Thr Tyr Gly Glu Thr Gly Gly
        1565                1570                1575

Asn Ser Pro Val Gln Glu Phe Thr Val Pro Gly Ser Lys Ser Thr
        1580                1585                1590

Ala Thr Ile Ser Gly Leu Lys Pro Gly Val Asp Tyr Thr Ile Thr
        1595                1600                1605

Val Tyr Ala Val Thr Gly Arg Gly Asp Ser Pro Ala Ser Ser Lys
        1610                1615                1620

Pro Ile Ser Ile Asn Tyr Arg Thr Glu Ile Asp Lys Pro Ser Gln
        1625                1630                1635

Met Gln Val Thr Asp Val Gln Asp Asn Ser Ile Ser Val Lys Trp
        1640                1645                1650
```

```
Leu Pro Ser Ser Pro Val Thr Gly Tyr Arg Val Thr Thr Thr
1655                 1660                 1665

Pro Lys Asn Gly Pro Gly Pro Thr Lys Thr Lys Thr Ala Gly Pro
1670                 1675                 1680

Asp Gln Thr Glu Met Thr Ile Glu Gly Leu Gln Pro Thr Val Glu
1685                 1690                 1695

Tyr Val Val Ser Val Tyr Ala Gln Asn Pro Ser Gly Glu Ser Gln
1700                 1705                 1710

Pro Leu Val Gln Thr Ala Val Thr Asn Ile Asp Arg Pro Lys Gly
1715                 1720                 1725

Leu Ala Phe Thr Asp Val Asp Val Asp Ser Ile Lys Ile Ala Trp
1730                 1735                 1740

Glu Ser Pro Gln Gly Gln Val Ser Arg Tyr Arg Val Thr Tyr Ser
1745                 1750                 1755

Ser Pro Glu Asp Gly Ile His Glu Leu Phe Pro Ala Pro Asp Gly
1760                 1765                 1770

Glu Glu Asp Thr Ala Glu Leu Gln Gly Leu Arg Pro Gly Ser Glu
1775                 1780                 1785

Tyr Thr Val Ser Val Val Ala Leu His Asp Asp Met Glu Ser Gln
1790                 1795                 1800

Pro Leu Ile Gly Thr Gln Ser Thr Ala Ile Pro Ala Pro Thr Asp
1805                 1810                 1815

Leu Lys Phe Thr Gln Val Thr Pro Thr Ser Leu Ser Ala Gln Trp
1820                 1825                 1830

Thr Pro Pro Asn Val Gln Leu Thr Gly Tyr Arg Val Arg Val Thr
1835                 1840                 1845

Pro Lys Glu Lys Thr Gly Pro Met Lys Glu Ile Asn Leu Ala Pro
1850                 1855                 1860

Asp Ser Ser Ser Val Val Ser Gly Leu Met Val Ala Thr Lys
1865                 1870                 1875

Tyr Glu Val Ser Val Tyr Ala Leu Lys Asp Thr Leu Thr Ser Arg
1880                 1885                 1890

Pro Ala Gln Gly Val Val Thr Thr Leu Glu Asn Val Ser Pro Pro
1895                 1900                 1905

Arg Arg Ala Arg Val Thr Asp Ala Thr Glu Thr Thr Ile Thr Ile
1910                 1915                 1920

Ser Trp Arg Thr Lys Thr Glu Thr Ile Thr Gly Phe Gln Val Asp
1925                 1930                 1935

Ala Val Pro Ala Asn Gly Gln Thr Pro Ile Gln Arg Thr Ile Lys
1940                 1945                 1950

Pro Asp Val Arg Ser Tyr Thr Ile Thr Gly Leu Gln Pro Gly Thr
1955                 1960                 1965

Asp Tyr Lys Ile Tyr Leu Tyr Thr Leu Asn Asp Asn Ala Arg Ser
1970                 1975                 1980

Ser Pro Val Val Ile Asp Ala Ser Thr Ala Ile Asp Ala Pro Ser
1985                 1990                 1995

Asn Leu Arg Phe Leu Ala Thr Thr Pro Asn Ser Leu Leu Val Ser
2000                 2005                 2010

Trp Gln Pro Pro Arg Ala Arg Ile Thr Gly Tyr Ile Ile Lys Tyr
2015                 2020                 2025

Glu Lys Pro Gly Ser Pro Pro Arg Glu Val Val Pro Arg Pro Arg
2030                 2035                 2040
```

```
Pro Gly Val Thr Glu Ala Thr  Ile Thr Gly Leu Glu  Pro Gly Thr
    2045                2050                 2055

Glu Tyr Thr Ile Tyr Val Ile  Ala Leu Lys Asn Asn  Gln Lys Ser
    2060                2065                 2070

Glu Pro Leu Ile Gly Arg Lys  Lys Thr Asp Glu Leu  Pro Gln Leu
    2075                2080                 2085

Val Thr Leu Pro His Pro Asn  Leu His Gly Pro Glu  Ile Leu Asp
    2090                2095                 2100

Val Pro Ser Thr Val Gln Lys  Thr Pro Phe Val Thr  His Pro Gly
    2105                2110                 2115

Tyr Asp Thr Gly Asn Gly Ile  Gln Leu Pro Gly Thr  Ser Gly Gln
    2120                2125                 2130

Gln Pro Ser Val Gly Gln Gln  Met Ile Phe Glu Glu  His Gly Phe
    2135                2140                 2145

Arg Arg Thr Thr Pro Pro Thr  Thr Ala Thr Pro Ile  Arg His Arg
    2150                2155                 2160

Pro Arg Pro Tyr Pro Pro Asn  Val Gly Glu Glu Ile  Gln Ile Gly
    2165                2170                 2175

His Ile Pro Arg Glu Asp Val  Asp Tyr His Leu Tyr  Pro His Gly
    2180                2185                 2190

Pro Gly Leu Asn Pro Asn Ala  Ser Thr Gly Gln Glu  Ala Leu Ser
    2195                2200                 2205

Gln Thr Thr Ile Ser Trp Ala  Pro Phe Gln Asp Thr  Ser Glu Tyr
    2210                2215                 2220

Ile Ile Ser Cys His Pro Val  Gly Thr Asp Glu Glu  Pro Leu Gln
    2225                2230                 2235

Phe Arg Val Pro Gly Thr Ser  Thr Ser Ala Thr Leu  Thr Gly Leu
    2240                2245                 2250

Thr Arg Gly Ala Thr Tyr Asn  Ile Ile Val Glu Ala  Leu Lys Asp
    2255                2260                 2265

Gln Gln Arg His Lys Val Arg  Glu Glu Val Val Thr  Val Gly Asn
    2270                2275                 2280

Ser Val Asn Glu Gly Leu Asn  Gln Pro Thr Asp Asp  Ser Cys Phe
    2285                2290                 2295

Asp Pro Tyr Thr Val Ser His  Tyr Ala Val Gly Asp  Glu Trp Glu
    2300                2305                 2310

Arg Met Ser Glu Ser Gly Phe  Lys Leu Leu Cys Gln  Cys Leu Gly
    2315                2320                 2325

Phe Gly Ser Gly His Phe Arg  Cys Asp Ser Ser Arg  Trp Cys His
    2330                2335                 2340

Asp Asn Gly Val Asn Tyr Lys  Ile Gly Glu Lys Trp  Asp Arg Gln
    2345                2350                 2355

Gly Glu Asn Gly Gln Met Met  Ser Cys Thr Cys Leu  Gly Asn Gly
    2360                2365                 2370

Lys Gly Glu Phe Lys Cys Asp  Pro His Glu Ala Thr  Cys Tyr Asp
    2375                2380                 2385

Asp Gly Lys Thr Tyr His Val  Gly Glu Gln Trp Gln  Lys Glu Tyr
    2390                2395                 2400

Leu Gly Ala Ile Cys Ser Cys  Thr Cys Phe Gly Gly  Gln Arg Gly
    2405                2410                 2415

Trp Arg Cys Asp Asn Cys Arg  Arg Pro Gly Gly Glu  Pro Ser Pro
    2420                2425                 2430

Glu Gly Thr Thr Gly Gln Ser  Tyr Asn Gln Tyr Ser  Gln Arg Tyr
```

-continued

```
                     2435                2440                2445

His Gln Arg Thr Asn Thr Asn  Val Asn Cys Pro Ile  Glu Cys Phe
          2450                2455                2460

Met Pro Leu Asp Val Gln Ala  Asp Arg Glu Asp Ser  Arg Glu
          2465                2470                2475

<210> SEQ ID NO 41
<211> LENGTH: 2296
<212> TYPE: PRT
<213> ORGANISM: Homo sapiens

<400> SEQUENCE: 41

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335
```

-continued

```
Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
        370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
```

-continued

```
             755                 760                 765
Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
                930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990

Gln Thr Thr Lys Leu Asp Ala Pro Thr Asn Leu Gln Phe Val Asn Glu
                995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170
```

```
Leu Ser Pro Pro Thr Asn Leu His Leu Glu Ala Asn Pro Asp Thr
    1175            1180                1185

Gly Val Leu Thr Val Ser Trp Glu Arg Ser Thr Thr Pro Asp Ile
    1190            1195                1200

Thr Gly Tyr Arg Ile Thr Thr Pro Thr Asn Gly Gln Gln Gly
    1205            1210                1215

Asn Ser Leu Glu Glu Val Val His Ala Asp Gln Ser Ser Cys Thr
    1220            1225                1230

Phe Asp Asn Leu Ser Pro Gly Leu Glu Tyr Asn Val Ser Val Tyr
    1235            1240                1245

Thr Val Lys Asp Asp Lys Glu Ser Val Pro Ile Ser Asp Thr Ile
    1250            1255                1260

Ile Pro Ala Val Pro Pro Pro Thr Asp Leu Arg Phe Thr Asn Ile
    1265            1270                1275

Gly Pro Asp Thr Met Arg Val Thr Trp Ala Pro Pro Pro Ser Ile
    1280            1285                1290

Asp Leu Thr Asn Phe Leu Val Arg Tyr Ser Pro Val Lys Asn Glu
    1295            1300                1305

Glu Asp Val Ala Glu Leu Ser Ile Ser Pro Ser Asp Asn Ala Val
    1310            1315                1320

Val Leu Thr Asn Leu Leu Pro Gly Thr Glu Tyr Val Val Ser Val
    1325            1330                1335

Ser Ser Val Tyr Glu Gln His Glu Ser Thr Pro Leu Arg Gly Arg
    1340            1345                1350

Gln Lys Thr Gly Leu Asp Ser Pro Thr Gly Ile Asp Phe Ser Asp
    1355            1360                1365

Ile Thr Ala Asn Ser Phe Thr Val His Trp Ile Ala Pro Arg Ala
    1370            1375                1380

Thr Ile Thr Gly Tyr Arg Ile Arg His His Pro Glu His Phe Ser
    1385            1390                1395

Gly Arg Pro Arg Glu Asp Arg Val Pro His Ser Arg Asn Ser Ile
    1400            1405                1410

Thr Leu Thr Asn Leu Thr Pro Gly Thr Glu Tyr Val Val Ser Ile
    1415            1420                1425

Val Ala Leu Asn Gly Arg Glu Glu Ser Pro Leu Leu Ile Gly Gln
    1430            1435                1440

Gln Ser Thr Val Ser Asp Val Pro Arg Asp Leu Glu Val Val Ala
    1445            1450                1455

Ala Thr Pro Thr Ser Leu Leu Ile Ser Trp Asp Ala Pro Ala Val
    1460            1465                1470

Thr Val Arg Tyr Tyr Arg Ile Thr Tyr Gly Glu Thr Gly Gly Asn
    1475            1480                1485

Ser Pro Val Gln Glu Phe Thr Val Pro Gly Ser Lys Ser Thr Ala
    1490            1495                1500

Thr Ile Ser Gly Leu Lys Pro Gly Val Asp Tyr Thr Ile Thr Val
    1505            1510                1515

Tyr Ala Val Thr Gly Arg Gly Asp Ser Pro Ala Ser Ser Lys Pro
    1520            1525                1530

Ile Ser Ile Asn Tyr Arg Thr Glu Ile Asp Lys Pro Ser Gln Met
    1535            1540                1545

Gln Val Thr Asp Val Gln Asp Asn Ser Ile Ser Val Lys Trp Leu
    1550            1555                1560
```

-continued

```
Pro Ser Ser Ser Pro Val Thr Gly Tyr Arg Val Thr Thr Thr Pro
    1565                1570                1575
Lys Asn Gly Pro Gly Pro Thr Lys Thr Lys Thr Ala Gly Pro Asp
    1580                1585                1590
Gln Thr Glu Met Thr Ile Glu Gly Leu Gln Pro Thr Val Glu Tyr
    1595                1600                1605
Val Val Ser Val Tyr Ala Gln Asn Pro Ser Gly Glu Ser Gln Pro
    1610                1615                1620
Leu Val Gln Thr Ala Val Thr Thr Ile Pro Ala Pro Thr Asp Leu
    1625                1630                1635
Lys Phe Thr Gln Val Thr Pro Thr Ser Leu Ser Ala Gln Trp Thr
    1640                1645                1650
Pro Pro Asn Val Gln Leu Thr Gly Tyr Arg Val Arg Val Thr Pro
    1655                1660                1665
Lys Glu Lys Thr Gly Pro Met Lys Glu Ile Asn Leu Ala Pro Asp
    1670                1675                1680
Ser Ser Ser Val Val Val Ser Gly Leu Met Val Ala Thr Lys Tyr
    1685                1690                1695
Glu Val Ser Val Tyr Ala Leu Lys Asp Thr Leu Thr Ser Arg Pro
    1700                1705                1710
Ala Gln Gly Val Val Thr Thr Leu Glu Asn Val Ser Pro Pro Arg
    1715                1720                1725
Arg Ala Arg Val Thr Asp Ala Thr Glu Thr Thr Ile Thr Ile Ser
    1730                1735                1740
Trp Arg Thr Lys Thr Glu Thr Ile Thr Gly Phe Gln Val Asp Ala
    1745                1750                1755
Val Pro Ala Asn Gly Gln Thr Pro Ile Gln Arg Thr Ile Lys Pro
    1760                1765                1770
Asp Val Arg Ser Tyr Thr Ile Thr Gly Leu Gln Pro Gly Thr Asp
    1775                1780                1785
Tyr Lys Ile Tyr Leu Tyr Thr Leu Asn Asp Asn Ala Arg Ser Ser
    1790                1795                1800
Pro Val Val Ile Asp Ala Ser Thr Ala Ile Asp Ala Pro Ser Asn
    1805                1810                1815
Leu Arg Phe Leu Ala Thr Thr Pro Asn Ser Leu Leu Val Ser Trp
    1820                1825                1830
Gln Pro Pro Arg Ala Arg Ile Thr Gly Tyr Ile Ile Lys Tyr Glu
    1835                1840                1845
Lys Pro Gly Ser Pro Pro Arg Glu Val Val Pro Arg Pro Arg Pro
    1850                1855                1860
Gly Val Thr Glu Ala Thr Ile Thr Gly Leu Glu Pro Gly Thr Glu
    1865                1870                1875
Tyr Thr Ile Tyr Val Ile Ala Leu Lys Asn Asn Gln Lys Ser Glu
    1880                1885                1890
Pro Leu Ile Gly Arg Lys Lys Thr Asp Glu Leu Pro Gln Leu Val
    1895                1900                1905
Thr Leu Pro His Pro Asn Leu His Gly Pro Glu Ile Leu Asp Val
    1910                1915                1920
Pro Ser Thr Val Gln Lys Thr Pro Phe Val Thr His Pro Gly Tyr
    1925                1930                1935
Asp Thr Gly Asn Gly Ile Gln Leu Pro Gly Thr Ser Gly Gln Gln
    1940                1945                1950
Pro Ser Val Gly Gln Gln Met Ile Phe Glu Glu His Gly Phe Arg
```

```
                1955                1960                1965

Arg Thr Thr Pro Pro Thr Thr Ala Thr Pro Ile Arg His Arg Pro
    1970                1975                1980

Arg Pro Tyr Pro Pro Asn Val Gly Glu Glu Ile Gln Ile Gly His
    1985                1990                1995

Ile Pro Arg Glu Asp Val Asp Tyr His Leu Tyr Pro His Gly Pro
    2000                2005                2010

Gly Leu Asn Pro Asn Ala Ser Thr Gly Gln Glu Ala Leu Ser Gln
    2015                2020                2025

Thr Thr Ile Ser Trp Ala Pro Phe Gln Asp Thr Ser Glu Tyr Ile
    2030                2035                2040

Ile Ser Cys His Pro Val Gly Thr Asp Glu Glu Pro Leu Gln Phe
    2045                2050                2055

Arg Val Pro Gly Thr Ser Thr Ser Ala Thr Leu Thr Gly Leu Thr
    2060                2065                2070

Arg Gly Ala Thr Tyr Asn Ile Ile Val Glu Ala Leu Lys Asp Gln
    2075                2080                2085

Gln Arg His Lys Val Arg Glu Glu Val Val Thr Val Gly Asn Ser
    2090                2095                2100

Val Asn Glu Gly Leu Asn Gln Pro Thr Asp Asp Ser Cys Phe Asp
    2105                2110                2115

Pro Tyr Thr Val Ser His Tyr Ala Val Gly Asp Glu Trp Glu Arg
    2120                2125                2130

Met Ser Glu Ser Gly Phe Lys Leu Leu Cys Gln Cys Leu Gly Phe
    2135                2140                2145

Gly Ser Gly His Phe Arg Cys Asp Ser Ser Arg Trp Cys His Asp
    2150                2155                2160

Asn Gly Val Asn Tyr Lys Ile Gly Glu Lys Trp Asp Arg Gln Gly
    2165                2170                2175

Glu Asn Gly Gln Met Met Ser Cys Thr Cys Leu Gly Asn Gly Lys
    2180                2185                2190

Gly Glu Phe Lys Cys Asp Pro His Glu Ala Thr Cys Tyr Asp Asp
    2195                2200                2205

Gly Lys Thr Tyr His Val Gly Glu Gln Trp Gln Lys Glu Tyr Leu
    2210                2215                2220

Gly Ala Ile Cys Ser Cys Thr Cys Phe Gly Gly Gln Arg Gly Trp
    2225                2230                2235

Arg Cys Asp Asn Cys Arg Arg Pro Gly Gly Glu Pro Ser Pro Glu
    2240                2245                2250

Gly Thr Thr Gly Gln Ser Tyr Asn Gln Tyr Ser Gln Arg Tyr His
    2255                2260                2265

Gln Arg Thr Asn Thr Asn Val Asn Cys Pro Ile Glu Cys Phe Met
    2270                2275                2280

Pro Leu Asp Val Gln Ala Asp Arg Glu Asp Ser Arg Glu
    2285                2290                2295

<210> SEQ ID NO 42
<211> LENGTH: 2176
<212> TYPE: PRT
<213> ORGANISM: Homo sapiens

<400> SEQUENCE: 42

Met Leu Arg Gly Pro Gly Pro Gly Leu Leu Leu Leu Ala Val Gln Cys
1               5                   10                  15
```

-continued

```
Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
 50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
```

```
                    435                 440                 445
Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                    485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
        530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
850                 855                 860
```

-continued

```
Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260
```

| | | | | | | | | | | | |
|---|---|---|---|---|---|---|---|---|---|---|---|
|Ile|Pro|Ala|Val|Pro|Pro|Thr|Asp|Leu|Arg|Phe|Thr|Asn|Ile|
|1265||||1270|||||1275|||

Ile Pro Ala Val Pro Pro Thr Asp Leu Arg Phe Thr Asn Ile
1265                1270                1275

Gly Pro Asp Thr Met Arg Val Thr Trp Ala Pro Pro Ser Ile
    1280                1285                1290

Asp Leu Thr Asn Phe Leu Val Arg Tyr Ser Pro Val Lys Asn Glu
1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Thr Ile Pro Ala Pro Thr Asp Leu
    1625                1630                1635

Lys Phe Thr Gln Val Thr Pro Thr Ser Leu Ser Ala Gln Trp Thr
    1640                1645                1650

Pro Pro Asn Val Gln Leu Thr Gly Tyr Arg Val Arg Val Thr Pro

-continued

```
              1655                1660                1665
Lys Glu Lys Thr Gly Pro Met Lys Glu Ile Asn Leu Ala Pro Asp
        1670                1675                1680
Ser Ser Ser Val Val Val Ser Gly Leu Met Val Ala Thr Lys Tyr
        1685                1690                1695
Glu Val Ser Val Tyr Ala Leu Lys Asp Thr Leu Thr Ser Arg Pro
        1700                1705                1710
Ala Gln Gly Val Val Thr Thr Leu Glu Asn Val Ser Pro Pro Arg
        1715                1720                1725
Arg Ala Arg Val Thr Asp Ala Thr Glu Thr Thr Ile Thr Ile Ser
        1730                1735                1740
Trp Arg Thr Lys Thr Glu Thr Ile Thr Gly Phe Gln Val Asp Ala
        1745                1750                1755
Val Pro Ala Asn Gly Gln Thr Pro Ile Gln Arg Thr Ile Lys Pro
        1760                1765                1770
Asp Val Arg Ser Tyr Thr Ile Thr Gly Leu Gln Pro Gly Thr Asp
        1775                1780                1785
Tyr Lys Ile Tyr Leu Tyr Thr Leu Asn Asp Asn Ala Arg Ser Ser
        1790                1795                1800
Pro Val Val Ile Asp Ala Ser Thr Ala Ile Asp Ala Pro Ser Asn
        1805                1810                1815
Leu Arg Phe Leu Ala Thr Thr Pro Asn Ser Leu Leu Val Ser Trp
        1820                1825                1830
Gln Pro Pro Arg Ala Arg Ile Thr Gly Tyr Ile Ile Lys Tyr Glu
        1835                1840                1845
Lys Pro Gly Ser Pro Pro Arg Glu Val Val Pro Arg Pro Arg Pro
        1850                1855                1860
Gly Val Thr Glu Ala Thr Ile Thr Gly Leu Glu Pro Gly Thr Glu
        1865                1870                1875
Tyr Thr Ile Tyr Val Ile Ala Leu Lys Asn Asn Gln Lys Ser Glu
        1880                1885                1890
Pro Leu Ile Gly Arg Lys Lys Thr Gly Gln Glu Ala Leu Ser Gln
        1895                1900                1905
Thr Thr Ile Ser Trp Ala Pro Phe Gln Asp Thr Ser Glu Tyr Ile
        1910                1915                1920
Ile Ser Cys His Pro Val Gly Thr Asp Glu Glu Pro Leu Gln Phe
        1925                1930                1935
Arg Val Pro Gly Thr Ser Thr Ser Ala Thr Leu Thr Gly Leu Thr
        1940                1945                1950
Arg Gly Ala Thr Tyr Asn Ile Ile Val Glu Ala Leu Lys Asp Gln
        1955                1960                1965
Gln Arg His Lys Val Arg Glu Glu Val Val Thr Val Gly Asn Ser
        1970                1975                1980
Val Asn Glu Gly Leu Asn Gln Pro Thr Asp Asp Ser Cys Phe Asp
        1985                1990                1995
Pro Tyr Thr Val Ser His Tyr Ala Val Gly Asp Glu Trp Glu Arg
        2000                2005                2010
Met Ser Glu Ser Gly Phe Lys Leu Leu Cys Gln Cys Leu Gly Phe
        2015                2020                2025
Gly Ser Gly His Phe Arg Cys Asp Ser Ser Arg Trp Cys His Asp
        2030                2035                2040
Asn Gly Val Asn Tyr Lys Ile Gly Glu Lys Trp Asp Arg Gln Gly
        2045                2050                2055
```

-continued

Glu Asn Gly Gln Met Met Ser Cys Thr Cys Leu Gly Asn Gly Lys
    2060                2065                2070

Gly Glu Phe Lys Cys Asp Pro His Glu Ala Thr Cys Tyr Asp Asp
    2075                2080                2085

Gly Lys Thr Tyr His Val Gly Glu Gln Trp Gln Lys Glu Tyr Leu
    2090                2095                2100

Gly Ala Ile Cys Ser Cys Thr Cys Phe Gly Gly Gln Arg Gly Trp
    2105                2110                2115

Arg Cys Asp Asn Cys Arg Arg Pro Gly Gly Glu Pro Ser Pro Glu
    2120                2125                2130

Gly Thr Thr Gly Gln Ser Tyr Asn Gln Tyr Ser Gln Arg Tyr His
    2135                2140                2145

Gln Arg Thr Asn Thr Asn Val Asn Cys Pro Ile Glu Cys Phe Met
    2150                2155                2160

Pro Leu Asp Val Gln Ala Asp Arg Glu Asp Ser Arg Glu
    2165                2170                2175

<210> SEQ ID NO 43
<211> LENGTH: 657
<212> TYPE: PRT
<213> ORGANISM: Homo sapiens

<400> SEQUENCE: 43

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu

```
            245                 250                 255
Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Val Ser Ile Pro Pro Arg Asn Leu Gly
                645                 650                 655

Tyr
```

<210> SEQ ID NO 44
<211> LENGTH: 2355
<212> TYPE: PRT
<213> ORGANISM: Homo sapiens

<400> SEQUENCE: 44

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
            85                  90                  95

Cys Phe Asp Lys Tyr Thr Gly Asn Thr Tyr Arg Val Gly Asp Thr Tyr
        100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
            165                 170                 175

Trp Thr Cys Lys Pro Ile Ala Glu Lys Cys Phe Asp His Ala Ala Gly
        180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
            245                 250                 255

Gln Cys Ile Cys Thr Gly Asn Gly Arg Gly Glu Trp Lys Cys Glu Arg
        260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
            325                 330                 335

Gly Asn Gly Val Ser Cys Gln Glu Thr Ala Val Thr Gln Thr Tyr Gly
        340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
370                 375                 380
```

```
Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
        420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
        450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
        690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
        770                 775                 780

Lys Tyr Ile Val Asn Val Tyr Gln Ile Ser Glu Asp Gly Glu Gln Ser
785                 790                 795                 800
```

Leu Ile Leu Ser Thr Ser Gln Thr Thr Ala Pro Asp Ala Pro Pro Asp
              805                 810                 815

Pro Thr Val Asp Gln Val Asp Asp Thr Ser Ile Val Val Arg Trp Ser
        820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
        930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly

```
                    1205                     1210                     1215
Asn  Ser  Leu  Glu  Glu  Val  Val  His  Ala  Asp  Gln  Ser  Ser  Cys  Thr
          1220                     1225                     1230

Phe  Asp  Asn  Leu  Ser  Pro  Gly  Leu  Glu  Tyr  Asn  Val  Ser  Val  Tyr
     1235                     1240                     1245

Thr  Val  Lys  Asp  Asp  Lys  Glu  Ser  Val  Pro  Ile  Ser  Asp  Thr  Ile
1250                     1255                     1260

Ile  Pro  Ala  Val  Pro  Pro  Thr  Asp  Leu  Arg  Phe  Thr  Asn  Ile
1265                     1270                     1275

Gly  Pro  Asp  Thr  Met  Arg  Val  Thr  Trp  Ala  Pro  Pro  Ser  Ile
1280                     1285                     1290

Asp  Leu  Thr  Asn  Phe  Leu  Val  Arg  Tyr  Ser  Pro  Val  Lys  Asn  Glu
     1295                     1300                     1305

Glu  Asp  Val  Ala  Glu  Leu  Ser  Ile  Ser  Pro  Ser  Asp  Asn  Ala  Val
     1310                     1315                     1320

Val  Leu  Thr  Asn  Leu  Leu  Pro  Gly  Thr  Glu  Tyr  Val  Val  Ser  Val
     1325                     1330                     1335

Ser  Ser  Val  Tyr  Glu  Gln  His  Glu  Ser  Thr  Pro  Leu  Arg  Gly  Arg
     1340                     1345                     1350

Gln  Lys  Thr  Gly  Leu  Asp  Ser  Pro  Thr  Gly  Ile  Asp  Phe  Ser  Asp
     1355                     1360                     1365

Ile  Thr  Ala  Asn  Ser  Phe  Thr  Val  His  Trp  Ile  Ala  Pro  Arg  Ala
     1370                     1375                     1380

Thr  Ile  Thr  Gly  Tyr  Arg  Ile  Arg  His  His  Pro  Glu  His  Phe  Ser
     1385                     1390                     1395

Gly  Arg  Pro  Arg  Glu  Asp  Arg  Val  Pro  His  Ser  Arg  Asn  Ser  Ile
     1400                     1405                     1410

Thr  Leu  Thr  Asn  Leu  Thr  Pro  Gly  Thr  Glu  Tyr  Val  Val  Ser  Ile
     1415                     1420                     1425

Val  Ala  Leu  Asn  Gly  Arg  Glu  Glu  Ser  Pro  Leu  Leu  Ile  Gly  Gln
     1430                     1435                     1440

Gln  Ser  Thr  Val  Ser  Asp  Val  Pro  Arg  Asp  Leu  Glu  Val  Val  Ala
     1445                     1450                     1455

Ala  Thr  Pro  Thr  Ser  Leu  Leu  Ile  Ser  Trp  Asp  Ala  Pro  Ala  Val
     1460                     1465                     1470

Thr  Val  Arg  Tyr  Tyr  Arg  Ile  Thr  Tyr  Gly  Glu  Thr  Gly  Gly  Asn
     1475                     1480                     1485

Ser  Pro  Val  Gln  Glu  Phe  Thr  Val  Pro  Gly  Ser  Lys  Ser  Thr  Ala
     1490                     1495                     1500

Thr  Ile  Ser  Gly  Leu  Lys  Pro  Gly  Val  Asp  Tyr  Thr  Ile  Thr  Val
     1505                     1510                     1515

Tyr  Ala  Val  Thr  Gly  Arg  Gly  Asp  Ser  Pro  Ala  Ser  Ser  Lys  Pro
     1520                     1525                     1530

Ile  Ser  Ile  Asn  Tyr  Arg  Thr  Glu  Ile  Asp  Lys  Pro  Ser  Gln  Met
     1535                     1540                     1545

Gln  Val  Thr  Asp  Val  Gln  Asp  Asn  Ser  Ile  Ser  Val  Lys  Trp  Leu
     1550                     1555                     1560

Pro  Ser  Ser  Ser  Pro  Val  Thr  Gly  Tyr  Arg  Val  Thr  Thr  Thr  Pro
     1565                     1570                     1575

Lys  Asn  Gly  Pro  Gly  Pro  Thr  Lys  Thr  Lys  Thr  Ala  Gly  Pro  Asp
     1580                     1585                     1590

Gln  Thr  Glu  Met  Thr  Ile  Glu  Gly  Leu  Gln  Pro  Thr  Val  Glu  Tyr
     1595                     1600                     1605
```

-continued

Val Val Ser Val Tyr Ala Gln Asn Pro Ser Gly Glu Ser Gln Pro
    1610            1615            1620

Leu Val Gln Thr Ala Val Thr Asn Ile Asp Arg Pro Lys Gly Leu
    1625            1630            1635

Ala Phe Thr Asp Val Asp Val Asp Ser Ile Lys Ile Ala Trp Glu
    1640            1645            1650

Ser Pro Gln Gly Gln Val Ser Arg Tyr Arg Val Thr Tyr Ser Ser
    1655            1660            1665

Pro Glu Asp Gly Ile His Glu Leu Phe Pro Ala Pro Asp Gly Glu
    1670            1675            1680

Glu Asp Thr Ala Glu Leu Gln Gly Leu Arg Pro Gly Ser Glu Tyr
    1685            1690            1695

Thr Val Ser Val Val Ala Leu His Asp Asp Met Glu Ser Gln Pro
    1700            1705            1710

Leu Ile Gly Thr Gln Ser Thr Ala Ile Pro Ala Pro Thr Asp Leu
    1715            1720            1725

Lys Phe Thr Gln Val Thr Pro Thr Ser Leu Ser Ala Gln Trp Thr
    1730            1735            1740

Pro Pro Asn Val Gln Leu Thr Gly Tyr Arg Val Arg Val Thr Pro
    1745            1750            1755

Lys Glu Lys Thr Gly Pro Met Lys Glu Ile Asn Leu Ala Pro Asp
    1760            1765            1770

Ser Ser Ser Val Val Val Ser Gly Leu Met Val Ala Thr Lys Tyr
    1775            1780            1785

Glu Val Ser Val Tyr Ala Leu Lys Asp Thr Leu Thr Ser Arg Pro
    1790            1795            1800

Ala Gln Gly Val Val Thr Thr Leu Glu Asn Val Ser Pro Pro Arg
    1805            1810            1815

Arg Ala Arg Val Thr Asp Ala Thr Glu Thr Thr Ile Thr Ile Ser
    1820            1825            1830

Trp Arg Thr Lys Thr Glu Thr Ile Thr Gly Phe Gln Val Asp Ala
    1835            1840            1845

Val Pro Ala Asn Gly Gln Thr Pro Ile Gln Arg Thr Ile Lys Pro
    1850            1855            1860

Asp Val Arg Ser Tyr Thr Ile Thr Gly Leu Gln Pro Gly Thr Asp
    1865            1870            1875

Tyr Lys Ile Tyr Leu Tyr Thr Leu Asn Asp Asn Ala Arg Ser Ser
    1880            1885            1890

Pro Val Val Ile Asp Ala Ser Thr Ala Ile Asp Ala Pro Ser Asn
    1895            1900            1905

Leu Arg Phe Leu Ala Thr Thr Pro Asn Ser Leu Leu Val Ser Trp
    1910            1915            1920

Gln Pro Pro Arg Ala Arg Ile Thr Gly Tyr Ile Ile Lys Tyr Glu
    1925            1930            1935

Lys Pro Gly Ser Pro Pro Arg Glu Val Val Pro Arg Pro Arg Pro
    1940            1945            1950

Gly Val Thr Glu Ala Thr Ile Thr Gly Leu Glu Pro Gly Thr Glu
    1955            1960            1965

Tyr Thr Ile Tyr Val Ile Ala Leu Lys Asn Asn Gln Lys Ser Glu
    1970            1975            1980

Pro Leu Ile Gly Arg Lys Lys Thr Asp Glu Leu Pro Gln Leu Val
    1985            1990            1995

Thr Leu Pro His Pro Asn Leu His Gly Pro Glu Ile Leu Asp Val
2000                2005                    2010

Pro Ser Thr Val Gln Lys Thr Pro Phe Val Thr His Pro Gly Tyr
2015                2020                    2025

Asp Thr Gly Asn Gly Ile Gln Leu Pro Gly Thr Ser Gly Gln Gln
2030                2035                    2040

Pro Ser Val Gly Gln Gln Met Ile Phe Glu His Gly Phe Arg
2045                2050                    2055

Arg Thr Thr Pro Pro Thr Thr Ala Thr Pro Ile Arg His Arg Pro
2060                2065                    2070

Arg Pro Tyr Pro Pro Asn Val Gly Gln Glu Ala Leu Ser Gln Thr
2075                2080                    2085

Thr Ile Ser Trp Ala Pro Phe Gln Asp Thr Ser Glu Tyr Ile Ile
2090                2095                    2100

Ser Cys His Pro Val Gly Thr Asp Glu Glu Pro Leu Gln Phe Arg
2105                2110                    2115

Val Pro Gly Thr Ser Thr Ser Ala Thr Leu Thr Gly Leu Thr Arg
2120                2125                    2130

Gly Ala Thr Tyr Asn Ile Ile Val Glu Ala Leu Lys Asp Gln Gln
2135                2140                    2145

Arg His Lys Val Arg Glu Glu Val Val Thr Val Gly Asn Ser Val
2150                2155                    2160

Asn Glu Gly Leu Asn Gln Pro Thr Asp Asp Ser Cys Phe Asp Pro
2165                2170                    2175

Tyr Thr Val Ser His Tyr Ala Val Gly Asp Glu Trp Glu Arg Met
2180                2185                    2190

Ser Glu Ser Gly Phe Lys Leu Leu Cys Gln Cys Leu Gly Phe Gly
2195                2200                    2205

Ser Gly His Phe Arg Cys Asp Ser Ser Arg Trp Cys His Asp Asn
2210                2215                    2220

Gly Val Asn Tyr Lys Ile Gly Glu Lys Trp Asp Arg Gln Gly Glu
2225                2230                    2235

Asn Gly Gln Met Met Ser Cys Thr Cys Leu Gly Asn Gly Lys Gly
2240                2245                    2250

Glu Phe Lys Cys Asp Pro His Glu Ala Thr Cys Tyr Asp Asp Gly
2255                2260                    2265

Lys Thr Tyr His Val Gly Glu Gln Trp Gln Lys Glu Tyr Leu Gly
2270                2275                    2280

Ala Ile Cys Ser Cys Thr Cys Phe Gly Gly Gln Arg Gly Trp Arg
2285                2290                    2295

Cys Asp Asn Cys Arg Arg Pro Gly Gly Glu Pro Ser Pro Glu Gly
2300                2305                    2310

Thr Thr Gly Gln Ser Tyr Asn Gln Tyr Ser Gln Arg Tyr His Gln
2315                2320                    2325

Arg Thr Asn Thr Asn Val Asn Cys Pro Ile Glu Cys Phe Met Pro
2330                2335                    2340

Leu Asp Val Gln Ala Asp Arg Glu Asp Ser Arg Glu
2345                2350                    2355

<210> SEQ ID NO 45
<211> LENGTH: 21
<212> TYPE: DNA
<213> ORGANISM: Artificial Sequence
<220> FEATURE:
<223> OTHER INFORMATION: siRNA oligonucleotide -continued

```
<400> SEQUENCE: 45
ccguuuucau ccaacaagat t                                              21

<210> SEQ ID NO 46
<211> LENGTH: 21
<212> TYPE: DNA
<213> ORGANISM: Artificial Sequence
<220> FEATURE:
<223> OTHER INFORMATION: siRNA oligonucleotide

<400> SEQUENCE: 46
ucuuguugga ugaaaacggg t                                              21

<210> SEQ ID NO 47
<211> LENGTH: 21
<212> TYPE: DNA
<213> ORGANISM: Artificial Sequence
<220> FEATURE:
<223> OTHER INFORMATION: siRNA oligonucleotide

<400> SEQUENCE: 47
guuacgacuu gggcaagaat t                                              21

<210> SEQ ID NO 48
<211> LENGTH: 21
<212> TYPE: DNA
<213> ORGANISM: Artificial Sequence
<220> FEATURE:
<223> OTHER INFORMATION: siRNA oligonucleotide

<400> SEQUENCE: 48
uucuugccca agucguaact g                                              21

<210> SEQ ID NO 49
<211> LENGTH: 21
<212> TYPE: DNA
<213> ORGANISM: Artificial Sequence
<220> FEATURE:
<223> OTHER INFORMATION: siRNA oligonucleotide

<400> SEQUENCE: 49
ccguuuucau ccaacaagag t                                              21

<210> SEQ ID NO 50
<211> LENGTH: 21
<212> TYPE: DNA
<213> ORGANISM: Artificial Sequence
<220> FEATURE:
<223> OTHER INFORMATION: siRNA oligonucleotide

<400> SEQUENCE: 50
tgggcaaaag uagguuguuc u                                              21
```

WNT7A COMPOSITIONS AND METHOD OF USING THE SAME

CROSS-REFERENCE TO RELATED APPLICATIONS

This application is a §371 U.S. national stage entry of international application no. PCT/US2012/055396, filed Sep. 14, 2012, which application claims the benefit under 35 U.S.C. §119(e) of U.S. Provisional Application No. 61/535,915, filed Sep. 16, 2011, each of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is FATE_110_01WO_ST25.txt. The text file is 122 KB, was created on Sep. 13, 2012, and is being submitted electronically via EFS-Web.

BACKGROUND

Technical Field

The present invention relates generally to compositions and methods for modulating stem cells, in particular, stem cell division symmetry, and uses thereof.

Description of the Related Art

Stem cells are undifferentiated or immature cells that are capable of giving rise to multiple specialized cell types and ultimately, to terminally differentiated cells. Most adult stem cells are lineage-restricted and are generally referred to by their tissue origin. Unlike any other cells, stem cells are able to renew themselves such that a virtually endless supply of mature cell types can be generated when needed over the lifetime of an organism. Due to this capacity for self-renewal, stem cells are therapeutically useful for the formation, regeneration, repair and maintenance of tissues.

It has recently been determined that satellite cells represent a heterogeneous population composed of stem cells and small mononuclear progenitor cells found in mature muscle tissue (Kuang et al., 2007). Satellite cells in adult skeletal muscle are located in small depressions between the sarcolemma of their host myofibers and the basal lamina. Satellite cells are involved in the normal growth of muscle, as well as the regeneration of injured or diseased tissue. In undamaged muscle, the majority of satellite cells are quiescent, meaning they neither differentiate nor undergo cell division. Satellite cells express a number of distinctive genetic markers, including the paired-box transcription factor Pax7, which plays a central regulatory role in satellite cell function and survival (Kuang et al., 2006; Seale et al., 2000). Pax7 can thus be used as a marker of satellite cells.

Upon damage, such as physical trauma or strain, repeated exercise, or in disease, satellite cells become activated, proliferate and give rise to a population of transient amplifying progenitors, which are myogenic precursors cells (myoblasts) expressing myogenic regulatory factors (MRF), such as MyoD and Myf5. In the course of the regeneration process, myoblasts undergo multiple rounds of division before committing to terminal differentiation, fusing with the host fibers or generating new myofibers to reconstruct damaged tissue (Charge and Rudnicki, 2004). In several diseases and conditions affecting muscle, a reduction in muscle mass is seen that is associated with reduced numbers of satellite cells and a reduced ability of the satellite cells to repair, regenerate and grow skeletal muscle. A few exemplary diseases and conditions affecting muscle include wasting diseases, such as cachexia, muscular attenuation or atrophy, including sarcopenia, ICU-induced weakness, surgery-induced weakness (e.g., following knee or hip replacement), and muscle degenerative diseases, such as muscular dystrophies. The process of muscle regeneration involves considerable remodeling of extracellular matrix and, where extensive damage occurs, is incomplete. Fibroblasts within the muscle deposit scar tissue, which can impair muscle function, and is a significant part of the pathology of muscular dystrophies.

Muscular dystrophies are genetic diseases characterized by progressive weakness and degeneration of the skeletal or voluntary muscles which control movement. The muscles of the heart and some other involuntary muscles are also affected in some forms of muscular dystrophy. In many cases, the histological picture shows variation in fiber size, muscle cell necrosis and regeneration, and often proliferation of connective and adipose tissue. The progressive muscular dystrophies include at least Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

Currently there is no cure for these diseases, but certain medications and therapies have been shown to be effective. For instance, corticosteroids have been shown to slow muscle destruction in Duchene muscular dystrophy patients. While corticosteroids can be effective in delaying progression of the disease in many patients, long-term corticosteroid use is undesirable due to unwanted side effects.

PCT Application No. WO 2004/113513 (Rudnicki et al.) discloses methods and compositions for modulating proliferation or lineage commitment of an atypical population of $CD45^+Sca1^+$ stem cells, located outside the satellite stem cell compartment, by modulating myogenic determination of Wnt proteins.

The Wnt family of genes encode over twenty cysteine-rich, secreted Wnt glycoproteins that act by binding to Frizzled (Fzd) receptors on target cells. Frizzled receptors are a family of G-protein coupled receptor proteins. Binding of different members of the Wnt-family to certain members of the Fzd family can initiate signaling by one of several distinct pathways. In the termed canonical pathway, activation of the signaling molecule, Disheveled, leads to the inactivation of glycogen synthase kinase-3 (GSK-3β), a cytoplasmic serine-threonine kinase. The GSK-3β target, β-catenin, is thereby stabilized and translocates to the nucleus where it activates TCF (T-cell-factor)-dependant transcription of specific promoters (Wodarz, 1998, Dierick, 1999). In the non-canonical, or planar cell polarity (PCP) pathway, binding of Wnt to Fzd also activates Disheveled, which in this case activates RhoA, a small g protein. Activation of the PCP pathway does not result in nuclear translocation of β-catenin.

Wnt signaling plays a key role in regulating developmental programs through embryonic development, and in regulating stem cell function in adult tissues (Clevers, 2006). Wnts have been demonstrated to be necessary for embryonic myogenic induction in the paraxial mesoderm (Borello et al., 2006; Chen et al., 2005; Tajbakhsh et al., 1998), as well in the control of differentiation during muscle fiber development (Anakwe et al., 2003). Recently, the Wnt planar cell polarity (PCP) pathway has been implicated in regulating elongation of differentiating myocytes in the developing myotome (Gros et al., 2009). In the adult, Wnt signaling is necessary for the myogenic commitment of adult CD45+/Sca1+ stem cells in muscle tissue following acute damage (Polesskaya et al., 2003; Torrente et al., 2004). Other studies suggest that canonical Wnt/β-catenin signaling regulates myogenic differentiation through activation and recruitment of reserve myoblasts. In addition, Wnt/β-catenin signaling in satellite cells within adult muscle appears to control myogenic lineage progression by limiting Notch signaling and thus promoting differentiation. Thus, traditionally, it has been assumed that Wnt proteins act as stem cell growth factors, promoting the proliferation and differentiation of stem cells and/or progenitor cells.

This has established a potential role for Wnts in the treatment of myodegenerative diseases. However, the poor protein solubility of Wnts has hindered their use in recombinant protein therapy. In addition, Wnt proteins are lipidated during posttranscriptional processing prior to secretion and contain a vast number of hydrophobic amino acid residues, leading to low water solubility and resultantly deterring systemic delivery. Thus, current strategies for delivering Wnts, such as Wnt7a, for example, limit the use of Wnt polypeptide therapies for treating myodegenerative diseases.

Accordingly, there is a need in the art for modified Wnt polypeptides having increased solubility and bioavailability to effectively treat myodegenerative diseases.

BRIEF SUMMARY

The present invention generally provides Wnt polypeptide fragments, and Wnt polypeptides or fragments thereof in combination with fibronectin. In addition, the present invention also provides methods for modulating stem cells, in particular, stem cell division symmetry using the Wnt7a polypeptides and compositions disclosed herein.

In one embodiment, the present invention contemplates, in part, a composition for increasing the symmetric expansion of a stem cell comprising a Wnt7a polypeptide fragment having the amino acid sequence set forth in SEQ ID NO: 5.

In another embodiment, the present invention contemplates, in part, composition for increasing the symmetric expansion of a stem cell comprising an N-terminal deletion of 210 to 219 amino acids of a Wnt7a polypeptide having the amino acid sequence set forth in SEQ ID NO: 3.

In a particular embodiment, the composition comprises a polynucleotide encoding a Wnt7a polypeptide according to any of the preceding embodiments.

In a certain embodiment, the polynucleotide comprises an expression vector.

In an additional embodiment, the composition comprises a stem cell or a population of stem cells.

In a further additional embodiment, the composition comprises one or more stem cell modulators.

In a particular additional embodiment, the modulator further increases the rate of stem cell division.

In a certain additional embodiment, the modulator comprises FGF.

In one embodiment, the stem cell is an adult stem cell.

In a particular embodiment, the adult stem cell is a satellite stem cell.

In various embodiments, any of the preceding compositions promote tissue formation, regeneration, maintenance or repair.

In a particular embodiment, the tissue is muscle.

In one particular embodiment, the muscle is skeletal muscle.

In one embodiment, the present invention contemplates, in part, a composition for enhancing tissue formation, regeneration or repair in a mammal comprising as an active agent (a) a Wnt7a polypeptide comprising the amino acid sequence set forth in SEQ ID NO: 3 and further comprising an N-terminal deletion of 210 to 219 amino acids, or (b) a polynucleotide encoding a Wnt7a polypeptide comprising the amino acid sequence set forth in (a).

In another embodiment, the present invention contemplates, in part, a composition for enhancing tissue formation, regeneration or repair in a mammal comprising as an active agent (a) a Wnt7a polypeptide fragment comprising the amino acid sequence set forth in SEQ ID NO: 5, or (b) a polynucleotide encoding a Wnt7a polypeptide comprising the amino acid sequence set forth in SEQ ID NO: 5.

In a particular embodiment, the composition comprises a physiologically acceptable carrier or diluent.

In a certain embodiment, the composition is formulated for injection.

In a certain particular embodiment, the composition is formulated for one or more of intravenous injection, intramuscular injection, intracardiac injection, subcutaneous injection, or intraperitoneal injection.

In a further embodiment, the composition is for promoting formation, maintenance, repair or regeneration of skeletal muscle in a human subject in need thereof.

In an additional embodiment, the subject has, is suspected of having, or is at risk of having, a degenerative disease.

In a related embodiment, the degenerative disease is a muscular dystrophy.

In a particular related embodiment, the muscular dystrophy selected from Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

In one embodiment, the subject has, is suspected of having, or is at risk of having a disease or condition affecting muscle.

In an additional embodiment, the disease or condition affecting muscle is a wasting disease (e.g., cachexia, which may be associated with an illness such as cancer or AIDS), muscular attenuation or atrophy (e.g., sarcopenia, which may be associated with aging), ICU-induced weakness, prolonged disuse (e.g., coma, injury, paralysis), surgery-induced weakness (e.g., following hip or knee replacement), or a muscle degenerative disease (e.g., muscular dystrophy).

In a further embodiment, subject has, is suspected of having, or is at risk of developing muscle wasting or atrophy associated with injury or illness.

In another embodiment, the present invention contemplates, in part, a composition for synergistically increasing the symmetric expansion of a stem cell comprising: (a) a Wnt7a polypeptide having the amino acid sequence set forth in SEQ ID NO: 3; (b) a Wnt7a polypeptide fragment having the amino acid sequence set forth in SEQ ID NO: 5; or (c) a Wnt7a polypeptide fragment having an N-terminal deletion of 210 to 219 amino acids of a Wnt7a polypeptide having the amino acid sequence set forth in SEQ ID NO: 3; and (d) a fibronectin polypeptide.

In a particular embodiment, the composition comprises a polynucleotide encoding (a) a Wnt7a polypeptide having the amino acid sequence set forth in SEQ ID NO: 3; (b) a Wnt7a polypeptide fragment having the amino acid sequence set forth in SEQ ID NO: 5; or (c) a Wnt7a polypeptide fragment having an N-terminal deletion of 210 to 219 amino acids of a Wnt7a polypeptide having the amino acid sequence set forth in SEQ ID NO: 3; and a polynucleotide encoding a fibronectin polypeptide.

In a certain embodiment, the composition comprises a Wnt7a polynucleotide and a fibronectin polynucleotide, wherein each polynucleotide comprises an expression vector.

In a certain particular embodiment, the composition comprises a stem cell or a population of stem cells.

In a related particular embodiment, the stem cell is an adult stem cell.

In a further particular embodiment, the adult stem cell is a satellite stem cell.

In an additional particular embodiment, the composition comprising a Wnt7a polypeptide or polynucleotide and a fibronectin polypeptide and polynucleotide is for promoting tissue formation, regeneration, maintenance or repair.

In one embodiment, the tissue is muscle.

In a related embodiment, the muscle is skeletal muscle.

In a particular embodiment, the composition comprises a physiologically acceptable carrier or diluent.

In a certain embodiment, the composition is formulated for injection.

In a certain particular embodiment, the composition is formulated for one or more of intravenous injection, intramuscular injection, intracardiac injection, subcutaneous injection, or intraperitoneal injection.

In an additional particular embodiment, the composition comprising a Wnt7a polypeptide or polynucleotide and a fibronectin polypeptide and polynucleotide is for promoting formation, maintenance, repair or regeneration of skeletal muscle in a human subject in need thereof.

In one embodiment, the subject has, is suspected of having, or is at risk of having, a degenerative disease.

In one embodiment, the present invention contemplates, in part, a method for increasing the symmetric expansion of a stem cell comprising contacting the stem cells with a composition comprising a Wnt7a polypeptide fragment having the amino acid sequence set forth in SEQ ID NO: 5, or an N-terminal deletion of 210 to 219 amino acids of a Wnt7a polypeptide having the amino acid sequence set forth in SEQ ID NO: 3.

In another embodiment, the present invention contemplates, in part, a method for increasing the symmetric expansion of a stem cell comprising contacting the stem cells with a composition comprising a polynucleotide encoding Wnt7a polypeptide fragment having the amino acid sequence set forth in SEQ ID NO: 5, or an N-terminal deletion of 210 to 219 amino acids of a Wnt7a polypeptide having the amino acid sequence set forth in SEQ ID NO: 3.

In one embodiment, the polynucleotide comprises an expression vector.

In a particular embodiment, the composition comprises a population of stem cells.

In a certain embodiment, the composition is administered to a subject in need thereof.

In a further embodiment, the stem cells are adult stem cells

In an additional embodiment, the adult stem cells comprise satellite stem cells.

In another embodiment, the composition comprises a physiologically acceptable carrier or diluent.

In one embodiment, the composition is formulated for injection.

In an additional embodiment, the method promotes tissue formation, regeneration maintenance, or repair.

In a particular embodiment, the tissue is muscle.

In a further embodiment, the muscle is skeletal muscle.

In a certain embodiment, the method promotes formation, maintenance, repair or regeneration of skeletal muscle in a human subject in need thereof.

In one particular embodiment, the subject has a degenerative disease.

In a related particular embodiment, the degenerative disease is a muscular dystrophy.

In one embodiment, the present invention contemplates, in part, a method for promoting muscle formation, regeneration, maintenance or repair in a mammal comprising administering to the mammal a therapeutically effective amount of a composition as defined in any one of the embodiments disclosed herein.

In a particular embodiment, the present invention contemplates, in part, a method for preventing muscle wasting, atrophy or degeneration in a subject in need thereof comprising administering to the subject a therapeutically effective amount of a composition as defined in any one of the embodiments disclosed herein.

In a certain embodiment, the present invention contemplates, in part, a method for expanding a population of satellite stem cells in vivo, ex vivo, or in vitro comprising contacting the stem cells with an effective amount of a composition as defined in any one of the embodiments disclosed herein.

In another embodiment, the present invention contemplates, in part, a method for synergistically increasing the symmetric expansion of a stem cell comprising contacting the stem cells with a composition comprising: (a) a Wnt7a polypeptide having the amino acid sequence set forth in SEQ ID NO: 3; (b) a Wnt7a polypeptide fragment having the amino acid sequence set forth in SEQ ID NO: 5; or (c) a Wnt7a polypeptide fragment having an N-terminal deletion of 210 to 219 amino acids of a Wnt7a polypeptide having the amino acid sequence set forth in SEQ ID NO: 3; and (d) a fibronectin polypeptide.

In another embodiment, the present invention contemplates, in part, a method for synergistically increasing the symmetric expansion of a stem cell comprising contacting the stem cells with a composition comprising: (a) a polynucleotide a Wnt7a polypeptide having the amino acid sequence set forth in SEQ ID NO: 3; (a Wnt7a polypeptide fragment having the amino acid sequence set forth in SEQ ID NO: 5; or a Wnt7a polypeptide fragment having an N-terminal deletion of 210 to 219 amino acids of a Wnt7a polypeptide having the amino acid sequence set forth in SEQ ID NO: 3; and (b) a polynucleotide encoding a fibronectin polypeptide.

In one embodiment, each polynucleotide comprises an expression vector.

In a particular embodiment, the composition comprises a population of stem cells.

In an additional particular embodiment, the composition is administered to a subject in need thereof.

In a certain particular embodiment, the stem cells are adult stem cells

In a further particular embodiment, the adult stem cells comprise satellite stem cells.

In a related particular embodiment, the composition comprises a physiologically acceptable carrier or diluent.

In a certain embodiment, the composition is formulated for injection.

In a certain further embodiment, the method promotes tissue formation, regeneration maintenance, or repair.

In a certain additional embodiment, the tissue is muscle.

In one certain embodiment, the muscle is skeletal muscle.

In an additional embodiment, the method promotes formation, maintenance, repair or regeneration of skeletal muscle in a human subject in need thereof.

In a particular embodiment, the subject has a degenerative disease.

In a further embodiment, the degenerative disease is a muscular dystrophy.

In one embodiment, the present invention contemplates, in part, a method for promoting muscle formation, regeneration, maintenance or repair in a mammal comprising administering to the mammal a therapeutically effective amount of a composition comprising a Wnt7a polynucleotide or polypeptide fragment or a Wnt7a polynucleotide or polypeptide or fragment thereof and a fibronectin polynucleotide or polypeptide according to any one of the embodiments disclosed herein.

In a particular embodiment, the present invention contemplates, in part, a method for preventing muscle wasting, atrophy or degeneration in a subject in need thereof comprising administering to the subject a therapeutically effective amount of a composition comprising a Wnt7a polynucleotide or polypeptide fragment or a Wnt7a polynucleotide or polypeptide or fragment thereof and a fibronectin polynucleotide or polypeptide according to any one of the embodiments disclosed herein.

In another embodiment, the present invention contemplates, in part, a method for expanding a population of satellite stem cells in vivo, ex vivo, or in vitro comprising contacting the stem cells with an effective amount of a composition comprising a Wnt7a polynucleotide or polypeptide fragment or a Wnt7a polynucleotide or polypeptide or fragment thereof and a fibronectin polynucleotide or polypeptide according to any one of the embodiments disclosed herein.

BRIEF DESCRIPTION OF THE SEVERAL VIEWS OF THE DRAWINGS

FIG. 20 shows the effect of FN, TEN and Wnt7a on Pax7$^+$/YFP$^+$ satellite cells. A) Fibers were cultured for 42 h in the presence of COL, FN, COL&Wnt7a or FN&Wnt7a. At this time point no detectable effect was observed on Pax7$^+$/YFP$^+$ cells. Bars represent means±SEM. n=3. B) At 72 h of fiber culture, FN&Wnt7a led to a slight increase in the number of Pax7$^+$/YFP$^+$ cells. Bars represent means±SEM. n=3. p value is *p<0.05. C) At 42 h of culture, PBS, TEN, Wnt7a nor TEN&Wnt7a had no effect on Pax7$^+$/YFP$^+$ cells. Bars represent means±SEM. n=3.

qPCR comparing Myf5 and FN expression in early passages of primary cells derived from Pax7$^+$/YFP$^-$ and Pax7$^+$/YFP$^+$ satellite cells. Pax7$^+$/YFP$^-$ cells expressed lower levels of Myf5 and FN. Bars represent means±SEM. n=3. p value is *p<0.05. D) Western blot showing that myoblasts derived from satellite stem cells (Pax7$^+$/YFP$^-$) expressed less FN than myoblasts derived from satellite myogenic cells (Pax7$^+$/YFP$^+$). GAPDH is shown as a loading control.

Figure 25D:
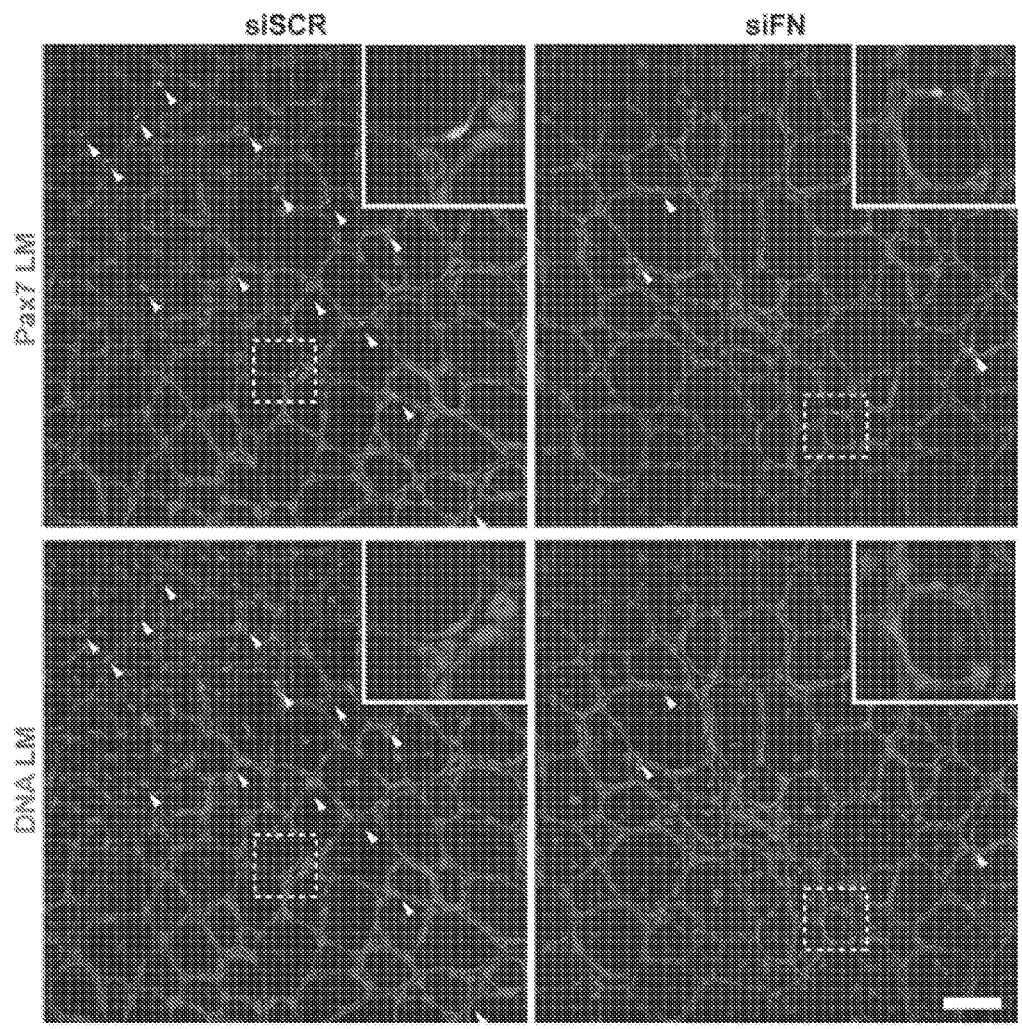

FIG. 25 shows the knockdown efficiency of FN siRNA and endogenous satellite cells after transplantation. A) siFN transfection of freshly FACS purified satellite cells from Pax7-zsGreen mice led to a significant knockdown after three days of plating when compared to siSCR. Bars represent means±SEM. n=3. p value is *p<0.05. B) The number of endogenous satellite cells was not significantly changed by transplantation of siFN or siSCR treated satellite cells. Bars represent means±SEM. n=3. C) Intramuscular injection of self-delivering siRNA at day two post CTX injury led to a significant knockdown of FN (siFN) by day five when compared to the scrambled control (siSCR). Bars represent means±SEM. n=3. p value is **p<0.01. D) Intramuscular injection of self-delivering siFN at day two post CTX injury led to a lower abundance of satellite cells (Arrowheads) in regenerating muscle. Scale bar=50 μm.

BRIEF DESCRIPTION OF THE SEQUENCE IDENTIFIERS

SEQ ID NO: 1 sets forth a cDNA sequence of human Wnt7a.

SEQ ID NO: 2 sets forth the amino acid sequence of a mouse Wnt7a polypeptide.

SEQ ID NO: 3 sets forth the amino acid sequence of the human Wnt7a polypeptide encoded by SEQ ID NO: 1.

SEQ ID NO: 4 sets forth amino acids 32-212 of SEQ ID NO: 3.

SEQ ID NO: 5 sets forth amino acids 213-349 of SEQ ID NO: 3.

SEQ ID NO: 6 sets forth the amino acid sequence of a rat Wnt7a polypeptide.

SEQ ID NO: 7 sets forth the amino acid sequence of a bovine Wnt7a polypeptide.

SEQ ID NO: 8 sets forth the amino acid sequence of a chicken Wnt7a polypeptide.

SEQ ID NOs: 9-38 set forth the polynucleotide sequences of oligonucleotide primers.

SEQ ID NO: 39 sets forth a cDNA sequence of human fibronectin.

SEQ ID NO: 40 sets forth the amino acid sequence encoded by the polynucleotide sequence of SEQ ID NO: 39.

SEQ ID NO: 41 sets forth the amino acid sequence of a human fibronectin splice variant.

SEQ ID NO: 42 sets forth the amino acid sequence of a human fibronectin splice variant.

SEQ ID NO: 43 sets forth the amino acid sequence of a human fibronectin splice variant.

SEQ ID NO: 44 sets forth the amino acid sequence of a human fibronectin splice variant.

SEQ ID NOs: 45-50 set forth the polynucleotide sequences for siRNA oligonucleotides.

DETAILED DESCRIPTION

Generally, the present invention provides compositions and methods for modulating stem cells, in particular, adult stem cells. More particularly, the present invention provides compositions and methods for modulating stem cell division. Various uses of the compositions and methods described herein are also provided, including therapeutic uses, for example, for promoting tissue formation, regeneration, repair or maintenance.

Stem cells, and therapies targeting stem cells, have the potential for providing benefit in a variety of clinical settings. A limitation of many potential therapeutic applications has been obtaining a sufficient number of undifferentiated stem cells, and stimulating terminal differentiation into mature tissue-specific cells without depleting the stem cell reservoir. Much current stem cell research focuses on directing the proliferation and differentiation of stem cells, in particular, transiently amplifying progenitors to repair or regenerate damaged tissue. In addition to concerns about stem cell depletion, another concern with stimulating proliferation and differentiation of stem cells is abnormal or poorly-formed tissue.

Activation of the planar cell polarity (PCP) pathway in stem cells, e.g., adult stem cells, promotes symmetrical stem cell division. Symmetrical division gives rise to two daughter cells and results in expansion of the stem cell pool. Conversely, inhibition of PCP signaling in stem cells inhibits symmetrical division, resulting in an increase in asymmetrical (apical-basal) cell division, which does not expand the stem cell pool. Promotion of symmetrical stem cell division via activation the PCP pathway does not appear to affect the rate of cell division.

Wnt7a is an important developmental factor regulates the satellite stem cell niche. Recently, Wnt signaling through the non-canonical Planar Cell Polarity (PCP) pathway was found to induce symmetric satellite stem cell expansion and increase muscle regeneration. Without wishing to be bound to any particular theory, it is thought that Wnt7a acts via the Frizzled7 (Fzd7) receptor and activates of PCP signaling in adult stem cells, e.g., satellite stem cells. Satellite stem cells are adult stem cells that give rise to muscle cells. Overexpression of Wnt7a by electroporation of CMV-Wnt7a plasmid into the Tibialis Anterior (TA) muscle of 3 month old mice increases muscle regeneration, marked by an 18% increase in muscle mass and a 50% increase in muscle fiber cross sectional area compared to control mice, suggesting that Wnt7a dramatically enhances muscle regeneration. Moreover, it has been shown that administration of Wnt7a polypeptide, or a polynucleotide encoding a Wnt7a polypeptide, increased satellite stem cell numbers in vitro and in vivo, and promoted tissue formation in vivo, leading to enhanced repair and regeneration in injured and diseased muscle tissue.

Thus, Wnt7a is a novel target that modulates stem cell division, and promotes tissue formation, regeneration, maintenance and repair. However, Wnt7a is poorly soluble because of post-translation lipidification and thus, use of Wnt7a polypeptides in recombinant protein therapy has been hindered. Delipidation of canonical Wnts through site-directed mutagenesis increases the water solubility of the protein to nearly 100% without compromising its activity. However, increased bioavailability of Wnt polypeptide therapies has yet to be realized. Surprisingly, the present inventors have identified that the N-terminal signal peptide is not necessary for Wnt7a signaling and that the C-terminal domain of Wnt7a is both sufficient and necessary to induce myofiber hypertrophy. Collectively, this novel Wnt7a comprising the C-terminal domain increases bioavailability in electroporated muscles and thus, offers advantages as a potential therapeutic modality over current Wnt7a polypeptides in the art.

In various embodiments, the present invention contemplates, in part, that compositions comprising novel Wnt7a polypeptide truncations or fragments and methods of using the same to increase stem cell expansion and provide therapy to subjects having myodegenerative disorders.

The invention also provides synergistic compositions and methods comprising the Wnt7a polypeptides of the invention. Using a microarray screening approach for ECM components synthesized by myogenic cells, the inventors discovered that during the initial proliferative response to injury, satellite cells release FN into their niche. FN activates the Fzd7/Sdc4 receptor complex in conjunction with Wnt7a leading to an expansion of the Myf5 negative satellite stem cell pool. It is contemplated that a high tissue content of satellite stem cells will ultimately facilitate the generation of committed daughter cells through asymmetric divisions.

Without wishing to be bound to any particular theory, the present invention contemplates, in part, that by expanding the satellite stem cell pool, the transient FN fibrosis during early adult myogenesis indirectly guarantees sufficient mitotically competent committed satellite myogenic cells which are available to resupply the myogenic pool for subsequent terminal differentiation.

Thus, the present invention contemplates, in part, a novel physiological mechanism to synergistically increase satellite cell pool during muscle regeneration. In various embodiments, the present invention contemplates, in part, compositions comprising a Wnt7a polypeptide or novel truncations or fragments thereof and a fibronectin polypeptide and methods of using the same to synergistically increase stem cell expansion and provide therapy to subjects having myodegenerative disorders.

A. Definitions

Unless defined otherwise, all technical and scientific terms used herein have the same meaning as commonly understood by one of ordinary skill in the art to which this invention pertains.

The term "stem cell", as used herein, refers to an undifferentiated cell that is capable of differentiating into a number of final, differentiated cell types. Different stem cells may have different potency. Totipotent stem cells typically have the capacity to develop into any cell type and are usually embryonic in origin. Pluripotent stem cells are capable of differentiating into cells of the endoderm, mesoderm, and ectoderm. Multipotent stem cells can differentiate into a number of cells, but only those of a single lineage. Unipotent stem cells can produce only one cell type, their own, but have the property of self-renewal which distinguishes them from non-stem cells. A muscle stem cell is an example of stem cell that is traditionally thought to be unipotent, giving rise to muscle cells only.

An "adult stem cell" is a stem cell found in a developed organism. Adult stem cells include, but are not limited to, hematopoietic stem cells, mesenchymal stem cells, neural stem cells, endothelial stem cells and muscle stem cells.

A "satellite stem cell" is an example of an adult stem cell that gives rise to muscle cells.

The term "progenitor cell", as used herein, refers to a cell that is committed to a particular cell lineage and which gives rise to cells of this lineage by a limited series of cell divisions. A myoblast is an example of a progenitor cell, which is capable of differentiation to only one type of cell, but is itself not fully mature or fully differentiated.

The term "symmetrical division", as used herein in reference to stem cells, refers to a cell division that increases the number of cells of the same type. The term "planar division" may also be used. Symmetrical stem cell division gives rise to two daughter stem cells, thereby expanding the stem cell pool. The term "expansion" therefore refers to an increase in the number of cells of a particular type as a result of symmetrical division.

The term "asymmetrical division", as used herein in reference to stem cells, refers to a cell division that gives rise to one daughter stem cell and one progenitor cell, with no increase in stem cell number. The term "apical-basal division" may also be used.

By "promoting", "enhancing" or "increasing" symmetrical stem cell division, it is meant that the ratio of symmetrical to asymmetrical cell division is increased compared to normal or control, e.g., the ratio in the absence of a particular active agent, composition or treatment method. For example, the ratio of symmetrical to asymmetrical cell division may be increased by at least 10%, 20%, 30%, 40%, 50%, 60%, 70%, 80%, 90%, 100%, 125%, 150%, 175%, 200%, or even greater.

The term "differentiation", as used herein, refers to a developmental process whereby cells become specialized for a particular function, for example, where cells acquire one or more morphological characteristics and/or functions different from that of the initial cell type. The term "differentiation" includes both lineage commitment and terminal differentiation processes. States of differentiation may be assessed, for example, by assessing or monitoring the presence or absence of biomarkers using immunohistochemistry or other procedures known to a person skilled in the art.

The term "lineage commitment", as used herein, refers to the process in which a stem cell becomes committed to forming a particular limited range of differentiated cell types. Lineage commitment arises, for example, when a stem cell gives rise to a progenitor cell during apical-basal division. Committed progenitor cells are often capable of self-renewal or cell division.

The term "terminal differentiation", as used herein, refers to the final differentiation of a cell into a mature, fully differentiated cell. Usually, terminal differentiation is associated with withdrawal from the cell cycle and cessation of proliferation.

The term "Wnt" refers to a family of related genes and proteins. The Wnt genes encode over twenty cysteine-rich, secreted, Wnt proteins (glycoproteins) that act by binding to Frizzled (Fzd) receptors on target cells. A number of Wnt polypeptides are known in the art, including Wnt 1, Wnt 2, Wnt 2b, Wnt 3, Wnt 3a, Wnt 4, Wnt 5a, Wnt 5b, Wnt 6, Wnt 7a, Wnt 7b, Wnt 8a, Wnt 8b, Wnt 9a, Wnt 9b, Wnt 10a, Wnt 10b, Wnt 11 and Wnt 16. Homologues from other species are also known and accessible to a person skilled in the art. Members of the Wnt family demonstrate marked evolutionary conversation and thus a high degree of homology is observed between species.

"Frizzled" (Fzd) receptors are a family of G-protein coupled receptor proteins to which Wnt molecules are known to bind. Sequences of various Fzd receptors are available to those skilled in the art. Fzd7 is expressed on satellite stem cells. Other stem cells that express Fzd7 include human embryonic stem cells (hESC) and neural stem cells (NSC).

Binding of different members of the Wnt family to certain members of the Fzd family on specific cells can initiate signaling by one of several distinct pathways, including canonical and non-canonical Wnt signaling pathways.

As used herein, the term "canonical pathway", refers to a Wnt signaling pathway comprising activation of the signaling molecule Disheveled, which inactivates glycogen synthase kinase-3 (GSK-3β), a cytoplasmic serine-threonine kinase. The GSK-3β target, β-catenin, is thereby stabilized and translocates to the nucleus where it activates TCF (T-cell-factor)-dependant transcription of specific promoters. This pathway is also described as the "Wnt/β-catenin" pathway herein. Canonical Wnt-signaling plays a well-documented role in regulating myogenic growth and differentiation.

As used herein, the term "non-canonical" refers to a Wnt signaling pathway, also referred to as the "planar cell polarity" (PCP) pathway; binding of Wnt to Fzd also activates Disheveled (Dvl), which in this case activates RhoA, a small g protein, triggering a cascade that is unique from the canonical pathway. For example, in contrast to the canonical pathway, activation or stimulation of the PCP pathway does not result in nuclear translocation of β-catenin.

As used herein, "effector" molecule refers to a post-receptor signaling molecule, also referred to as a "downstream effector" molecule. Effector molecules may include, for example, cytosolic signaling molecules or nuclear signaling molecules and transcription factors, or molecules in a cell membrane, such as receptors or co-receptors.

Illustrative examples of effectors include, but are not limited to proteins, polynucleotides and peptides. Further illustrative examples of effector molecules in the PCP pathway include CelsM, Celsr2, Celsr3, DvM, Dvl2, Dvl3, Pk1, Pk2, Pk3, Pk4, Rac/RhoA, VangM, Vangl2, Syndecan 4 (Sdc4) and α7-β1-integrin.

In the context of a signaling pathway, "activation" may include one or more of, e.g., changes in phosphorylation, conformation, polarization, localization or distribution of a molecule within the cell or cell membrane. Activation may occur directly via activation, stimulation or upregulation of an activating component of a signaling pathway, or may occur indirectly by inhibiting an inhibitory component. The converse is also true where "inhibition" may occur directly or indirectly.

The term "modulator", as used herein, refers to both "activators" and "inhibitors" of a signaling event or pathway, e.g., modulators of the Wnt7a signaling pathway. A modulator of the Wnt7a signaling pathway may be a compound or molecule that stimulates or inhibits the activity or expression of a Wnt7a polypeptide, or an upstream (activator) or downstream (effector) molecule in the Wnt7a signaling pathway, including modulators of the Frizzled7 (Fzd7) receptor. Candidate modulators of the Wnt7a signaling pathway may stimulate or inhibit the activity of a Wnt7a polypeptide directly or indirectly. Direct modulators may act on a Wnt7a polypeptide, or a gene encoding a Wnt7a polypeptide, whereas indirect modulators may act on one or more proteins, or genes encoding proteins, that act upstream ("activators") or downstream ("effectors") of a Wnt7a polypeptide in the Wnt7a signaling pathway. A modulator can act at a genetic level, for example to upregulate or downregulate the expression of a gene encoding a Wnt7a polypeptide or an activator or effector of Wnt7a signaling, or at the protein level to interfere with the activity of a Wnt7a polypeptide or an activator or effector of Wnt7a signaling. Modulators may themselves be Wnt polypeptides, or active fragments, derivatives or variants thereof. A modulator can be, for example, a polypeptide, peptide, polynucleotide, oligonucleotide, antibody or antibody fragment, or a small molecule activator or inhibitor. Small molecule modulators can be organic or inorganic.

A "stem cell modulator" is a modulator that activates or inhibits a function of a stem cell. For example, a stem cell modulator may modify stem cell division, proliferation, differentiation, or survival. For example, Wnt7a, is a modulator of stem cell division.

The term "Wnt7a signaling pathway," as used herein in reference to stem cells, refers to the Wnt7a-Fzd7 signaling pathway in adult stem cells, e.g., satellite stem cells, which was shown to activate PCP signaling. Wnt7a signaling was shown to induce polarized distribution of Vangl2 and α7-integrin, two known effector molecules in the PCP pathway, thereby promoting symmetrical stem cell division. Thus, the Wnt7a signaling pathway referred to herein is the PCP signaling pathway. In certain other cell types, Wnt7a may activate other Wnt signaling pathways.

Component members of the Wnt7a signaling pathway demonstrate marked evolutionary conservation, e.g., in vertebrates and mammals. Human and mouse Wnt7a proteins share about 98% sequence identity, while corresponding Fzd7 homologues are about 96% identical and Vangl2 homologues are about 99% identical. Such high degree of homology often results in cross-species activity. For instance, it has been demonstrated that human Wnt7a is active in the mouse system. Therefore, experimental findings can often be extrapolated across species.

The terms "protein", "polypeptide", and "peptide," as used herein, refer to a sequence of amino acid residues linked together by peptide bonds or modified peptide bonds. Polypeptides of the invention include, but are not limited to Wnt, e.g., Wnt7a, and fibronectin polypeptides as described elsewhere herein. Typically, a polypeptide is at least six amino acids long and a peptide is at least 3 amino acids long. The polypeptide or peptide can be naturally occurring, recombinant, synthetic, or a combination of these. The polypeptide or peptide can be a fragment of a naturally occurring protein or polypeptide.

The present invention further contemplates that polypeptides of the invention may be isolated from a number of sources, e.g., mouse, cow, sheep, goat, pig, dog, cat, rat, rabbit, primate, or human.

The terms polypeptide and peptide also encompass analogues, derivatives and peptidomimetic compounds. Such compounds are well known in the art and may have significant advantages over naturally occurring peptides, including, for example, greater chemical stability, increased resistance to proteolytic degradation, enhanced pharmacological properties (such as, half-life, absorption, potency and efficacy), altered specificity (for example, a broad-spectrum of biological activities) or reduced antigenicity.

Specific proteins or polypeptides referred to herein, e.g., Wnts and fibronectins, encompass proteins and polypeptides having amino acid sequences corresponding to naturally occurring sequences, as well as variant or homologous polypeptide sequences, fragments, and derivatives having an activity at least substantially identical to a wild-type protein. Likewise, specific genes (e.g., Wnt7a, fibronectin) encompass nucleic acid sequences or partial sequences encoding proteins having a polypeptide sequence corresponding to naturally occurring sequences as well as variant or homologous polypeptide sequences, fragments, analogies and derivatives having an activity at least substantially identical to a wild-type protein. Polypeptides, including variants, fragments, analogues and derivatives thereof, having an increased activity compared to wild-type polypeptides are also contemplated.

A functional "activity", as used herein in reference to a polypeptide or gene or portion thereof, refers to a polypeptide, gene or portion thereof that displays one or more activities associated with a naturally-occurring protein or gene. Functional activity in regard to a polypeptide or portion thereof may include, for example, the ability to specifically bind to and/or activate a receptor or ligand for the polypeptide.

"Naturally occurring", as used herein in reference to an object, indicates that the object can be found in nature. For example, a naturally occurring polypeptide or polynucleotide sequence would be one that is present in an organism, and can be isolated from the organism, and which has not been intentionally modified by man in the laboratory. The term "wild-type" is often used interchangeably with naturally occurring.

In the context of the present invention, a polypeptide, or fragment, variant, analogue or derivative thereof, is considered to have at least substantially the same activity as the wild-type protein when it exhibits about 50% of the activity of the wild-type protein, preferably at least 60%, 75%, or 80% of the activity of the wild-type protein. In preferred embodiments, the polypeptide, variant, fragment, analogue or derivative exhibits at least about 85% of the activity of the wild-type protein, e.g. 88%, 90%, 95%, 99%, 100%. In certain embodiments, an activity greater than wild-type activity may be achieved. Activity of a Wnt7a polypeptide, variant, fragment, analogue or derivative, for example, can be determined by measuring its ability to promote symmetrical stem cell expansion and comparing to a wild-type protein. Methods of measuring and characterizing stem cell division are known in the art.

A "fragment" of a polypeptide includes, but is not limited to, an amino acid sequence wherein one or more amino acids are deleted in comparison to the wild-type sequence or another reference sequence. In various embodiments, polypeptide fragments include, but are not limited to truncated Wnt polypeptides, e.g., a Wnt polypeptide, e.g., Wnt7a, comprising one or more N-terminal or C-terminal amino acid deletions. Without wishing to be bound to any particular theory, the present invention contemplates that Wnt7a comprises two polypeptide domains: a hydrophobic N-terminal region (amino acids 32-212; amino acids 1-31 comprise a Wnt7a signal peptide, which is likely cleaved during protein processing) and a hydrophilic C-terminal region (amino acids 213-349), which retain the Wnt signaling activity of the naturally occurring Wnt7a.

In particular embodiments, polypeptide fragments include, but are not limited to fibronectin polypeptides comprising one or more N-terminal or C-terminal amino acid deletions.

In one embodiment, a Wnt polypeptide fragment comprises a deletion of 210, 211, 212, 213, 214, 215, 216, 217, 218, or 219 N-terminal amino acids. In another embodiment, a fragment exists when one or more amino acids from the amino terminal, carboxy terminal or both are removed. In a particular embodiment, the Wnt polypeptide fragment is a Wnt7a polypeptide fragment. Further, one or more amino acids internal to the polypeptide may be deleted. Active fragments are fragments that retain functional characteristics, e.g., of the native sequence or other reference sequence. Typically, active fragments are fragments that retain substantially the same activity as the wild-type protein. A fragment may, for example, contain a functionally important domain, e.g., Wnt7a C-terminal domain, such as a domain that is important for receptor or ligand binding.

A "variant" polypeptide or variant fragment is one in which one or more amino acid residues have been deleted, added, or substituted for those that appear in the amino acid sequence of a wild-type sequence or another reference sequence. In the context of the present invention, a variant preferably retains substantially the same activity as the wild-type sequence or other reference sequence, or has better activity than the wild type protein. The present invention includes, but is not limited to variants of Wnt7a and fibronectin.

A variant may contain one or more amino acid substitutions, which may be "conservative" or "non-conservative" substitutions. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group, while a non-conservative substitution involves the substitution of an amino acid with another amino acid from a different group.

Typically, variant amino acid sequences comprise greater than about 70%, more preferably greater than about 80%, 85%, 90%, 91%, 92%, 93%, 94%, 95%, 96%, 97%, 98% or 99% identity to the wild-type or reference sequence. The degree of identity may also be represented by a range defined by any two of the values listed above or any value therein between. Variants include "mutants" in which the reference sequence is the wild-type sequence.

A "derivative" is a peptide or polynucleotide containing additional chemical or biochemical moieties not normally a part of a naturally occurring molecule. Peptide derivatives include peptides in which one or more amino acid side chain and/or the amino-terminus and/or the carboxy-terminus has been derivatized with a suitable chemical substituent group, as well as cyclic peptides, dual peptides, multimers of the peptides, peptides fused to other proteins or carriers glycosylated peptides, phosphorylated peptides, peptides conjugated to lipophilic moieties (for example, caproyl, lauryl, stearoyl moieties) and peptides conjugated to an antibody or other biological ligand. Examples of chemical substituent groups that may be used to derivatize a peptide include, but are not limited to, alkyl, cycloalkyl and aryl groups; acyl groups, including alkanoyl and aroyl groups; esters; amides; halogens; hydroxyls; carbamyls, and the like. The substituent group may also be a blocking group such as Fmoc (fluorenylmethyl-O—CO—), carbobenzoxy(benzyl-CO—), monomethoxysuccinyl naphthyl-NH—CO~, acetylaminocaproyl and adamantyl-NH—CO—. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

An "analogue" is a polypeptide or peptide comprising one or more non-naturally occurring amino acids. As is known in the art, substitution of all D-amino acids for all L-amino acids within a peptide can result in an "inverse" peptide, or in a "retro-inverso" peptide (see Goodman et al. "Perspectives in Peptide Chemistry" pp. 283-294 (1981); U.S. Pat. No. 4,544,752), both of which are considered to be analogues in the context of the present invention. An "inverse" peptide is one in which all L-amino acids of a sequence have been replaced with D-amino acids, and a "retro-inverso" peptide is one in which the sequence of the amino acids has been reversed ("retro") and all L-amino acids have been replaced with D-amino acids.

"Peptidomimetics" are compounds that are structurally similar to peptides and contain chemical moieties that mimic the function of the polypeptide or peptide of the invention. For example, if a polypeptide contains two charged chemical moieties having functional activity, a mimetic places two charged chemical moieties in a spatial orientation and constrained structure so that the charged chemical function is maintained in three-dimensional space. The term peptidomimetic thus is intended to include isosteres. The term "isostere" refers to a chemical structure that can be substituted for a polypeptide or peptide because the steric conformation of the chemical structure is similar to that of the peptide or polypeptide, for example, the structure fits a binding site specific for the polypeptide or peptide.

One skilled in the art will appreciate that not all amino acids in a peptide or polypeptide need be modified. Similarly not all amino acids need be modified in the same way. Peptide derivatives, analogues and peptidomimetics of the present invention include chimeric molecules which contain two or more chemically distinct regions, each region comprising at least one amino acid or modified version thereof.

A "Wnt7a polypeptide," as used herein, encompasses a Wnt7a protein or fragments thereof, having a polypeptide sequence corresponding to a wild-type Wnt7a sequence, or having a sequence that is at least about as 70%, more preferably about 80%, 85%, 90%, 91%, 92%, 93%, 94%, 95%, 96%, 97%, 98%, 99% or about 100%, identical to a naturally occurring Wnt7a sequence. Identity may be assessed over at least about 50, 100, 200, 300, or more contiguous amino acids, or may be assessed over the full length of the sequence. Methods for determining % identity or % homology are known in the art and any suitable method may be employed for this purpose. Wnt7a polypeptides also include variants, fragments, analogues and derivatives having an activity substantially identical to a wild-type Wnt7a polypeptide, e.g., binding to Fzd7. Exemplary Wnt7a polypeptides include polypeptides comprising the amino acid sequence shown in SEQ ID NO: 2-5, as well as active fragments, variants or derivatives thereof.

A "fibronectin polypeptide," as used herein, encompasses a fibronectin protein or fragments thereof, splice variants, e.g., EIIIA, EIIIB, having a polypeptide sequence corresponding to a wild-type fibronectin sequence, or having a sequence that is at least about as 70%, more preferably about 80%, 85%, 90%, 91%, 92%, 93%, 94%, 95%, 96%, 97%, 98%, 99% or about 100%, identical to a naturally occurring fibronectin sequence. Identity may be assessed over at least about 50, 100, 200, 300, or more contiguous amino acids, or may be assessed over the full length of the sequence. Methods for determining % identity or % homology are known in the art and any suitable method may be employed for this purpose.

Fibronectin contributes to survival of cells in vitro, ex vivo, and in vivo. It is expressed by fibroblasts in skin, in most other tissues and may other cell types (e.g., endothelial cells) and made in the liver. Fibronectin, (m.w. 440,000) is a dimer of two large subunits joined by disulfide bonds at one end. The single large gene contains about 50 exons of similar size. Over 50 alternately spliced variants exist and are known in the art. The tetrapeptide, Arg-Gly-Asp-Ser, assists cell adhesion. Fibronectin has fibrin, Clq, heparin, transglutaminase, collagen types I, II, III, V, VI and sulfated proteoglycans binding sites. Fibronectin functions in cell-substrate adhesion, contact inhibition, cell migration, cell differentiation, inflammation and wound healing. Plasma fibronectin is soluble and differs from insoluble cellular fibronectin by the absence of the two commonly spliced domains EIIIA and EIIIB.

Fibronectin polypeptides also include variants, fragments, analogues and derivatives having an activity substantially identical to a wild-type Fibronectin polypeptide, e.g., binding to Fzd7/Sdc4 and/or Wnt7a. Exemplary fibronectin polypeptides include polypeptides comprising the amino acid sequence shown in SEQ ID NO: 40-44, as well as active fragments, variants or derivatives thereof.

The polypeptides of the present invention can be prepared by methods known in the art, such as purification from cell extracts or the use of recombinant techniques. Polypeptides as described herein will preferably involve purified or isolated polypeptide preparations. In certain embodiments, purification of the polypeptide may utilize recombinant expression methods well known in the art, and may involve the incorporation of an affinity tag into the expression construct to allow for affinity purification of the target polypeptide.

Shorter sequences can also be chemically synthesized by methods known in the art including, but not limited to, exclusive solid phase synthesis, partial solid phase synthesis, fragment condensation or classical solution synthesis (Merrifeld (1963) *Am. Chem. Soc.* 85:2149; Merrifeld (1986) *Science* 232:341). The polypeptides of the present invention can be purified using standard techniques such as chromatography (e.g., ion exchange, affinity, and sizing column chromatography or high performance liquid chromatography), centrifugation, differential solubility, or by other techniques familiar to a worker skilled in the art. The polypeptides can also be produced by recombinant techniques. Typically this involves transformation (including transfection, transduction, or infection) of a suitable host cell with an expression vector comprising a polynucleotide encoding the protein or polypeptide. The nucleic acid sequences for human and mouse Wnt7a gene and various other components of the PCP signaling pathway are known in the art (see, for example, GenBank Accession Nos 000755, P24383, NPJD04616, G36470, PF6706, P28047, H36470, NM_004625, and M89801) and may be used as a basis for the polynucleotides of the invention.

The polypeptides and peptides of the present invention can also be produced as fusion proteins. One use of such fusion proteins is to improve the purification or detection of the polypeptide or peptide. For example, a polypeptide or peptide can be fused to an immunoglobulin Fc domain and the resultant fusion protein can be readily purified using a protein A column. Other examples of fusion proteins include polypeptides or peptides fused to histidine tags (allowing for purification on Nickel resin columns), to glutathione-S-transferase (allowing purification on glutathione columns) or to biotin (allowing purification on streptavidin columns or with streptavidin labeled—19 magnetic beads). Once the fusion protein has been purified, the tag may be removed by site-specific cleavage using chemical or enzymatic methods known in the art.

As used herein, the term "polynucleotide sequence" or "nucleic acid sequence," refers to any nucleotide sequence (e.g., RNA or DNA), the manipulation of which may be deemed desirable for any reason (e.g., modulate cell function, treat disease, etc.), by one of ordinary skill in the art. Such nucleotide sequences include, but are not limited to, coding sequences of genes (e.g., reporter genes, selection marker genes, oncogenes, disease resistance genes, growth factors, etc.), and non-coding regulatory sequences which may not encode an mRNA (e.g., promoter sequence, polyadenylation sequence, termination sequence, enhancer sequence, etc.).

By the terms "regulatory sequence", "regulatory region", "regulatory element" it is meant a portion of nucleic acid typically, but not always, upstream of the protein or polypeptide coding region of a nucleotide sequence, which may be comprised of either DNA or RNA, or both DNA and RNA. When a regulatory region is active, and in operative association with a nucleotide sequence of interest, this may result in expression of the nucleotide sequence of interest. A regulatory element may be capable of mediating organ specificity, or controlling developmental or temporal nucleotide sequence activation. A "regulatory region" includes promoter elements, core promoter elements exhibiting a basal promoter activity, elements that are inducible in response to a stimulus, elements that mediate promoter activity such as negative regulatory elements or transcriptional enhancers. "Regulatory region", as used herein, also includes elements that are active following transcription, for example, regulatory elements that modulate nucleotide sequence expression such as translational and transcriptional enhancers, translational and transcriptional repressors, upstream activating sequences, and mRNA instability determinants. Several of these latter elements may be located proximal to the coding region.

The terms "complementary" and "complementarity" refer to polynucleotides (i.e., a sequence of nucleotides) related by the base-pairing rules. For example, the sequence "A-G-T-" is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The term "isolated" when used in relation to a polynucleotide, refers to a nucleic acid sequence that is identified and separated from at least one contaminant nucleic acid with which it is ordinarily associated in its natural source. Isolated nucleic acid molecule is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid molecule encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid may be present in single-stranded or double-stranded form. When an isolated nucleic acid is to be utilized to express a protein, the polynucleotide will contain at a minimum the sense or coding strand (i.e., the polynucleotide may be single-stranded), but may contain both the sense and anti-sense strands (i.e., the polynucleotide may be double-stranded).

The term "purified" refers to molecules, including nucleic or amino acid sequences that are removed from their natural environment isolated or separated. An "isolated nucleic acid sequence" is therefore a purified nucleic acid sequence. "Substantially purified" molecules are at least 60% free, at least 75% free, or typically at least 90%, 95% or 99% free from other components with which they are naturally associated. As used herein, the terms "purified" and "to purify" also refer to the removal of contaminants from a sample. The removal of contaminating molecules, including proteins, results in an increase in the percent of polypeptide of interest in the sample. In another example, recombinant polypeptides are expressed in bacteria, yeast, or mammalian host cells and the polypeptides are purified by the removal of host cell proteins; the percent of recombinant polypeptides is thereby increased in the sample.

Nucleic acid sequences corresponding to genes or encoding polypeptides relating to the present invention can be readily purchased or purified from a suitable source by standard techniques, or can be synthesized chemically. The nucleic acids can be genomic DNA, RNA, cDNA prepared from isolated mRNA, or DNA amplified from a naturally occurring nucleic acid sequence by standard techniques. Alternatively, the known sequences may be used to prepare probes to obtain other nucleic acid sequences encoding a Wnt7a polypeptide or fragment thereof or a fibronectin polypeptide from various sources using standard techniques. Suitable sources for obtaining the nucleic acids are those cells or tissues which are known to express the proteins of interest, such as skeletal muscle tissue and other tissues with measurable Wnt7a or fibronectin transcripts.

Polynucleotides encoding fragments or variants of the naturally occurring Wnt7a or fibronectin proteins can be constructed by deletion, addition, and/or substitution of one or more nucleotides within the coding sequence using standard techniques, such as site-directed mutagenesis techniques.

Specific initiation signals may be required for efficient translation of cloned polynucleotide. These signals include the ATG initiation codon and adjacent sequences. In cases where an entire wild-type gene or cDNA, including its own initiation codon and adjacent sequences, is inserted into the appropriate expression vector, additional translational control signals may not be needed. In other cases, exogenous translational control signals, including, perhaps, the ATG initiation codon, must be provided. Furthermore, the initiation codon must be in phase with the reading frame of the desired coding sequence to ensure translation of the entire insert. The exogenous translational control signals and initiation codons can be natural or synthetic. The efficiency of expression may be enhanced by the inclusion of appropriate transcription enhancer elements and/or transcription terminators (Bittner et al. (1987) *Methods in Enzymol.* 153, 516).

In some instances, it may be desirable to link the coding sequence of a particular gene to an amino- or carboxyl-terminal epitope tag to facilitate detection or purification of expressed protein. Suitable epitope tags may include, but are not limited to, hemagglutinin (HA), myc, FLAG, 6× His, V5, glutathione-S-transferase (GST), etc.

An "expression vector", also known as an expression construct, is used to introduce a specific gene into a target cell. Once the expression vector is inside the cell, the protein that is encoded by the gene is produced by the cellular-transcription and translation machinery. The vector is frequently engineered to contain regulatory sequences that act as enhancer and promoter regions and lead to efficient transcription of the gene carried on the expression vector. The goal of a well-designed expression vector is the production of large amounts of stable messenger RNA.

Suitable expression vectors include, but are not limited to, plasmids, phagemids, viral particles and vectors, phages and the like. The entire expression vector, or a part thereof, can be integrated into the host cell genome. In some circumstances, it is desirable to employ an inducible expression vector as are known in the art, e.g., the LACSWITCH Inducible Expression System (Stratagene, LaJolla, Calif.). Suitable expression vectors may comprise promoters for driving expression in a particular host cell. Some expression vectors may comprise a CMV promoter. The expression vectors may be, for example, pCMV or pCMV-Sportβ.

Those skilled in the field of molecular biology will understand that a wide variety of expression systems can be used to provide the recombinant polypeptide or peptide. The polypeptide or peptide can be produced in a prokaryotic host (e.g., *E. coli* or *B. subtilis*) or in a eukaryotic host (e.g., *Saccharomyces* or *Pichia*; mammalian cells, such as COS, NIH 3T3, CHO, BHK, 293, or HeLa cells, insect cells, or plant cells). The methods of transformation or transfection and the choice of expression vector will depend on the host system selected and can be readily determined by one skilled in the art. Transformation and transfection methods are described, for example, in Ausubel et al. (1994) *Current Protocols in Molecular Biology*, John Wiley & Sons, New York; and various expression vectors may be chosen from those provided, e.g. in *Cloning Vectors: A Laboratory Manual* (Ponwels et al., 1985, Supp. 1987) and by various commercial suppliers.

In addition, a host cell may be chosen which modulates the expression of the inserted sequences, or modifies and processes the gene product in a specific, desired fashion. Such modifications (e.g. glycosylation) and processing (e.g. cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed heterologous protein. The host cells harboring the expression vehicle can be cultured in conventional nutrient media adapted as needed for activation of a chosen gene, repression of a chosen gene, selection of transformants, or amplification of a chosen gene according to known procedures.

With reference to the polypeptide and polynucleotide sequences defined herein, the term "substantially identical" in reference to sequence identity means at least 70%, preferably at least 80%, 85%, 90%, 91%, 92%, 93%, 94%, 95%, 96%, 97%, 98% or 99% sequence identity. By "identity" is meant the number of conserved amino acids or nucleotides as determined by standard alignment algorithms or programs known in the art, used with default parameters established by each supplier. It will be understood that the degree of identity may be represented by a range defined by any two of the values listed above or any value therebetween. Identity may be assessed, for example, over at least about 50, 100, 200, 300, or more contiguous amino acids, or at least about 50, 100, 200, 300, 500, 750, 1000 or more nucleotides, or may be assessed over the full length of the sequence. The terms "homology" and "identity" are often used interchangeably. Methods for determining % identity or % homology are known in the art and any suitable method may be employed for this purpose. In general, sequences are aligned so that an optimized match is obtained. An example of an algorithm that is suitable for determining percent sequence identity is algorithms such as the BLAST algorithm, as is well known to those skilled in the art. Software for performing BLAST analyses is publicly available through the National Center for Biotechnology Information (www.ncbi.nlm.nih.gov). Other commercially or publicly available programs include the DNAStar MegAlign program (Madison, Wis.) and the University of Wisconsin Genetics Computer Group (UWG) Gap program (Madison Wis.).

As used herein, the term at "least 90% identical" would refer to percent identities from 90 to 99.99% relative to a reference polynucleotide or polypeptide. Identity at a level of 90% or more is indicative of the fact that, assuming for exemplification purposes a test and reference polynucleotide or polypeptide length of 100 nucleotides or amino acids are compared, no more than 10% of the respective nucleotides or amino acids in the test polypeptide would differ from corresponding aligned positions of the reference nucleotides/polypeptides. Differences may be represented as point mutations randomly distributed over the entire length of an polynucleotide or amino acid sequence or may be clustered in one or more locations of varying length up to the maximum allowable, e.g., 10 of 100 nucleotide/amino acid differences for the above "at least 90% identity" example. Differences may be defined as nucleic acid or amino acid substitutions or deletions.

Substantially identical nucleic acid molecules would hybridize typically at moderate stringency or at high stringency conditions along the length of the nucleic acid or along at least about 70%, 80%, 85%, 90%, 95%, 96%, 97%, 98%, or 99% of the full length nucleic acid molecule of interest. In the case of coding sequences, also contemplated are nucleic acid molecules that contain degenerate codons in place of codons in the hybridizing nucleic acid molecule.

As used herein, "domain" refers to a portion of a molecule, e.g., polypeptide or the encoding polynucleotide that is structurally and/or functionally distinct from other portions of the molecule. For example, Wnt7a comprises and N-terminal hydrophobic domain (SEQ ID NO: 4) and a C-terminal hydrophobic domain (SEQ ID NO: 5).

As used herein, "gene therapy" includes both ex vivo and in vivo techniques. Thus host cells can be genetically engineered ex vivo with a polynucleotide, with the engineered cells then being provided to a patient to be treated. Delivery of the active agent in vivo may involve a process that effectively introduces a molecule of interest (e.g., Wnt-7a polypeptide or other activator of PCP-signaling) into the cells or tissue being treated. In the case of polypeptide-based active agents, this can be effected directly or, alternatively, by transfecting transcriptionally active DNA into living cells such that the active polypeptide coding sequence is expressed and the polypeptide is produced by cellular machinery. Transcriptionally active DNA may be delivered into the cells or tissue, e.g., muscle, being treated using transfection methods including, but not limited to, electroporation, microinjection, calcium phosphate coprecipitation, DEAE dextran facilitated transfection, cationic liposomes and retroviruses. In certain embodiments, the DNA to be transfected is cloned into a vector. Such vectors may include plasmids effective for delivery and expression of the DNA within a host cell. Such vectors may include but are not limited to plasmids derived from human cytomegalovirus (hCMV) or other suitable promoters such as hPGK-1 or hACT.

Alternatively, cells can be engineered in vivo by administration of the polynucleotide using techniques known in the art. For example, by direct injection of a "naked" polynucleotide (Feigner and Rhodes, (1991) *Nature* 349: 351-352; U.S. Pat. No. 5,679,647) or a polynucleotide formulated in a composition with one or more other agents which facilitate uptake of the polynucleotide by the cell, such as saponins (see, for example, U.S. Pat. No. 5,739,118) or cationic polyamides (see, for example, U.S. Pat. No. 5,837,533); by microparticle bombardment (for example, through use of a "gene gun", Biolistic, Dupont); by coating the polynucleotide with lipids, cell-surface receptors or transfecting agents; by encapsulation of the polynucleotide in liposomes, microparticles, or microcapsules; by administration of the polynucleotide linked to a peptide which is known to enter the nucleus; or by administration of the polynucleotide linked to a ligand subject to receptor-mediated endocytosis (see, for example, Wu and Wu, (1987) *J. Biol. Chem.* 262:4429-4432), which can be used to target cell types specifically expressing the receptors.

Alternatively, a polynucleotide-ligand complex can be formed in which the ligand comprises a fusogenic viral peptide to disrupt endosomes, allowing the polynucleotide to avoid lysosomal degradation; or the polynucleotide can be targeted for cell specific uptake and expression in vivo by targeting a specific receptor (see, for example, International Patent Applications WO 92/06180, WO 92/22635, WO92/203167 WO93/14188 and WO 93/20221). The present invention also contemplates the intracellular introduction of the polynucleotide and subsequent incorporation within host cell DNA for expression by homologous recombination (see, for example, Koller and Smithies (1989) *Proc. Natl. Acad. Sci. USA* 86:8932-8935; Zijlstra et al. (1989) *Nature* 342: 435-438).

The polynucleotide can be incorporated into a suitable expression vector. A number of vectors suitable for gene therapy applications are known in the art (see, for example, *Viral Vectors: Basic Science and Gene Therapy*, Eaton Publishing Co. (2000)) and may be used. The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise. A variety of plasmids are now readily available commercially and include those derived from *Escherichia coli* and *Bacillus subtilis*, with many being designed particularly for use in mammalian systems. Examples of plasmids that may be used in the present invention include, but are not limited to, the expression vectors pRc/CMV (Invitrogen), pCR2. 1 (Invitrogen), pAd/CMV and pAd/TR5/GFPq (Massie et al., 1998) *Cytotechnology* 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or pVAX (Invitrogen).

Alternatively, the expression vector can be a viral-based vector. Examples of viral-based vectors include, but are not limited to, those derived from replication deficient retrovirus, lentivirus, adenovirus and adeno-associated virus. These vectors provide efficient delivery of genes into cells, and the transferred polynucleotides are stably integrated into the chromosomal DNA of the host.

As used herein, "subject" may be a mammalian subject, for example, but not limited to mouse, cow, sheep, goat, pig, dog, cat, rat, rabbit, primate, or human.

A "pharmaceutical composition", often used interchangeably with composition, includes at least one active agent for carrying out a desired effect. The pharmaceutical composition further comprises one or more physiologically acceptable diluents, carriers or excipients. Pharmaceutical compositions and methods of preparing pharmaceutical compositions are known in the art and are described, for example, in "Remington: The Science and Practice of Pharmacy" (formerly "Remington's Pharmaceutical Sciences"); Gennaro, A., Lippincott, Williams & Wilkins, Philadelphia, Pa. (2000).

A "cell composition" is a composition that contains cells together with one or more physiologically acceptable diluents, carriers or excipients. The cell composition may further comprise one or more active agents. In some cases, the cells may be transformed to express a gene or protein of interest.

A "stem cell composition" is a composition that contains stem cells together with one or more physiologically acceptable diluents, carriers or excipients. The stem cell composition may comprise one or more active agents, such as a stem cell modulator. In some cases, the stem cells may be transformed to express a gene or protein of interest.

An "effective amount" is an amount sufficient to achieve a beneficial or desired result. An effective amount may be effective amount in vitro or in vivo. In vivo, an effective amount may also be referred to as a "therapeutically effective amount", which can be administered to a patient in one or more doses. In terms of treatment of disease or damage, an effective amount may be an amount that is sufficient to palliate, ameliorate, stabilize, reverse or slow the progression of the disease or damage. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition and the form and effective concentration of the antigen-binding fragment administered.

As used herein, the term "about" refers to a +/−5% variation from the nominal value. It is to be understood that such a variation is always included in any given value provided herein, whether or not it is specifically referred to.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

Embodiments of the invention are included within the definitions above, which may be relied upon to define the invention.

B. Compositions and Formulations

In one aspect, there is provided a composition for modulating the division symmetry of a stem cell comprising as an active agent, a Wnt7a polypeptide fragment that modulates planar cell polarity (PCP) signaling in the stem cell. In another aspect, a composition for modulating the division symmetry of a stem cell comprising one or more active agents selected from the group consisting of a Wnt7a polypeptide or fragment thereof and a fibronectin polypeptide that synergistically modulates planar cell polarity (PCP) signaling in the stem cell. Preferably, the stem cell is an adult stem cell, for example, a satellite stem cell.

In particular embodiments, the compositions of the invention further comprise a stem cell or population of stem cells. Preferably, the stem cell is an adult stem cell, for example, a satellite stem cell.

In some embodiments, a Wnt7a polypeptide fragment is an activator of PCP signaling capable of promoting symmetrical division of the stem cell. Polypeptide and peptide activators of the PCP signaling pathway include direct activators, as well as activators that exert their activating effect by inhibiting the activity or expression of proteins that inhibit Wnt7a signaling, i.e., indirect activators.

In other embodiments, a Wnt7a polypeptide or fragment thereof and a fibronectin polypeptide are a synergistic activator of PCP signaling capable of promoting symmetrical division of the stem cell.

The compositions described herein are useful in vitro or in vivo to promote stem cell expansion. It was demonstrated that activation of the PCP pathway, or components thereof, in satellite stem cells promotes symmetrical stem cell division, largely expanding the stem cell pool without affecting the rate of cell division.

The active agent may, for example, comprise a small molecule, a polynucleotide, a peptide, a polypeptide, a macromolecule, or a combination thereof, e.g., a Wnt7a polypeptide or fragment thereof, a fibronectin polypeptide.

The components of the PCP pathway, including Wnt7a, Fzd7, fibronectin, and syndecan-4 (Sdc4) tend to be highly conserved across species. Therefore, polypeptides and polynucleotides derived from various species are contemplated within the scope of the invention so long as they have the desired characteristics and activity.

In some embodiments, the active agent comprises a peptide or polypeptide capable of binding to and/or activating Fzd7 on the stem cell, e.g., a Wnt7a polypeptide fragment. Fzd7 may be particularly important for interaction with Wnt7a. Thus, a polypeptide capable of activating Fzd7 may comprise a polypeptide capable of binding to a Wnt-binding domain of Fzd7.

In other embodiments, the composition comprises one or more active agents that are peptides or polypeptides capable of binding to and/or activating Fzd7/Sdc4 receptor complex on the stem cell, e.g., a Wnt7a polypeptide or fragment thereof and a fibronectin polypeptide. The Fzd7/Sdc4 receptor complex may be particularly important for interaction with Wnt7a and fibronectin that drives a synergistic increase in stem cell expansion.

In some embodiments, the active agent is a Wnt7a polypeptide fragment or an active analogue, variant, or derivative thereof capable of binding to and activating Fzd7. In some embodiments, the active agent is a polypeptide having a sequence of a Wnt7a polypeptide, or a sequence that is at least about 70%, 80%, 85%, 90%, 91%, 92%, 93%, 94%, 95%, 96%, 97%, 98% or 99% identical to a Wnt7a polypeptide. Exemplary Wnt7a polypeptides are set forth in SEQ ID NO: 3 and 5. In related embodiments, the composition further comprises a fibronectin polypeptide or active fragment thereof as another active agent. An exemplary fibronectin polypeptide is shown in SEQ ID NO: 7.

In some embodiments, the % identity is assessed over at least about 50, 100, 200, 300, or more contiguous amino acids. In some embodiments, the % identity is assessed over the full length of the mature peptide sequence.

In certain embodiments, the active agent comprises a Wnt7a polypeptide. In some embodiments, the Wnt7a polypeptide is a human Wnt7a polypeptide. In some embodiments, the Wnt7a polypeptide is a murine Wnt7a polypeptide. Other species are also contemplated. In certain embodiments, a composition comprises one or more active agents selected from the group consisting of: a human or murine Wnt7a polypeptide and a fibronectin polypeptide.

In some embodiments, the Wnt7a polypeptide has an amino acid sequence comprising or consisting of SEQ ID NO: 3 or 5. In some embodiments, the active agent comprises an isolated polynucleotide encoding a peptide or polypeptide capable of binding to and/or activating Fzd7. The peptide or polypeptide capable of binding to and/or activating Fzd7 may be as described above. Thus, in some embodiments, the polynucleotide encodes a Wnt7a polypeptide or an active analogue, variant, fragment, or derivative thereof capable of binding to and activating Fzd7. In particular embodiments, the composition comprises one or more active agents comprising a polynucleotide encoding a Wnt7a polypeptide or an active analogue, variant, fragment, or derivative thereof and a polynucleotide encoding a fibronectin polypeptide, where the Wnt7a polypeptide and fibronectin polypeptide synergistically bind to and activate a Fzd7/Sdc4 complex.

An exemplary Wnt7a polynucleotide is shown in SEQ ID NO: 1. An exemplary fibronectin polynucleotide is shown in SEQ ID NO: 6.

In some embodiments, the active agent comprises a polynucleotide encoding a Wnt7a polypeptide having an amino acid sequence comprising SEQ ID NO: 5, or a sequence that is at least about 70%, 80%, 85%, 90%, 91%, 92%, 93%, 94%, 95%, 96%, 97%, 98% or 99% identical to SEQ ID NO: 3 or 5. In some embodiments, the active agent comprises a polynucleotide having an amino acid sequence comprising SEQ ID NO: 1, or a sequence that is at least about 70%, 80%, 85%, 90%, 91%, 92%, 93%, 94%, 95%, 96%, 97%, 98% or 99% identical to SEQ ID NO: 1.

In some embodiments, the % identity is assessed over at least about 50, 100, 200, 300, 500, 750 or 100 or more contiguous nucleotides. In some embodiments, the % identity is assessed over the full length of the polynucleotide. In some embodiments, the polynucleotide comprises a Wnt7a polynucleotide sequence comprising or consisting of SEQ ID NO: 1, or a fragment thereof.

In some embodiments, the polypeptides correspond to modulators of Wnt7a signaling, for example, fibronectin and/or Syndecan 4 (Sdc4) and α7-β1-integrin, or active fragments, variants or derivatives thereof.

In some embodiments, the active agent comprises a polynucleotide or polypeptide capable of modulating a downstream effector molecule in the PCP pathway to thereby promote or inhibit symmetrical cell division. Exemplary polarity effectors that may be modulated to affect cell division in adult stem cells include Prickle, Flamingo (Celsr2), Disheveled (Dsh) or PTK7. Exemplary targets of modulation in the PCP pathway include, but are not limited to, fibronectin, Fzd7, Vangl1, Vangl2, Dvl2, Dvl3, PM, Pk2, Celsr2, Sdc4 and α7-integrin.

In some embodiments, the active agent comprises a polynucleotide or polypeptide capable of activating a downstream effector molecule in the PCP pathway to thereby promote symmetrical stem cell division. The downstream effector molecule may, for example be, Fzd7, Vangl1, Vangl2, Dvl2, Dvl3, PM, Pk2, Celsr2, Sdc4 and α7-integrin.

In some embodiments, the composition additionally comprises one or more stem cell modulators. The stem cell modulator may, for example, promote one more of stem cell proliferation, differentiation, lineage commitment, or terminal differentiation of committed progenitor cells.

In some embodiments, the modulator increases the rate of stem cell division. Any suitable activator of stem cell division rate can be used, such as a suitable growth factor. Known growth factors include FGF, HGF and SDF. In some embodiments, a growth factor that increases stem cell division rate without promoting differentiation is selected.

In some embodiments, the modulator is one that increases proliferation in a population of expanding stem cells, or one that promotes differentiation in a population of stem cells that have been previously expanded by treatment with a Wnt7a polypeptide or a Wnt7a truncated polypeptide and a fibronectin polypeptide as discussed elsewhere herein.

In one embodiment, there is provided a composition for enhancing tissue formation, regeneration, maintenance or repair in a mammal comprising as an active agent (a) a Wnt7a polypeptide fragment, or variant, analogue or derivative thereof capable of binding to and activating Fzd7, or (b) a polynucleotide encoding a Wnt7a polypeptide fragment, or variant, analogue or derivative thereof capable of binding to and activating Fzd7. In a particular embodiment the Wnt7a polypeptide fragment comprises the amino acid sequence set forth in SEQ ID NO: 5.

In another embodiment, there is provided a composition for promoting symmetrical stem cell division comprising as active agents, a) a Wnt7a polypeptide or fragment thereof and b) a fibronectin polypeptide, wherein the composition activates a Fzd7/Sdc4 receptor signaling complex in adult stem cells. In other embodiments, a composition comprises a stem cell or population of stem cells, a Wnt7a polypeptide or fragment thereof, and/or a fibronectin polypeptide.

In some embodiments, the adult stem cells are satellite stem cells.

The compositions described herein may be used to deliver one or more polynucleotides of interest into a cell or tissue. In some embodiments, the composition comprises an expression vector carrying a polynucleotide encoding a Wnt7a polypeptide or fragment thereof and/or a polynucleotide encoding a fibronectin polypeptide, wherein the composition is capable of activating PCP signaling in a stem cell, to thereby promote symmetrical stem cell expansion. The composition may be administered in vitro, for example, to expand a population of stem cells, or in vivo, for example, in a gene therapy method. A number of exemplary modulators have been described above, e.g., Wnt7a polypeptides and fragments, Frz7, fibronectin and Sdc4.

In some embodiments, a cell or tissue is transformed to overexpress a Wnt7a polypeptide or fragment thereof and/or a polynucleotide encoding a fibronectin polypeptide, thereby inducing symmetrical division of a stem cell. Wnt7a polypeptides and/or fibronectin polypeptides may be secreted from the transformed cell and may act on the cell from which is it secreted or may act on a nearby stem cell. In some embodiments, the transformed cell is a helper cell that may be co-cultured or co-administered with the stem cell. The helper cell may also be a resident cell in a tissue that is transformed to overexpress Wnt7a or a fragment thereof and/or a fibronectin polypeptide. In some embodiments, the helper cell is a myoblast or muscle cell transformed to overexpress Wnt7a and/or fibronectin polypeptides of the invention. The inventive Wnt7a polypeptides comprise increased solubility compared to naturally occurring Wnt7a polypeptides.

In some embodiments, muscle tissue is transformed to overexpress truncated Wnt7a polypeptides or Wnt7a polypeptide fragments that expand the satellite stem cell pool in vivo, increase satellite cell numbers, and promote muscle regeneration and repair compared to the naturally occurring Wnt7a. In certain embodiments, the tissue is further transformed to transiently overexpress fibronectin.

In some embodiments, a composition comprises cells and may therefore be a cell composition. For example, the composition may comprise a cell transformed to express and secrete Wnt7a polypeptide fragments and/or Wnt7a polypeptides and fragments thereof and a fibronectin polypeptide. In some embodiments, the cell is a myoblast or muscle cell. In some embodiments, the composition comprises stem cells and is therefore a stem cell composition.

In some embodiments, stem cells may be expanded in vitro using a method according to the invention and may subsequently be added to a composition of the invention to form a stem cell composition. For instance, stem cells can be cultured and expanded in vitro using methods of the invention and then administered to a subject as a therapeutic stem cell composition according to methods known to skilled persons.

In some embodiments, the composition comprises: a stem cell; and one or more activators of PCP signaling in the stem cell, e.g., a Wnt7a polypeptide or fragment thereof and/or fibronectin. In some embodiments, the stem cell is a satellite stem cell.

In some embodiments, the composition comprises a stem cell transformed to express a polynucleotide of interest that encodes a Wnt7a polypeptide or fragment thereof and/or fibronectin. Any suitable transformation method known in the art may be employed.

In one embodiment, there is provided a composition for enhancing tissue regeneration or repair comprising: a stem cell; and one or more activators or effectors of PCP signaling such as, for example, a Wnt7a polypeptide or fragment thereof and/or fibronectin.

In some embodiments, the composition comprises a stem cell transformed to overexpress an activator or effector of the PCP pathway, for example, a Wnt7a polypeptide fragment. In particular embodiments, the stem cell is further transformed to overexpress fibronectin.

The composition may comprise a physiologically acceptable diluent, carrier or excipient. Methods of making various pharmaceutical compositions for various routes of administration are known in the art and are further described elsewhere herein.

The present invention further provides pharmaceutical compositions comprising one or more active agents selected from the group consisting of a Wnt7a polypeptide, an analogue, derivative, variant or active fragment thereof, a fibronectin polypeptide, and another activator or effector of PCP signaling; and a pharmaceutically acceptable diluent or excipient. Pharmaceutical compositions and methods of preparing pharmaceutical compositions are known in the art and are described, for example, in "Remington: The Science and Practice of Pharmacy" (formerly "Remington's Pharmaceutical Sciences"); Gennaro, A., Lippincott, Williams & Wilkins, Philadelphia, Pa. (2000).

The pharmaceutical compositions may optionally further comprise one or more stem cell modulators, one or more stem cells, or a combination thereof. Administration of the pharmaceutical compositions may be via a number of routes depending upon whether local or systemic treatment is desired and upon the area to be treated. Typically, the compositions are administered systemically or locally to the area to be treated.

Administration may be topical (including ophthalmic and to mucous membranes including vaginal and rectal delivery), pulmonary (e.g., by inhalation or insufflation of powders or aerosols, including by nebulizer), intratracheal, intranasal, epidermal and transdermal, oral or parenteral. Parenteral administration includes intravenous, intraarterial, subcutaneous, intraperitoneal or intramuscular injection, for example, but not limited to intracardial injection or infusion, or intracranial, e.g., intrathecal or intraventricular administration. In some embodiments, compositions are administered by injection or infusion.

The compositions of the present invention may be delivered in combination with a pharmaceutically acceptable vehicle. Preferably, such a vehicle would enhance the stability and/or delivery properties. Examples include liposomes, microparticles or microcapsules. In various embodiments of the invention, the use of such vehicles may be beneficial in achieving sustained release of the active component. When formulated for parenteral injection, the pharmaceutical compositions are preferably used in the form of a sterile solution, containing other solutes, for example, enough saline or glucose to make the solution isotonic.

For administration by inhalation or insufflation, the pharmaceutical compositions can be formulated into an aqueous or partially aqueous solution, which can then be utilized in the form of an aerosol. For topical use, the modulators or pharmaceutical compositions comprising the modulators can be formulated as dusting powders, creams or lotions in pharmaceutically acceptable vehicles, which are applied to effected portions of the skin.

The dosage requirements for the pharmaceutical compositions vary with the particular compositions employed, the route of administration and the particular subject being treated. Dosage requirements can be determined by standard clinical techniques known to a worker skilled in the art. Treatment will generally be initiated with small dosages less than the optimum dose of each compound. Thereafter the dosage is increased until the optimum effect under the circumstances is reached. In general, the pharmaceutical compositions are administered at a concentration that will generally afford effective results without causing any harmful or deleterious side effects. Administration can be either as a single unit dose or, if desired, the dosage can be divided into convenient subunits that are administered at suitable times throughout the day.

When in vitro or ex vivo methods of treating the stem cells are employed, the stem cells can be administered to the subject by a variety of procedures. Typically, administration of the stem cells is localized. The stem cells can be administered by injection as a cell suspension in a pharmaceutically acceptable liquid medium. Alternatively, the stem cells can be administered in a biocompatible medium which is, or becomes in site a semi-solid or solid matrix. For example, the matrix maybe an injectable liquid which forms a semi-solid gel at the site of tissue damage or degeneration, such as matrices comprising collagen and/or its derivatives, polylactic acid or polyglycolic acid, or it may comprise one or more layers of a flexible, solid matrix that is implanted in its final boron, such as impregnated fibrous matrices. Such matrices are letdown in the art (for example, Gelfoam available from Upjohn, Kalamazoo, Mich.) and function to hold the cells in place at the site of injury, which enhances the opportunity for the administered cells to expand and thereby for a reservoir of stem cells, to develop.

The stem cells may or may not be cryopreserved prior to, or after treatment of the cells.

In some embodiments, the stem cells are administered with a compound for promoting stem cell expansion to minimize risk of stem cell depletion following transplantation. In some embodiments, the transplanted stem cells have been transformed to overexpress an activator of PCP signaling, as described elsewhere herein. In some embodiments, the stem cells are co-administered with muscle cells or other satellite cells transformed to overexpress and secrete a Wnt7a polypeptide or fragment thereof and/or a fibronectin polypeptide. In some embodiments, the stem cells are injected intramuscularly.

In a preferred embodiment, satellite stem cells or a composition comprising satellite stem cells is injected into muscle tissue, preferably in an area proximal to diseased, injured or damaged tissue. However, injection into the circulation or at a distal site is also contemplated. Intracardiac administration is also contemplated.

C. Methods

The invention provides, in part, for methods of modulating stem cells, in particular, methods of modulating division symmetry of adult stem cells, such as satellite stem cells comprising contacting the stem cells with a composition comprising a Wnt7a polypeptide fragment as described elsewhere herein. The invention also provides a method of synergistically modulating division symmetry of adult stem cells, such as satellite stem cells comprising contacting the stem cells with a composition comprising a Wnt7a polypeptide or fragment thereof and a fibronectin polypeptide as described elsewhere herein.

In particular embodiments, it is therapeutically beneficial to pharmacologically treat fibrotic muscle pathology in intervals. Such treatment would simulate both physiological states of muscle regeneration, fibrotic conditions triggering satellite stem cell expansion, and lower levels of FN fostering lineage progression and the differentiation of myoblasts.

In some embodiments, stem cell division symmetry is modulated by the compositions of the invention in vivo, ex vivo, or in vitro.

In some embodiments, there is provided a use of a composition a Wnt7a polypeptide fragment as described herein for the manufacture of a medicament for promoting stem cell expansion. In some embodiments, there is provided a use of a composition a Wnt7a polypeptide or fragment thereof and a fibronectin polypeptide as described herein for the manufacture of a medicament for promoting stem cell expansion.

In some embodiments, there is provided a composition a Wnt7a polypeptide fragment as described herein for use in the manufacture of a medicament for promoting stem cell expansion. In some embodiments, there is provided a use of a composition a Wnt7a polypeptide fragment as described herein for the manufacture of a medicament for promoting muscle formation, maintenance, repair, or regeneration of muscle in a subject in need thereof. In some embodiments, there is provided a composition a Wnt7a polypeptide fragment as described herein for use in the manufacture of a medicament for promoting muscle formation, maintenance, repair, or regeneration of muscle in a subject in need thereof. In related embodiments, the compositions comprise a Wnt7a polypeptide or fragment thereof and a fibronectin polypeptide.

In some embodiments, the inventive compositions are used for promoting muscle regeneration or repair in a subject.

The composition may be administered in an effective amount, such as a therapeutically effective amount.

As described in the embodiments above, the composition comprises a Wnt7a polypeptide or a fragment thereof and/or a fibronectin polypeptide as an active agent a modulator of planar cell polarity (PCP) signaling in the stem cell. In some embodiments, the method thereby promotes stem cell expansion. Such methods are useful, for example, for increasing the relative proportion of symmetrical to asymmetrical cell divisions in a population of stem cells in vivo or in vitro. Such methods are therefore useful for expanding a population of stem cells in vivo or in vitro.

In some embodiments, the methods disclosed herein are capable of promoting symmetrical stem cell division without altering the rate of stem cell division. In some embodiments, the methods may be useful for promoting survival of a population of stem cells. In some embodiments, the methods are administered in vitro.

In some embodiments, the methods are administered in vivo. In some embodiments, the in vivo method comprises administering the composition to a subject in need thereof. In some embodiments, a method for expanding a population of satellite stem cells in vivo or in vitro comprises contacting the stem cells with an effective amount of a composition comprising (a) a Wnt7a polypeptide fragment, or an active variant, analogue or derivative thereof capable of binding to and activating Fzd7, or (b) a polynucleotide encoding a Wnt7a polypeptide fragment, or an active variant, analogue or derivative thereof capable of binding to and activating Fzd7.

In other embodiments, the invention provides an in vivo, ex vivo, or in vitro method for expanding a population of satellite stem cells comprising administering or contacting the population of satellite stem cells with a composition comprising (a) a Wnt7a polypeptide or fragment thereof and a fibronectin polypeptide capable of binding to and activating Fzd7/Sdc4 receptor complex, or (b) one or more polynucleotides encoding a Wnt7a polypeptide or fragment thereof and a fibronectin polypeptide capable of binding to and activating Fzd7/Sdc4 receptor complex.

In some embodiments, the active agent is a Wnt7a polypeptide fragment, or an analogue, derivative, variant or active thereof. In other embodiments, a composition comprises one or more active agents selected from the group consisting of: a Wnt7a polypeptide or fragment thereof and a fibronectin polypeptide.

In some embodiments, there is provided a method of promoting satellite stem cell expansion comprising contacting the satellite stem cell with a composition comprising one or more active agents. In particular embodiments, it is contemplated that one or more agents may synergistically promote satellite stem cell expansion.

In another embodiment, a method of increasing the number of satellite cells in a tissue, and thereby providing enhanced regeneration potential of the tissue, comprises contacting the stem cells with a composition as described herein. In particular embodiments, it is contemplated that one or more agents may synergistically promote tissue regeneration.

In some embodiments, the methods of the invention are used in vivo for treatment of resident stem cells in a tissue, e.g. resident satellite stem cells in muscle tissue.

In some embodiments, the method may additionally comprise contacting the stem cell with one or more stem cell modulators, for example, a modulator that increases the rate of stem cell division or increases stem cell survival. In some embodiments, the method comprises administering cells to a subject. The cells may, for example, be administered simultaneously or sequentially with a composition described herein.

In some embodiments, the method comprises administering stem cells to a subject. The stem cells may, for example, be administered simultaneously or sequentially with a composition described herein that promotes stem cell expansion. For example, the stem cells may be administered prior to administration of the composition (i.e. the composition may be administered after a desired period). In some embodiments, the composition itself may comprise the stem cells to be administered.

Stem cells may be maintained and expanded in vitro for subsequent experimental or therapeutic uses. In some embodiments, stem cells, e.g., satellite stem cells, are expanded in vitro or ex vivo and are subsequently administered to a subject in need thereof. For instance, stem cells can be cultured and expanded in vitro or ex vivo using methods of the invention and then administered to a patient as a therapeutic stem cell composition according to methods known to skilled persons.

In some embodiments, stem cells may be obtained from an individual and maintained in culture. The population of cultured stem cells may be treated with a Wnt7a polypeptide fragment or polynucleotide encoding the same, and/or another activator of PCP signaling, e.g., fibronectin, to promote symmetrical expansion in vitro or ex vivo.

In some embodiments, the method may comprise administering helper cells to a subject, such as cells of the stem cell niche. The helper cells may, for example, be administered simultaneously or sequentially with the composition. In some embodiments, the composition itself may comprise helper cells. The present invention also contemplates administration of polynucleotides encoding Wnt7a active fragment, a variant or thereof, or another activator of PCP signaling, e.g., fibronectin, and optionally a stem cell modulator, which then express the encoded product in vivo, by various gene therapy methods known in the art.

In one embodiment, satellite stem cells are co-cultured with muscle cells transformed with a CMV-Wnt7a polypeptide fragment construct to overexpress and secrete the Wnt7a polypeptide fragment. Any suitable expression vector may be used, including but not limited to those described previously. Where in vivo methods are performed, cell- or tissue-specific vectors or promoters may also be used. In one embodiment, the vector is a muscle-specific AAV vector. An inducible promoter may optionally be used. Polypeptide activators or effectors of PCP-signaling may be directly introduced into cells, bypassing the DNA transfection step. Means to directly deliver polypeptides into cells include, but are not limited to, microinjection, electroporation, cationic lipids and the construction of viral fusion proteins. Typically, transfection of a suitable expression system carrying a polynucleotide will be used.

The methods of promoting stem cell expansion can be used to stimulate the ex vivo or in vitro expansion of stem cells and thereby provide a population of cells suitable for transplantation or administration to a subject in need thereof. The stem cells to be administered may be treated with a stem cell modulator, for example, a modulator that promotes survival of a stem cell. Sequential methods that promote expansion followed by proliferation and/or differentiation of stem cells are also contemplated. For example, a stem cell population may be expanded in vitro by contacting the cells, directly or indirectly, with a Wnt7a polypeptide fragment or a Wnt7a polypeptide or fragment thereof and a fibronectin polypeptide. The expanded population of cells may then be treated with one or more stem cell modulators in vitro or in vivo, e.g., that promotes proliferation and/or differentiation of the stem cells in situ or promotes stem cell survival. Alternatively, both steps may be conducted in vitro prior to administration of the cells to a subject.

For in vivo and ex vivo transplant methods, the stem cells can be autologous, allogeneic or xenogeneic. In embodiments where stem cells from a donor subject are transplanted into a recipient subject in need thereof, preferably, the donor and recipient are matched for immunocompatibility. Not wishing to be limiting, it is preferable that the donor and the recipient are matched for compatibility to the major histocompatibility complex (MHC) (human leukocyte antigen (HLA))-class I (e.g., loci A, B, C) and -class II (e.g., loci DR, DQ, DRW) antigens. Immunocompatibility between donor and recipient may be determined according to methods generally known in the art (see, e.g., Charron, D. J., *Curr. Opin. Hematol.*, 3: 416-422 (1996); Goldman, J., *Curr. Opin. Hematol.*, 5: 417-418 (1998); and Boisjoly, H. M. et al., *Opthalmology*, 93: 1290-1297 (1986)).

In one embodiment of the present invention, the gene therapy vector is an adenovirus-derived vector or a lentiviral vector. In one embodiment, the gene therapy vector is administered to a patient, wherein the vector comprises a Wnt7a polypeptide fragment under the control of a muscle-specific promoter or vector.

The methods described herein have a number of applications. For example, the methods can be used in vitro to promote expansion of stem cells wherein the cells are destined for further in vitro use, for example, for research or diagnostic purposes. The methods can be used for maintaining stem cell cultures in vitro and also have potential application in the development of new in vitro models for drug testing or screening.

The compositions and methods described herein are also useful for various therapeutic applications. In particular, the compositions and methods described herein are useful for promoting tissue formation, regeneration, repair or maintenance in a subject in need thereof. In some embodiments, the tissue is muscle. In some embodiments, the muscle is skeletal muscle.

Relevant therapeutic applications may pertain to situations where there is a need to regenerate lost or damaged muscle tissue, for example, after chemotherapy or radiation therapy, after muscle injury, or in the treatment or management of diseases and conditions affecting muscle. In some embodiments, the disease or condition affecting muscle may include a wasting disease (e.g. cachexia, which may be associated with an illness such as cancer or AIDS), muscular attenuation or atrophy (e.g. sarcopenia, which may be associated with aging), ICU-induced weakness, prolonged disuse (e.g. coma, paralysis), surgery-induced weakness (e.g. following hip or knee replacement), or a muscle degenerative disease (e.g. muscular dystrophies). This list is not exhaustive.

In some embodiments, compositions and methods described herein are employed where there is a need to prevent loss of tissue, as in wasting diseases or atrophy.

In some embodiments, compositions and methods described herein are employed where there is a need or desire to increase the proportion of resident stem cells, or committed precursor cells, in a muscle tissue, for example, to replace damaged or defective tissue, or to prevent muscle atrophy or loss of muscle mass, in particular, in relation to diseases and disorders such as muscular dystrophy, neuromuscular and neurodegenerative diseases, muscle wasting diseases and conditions, atrophy, cardiovascular disease, stroke, heart failure, myocardial infarction, cancer, HIV infection, AIDS, and the like.

In some embodiments, the methods can be used with satellite stem cells in the treatment, management or prevention of degenerative muscle disorders.

In some embodiments, the compositions and methods are useful for promoting muscle cell formation, for example, for repairing or regenerating dysfunctional skeletal muscle, for instance, in subjects having muscle degenerative diseases.

The subject may therefore have, be suspected of having, or be at risk of at having skeletal muscle damage, degeneration or atrophy. The skeletal muscle damage may be disease related or non-disease related. The human subject may exhibit or be at risk of exhibiting muscle degeneration or muscle wasting. The muscle degeneration or muscle wasting may be caused in whole or in part by a disease, for example aids, cancer, a muscular degenerative disease, or a combination thereof. Muscle degeneration may be due to a muscle degeneration disease such as muscular dystrophy.

Illustrative examples of muscular dystrophies include, but are not limited to: Duchenne muscular dystrophy (DMD), Becker muscular dystrophy (BMD), myotonic dystrophy (also known as Steinert's disease), limb-girdle muscular dystrophies, facioscapulohumeral muscular dystrophy (FSH), congenital muscular dystrophies, oculopharyngeal muscular dystrophy (OPMD), distal muscular dystrophies and Emery-Dreifuss muscular dystrophy.

In some forms of urinary continence, the culprit muscle can be treated with a composition or method of the invention, for example, by electroporation of the muscle. Thus, in one embodiment, the method is useful for treating urinary incontinence.

In one aspect, there is provided a method for promoting muscle formation, regeneration or repair in a subject in need thereof comprising administering to the mammal a composition comprising one or more active agents as disclosed elsewhere herein.

In another aspect, there is provided a method for preventing muscle wasting, atrophy or degeneration in a subject in need thereof comprising administering to the mammal a therapeutically effective amount of a composition as disclosed elsewhere herein.

In some aspects, the compositions and methods described herein are useful for promoting formation, maintenance, repair or regeneration of skeletal muscle in a human subject in need thereof. In one aspect, there is provided a method for enhancing tissue formation, regeneration, maintenance or repair in a mammal comprising administering to a subject in need thereof a composition as described elsewhere herein.

The promotion of muscle cell formation can further be, in an embodiment, for preventing or treating muscle destruction or atrophy of a subject, e.g., in subjects with disuse atrophy or sarcopenia. In some embodiments, the compositions are used to treat or prevent atrophy and to maintain muscle mass. The promotion of muscle cell formation can also be, in an embodiment, for repairing damaged muscle tissue. In an alternative embodiment, the promotion of muscle cell formation can be for increasing muscle mass in a subject.

In a further embodiment, damaged or dysfunctional muscle tissue may be caused by an ischemic event. For instance, the damaged muscle tissue may be cardiac muscle damaged by a cardiovascular event such as myocardial infarct, or heart failure.

In a further embodiment, damaged or dysfunctional muscle tissue may be cardiac muscle. For instance, the damaged muscle tissue may be cardiac muscle damaged by a cardiovascular event such as myocardial infarct, or heart failure, where the target stem cell would be a cardiac stem sell. In accordance with another aspect of the present invention, there is provided a method of promoting cardiac stem cell expansion in a mammal comprising administering to said mammal an effective amount of a composition as described herein.

The compositions and methods described herein may be used in combination with other known treatments or standards of care for given diseases, injury, or conditions. For example, in the context of muscular dystrophy, a composition of the invention for promoting symmetrical stem cell expansion can be administered in conjunction with such compounds as cardiotrophin polypeptide (CT-1), pregnisone or myostatin. The treatments may be administered together, separately or sequentially.

The dosage regimen and treatment regime will vary depending on the disease being treated, based on a variety of factors, including the type of injury, the age, weight, sex, medical condition of the individual, the severity of the condition, the route of administration, and the particular compound employed. Thus, the dosage regimen and treatment regimes can vary, but can be determined routinely by a physician using standard methods. Dosage levels of the order of between 0.1 ng/kg and 10 mg/kg body weight of the active agents per body weight are useful for all methods of use disclosed herein.

Treatment may continue with subsequent administration of a composition of the invention. In a particular embodiment of the invention, a subject undergoes repeated cycles of treatment according to the method of this invention. Therapy may be administered for 1, 2, 3, 4, 5, 6, 7, 8, 9, 10, 11, or 12 times per day, per week, per month, or per year at dosages determined based on the disease or condition being treated, age, weight, route of administration, and other factors. In all of these embodiments, the compositions of the invention can be administered either prior to, simultaneously with, or subsequent to a planned medical procedure, onset of disease or injury.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Wnt7a Modeling

Background

Therapeutic application of Wnt7a has been hindered by the hydrophobicity of the protein, preventing its use in systemic delivery. Understanding the structure of the protein is difficult due to the complex posttranscriptional modification of Wnt proteins, which renders Wnts insoluble and hard to crystallize. Consequently, the structure of these proteins remains unknown.

Experimental Results

Figure 1A:
FIG. 1 show an in-silico protein modeling of Wnt7a that predicts two distinct protein domains. (A) Protein modeling with I-TASSER software predicts the presence of a helicoid N-terminal region and globular C-terminal region in Wnt7a tertiary protein structure. (B) Kyte-Doolitle hydropathy plot of amino acid hydrophobicity reveals a concentration of hydrophobic residues in the N-terminal domain and an almost exclusively hydrophilic C-terminal domain.

A model of Wnt7a's tertiary structure using I-TASSER homology protein modeling software was created (FIG. 1A). This predicted structure indicated that at least two functional domains are present in Wnt7a: a helicoid N-terminal domain (NT) which contained the two lipid adducts that are added to Wnt7a posttranslationally; and a globular C-terminal domain (CT). Although a number of recent studies have shown that lipidation of the NT region of Wnts are necessary Wnt secretion and activation of canonical signaling pathways, the inventors have surprisingly discovered that Wnt7a function may not be entirely dependent on the N-terminal domain and that Wnt7a function is independent of lipidation.

Figure 1B:
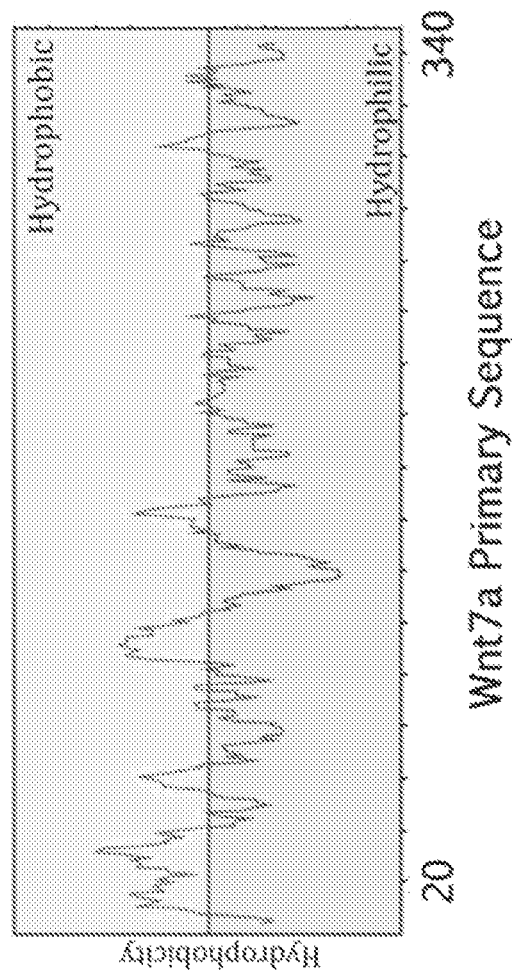

To investigate the differences in the two proposed Wnt7a domains a Kyte-Doolittle Hydropathy Plot was used to examine the solubility of these regions based on their primary amino acid sequence. The N-terminal region contained a significant number of hydrophobic residues, which were virtually absent from the highly hydrophilic C-terminus (FIG. 1B).

These results indicated that the C-terminal domain could be the receptor-binding region of the protein, and may be able to induce a response in the absence of the hydrophobic N-terminus.

Example 2

Wnt7a-CT Activates Wnt7a Signaling Pathways In Vivo

Background

Figure 2:
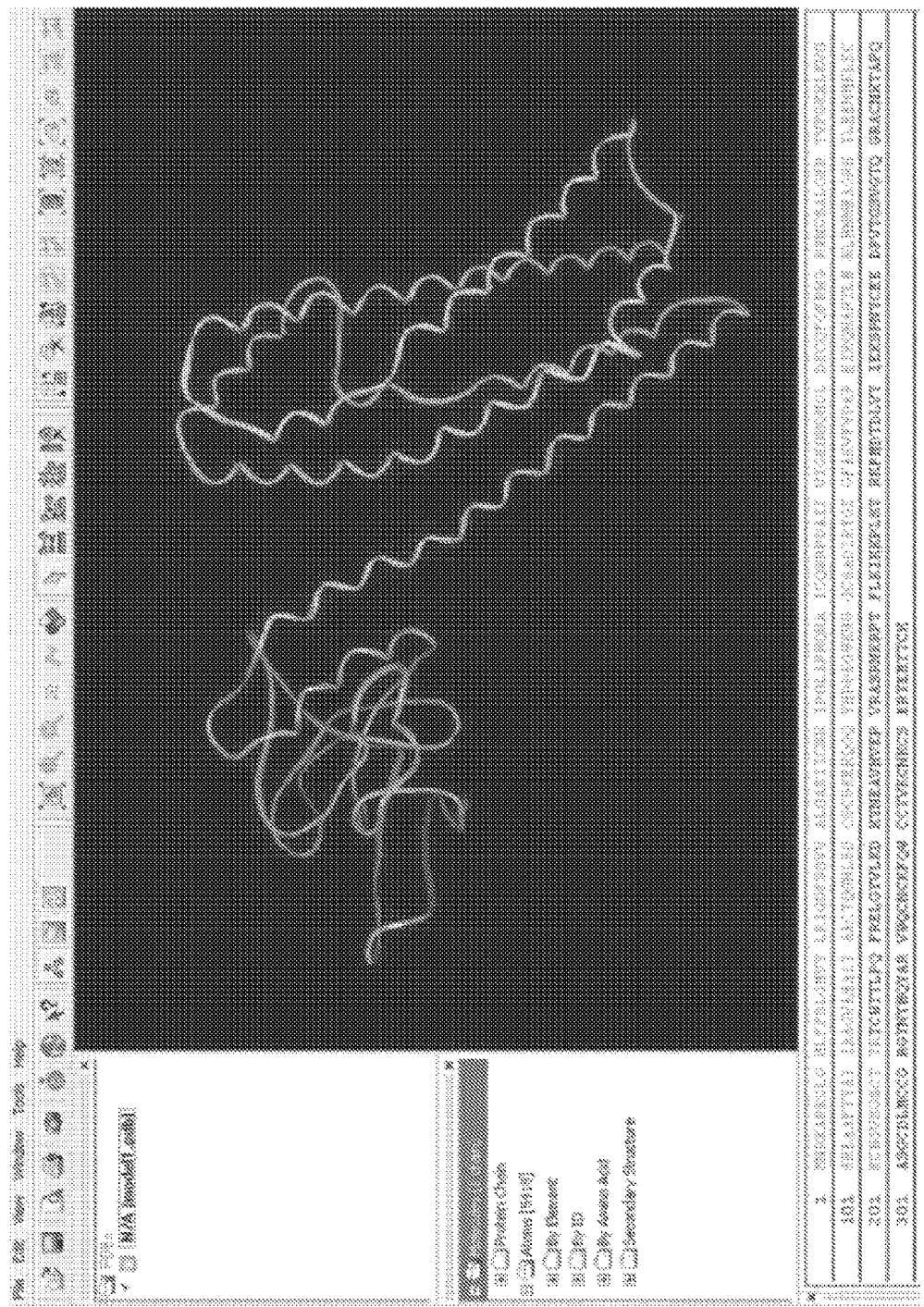
FIG. 2 shows a computer screen snapshot of 3D Molecule Viewer's rendering of Wnt7a structure. Wnt7a was divided in two regions: the N-terminal region (amino acids 32-212) and the globular C-terminal region (amino acids 213-349). The corresponding amino acid sequence is shown in the bottom panel. Truncated Wnt7a polypeptides representing the two suggested domains were prepared.

Two truncated mutants were created to verify that the C-terminal domain of Wnt7a is the receptor binding region of the protein: the NT region comprised amino acids 32-212 of Wnt7a, which includes the two lipidation sites on Wnt7a, and the CT region comprised amino acids 213-349; the full length processed Wnt7a protein contains amino acid residues 32-349 (FIG. 2). Amino acids 1-31 form the signal peptide that targets Wnt7a for secretion, which is likely cleaved off during processing of the protein.

Experimental Results

Wnt7a CT Increases TA Weight and Fiber Diameter Compared to LacZ Controls

In order to preserve protein secretability, both regions, as well as the full length protein were cloned with the signal peptide fused to the N-terminus of the coding sequence tested. A large quantity of plasmid was prepared using a plasmid prep kit and dissolved in saline solution (0.9% NaCl). Before injection, an equal quantity of LacZ plasmid DNA was added to each Wnt7a sample to be used as a marker of electroporation efficiency. A total volume of 504, of solution containing 17.5 µg of a Wnt7a construct and 17.5 µg of LacZ was electroporated into the TA muscle of adult mice. A small quantity of plasmid was used to endure that only a fraction of the fibers in the muscle were electroporated, thus, creating a contrast between fibers affected by Wnt7a and the remaining fibers.

Figure 3A:
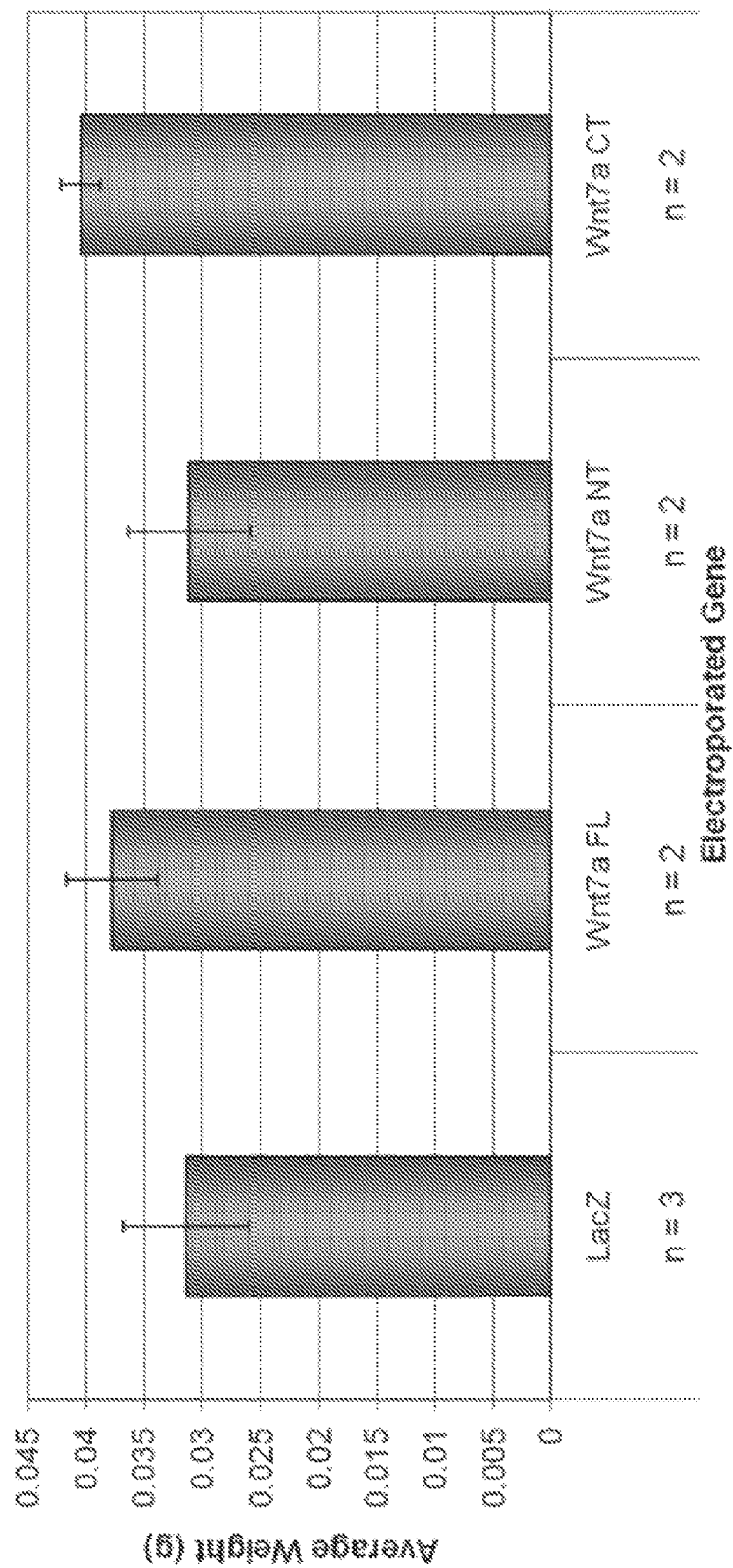
FIG. 3 shows that the C-terminal domain of Wnt7a is sufficient and necessary to induce myofiber hypertrophy. (A) Weight of mouse tibialis anterior (TA) muscles electroporated with 17.5 µg of vector encoding a truncated, C-terminal Wnt7a-HA tagged polypeptide (Wnt7a CT; lacks N-terminal domain), a full-length Wnt7a (Wnt7a FL), or a truncated, N-terminal (Wnt7a NT; lacks C-terminal domain). TA muscles that were electroporated with Wnt7a CT or Wnt7a FL were heavier compared to LacZ or Wnt7a NT electroporated muscle six days after electroporation. (B) Wnt7a CT induces hypertrophy (measured as an increase in muscle fiber diameter) in electroporated muscle fibers, while Wnt7a NT electroporated fibers do not differ from the LacZ control.

Six days after electroporation, the electroporated TA muscles were collected and divided in two, with one half sectioned for staining and the other half crushed and used for Western Blotting. Following excision, muscles electroporated with Wnt7a CT or FL genes were significantly heavier than Wnt7a NT and LacZ control muscles, which were the same weight (FIG. 3A).

Muscle sections were stained with X-Gal staining solution to confirm that the electroporation had only affected select muscle fibers (FIG. 4). The positive X-Gal staining also indicated that the mice used in the study had been successfully electroporated. Muscle sections were then stained with α2-laminin and αHA antibodies to outline the perimeter of muscle fibers and to mark fibers expressing Wnt7a, respectively.

Figure 3B:
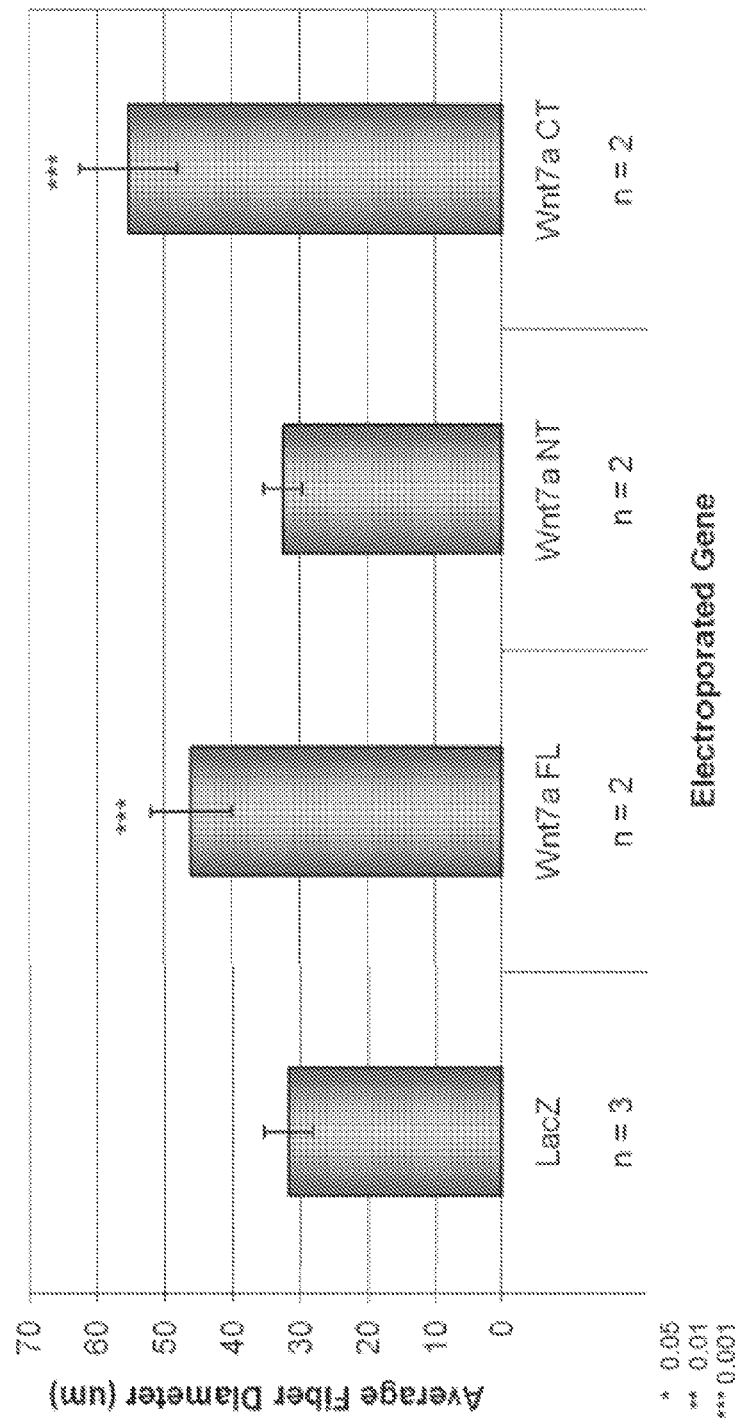
Figure 4A:
FIG. 4 shows X-Gal staining in muscles electroporated with Wnt7a constructs. X-Gal staining for LacZ in TA muscle electroporated with 17.5 µg of (A) LacZ (B) Wnt7a FL, (C) Wnt7a NT or (D) Wnt7a CT indicates that all constructs had similar electroporation efficiency. Scale bar is 200 µm.
Figure 4B:
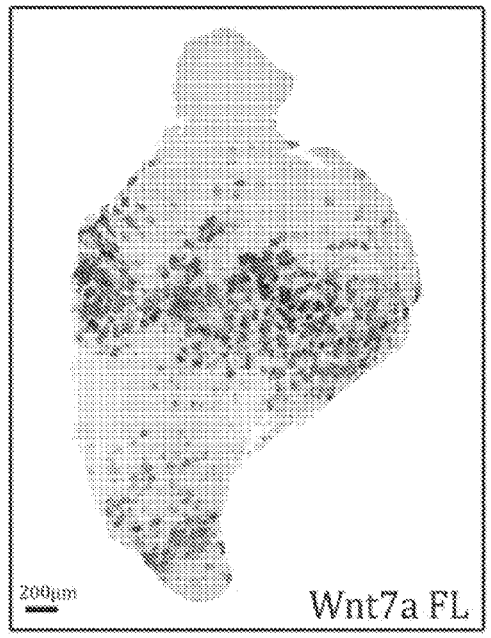
Figure 4C:
Figure 4D:
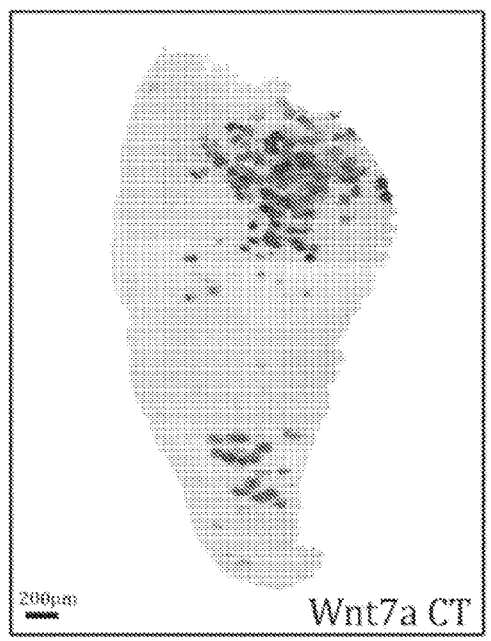
Figure 5A:
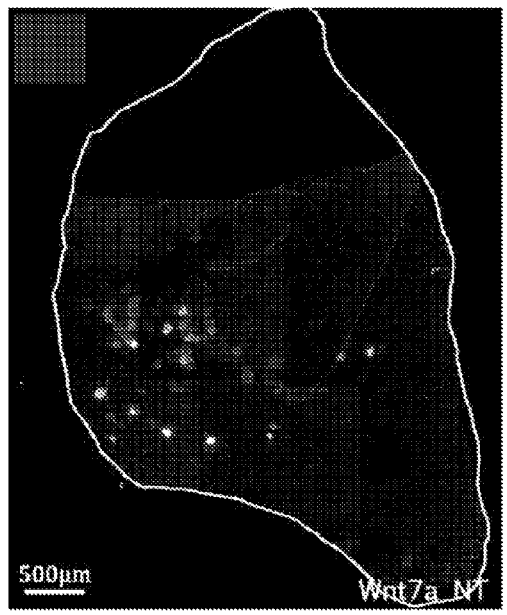
FIG. 5 shows that the Wnt7a CT polypeptide has increased biodistribution. A), B), and C) Myofibers expressing were stained with an antibody recognizing Wnt7a; Wnt7a CT expressing fibers are larger, and comprise a greater portion of total muscle fibers than the Wnt7a FL or Wnt7a NT expressing fibers. Scale bar is 500 µm. (D) Lysate from electroporated muscles shows comparable levels of Wnt expression for LacZ, Wnt7a FL, Wnt7a CT, and Wnt7a NT.
Figure 5B:
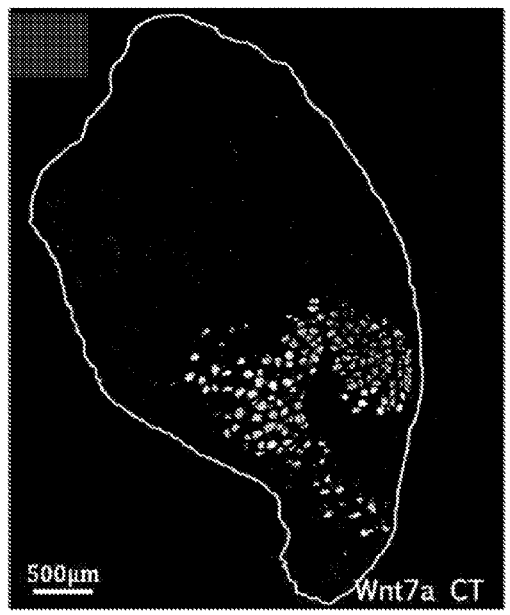
Figure 5C:
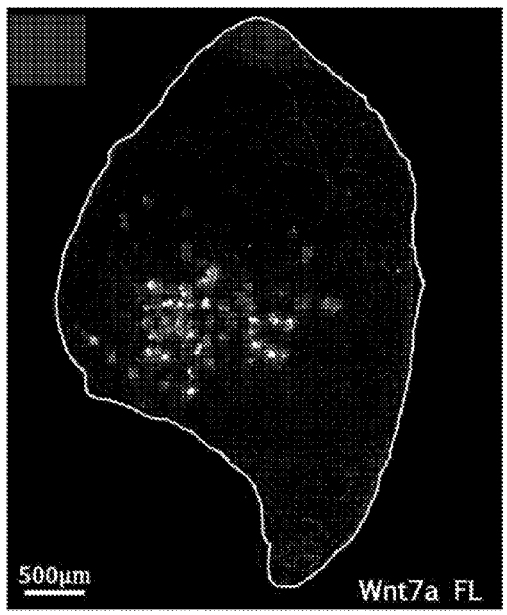
Figure 5D:
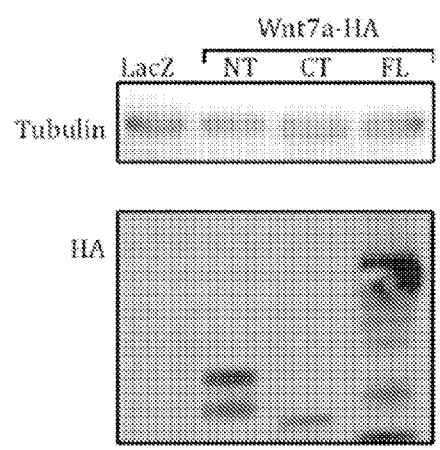

Selectively measuring the diameter of Wnt7a-HA expressing fibers revealed a significant increase in hypertrophy in Wnt7a FL-electroporated fibers over the LacZ control (FIG. 3B). The introduction of two exogenous amino acids following the signal peptide, which likely prevented its cleavage, did not compromise the functioning of the protein. This indicated that cleavage of the signal peptide on Wnt7a was not a necessary event during trafficking and excretion of the protein.

The measured diameter of Wnt7a CT expressing muscles resembled that of the full length Wnt7a (FIG. 3B), whereas Wnt7a NT did not induce hypertrophy over the size of fibers observed in the LacZ control. Muscles electroporated with Wnt7a FL and the Wnt7a CT truncated mutant had an average fiber diameter of 46.0 µm±6.0 µm and 55.3 µm±7.2 µm, respectively, compared to a control fiber diameter of 31.8 µm±3.6 µm (LacZ), indicating an overall increase in fiber caliber of 44% (Wnt7a FL) and 74% (Wnt7a CT).

These data indicated that the C-terminal domain of Wnt7a has retained the activity of the full length protein and was both necessary and sufficient to induce hypertrophy in myofibers; conversely, the N-terminal domain was not necessary for Wnt7a signaling. In addition, the removal of the N-terminal region may have increased the activity of the protein.

Wnt7a CT has Increased Bioavailability Compared to Wnt7a FL

Examination of the entire muscle sections revealed that Wnt7a CT had an increased biodistribution profile, i.e., Wnt7a CT was secreted over a much greater area in the electroporated muscle when compared to Wnt7a WT (FIG. 5). Although the same number of fibers was initially electroporated as shown by the X-Gal staining (FIG. 4), the delipidated Wnt7a (Wnt7a CT) had dispersed to adjacent fibers that endocytosed the protein, resulting in the observed sarcoplasmic staining and increased biodistribution profile.

It was confirmed that the Wnt7a CT biodistribution profile was not a location-dependent observation by staining sections from both the middle ("belly") and tip of the muscle. The muscle lysate was probed with αHA antibody and it was confirmed that all Wnt7a variants were being expressed to the same extent (FIG. 5D), showing that the widespread staining is due to increased dispersion of the hydrophilic protein rather than differences in expression levels.

Summary

The results indicated that Wnt7a is composed of two protein domains, where the C-terminal region (amino acids 213-349) is significantly more hydrophilic than the N-terminus (amino acids 32-212). The CT domain was both necessary and sufficient to induce muscle cell hypertrophy. The truncated Wnt7a CT mutant was significantly more water soluble than the full length protein, had greater affectability in muscles and was sufficiently small to more easily circumvent the capillary endothelium, which would augment Wnt7a's therapeutic effects in treatment of myodegenerative disorders.

Example 3

Secreted Wnt7a-CT Activates Wnt7a Signaling Pathways in C2C12 Cells

Figure 6:
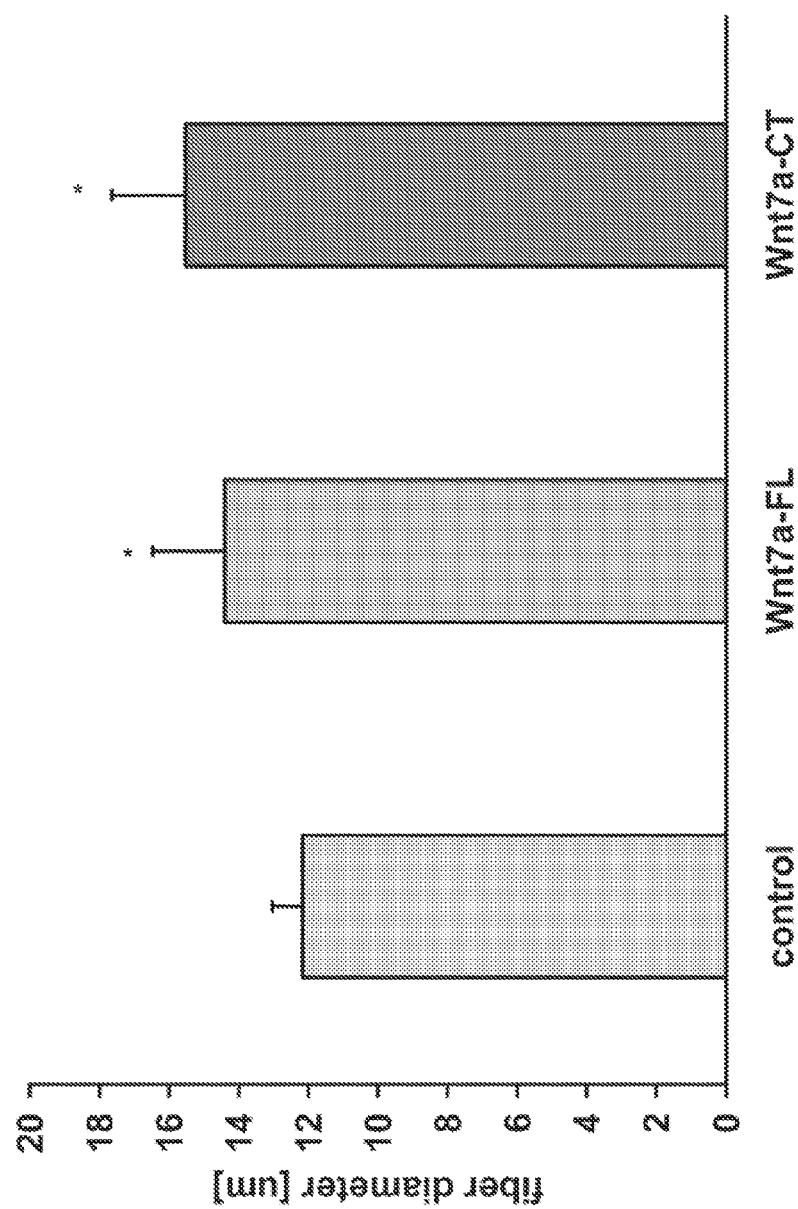
FIG. 6 shows the effect on muscle fiber diameter in C2C12 cells cultured for two days with concentrated supernatant from COS cells expressing Wnt7a CT, Wnt7a FL, or control supernatant.

COS cells were transfected with Wnt7a FL, Wnt7a C73A (a Wnt7a delipidation mutant), or Wnt7a CT. After allowing for expression of transfected genes, tissue culture supernatants from the transfected COS cells was harvested and applied to C2C12 primary myoblast cells that had been growing in differentiation conditions for three days. The fiber diameter of the C2C12 cells was measured two days after addition of the COS cell supernatants that contained the secreted Wnt7a proteins that were tested. FIG. 6 shows that Wnt7a CT, Wnt7a C73A, or Wnt7a FL supernatants increased muscle fiber diameter in C2C12 cells compared to the control COS cell supernatant.

Example 4

Wnt7a-CT Activates Wnt7a Signaling Pathways in C2C12 Cells

Figure 7:
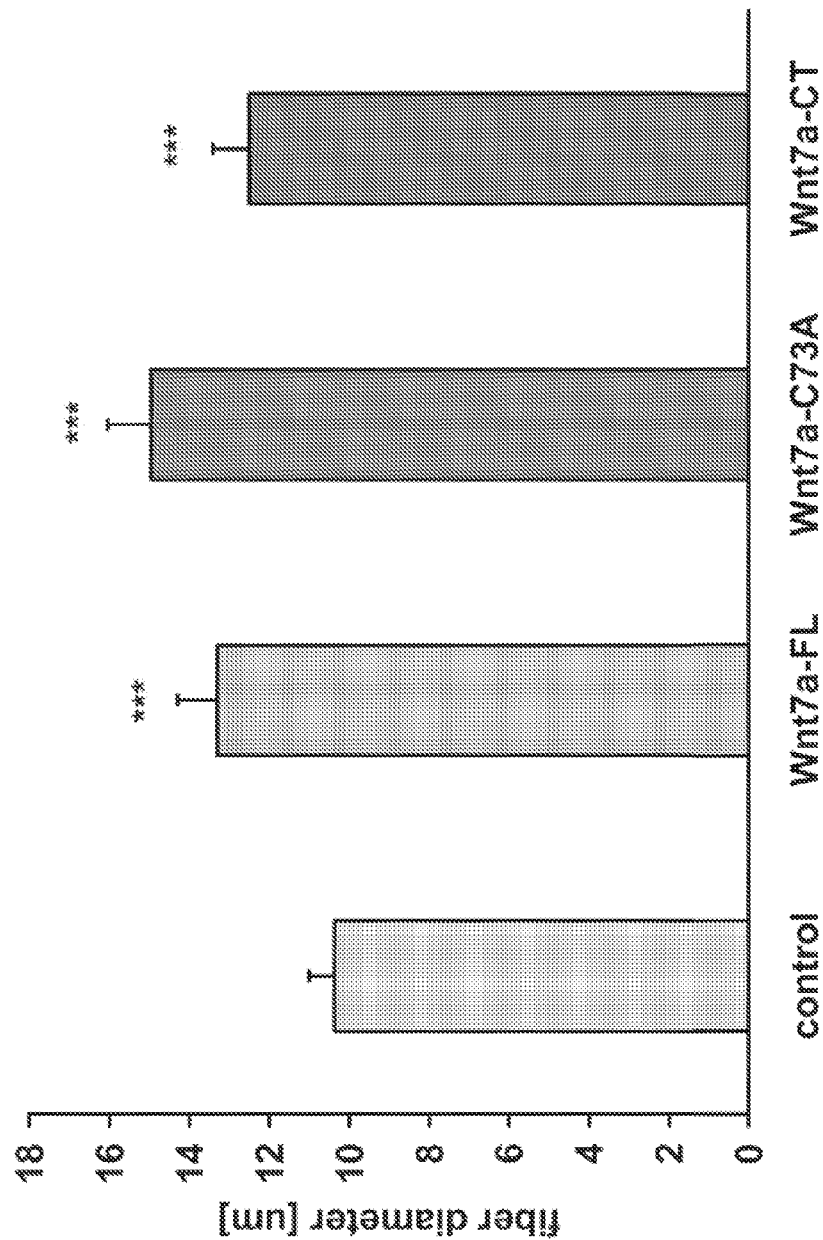
FIG. 7 shows the effect on muscle fiber diameter in C2C12 cells cultured for two days with concentrated supernatant from COS cells expressing Wnt7a CT, Wnt7a FL, a Wnt7a C73A mutant, or control supernatant.

C2C12 cells were transiently transfected with Wnt7a FL, Wnt7a C73A (a Wnt7a delipidation mutant), or Wnt7a CT. The transfected C2C12 primary myoblast cells were grown in differentiation conditions for five days. The fiber diameter of the C2C12 cells was measured on day five. FIG. 7 shows that C2C12 cells transfected with Wnt7a CT, Wnt7a C73A, or Wnt7a FL supernatants had increased muscle fiber diameter compared to the control transfected C2C12 cells.

Example 5

Activated Satellite Cells Remodel their Niche with FN

Introduction

The spatiotemporal regulation of satellite cells during muscle regeneration is remarkably fine-tuned and highly dependent on a variety of extrinsic signals (Bentzinger et al., 2010; Kuang et al., 2008). Apart from classic signaling molecules, mechanical and structural properties of the niche play an important role for satellite cell function (Cosgrove et al., 2009).

Structural properties of the satellite cell niche are largely determined by the fiber sarcolemma and the complex extracellular matrix (ECM) secreted by myogenic cells, which surrounds muscle fibers as the basement membrane. The basement membrane is primarily composed of collagens, laminins and non-collagenous glycoproteins (Sanes, 2003).

A screening approach was used to identify ECM components synthesized by myogenic cells and lead to the discovery of the glycoprotein Fibronectin (FN) as a transient component of the satellite cell niche during muscle regeneration. Upon muscle injury, the inventors found that FN modulated the initial proliferative response of satellite stem cells in cooperation with Wnt signaling, whereas in later stages of regeneration FN levels drop and allow lineage progression and differentiation of committed satellite myogenic cells for tissue repair.

Results

Figures 8A, 8B:
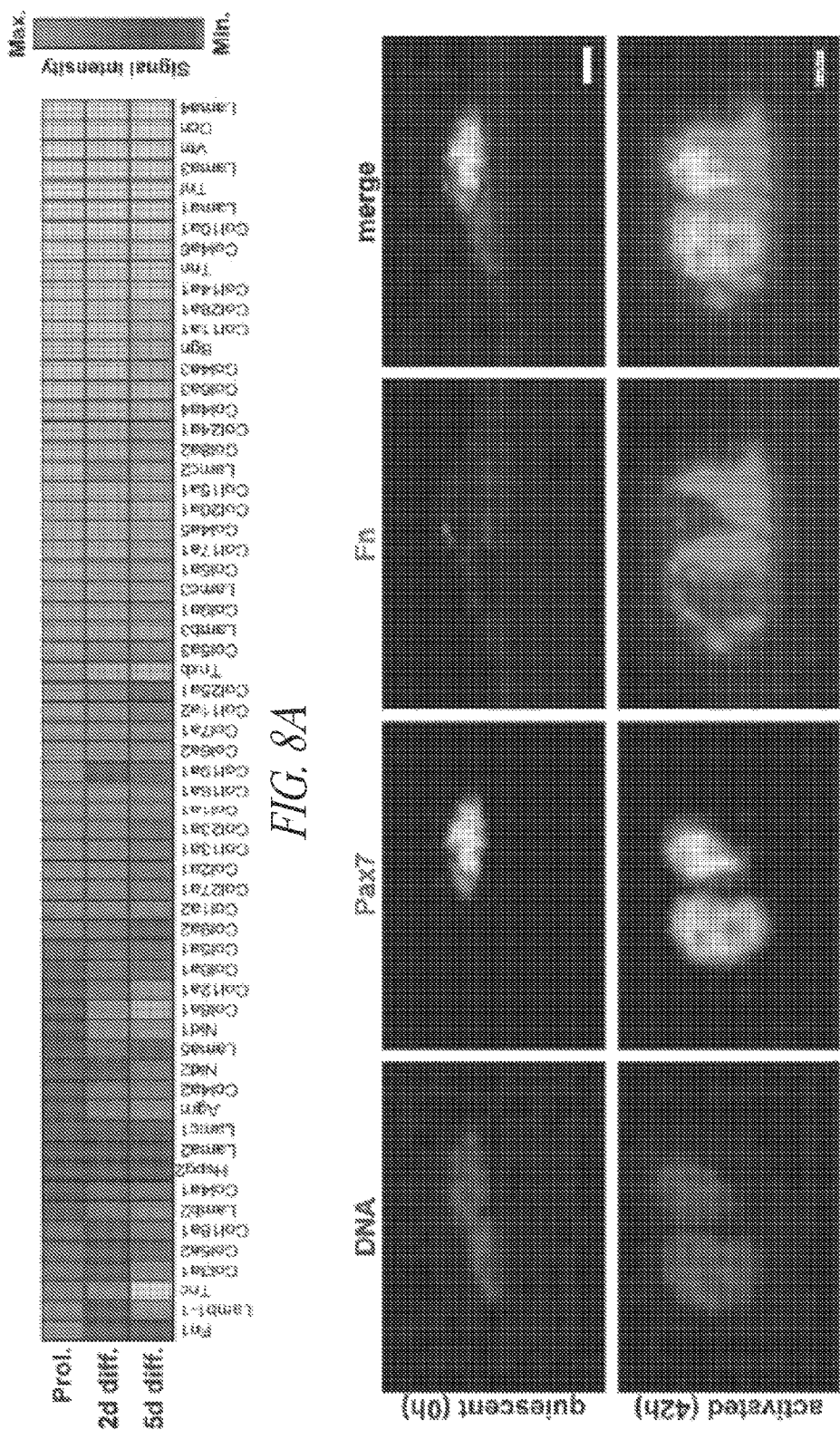
FIG. 8 shows the microarray-based identification of FN as an ECM molecule that is transiently expressed by satellite cells during their activation. A) Microarray heat map from proliferating myoblasts (Prol.) and 2 or 5 day differentiated (2 d diff./5 d diff.) myofibers. The probe for FN (Fn1) shows the highest signal in proliferating myogenic cells, but substantially downregulated during differentiation. Signal intensities represent the average of N=3 microarrays per condition. B) Quiescent satellite cells which were directly fixed after fiber isolation, only express marginal amounts of FN, whereas proliferating activated satellite cells after 48 hours of fiber culture express high levels of FN. Scale bar=2.5 µm. C) Regeneration time course after CTX injury of the TA muscle. FN expression increases at day 5 after CTX compared to the ECM component Lm. Scale bar=50 µm. D) qPCR from whole muscle cDNA at the given time points after CTX injury. The expression of FN correlates with Pax7. Data points represent means±SEM. n=3. "no injury" was set to 100% for both genes. E) In homeostatic muscle tissue satellite cells are found in close proximity of FN rich areas. Upon injury the muscle is saturated with FN and the satellite cells are embedded within it. Arrows denote Pax7$^+$ satellite cells. Scale bar=50 µm. F) Microarray heat map representing ECM genes from quiescent satellite cells (Quie.), proliferating myoblasts (Prol.) and 2 or 5 day differentiated (2 d diff./5 d diff.) myofibers. The probe for FN (Fn1) shows the highest signal in proliferating myogenic cells and is substantially lower in Quie. and diff. (Asterisk). Signal intensities represent the average of n=3 microarrays per condition for Prol. and diff. and n=1 microarray for Quie.
Figure 15:
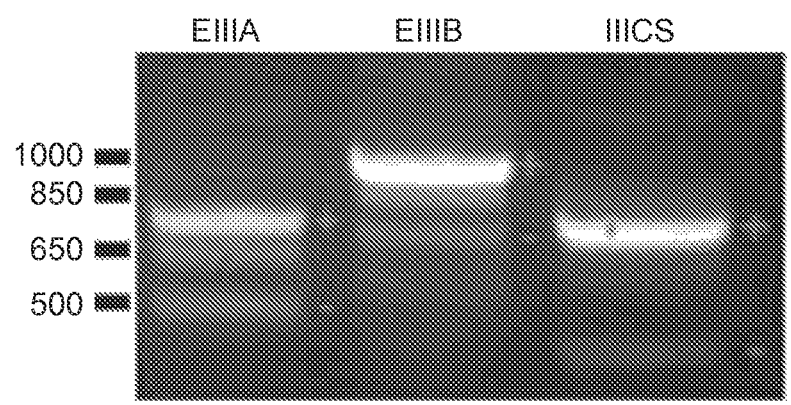
FIG. 15 shows that myoblasts express mainly cellular FN. PCR to detect splice variants of FN1. Proliferating myoblasts express mainly cellular FN1 containing the EIIIA and EIIIB inserts (+). The weaker (−) band reveals that the cells also express low levels of plasma FN1.

A microarray analysis of proliferating and differentiating satellite cell derived primary myoblasts was performed to determine how myogenic cells contribute to the ECM (FIG. 8A). FN showed the highest signal intensity among a selection of classic ECM components, and was substantially downregulated during myotube differentiation (Table 2). PCR over potential splice sites revealed that the majority of FN transcripts in proliferating myogenic cells code for cellular FN containing EIIIA and EIIIB inserts (FIG. 15).

TABLE 2

| Gene name | Prol. 1 | Prol. 2 | Prol. 3 | AV Prol. | SE Prol. | 2d diff. 1 | 2d diff. 2 | 2d diff. 3 | AV 2d diff. | SE 2d diff. | 5d diff. 1 | 5d diff. 2 | 5d diff. 3 | AV 5d diff. | SE 5d diff. |
|---|---|---|---|---|---|---|---|---|---|---|---|---|---|---|---|
| Fn1 | 761 | 911 | 821 | 828 | 44 | 244 | 256 | 237 | 245 | 6 | 53 | 70 | 62 | 61 | 5 |
| Lamb1-1 | 448 | 523 | 471 | 480 | 22 | 86 | 87 | 87 | 87 | 1 | 33 | 33 | 28 | 32 | 2 |
| Tnc | 379 | 457 | 406 | 413 | 23 | 40 | 40 | 39 | 39 | 0 | 10 | 12 | 10 | 11 | 1 |
| Col4a3bp | 346 | 403 | 390 | 379 | 17 | 718 | 766 | 684 | 722 | 24 | 333 | 400 | 393 | 374 | 21 |
| Col3a1 | 367 | 378 | 359 | 368 | 6 | 67 | 68 | 68 | 68 | 0 | 41 | 32 | 36 | 36 | 2 |
| Col5a2 | 332 | 369 | 344 | 348 | 11 | 129 | 140 | 140 | 136 | 4 | 57 | 59 | 53 | 56 | 2 |
| Col18a1 | 318 | 352 | 320 | 330 | 11 | 68 | 69 | 69 | 68 | 0 | 51 | 42 | 47 | 46 | 3 |
| Lamb2 | 168 | 189 | 169 | 175 | 7 | 362 | 368 | 359 | 363 | 3 | 511 | 443 | 442 | 464 | 23 |
| Col4a1 | 163 | 192 | 147 | 167 | 13 | 50 | 53 | 51 | 51 | 1 | 47 | 46 | 39 | 44 | 2 |
| Hspg2 | 155 | 167 | 160 | 161 | 4 | 170 | 177 | 172 | 173 | 2 | 149 | 142 | 153 | 148 | 3 |
| Lama2 | 147 | 163 | 159 | 156 | 5 | 159 | 159 | 159 | 159 | 0 | 159 | 162 | 174 | 165 | 4 |
| Lamc1 | 109 | 125 | 119 | 117 | 5 | 130 | 131 | 126 | 129 | 1 | 104 | 90 | 101 | 98 | 4 |
| Agrn | 112 | 116 | 111 | 113 | 2 | 45 | 42 | 42 | 43 | 1 | 36 | 33 | 32 | 34 | 1 |
| Col4a2 | 108 | 113 | 97 | 106 | 5 | 43 | 45 | 46 | 44 | 1 | 44 | 37 | 42 | 41 | 2 |
| Nid2 | 93 | 107 | 102 | 100 | 4 | 167 | 163 | 165 | 165 | 1 | 37 | 49 | 54 | 46 | 5 |
| Lama5 | 90 | 105 | 100 | 98 | 4 | 47 | 49 | 46 | 47 | 1 | 61 | 61 | 62 | 61 | 0 |
| Nid1 | 89 | 105 | 95 | 96 | 4 | 38 | 37 | 28 | 34 | 3 | 31 | 31 | 32 | 31 | 0 |
| Col8a1 | 74 | 85 | 74 | 77 | 4 | 34 | 34 | 32 | 34 | 1 | 26 | 19 | 16 | 20 | 3 |
| Col12a1 | 58 | 72 | 66 | 65 | 4 | 46 | 45 | 46 | 46 | 0 | 25 | 31 | 30 | 29 | 2 |
| Col6a1 | 65 | 56 | 65 | 62 | 3 | 47 | 44 | 52 | 47 | 2 | 56 | 50 | 48 | 51 | 2 |
| Col5a1 | 55 | 54 | 52 | 54 | 1 | 46 | 49 | 48 | 48 | 1 | 57 | 51 | 51 | 53 | 2 |
| Col9a2 | 45 | 39 | 40 | 41 | 2 | 48 | 51 | 49 | 49 | 1 | 70 | 62 | 51 | 60 | 5 |
| Col1a2 | 37 | 40 | 40 | 39 | 1 | 37 | 40 | 39 | 39 | 1 | 41 | 39 | 37 | 39 | 1 |
| Col27a1 | 40 | 34 | 39 | 38 | 2 | 35 | 40 | 36 | 37 | 1 | 49 | 46 | 41 | 45 | 2 |
| Col13a1 | 38 | 31 | 38 | 36 | 2 | 38 | 38 | 35 | 37 | 1 | 50 | 44 | 40 | 45 | 3 |
| Col2a1 | 38 | 35 | 36 | 36 | 1 | 35 | 38 | 38 | 37 | 1 | 49 | 43 | 46 | 46 | 2 |
| Col1a1 | 37 | 32 | 36 | 35 | 2 | 34 | 38 | 37 | 36 | 1 | 42 | 39 | 37 | 39 | 2 |
| Col23a1 | 39 | 31 | 36 | 35 | 2 | 36 | 39 | 42 | 39 | 2 | 60 | 46 | 46 | 50 | 5 |
| Col16a1 | 36 | 29 | 32 | 33 | 2 | 33 | 31 | 33 | 32 | 1 | 41 | 38 | 33 | 37 | 2 |
| Col19a1 | 29 | 36 | 32 | 33 | 2 | 68 | 65 | 73 | 68 | 2 | 49 | 53 | 53 | 52 | 1 |
| Col11a2 | 33 | 26 | 31 | 30 | 2 | 35 | 35 | 35 | 35 | 0 | 49 | 45 | 40 | 44 | 2 |
| Col6a2 | 32 | 31 | 28 | 30 | 1 | 32 | 31 | 29 | 31 | 1 | 38 | 32 | 35 | 35 | 2 |
| Col7a1 | 32 | 27 | 30 | 30 | 2 | 31 | 32 | 32 | 32 | 1 | 40 | 38 | 38 | 39 | 1 |
| Col25a1 | 33 | 27 | 24 | 28 | 3 | 40 | 40 | 40 | 40 | 0 | 50 | 57 | 53 | 53 | 2 |
| Lamb3 | 27 | 26 | 28 | 27 | 1 | 24 | 26 | 24 | 25 | 1 | 26 | 27 | 25 | 26 | 1 |
| Col5a3 | 27 | 24 | 30 | 27 | 2 | 33 | 39 | 35 | 36 | 2 | 41 | 38 | 34 | 38 | 2 |
| Col9a1 | 24 | 25 | 25 | 25 | 0 | 27 | 25 | 26 | 26 | 1 | 35 | 31 | 27 | 31 | 2 |
| Lamc3 | 25 | 22 | 26 | 24 | 1 | 25 | 23 | 25 | 24 | 1 | 33 | 27 | 24 | 28 | 3 |
| Col5a1 | 24 | 21 | 24 | 23 | 1 | 24 | 24 | 24 | 24 | 0 | 31 | 28 | 24 | 28 | 2 |
| Col17a1 | 22 | 22 | 22 | 22 | 0 | 21 | 23 | 22 | 22 | 1 | 29 | 29 | 24 | 27 | 2 |
| Col4a5 | 22 | 20 | 24 | 22 | 1 | 24 | 24 | 24 | 24 | 0 | 28 | 29 | 24 | 27 | 1 |
| Col20a1 | 22 | 20 | 23 | 21 | 1 | 23 | 23 | 23 | 23 | 0 | 23 | 23 | 22 | 23 | 0 |
| Lamc2 | 21 | 19 | 19 | 19 | 1 | 33 | 30 | 28 | 31 | 1 | 24 | 25 | 25 | 25 | 0 |
| Col15a1 | 21 | 16 | 21 | 19 | 2 | 21 | 21 | 21 | 21 | 0 | 26 | 26 | 25 | 26 | 0 |
| Col24a1 | 22 | 19 | 17 | 19 | 2 | 21 | 22 | 22 | 22 | 0 | 31 | 31 | 23 | 28 | 3 |
| Col8a2 | 22 | 18 | 18 | 19 | 1 | 22 | 22 | 21 | 22 | 0 | 31 | 29 | 32 | 30 | 1 |
| Col4a4 | 20 | 16 | 19 | 18 | 1 | 19 | 19 | 19 | 19 | 0 | 20 | 20 | 23 | 21 | 1 |
| Col4a3 | 18 | 15 | 17 | 17 | 1 | 17 | 18 | 18 | 18 | 0 | 21 | 20 | 22 | 21 | 1 |
| Col6a3 | 18 | 15 | 17 | 17 | 1 | 19 | 19 | 19 | 19 | 0 | 21 | 20 | 20 | 20 | 0 |
| Bgn | 17 | 17 | 15 | 16 | 1 | 17 | 16 | 13 | 15 | 1 | 20 | 24 | 23 | 22 | 1 |
| Col11a1 | 18 | 16 | 16 | 16 | 1 | 16 | 18 | 18 | 17 | 1 | 22 | 22 | 19 | 21 | 1 |
| Tnn | 15 | 14 | 15 | 15 | 0 | 15 | 15 | 15 | 15 | 0 | 15 | 17 | 15 | 16 | 1 |
| Col14a1 | 15 | 14 | 15 | 15 | 1 | 15 | 15 | 15 | 15 | 0 | 19 | 16 | 15 | 17 | 1 |
| Col28a1 | 18 | 14 | 15 | 15 | 1 | 18 | 19 | 17 | 18 | 0 | 24 | 25 | 18 | 22 | 2 |
| Tnxb | 12 | 12 | 15 | 13 | 1 | 15 | 15 | 15 | 15 | 0 | 20 | 17 | 16 | 18 | 1 |
| Col4a6 | 15 | 12 | 13 | 13 | 1 | 15 | 15 | 14 | 15 | 0 | 20 | 17 | 15 | 17 | 2 |
| Lama1 | 13 | 11 | 12 | 12 | 1 | 13 | 12 | 12 | 12 | 0 | 14 | 13 | 13 | 14 | 0 |
| Col10a1 | 11 | 13 | 13 | 12 | 0 | 13 | 15 | 12 | 13 | 1 | 14 | 13 | 16 | 14 | 1 |
| Tnf | 9 | 11 | 13 | 11 | 1 | 13 | 13 | 13 | 13 | 0 | 13 | 11 | 17 | 13 | 2 |
| Lama3 | 11 | 11 | 11 | 11 | 0 | 11 | 11 | 10 | 10 | 0 | 12 | 11 | 12 | 12 | 0 |
| Vtn | 9 | 10 | 11 | 10 | 1 | 11 | 11 | 11 | 11 | 0 | 12 | 16 | 11 | 13 | 1 |
| Dcn | 9 | 8 | 8 | 9 | 0 | 8 | 8 | 8 | 8 | 0 | 9 | 8 | 12 | 10 | 1 |
| Lama4 | 8 | 8 | 8 | 8 | 0 | 9 | 9 | 8 | 8 | 0 | 9 | 10 | 8 | 9 | 1 |

Replicates are from primary myoblasts in proliferation (Prol.) and differentiation (diff.).
AV = Average, SE = Standard error.

Figure 8C:
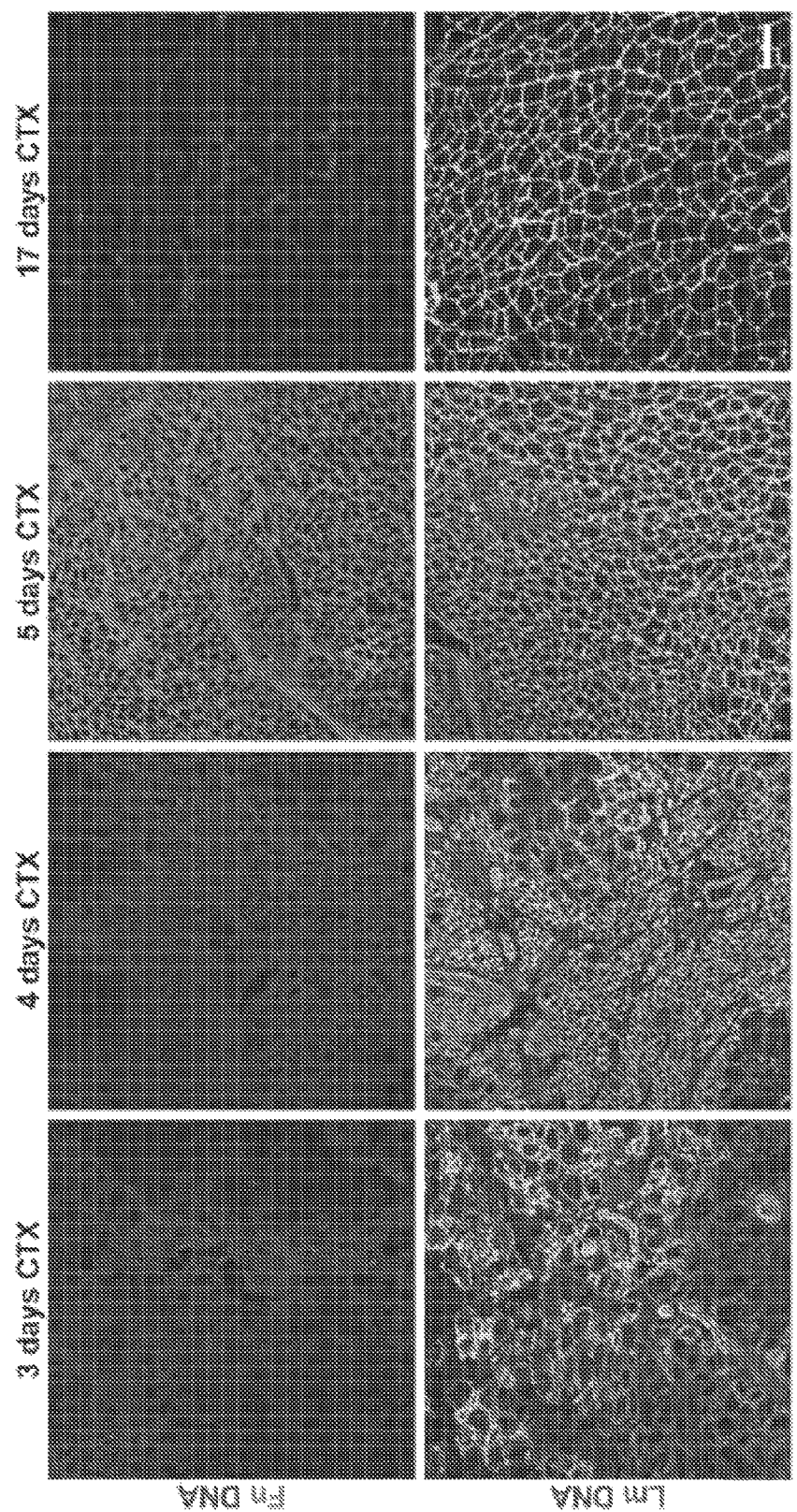

The expression pattern of FN and other ECM components by myogenic cells were determined using an additional gene expression analysis on prospectively isolated quiescent satellite cells (Quie.), versus established proliferating satellite cell-derived myoblasts (Prol.), and differentiated myotubes (2 d and 5 d diff.) (FIG. 8F, Table 4).

TABLE 4

Affymetrix microarray probe signal intensity of ECM components synthesized by myogenic cells.

| Gene | Quie. | Prol. | 2d diff. | 5d diff. |
|------|-------|-------|----------|----------|
| Vtn | 1953.1 | 11.5 | 13.4 | 14.7 |
| Bgn | 1618.3 | 18.2 | 17 | 25.7 |
| Dcn | 1323.8 | 9.7 | 9 | 12 |
| Hspg2 | 1130.8 | 181.8 | 200.3 | 167.4 |
| Lama2 | 1093.8 | 178 | 178.6 | 188 |
| Lamc1 | 1028.3 | 135.1 | 150.5 | 109.7 |
| Nid1 | 873.2 | 115.5 | 39.8 | 36.2 |
| Lamb2 | 577.4 | 187.1 | 384.8 | 497.9 |
| Tnxb | 521.8 | 13.4 | 17.4 | 20.5 |
| Col6a1 | 447.8 | 67.1 | 50.1 | 55.1 |
| Col3a1 | 357.6 | 400 | 74.2 | 38.6 |
| Col15a1 | 354.3 | 21 | 22.9 | 28.9 |
| Fn1 | 331 | 884.4 | 266.6 | 69.9 |
| Col6a3 | 297.9 | 18.5 | 21.5 | 24.6 |
| Col4a1 | 286.2 | 184.4 | 55.8 | 50.6 |
| Col4a2 | 250.3 | 125.5 | 51.4 | 48.4 |
| Col6a2 | 229.5 | 35.7 | 38.5 | 45.3 |
| Lamb1 | 212 | 510.2 | 95.7 | 35.1 |
| Col1a2 | 206.1 | 46.3 | 45.5 | 44.8 |
| Col1a1 | 174.4 | 37.7 | 39.5 | 44.8 |
| Lama4 | 158.9 | 8.2 | 9.5 | 9.5 |
| Nid2 | 158.8 | 114.5 | 187.4 | 53.7 |
| Agrn | 148.1 | 128.5 | 49.8 | 40.3 |
| Lama5 | 135 | 117.5 | 54.4 | 70 |
| Col8a1 | 130.2 | 91.6 | 38.4 | 22.2 |
| Lama3 | 127 | 11.3 | 11.4 | 13.7 |
| Col4a3bp | 122.8 | 408.6 | 769.4 | 403.7 |
| Col5a1 | 109.2 | 67 | 57 | 64.6 |
| Col5a2 | 95.6 | 380.4 | 155.9 | 64 |
| Col12a1 | 71.7 | 77.6 | 54.5 | 32.1 |
| Col5a3 | 68.2 | 30.4 | 41.4 | 43.1 |
| Col18a1 | 64.4 | 367.2 | 76.7 | 54.1 |
| Lamc3 | 55.5 | 27.5 | 27.7 | 34.1 |
| Col19a1 | 49.5 | 37.9 | 81.7 | 62.2 |
| Col20a1 | 44.2 | 22.8 | 25 | 26 |
| Tnc | 42.5 | 446.5 | 45 | 12 |
| Col27a1 | 38.1 | 42 | 42.2 | 52.7 |
| Col16a1 | 34.9 | 36.1 | 36.1 | 43.9 |
| Col6a6 | 34.8 | 32.9 | 35.8 | 42.4 |
| Col11a2 | 31.3 | 37 | 43 | 55.6 |
| Col2a1 | 31.3 | 44 | 44.3 | 56 |
| Col9a3 | 30.7 | 53 | 55.3 | 75.4 |
| Col5a1 | 30.6 | 29.6 | 29.5 | 36.2 |
| Col14a1 | 30.4 | 16.9 | 17 | 20.7 |
| Col9a2 | 29.5 | 46.5 | 56.6 | 70.8 |
| Col7a1 | 28.3 | 33.9 | 35.9 | 46.2 |
| Col23a1 | 25.7 | 41.8 | 45.9 | 62.1 |
| Col25a1 | 23.9 | 31.5 | 45.2 | 61.7 |
| Col17a1 | 23.7 | 23.1 | 23.4 | 30.3 |
| Col22a1 | 22.8 | 26.8 | 28.4 | 37.1 |
| Col13a1 | 22.5 | 41.3 | 43.3 | 55.9 |
| Col9a1 | 20.6 | 24.3 | 24.9 | 32.3 |
| Lamc2 | 20.4 | 21.1 | 34.7 | 26.6 |
| Col4a5 | 20.2 | 23.3 | 25.3 | 30 |
| Col4a3 | 20.1 | 19.1 | 20.1 | 24.8 |
| Col4a4 | 20.1 | 20.7 | 21.8 | 23.6 |
| Col11a1 | 19.3 | 19.3 | 20.1 | 25.9 |
| Col6a4 | 18.2 | 19.5 | 21.1 | 28.9 |
| Col24a1 | 17.3 | 20.2 | 23.6 | 30.3 |
| Lamb3 | 15.6 | 30.1 | 26 | 29.4 |
| Tnf | 15.6 | 12.6 | 14.7 | 15.4 |
| Col28a1 | 15.6 | 17.1 | 20.2 | 25.9 |
| Col6a6 | 15.2 | 14.3 | 14 | 14.8 |
| Col10a1 | 13.4 | 13.2 | 14.9 | 15.7 |
| Tnn | 12.5 | 14.3 | 14.9 | 16.6 |
| Col4a6 | 12.1 | 14.6 | 18 | 21.2 |
| Col8a2 | 11.5 | 17.8 | 21 | 29.8 |
| Lama1 | 10.7 | 11.3 | 11.9 | 13.8 |

Several probes, including Vitronectin (Vtn), Biglycan (Bgn), Decorin (Dcn), Perlecan (HSPG2), Laminin subunits (Lama2 and Lamc1) and Nidogen (Nid1) showed a high hybridization signal in quiescent satellite cells when compared to primary myoblasts or differentiated myotubes. In proliferating primary myoblasts the probe for FN (Fn1) showed a strong hybridization signal, which was 60-70% lower in quiescence or differentiation. These data indicate that proliferating myogenic progenitors are a potential source of FN within the satellite cell niche.

To confirm that satellite cells express FN single fibers from mouse EDL muscles were isolated. Quiescent satellite cells on fibers that were immediately fixed after isolation showed marginal immunostaining with FN antibodies (FIG. 8B). However, activated proliferating satellite cells found on fibers that were cultured under free floating conditions for 42 hours stained strongly for FN.

Numerous cell types have been noted to express FN including fibroblasts, chondrocytes, endothelial cells, macrophages, as well as certain epithelial cells (Hynes and Yamada, 1982). Low levels of FN expression have been described in the interstitium and in capillaries of adult skeletal muscle (Peters et al., 1996). Satellite cells reside closely juxtaposed to muscle fibers in a niche between the sarcolemma and the basal lamina (Charge and Rudnicki, 2004).

FN expression dynamics during regeneration were studied: the TA muscle was injured by injection of CTX and analyzed at several time-points after injury. In contrast to the unrelated ECM component Laminin (LM), FN in muscle cross sections peaked at five days post injury and declined to baseline thereafter (FIG. 8C). Immunostaining performed with antibodies directed to Pax7 and FN revealed that the satellite cell niche does not contain detectable levels of FN in resting tibialis anterior (TA) muscle. However, FN staining was present in ring-like structures reminiscent of capillaries (FIG. 8E). In contrast, five days after acute cardiotoxin (CTX) muscle injury, satellite cells were embedded in a extracellular milieu containing high levels of FN.

Figure 8D:
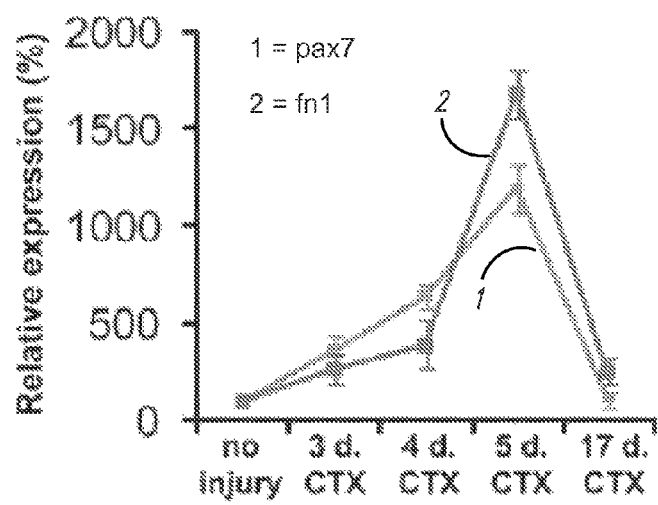
Figure 8E:
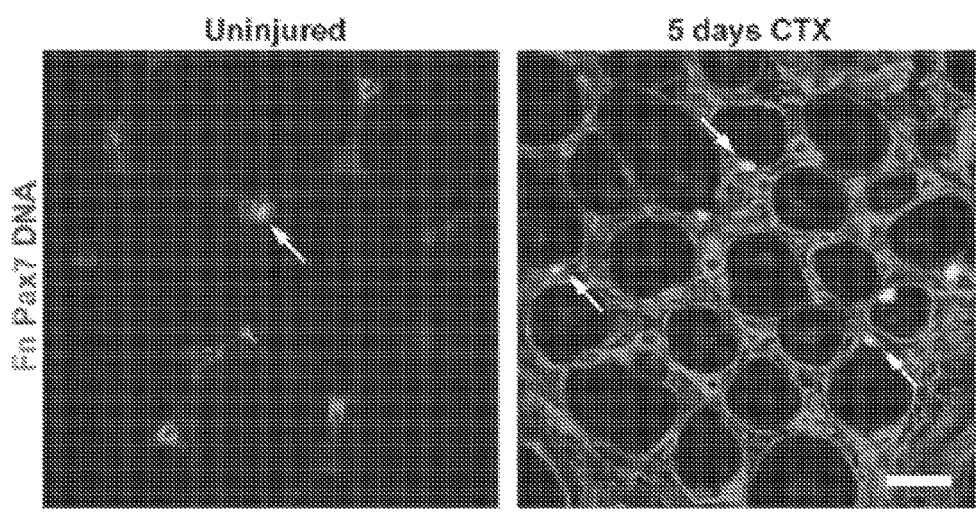
Figure 8F:
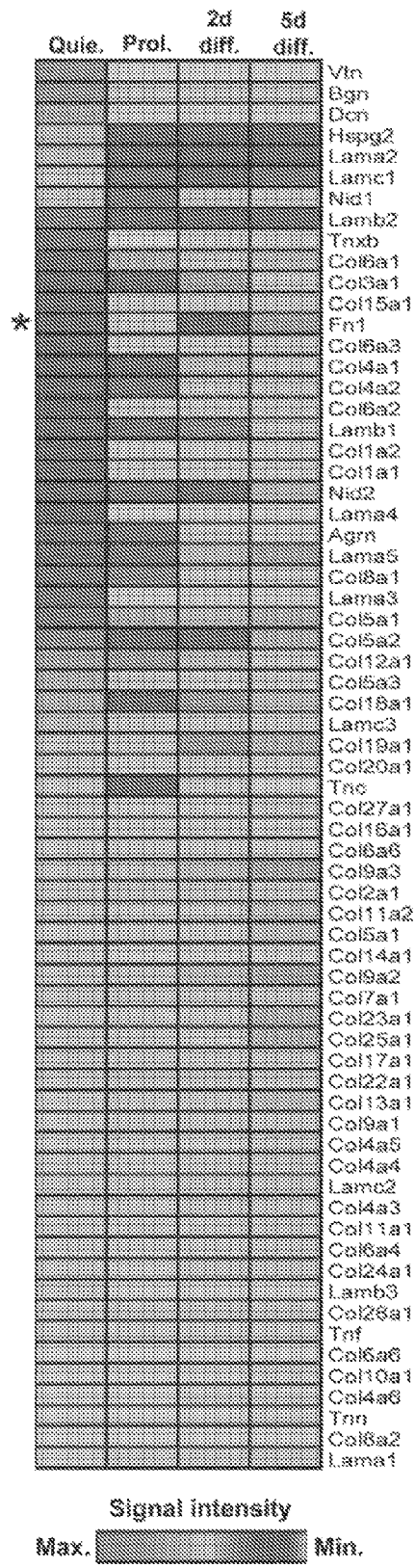

Quantitative real-time PCR (qPCR) using whole muscle lysates confirmed that maximal FN expression after injury correlated with Pax7 expression and therefore with tissue satellite cell content (FIG. 8D). These results suggested that satellite cells are a source of FN during muscle regeneration.

Figure 21B:
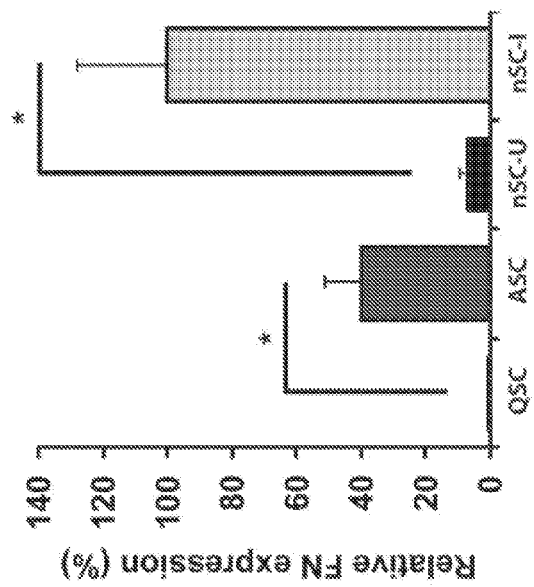
FIG. 21 shows that activated satellite cells express FN to remodel their niche. A) Quiescent satellite cells were directly fixed after fiber isolation, and expressed marginal amounts of FN, whereas proliferating activated satellite cells expressed higher levels of FN than quiescent cells after 42 h of fiber culture. Scale bar=5 μm. B) FN expression in freshly FACS isolated cells from injured and uninjured muscle. Quiescent satellite cells (QSC) and activated satellite cells (ASC) are compared to non-satellite cells from uninjured (nSC-U) and injured (nSC-I) muscle. Bars represent means±SEM. n=3. p value is *p<0.05. C) 42 h activated satellite cells were stained with FN antibody before permeabilization (non perm.). Scale bar=10 μm. D) Activated satellite cells on fibers were directly fixed after isolation from regenerating muscle five days after CTX injury and expressed high levels of FN underneath the intact basal-lamina. Scale bar=5 μm. E) After 42 hours of culture, satellite stem cells (Pax7$^+$/YFP$^-$) in dividing asymmetric satellite cell doublets on fibers contained lower levels of FN than the apical satellite myogenic cell (Pax7$^+$/YFP$^+$). Scale bar=5 μm. F) Background corrected, pooled average grey values of FN staining from >10 asymmetric divisions (as illustrated in FIG. 24A). The area that was densitometrically analyzed for each cell in an individual division was kept constant. The YFP+ cell was set to 100% for each individual division.
Figure 21A:
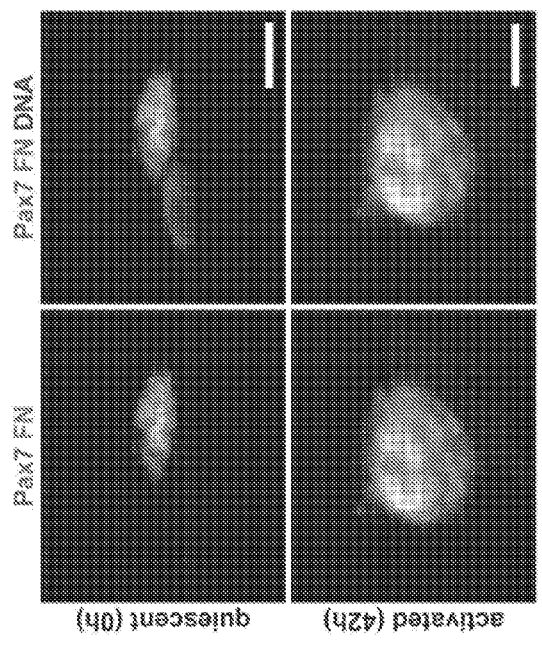

FN expression in activated satellite cells was determined. Quiescent satellite cells on freshly isolated single myofibers (0 h) or activated satellite cells on cultured fibers for 42 h were stained with anti-FN antibody (FIG. 21A). FN was barely detectable in quiescent satellite cells, but was upregulated in activated satellite cells at 42 h in culture. After 72 h of culture, the majority of satellite cells on single fibers were identified by high-level FN expression (FIG. 21B).

Figure 21C:
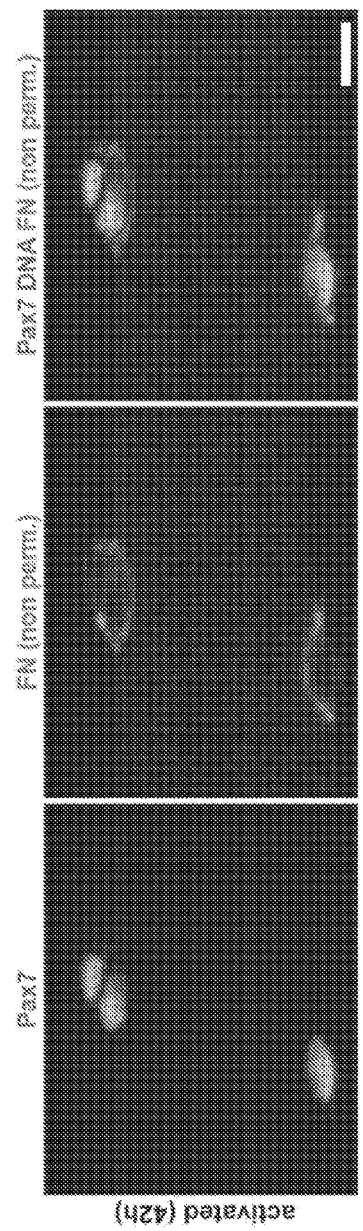
Figure 21D:
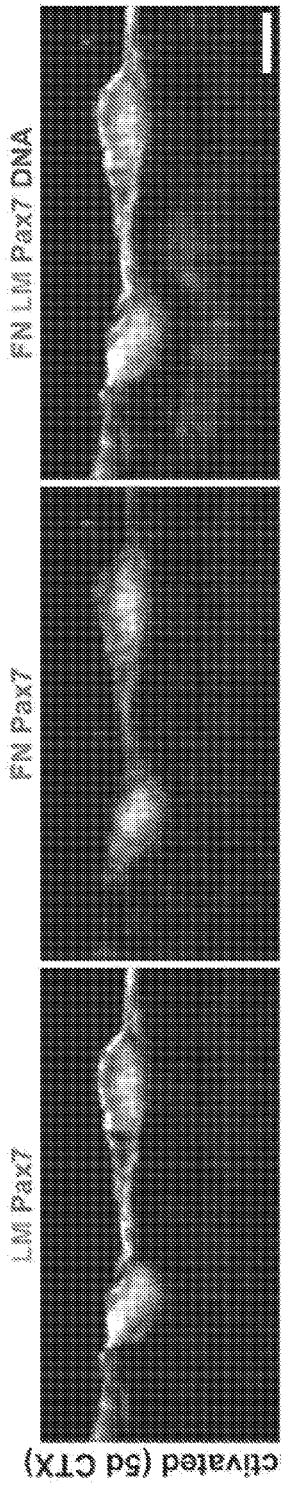

Activated satellite cells incubated with FN antibody before permeabilization showed that a large fraction of FN protein was extracellularly localized (FIG. 21C). FN expression by satellite cells on isolated myofibers was not induced by cultivation. Isolated muscle fibers with activated satellite cells from mice that had been injured for five days with cardiotoxin (CTX) showed detectable FN expression in discrete domains around activated satellite cells within their niche beneath the intact basal-lamina (FIG. 21D).

Figure 21F:
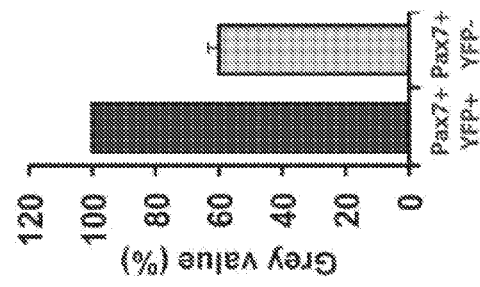
Figure 21E:
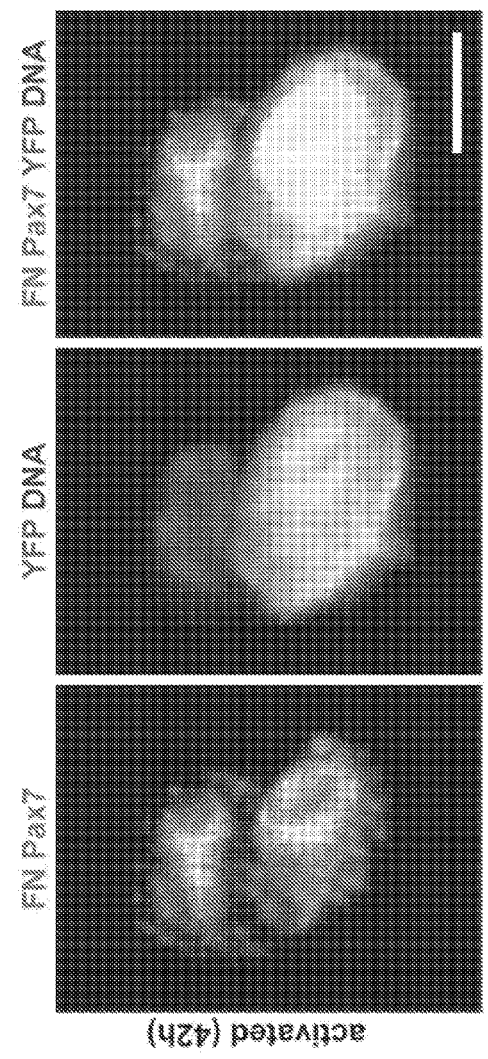

The FN expression in Pax7+/YFP− satellite stem cells versus Pax7+/YFP+ satellite myogenic cells was assessed by analyzing asymmetric satellite cell divisions found on cultured individual myofibers at 42 h after isolation. This experiment showed that FN expression was markedly up regulated in Pax7+/YFP+ satellite myogenic cells relative to Pax7+/YFP− satellite stem cells (FIG. 21E). Stringent washing conditions used during the staining procedure enriched intracellular FN in the secretory pathway and allowed for the quantification of protein levels in doublets resulting from asymmetric cell divisions (FIG. 22A).

Figures 22A, 22B, 22C:
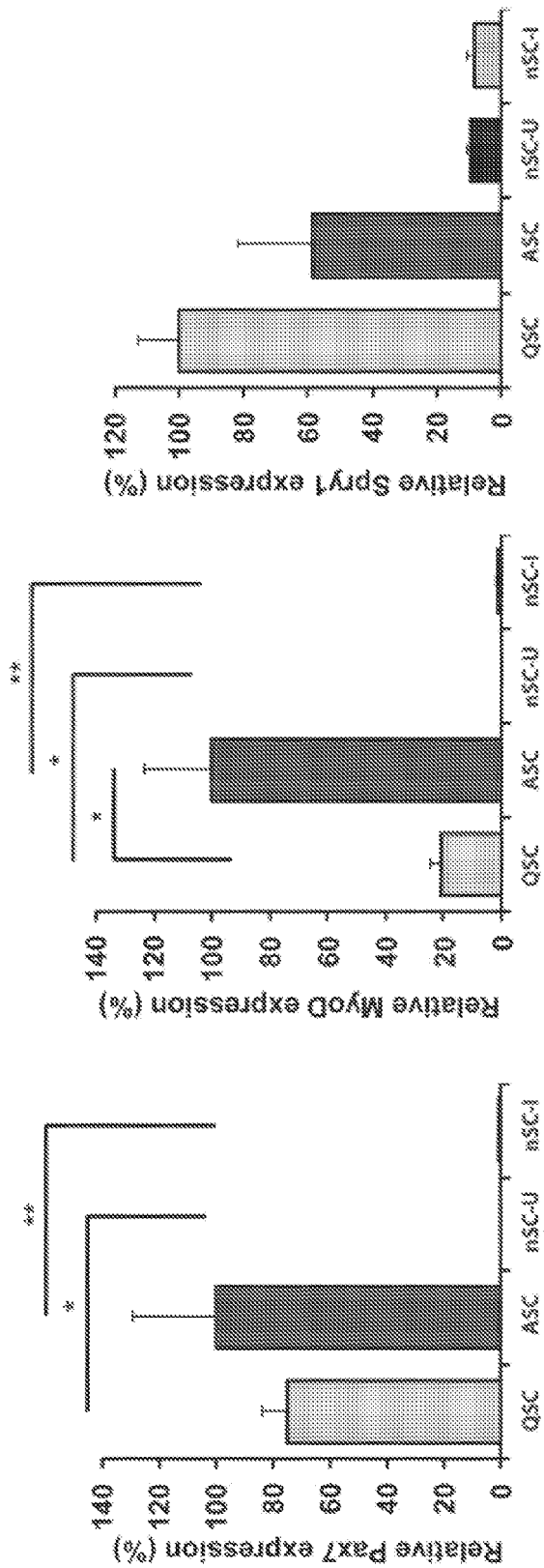
FIG. 22 shows a comparison of expression markers in freshly isolated quiescent and activated cells and FN expression in newly activated satellite cells. A), B) and C) Pax7, MyoD and Srpy1 expression in freshly FACS isolated cells from injured and uninjured muscle. Quiescent satellite cells (QSC) and activated satellite cells (ASC) were compared to non-satellite cells from uninjured (nSC-U) and injured (nSC-I) muscle. Bars represent means±SEM. n=3. p value are **p<0.01; *p<0.05. D) PCR over the EIIIA and EIIIB splice sites revealed that myogenic cells mostly express cellular FN containing both splice inserts (+). EIIIA and EIIIB negative transcripts are expressed at low levels (−). E) Western blot for FN in gelatin-sepharose treated fiber culture medium confirms removal of pFN from treated medium. F) After 8 h of isolation of single fibers, activated satellite cells expressed high levels of FN in pFN free culture conditions. Scale bar=5 μm.

Immunostaining grey values from >10 randomly selected asymmetric doublets were quantitated using non-saturating concentrations of FN antibody and revealed that Pax7+/YFP− cells contain about 60% of the FN levels found in Pax7+/YFP+ cells (FIG. 22B). In addition, FACS-purified Pax7/YFP− primary cells expressed 66% of FN mRNA compared to Pax7+/YFP+ cells and contained lower levels of protein (FIGS. 22C and 21F).

The observation that Pax7+/YFP+ satellite myogenic cells expressed elevated levels of FN relative to Pax7+/YFP− satellite stem cells indicated that Wnt7a signaling is primed in satellite stem cells by FN originating from satellite myogenic cells following an asymmetric division.

Example 6

Sdc4 is an FN Receptor on Satellite Cells

Background

Syndecan 4 (Sdc4) and the related syndecan 3 (Sdc3) are known to be important for myogenesis (Cornelison et al., 2001). Syndecans are highly glycosylated single transmembrane proteins which have been reported to act as co-receptors for Integrins and the FGF receptor (Murakami et al., 2008; Xian et al., 2010). Several ECM proteins, including FN, Tenascin-c, Vitronectin, Fibrillin-1 and Thrombospondin-1 can bind to Syndecans through their heparin-binding sites (Xian et al., 2010). Protein kinase C (PKC) binds directly to the cytoplasmatic tail of Sdc4 to modulate small GTPases (Lim et al., 2003; Xian et al., 2010).

In *Xenopus laevis*, Sdc4 is required for convergent extension movement and influences PCP signaling by binding to Fzd7 and Dishevelled (Davidson et al., 2006; Munoz et al., 2006). Sdc4 is highly expressed in myogenic cells.

Results

Figure 9A:
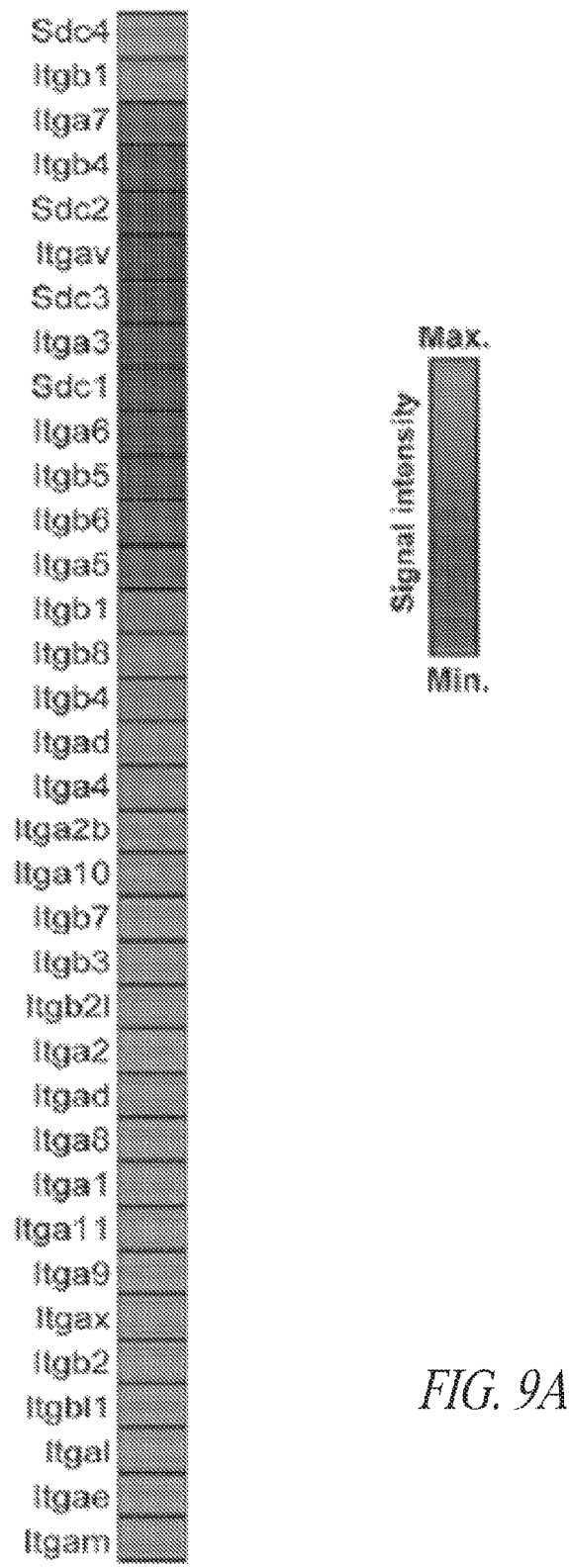
FIG. 9 shows the microarray based identification of Sdc4 as a candidate receptor for FN on satellite cells and as a component involved in myogenic Wnt signaling. A) Heat map of microarray data from proliferating myoblasts representing all integrin subunits as well as Syndecans. Sdc4 has the strongest signal while putative FN binding integrin combinations are expressed at lower levels. Signal intensities represent the average of N=3 microarrays per condition. B) qPCR from proliferating myoblasts (Prol.) and 2 or 4 day differentiated (2 d diff./4 d diff.) myofibers comparing Sdc4 expression to the expression of Itgα5. Bars represent means±SEM. n=3. p values are *p<0.001; p<0.01. C) Sdc4 colocalizes with FN on proliferating satellite cells. Scale bar=2.5 µm. D) Itgβ1 does not colocalize with FN on proliferating satellite cells. Scale bar=2.5 µm. E) Western blot demonstrating that Sdc4 immunoprecipitates with Wnt7a receptor Fzd7 in mammalian cells. F) Western blot demonstrating that Pax7$^+$/YFP$^-$ cells express less FN in culture. GAPDH is shown as a loading control. G) In dividing asymmetric satellite cell doublets the Pax7$^+$/YFP$^-$ cell (asterisk) stains less bright for FN. Scale bar=2.5 µm.
Figure 9B:
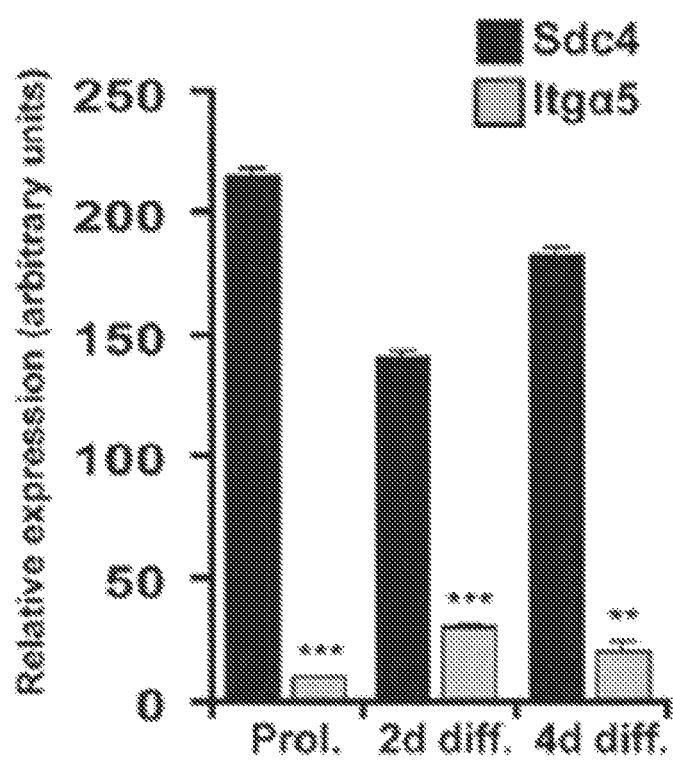

No Integrin (Itg) subunits involved in FN binding showed a high signal in proliferating myogenic cells in the microarray data (FIG. 9A; Table 3). The Lm binding α7β1 Itg appeared to be present in substantial levels. However, a strong signal was obtained for the high affinity FN receptor Sdc4. qPCR subsequently confirmed that Sdc4 expression was substantially higher than the classic FN receptor Itg subunit α5 (FIG. 9B). In addition, the expression level between Sdc4 and Itgα5 was maintained through differentiation of myoblasts into myofibers. Immunostaining of 42 hour activated satellite cells on free floating fiber cultures showed a co-localization of FN with Sdc4 (FIG. 9C). Itgβ1 was not observed to colocalize with FN (FIG. 9D).

The data demonstrated that the Fzd7/Sdc4 receptor complex exists in mammalian muscle cells.

TABLE 3

| Gene Name | Prol. 1 | Prol. 2 | Prol. 3 | Av Prol. | SE |
|---|---|---|---|---|---|
| Sdc4 | 1274 | 1273 | 1177 | 1240 | 32 |
| Itgb1 | 1072 | 1174 | 1056 | 1099 | 37 |
| Itga7 | 629 | 815 | 705 | 712 | 54 |
| Itgb4 | 508 | 556 | 516 | 526 | 15 |
| Sdc2 | 305 | 342 | 364 | 336 | 17 |
| Itgav | 284 | 358 | 331 | 323 | 22 |
| Sdc3 | 260 | 310 | 250 | 272 | 19 |
| Itga3 | 172 | 222 | 188 | 193 | 15 |
| Sdc1 | 189 | 187 | 177 | 184 | 3 |
| Itga6 | 125 | 136 | 123 | 128 | 4 |
| Itgb5 | 102 | 114 | 106 | 107 | 4 |
| Itgb6 | 77 | 91 | 82 | 83 | 4 |
| Itga5 | 74 | 84 | 80 | 79 | 3 |
| Itgb1 | 42 | 46 | 47 | 45 | 2 |
| Itgb8 | 30 | 37 | 32 | 33 | 2 |
| Itgb4 | 37 | 26 | 28 | 30 | 3 |
| Itgad | 27 | 25 | 25 | 26 | 1 |
| Itga4 | 24 | 28 | 26 | 26 | 1 |
| Itga2b | 22 | 22 | 20 | 22 | 1 |
| Itga10 | 17 | 19 | 18 | 18 | 0 |
| Itgb7 | 16 | 16 | 16 | 16 | 0 |
| Itgb3 | 15 | 14 | 16 | 15 | 1 |
| Itgb2l | 16 | 12 | 15 | 14 | 1 |
| Itga2 | 12 | 14 | 12 | 13 | 1 |
| Itgad | 11 | 11 | 13 | 12 | 0 |
| Itga8 | 11 | 11 | 11 | 11 | 0 |
| Itga1 | 12 | 10 | 12 | 11 | 0 |
| Itga11 | 11 | 11 | 11 | 11 | 0 |
| Itga9 | 15 | 9 | 9 | 11 | 2 |
| Itgax | 10 | 10 | 11 | 10 | 0 |
| Itgb2 | 11 | 9 | 9 | 10 | 1 |
| Itgbl1 | 10 | 9 | 9 | 10 | 0 |
| Itgal | 11 | 11 | 8 | 10 | 1 |
| Itgae | 9 | 9 | 8 | 9 | 0 |
| Itgam | 10 | 7 | 7 | 8 | 1 |

Replicates are from primary myoblasts in proliferation (Prol.).
AV = Average,
SE = Standard error.

Example 7

Sdc4 Forms a Complex with the Satellite Stem Cell Receptor Fzd7

The inventors previously identified Fzd7 and its ligand Wnt7a as components for the symmetric expansion of the Pax7 positive and Myf5-Cre-ROSA-YFP negative (Pax7+/YFP−) satellite stem cell pool (Le Grand et al., 2009).

Figure 9E:
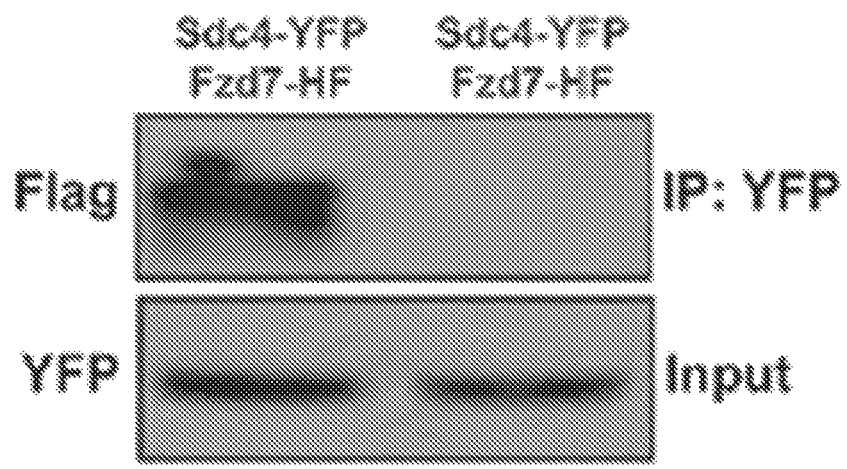
Figure 19A:
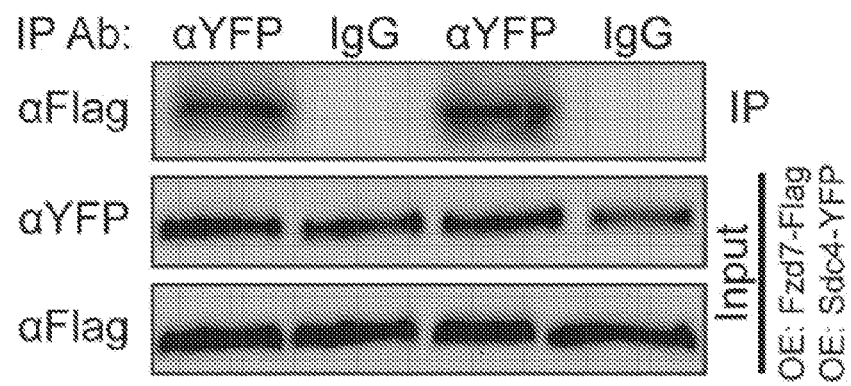
FIG. 19 shows that the FN receptor Sdc4 forms a functional complex with Fzd7. A) Co-IP of Sdc4 with the Wnt7a receptor Fzd7 from satellite cell derived primary myoblasts overexpressing (OE) Fzd7-Flag and Sdc4-YFP. Co-IP was performed with an anti-YFP antibody or with an IgG control. B) Proximity ligation assay (PLA) of Sdc4 and Fzd7 in activated satellite cells after 42 hours of fiber culture. No interaction was observed in siSdc4 treated cells. Scale bar=5 μm. C) Proximity ligation assay (PLA) of Sdc4 and FN in activated satellite cells after 42 hours of fiber culture. No interaction was observed in siSdc4 treated cells. Scale bar=5 μm. D) Co-IP of Fzd7 with FN from satellite cell derived primary myoblasts overexpressing (OE) Fzd7-Flag and FN. Co-IP was performed with an anti-YFP antibody. siRNA knockdown of endogenous Sdc4 (siSdc4) prevented Co-IP of FN with Fzd7 when compared to siSCR. E) Co-IP of Sdc4 with Wnt7a from satellite cell derived primary myoblasts that overexpress (OE) Sdc4-YFP and Wnt7a-HA. Co-IP was performed with an anti-flag antibody. siRNA knockdown of endogenous Fzd7 prevented Co-IP of Sdc4 with Wnt7a. F) Rac1 activation assay. Total Rac1 is shown as a loading control. Densitometric quantification represents average grey values±SEM after subtraction of the background and normalization to total Rac1. The average grey value obtained for empty vector (EV) was set to 100%, n=3, p values are *p<0.001, p<0.01, *p<0.05.
Figure 19B:
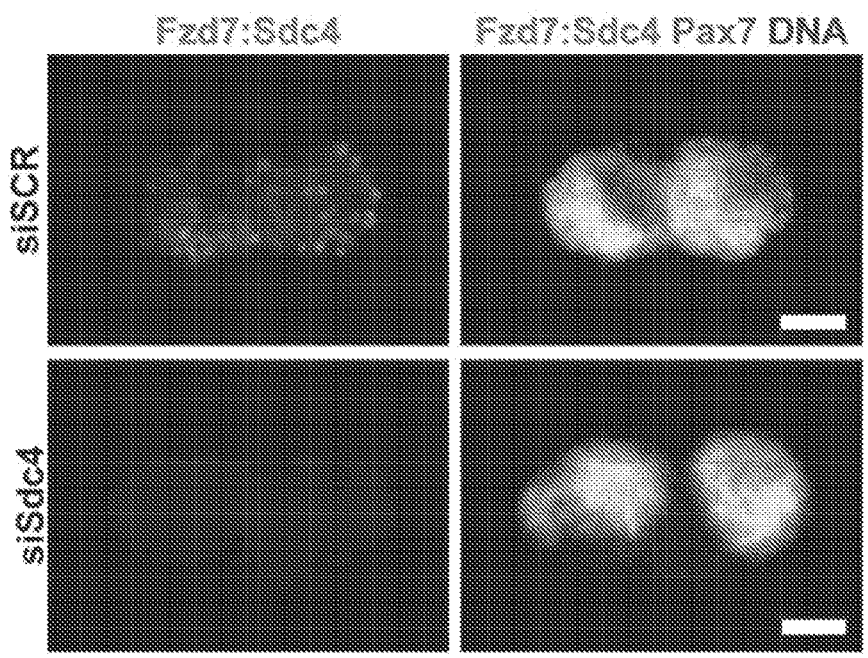

Mouse Fzd7 immunoprecipitated with mouse Sdc4 in mammalian myogenic cells. Immunoprecipitation of transfected Flag-tagged Fzd7 from primary myoblasts coprecipitated transfected YFP-tagged Sdc4 (FIG. 9E and FIG. 19A). Endogenous Fzd7 and Sdc4 were also found to form a receptor complex in satellite cells using an in-situ proximity ligation assay (PLA) (Fredriksson et al., 2002; Pisconti et al., 2010). PLA detection of endogenous Fzd7 and Sdc4 with antibodies resulted in a strong signal in activated satellite cells on cultured myofibers (FIG. 19B). This signal was abolished by knocking down Sdc4 with siRNA (siSdc4). These data indicated that Pax7+/YFP− satellite stem cells contain a Fzd7/Sdc4 receptor complex that integrates Wnt and FN signals.

Figure 9F:
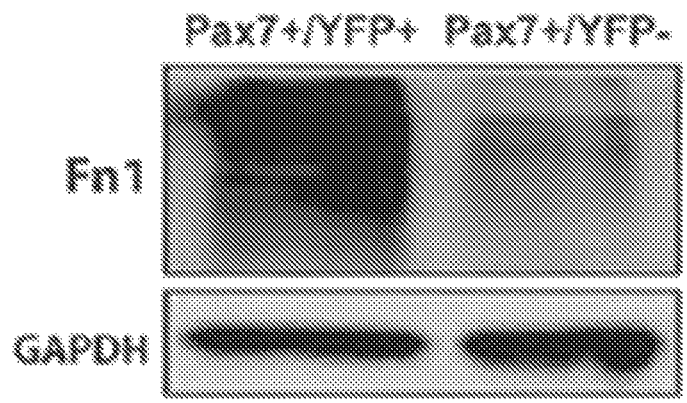
Figure 9G:
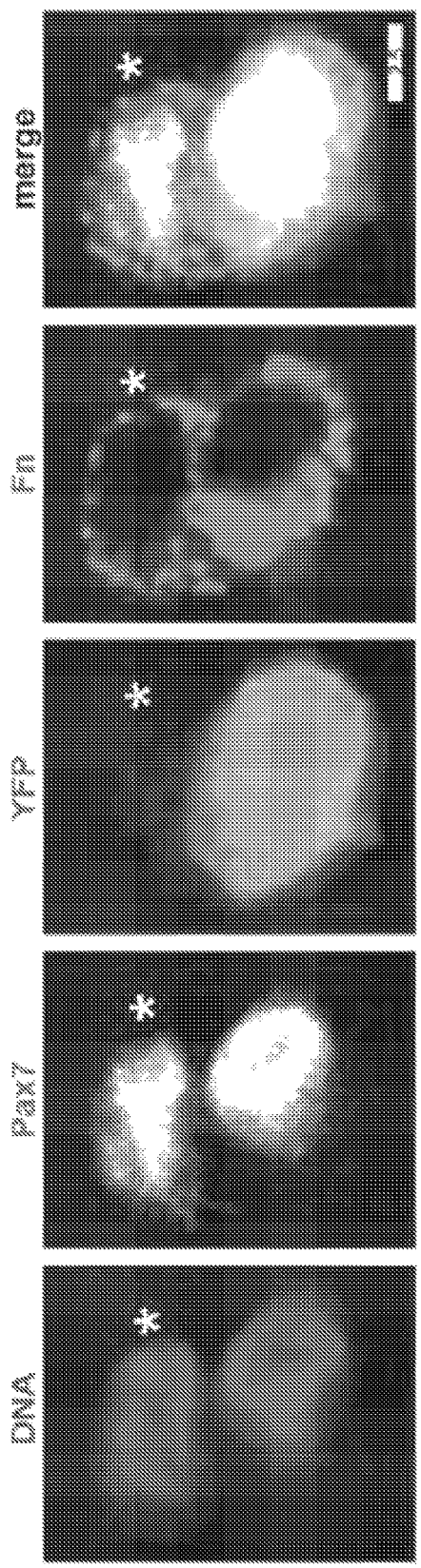
Figure 16B:
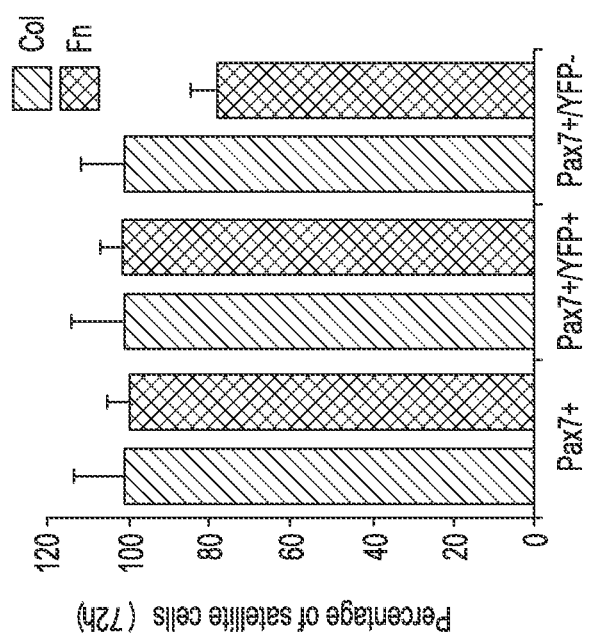
FIG. 16 shows that qPCR demonstrates lower levels of FN expression in cultured Pax7+/YFP− cells. FN alone has no significant effect on satellite cell populations. A) qPCR comparing FN expression of cultured Pax7+YFP− and Pax7+YFP+ cells. Lower expression of FN is observed in Pax7+YFP− cells. Bars represent means±SEM. n=3 replicates. p value is *p<0.05. B) Fibers were cultured for 72 hours in the presence of COL or FN. The presence of FN did not change the proportions of the different satellite cell populations significantly. Bars represent means±SEM. n=3 replicates.
Figure 16A:
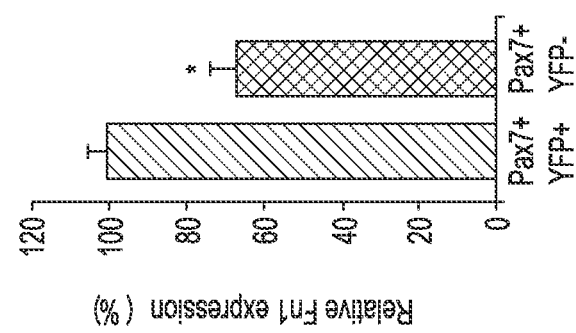

Cultured Pax7+/YFP− cells contained lower levels of FN protein and mRNA when compared to committed Pax7+/YFP+ cells (FIG. 9F, FIG. 16A). Pax7+/YFP− satellite stem cells divide asymmetrically to give rise to a committed Pax7+/YFP+ daughter cell (Kuang et al., 2007). Dividing asymmetric doublets on 42 hour fiber cultures were immunostained to confirm that satellite stem cells express lower levels of FN (FIG. 9G). These results indicated that Pax7+/YFP− satellite stem cells were responsive to FN that is released from Pax7+/YFP+ committed cells.

Figure 19C:
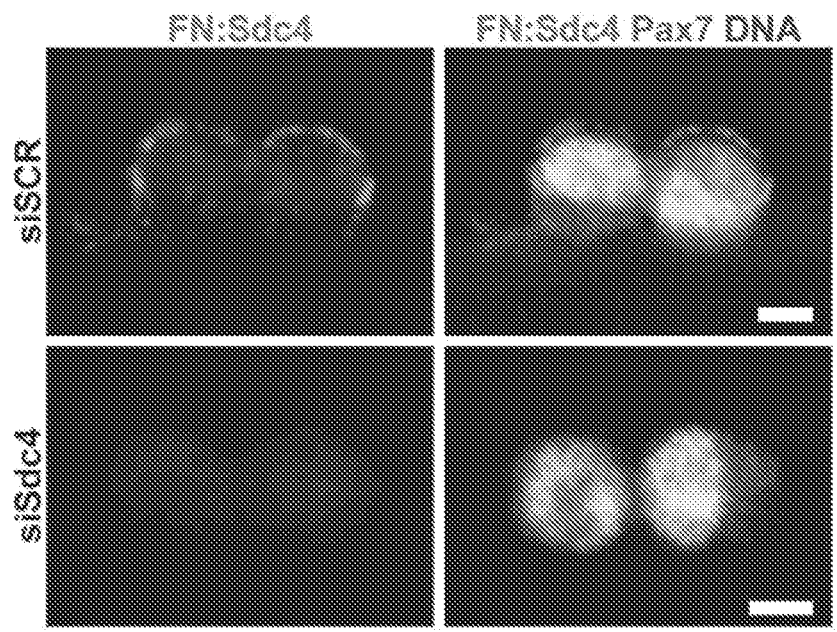

Fzd7 is expressed abundantly in Pax7+/YFP− satellite stem cells and only marginal transcript levels are detected in Pax7+/YFP+ satellite myogenic cells (Le Grand et al., 2009). Sdc4 on the other hand was expressed at relatively high levels throughout differentiation. Sdc4 is a high affinity receptor for fibronectin (FN) (Lyon et al., 2000; Woods et al., 2000). PLA was used to assess the binding of FN to Sdc4 in satellite cells, and similarly detected a strong signal in satellite cells on cultured myofibers (FIG. 19C). PLA reactivity of Sdc4 and FN antibodies on satellite cells was completely abrogated by siSdc4 treatment. Therefore, the inventors concluded that Sdc4 binds FN on activated satellite cells.

Figure 19D:
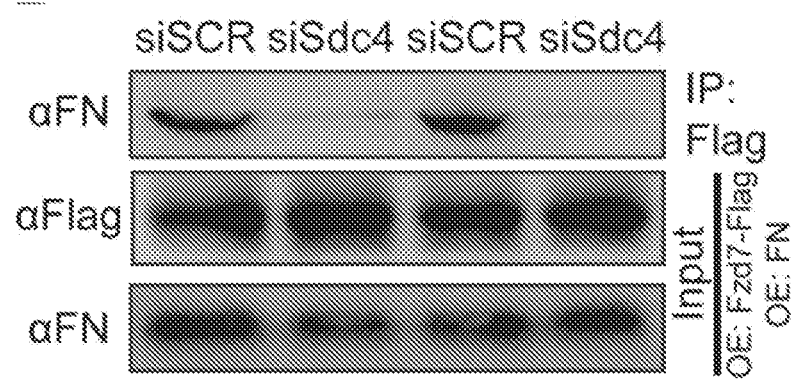
Figure 19F:
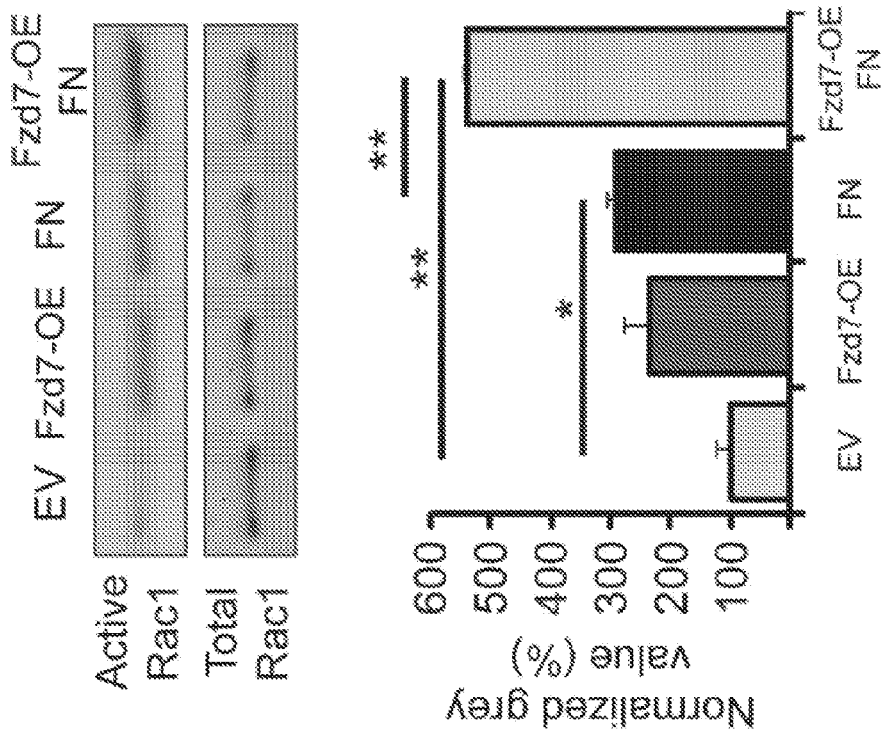
Figure 19E:
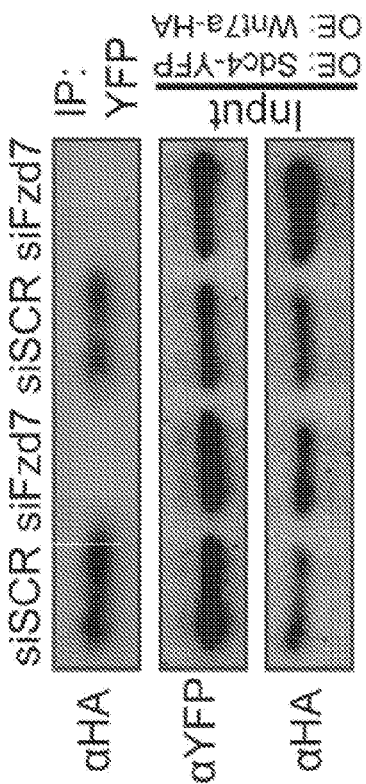

To determine whether binding of Wnt7a to Fzd7 in primary myoblasts was dependent on the presence of Sdc4 as a co-receptor, co-immunoprecipitation experiments were performed. Immunoprecipitation of Flag-tagged Fzd7 from primary myoblasts co-precipitated FN and this interaction was lost following siRNA knockdown of endogenous Sdc4 (FIG. 19D). In addition, immunoprecipitation of YFP-tagged Sdc4 co-precipitated overexpressed Wnt7a-HA, and this interaction was lost following siRNA knockdown of endogenous Fzd7 (FIG. 19E). These data indicated that Fzd7/Sdc4 co-receptor complex binds both Wnt7a and FN.

In addition, this data indicated that Fzd7 was a limiting factor for the specific function of the Fzd7/Sdc4 receptor complex in satellite stem cells. Moreover, Pax7+/YFP− satellite stem cells produced lower amounts of FN than committed Pax7+/YFP+ satellite myogenic cells. This further indicated that satellite stem cells were more sensitive to exogenous FN and that the bulk of satellite cell derived FN during muscle regeneration was released by proliferating committed cells.

Rac1 is associated with Sdc4 and is activated by FN binding (Bass et al., 2007). Rac1 is also a known effector of the PCP pathway (Seifert and Mlodzik, 2007). FN stimulation of Sdc4 facilitated Fzd7 dependent Rac1 activation. Fzd7 overexpression, or stimulation with FN resulted in increased levels of active Rac1 in primary myoblasts (FIG. 19F). In addition, FN stimulation of cells over-expressing Fzd7 resulted in markedly increased levels of Rac1 activation. These data show that Fzd7/Sdc4-Rac1 coreceptor complex integrated Wnt7a and FN signals to activate PCP signaling.

Example 8

FN and Wnt7a Signal Through the Fzd7/Sdc4 Complex to Stimulate Satellite Stem Cell Symmetric Divisions Co-activation of the Fzd7/Sdc4 receptor complex by FN and Wnt7a was determined by applying FN and Wnt7a to Pax7+/YFP− satellite stem cells in culture.

Both plasma and cellular FN contain the Hep II domain for binding to Sdc4 (Singh et al., 2010; Woods et al., 2000). Standard fiber medium contains 20% Fetal bovine serum (FBS) resulting in a final concentration around 5-15 μg/ml in the medium (Hayman and Ruoslahti, 1979; Sochorova et al., 1983). The medium was supplemented with an additional 25 μg/ml FN to determine the effect of FN on Pax7+/YFP− satellite stem cells. As a control, the concentration of the ECM component Collagen (COL) was similarly increased. Neither FN nor COL alone significantly affected Pax7+/YFP− satellite stem cells in 42 hour fiber cultures (FIG. 10A).

It was previously described that the COL control in combination with Wnt7a (COL&Wnt7a) lead to an increase in the number of Pax7+/YFP− satellite stem cells (Le Grand et al., 2009). After 42 h of culture, addition of Wnt7a with COL (COL&Wnt7a) resulted in a 73% increase in the number of Pax7+/YFP− satellite stem cells (FIG. 10A), and a 108% increase in the proportion of symmetric cell divisions when compared to COL alone (FIG. 10B). Surprisingly, FN applied together with Wnt7a (FN&Wnt7a) lead to a synergistic increase in the number of Pax7+/YFP− satellite stem cells that was significantly higher than that observed for COL&Wnt7a: a 147% increase in the number of satellite stem cells (FIG. 10A). This synergistic effect was confirmed by scoring a 163% increase in the proportion of symmetric Pax7+/YFP− cell divisions (FIG. 10B).

Figure 10D:
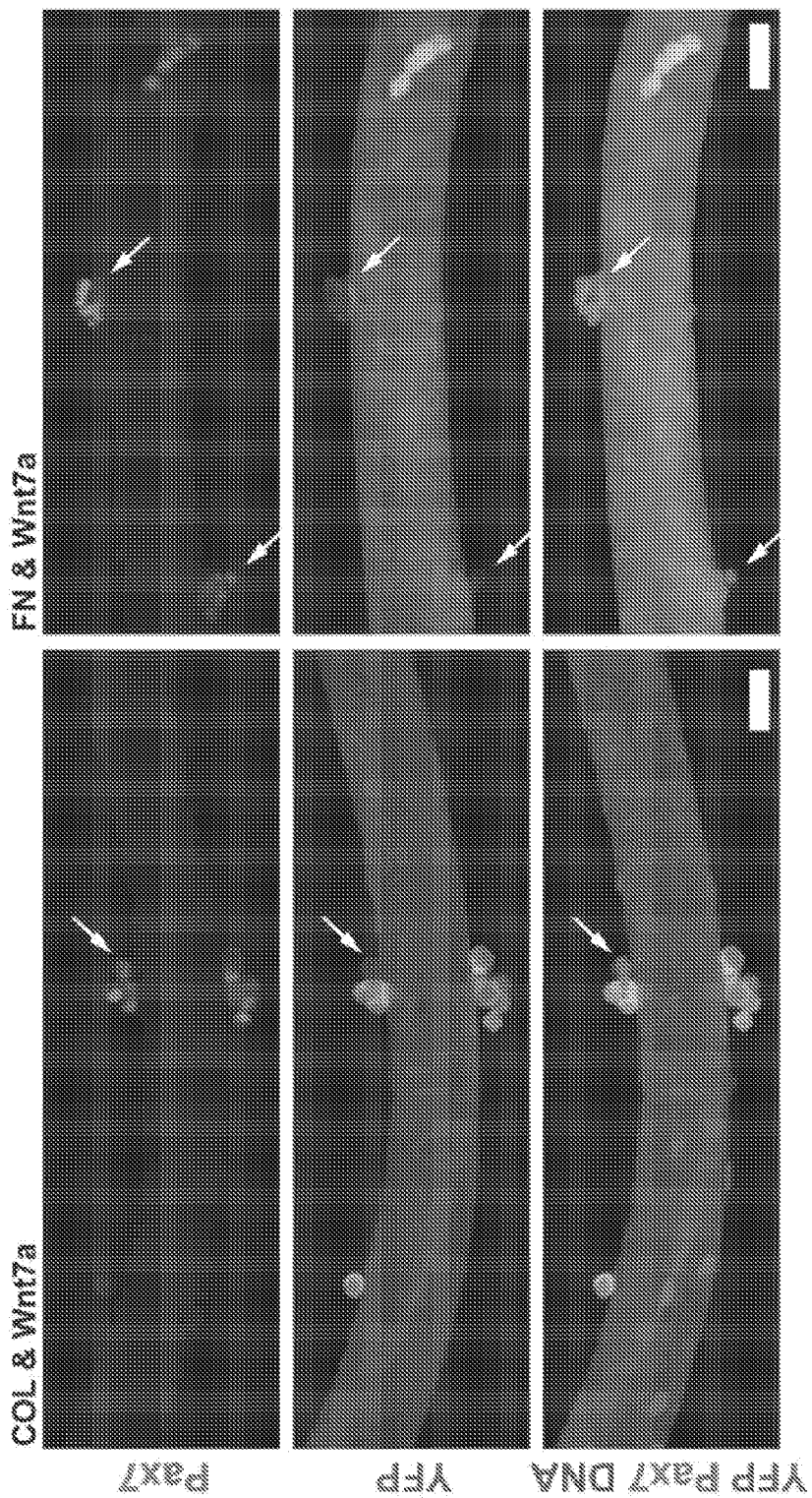
FIG. 10 shows that Sdc4 and Fzd7 synergize to activate the symmetric expansion of Pax7$^+$/YFP$^-$ satellite stem cells. A) Myofibers were isolated and cultured for 42 hours in the presence of Collagen (COL), FN, COL and Wnt7a (COL&Wnt7a) or FN and Wnt7a (FN&Wnt7a). FN synergizes with Wnt7a to drive the expansion of Pax7$^+$/YFP$^-$ cells. Bars represent means±SEM. n=4. p values are ***p<0.001; *p<0.05. B) Quantification of Pax7$^+$/YFP$^-$ symmetric divisions after 42 hours in the presence of COL, FN, COL&Wnt7a or FN&Wnt7a. Bars represent means±SEM. n=4. p values are **p<0.01; *p<0.05. C) Quantification of satellite cell populations after 72 hours in the presence of COL, FN, COL&Wnt7a or FN&Wnt7a. Bars represent means±SEM. n=3. p values are **p<0.01; *p<0.05. D) Representative pictures illustrating the effect of FN & Wnt7a after 72 hours culture. Arrows indicate Pax7$^+$/YFP$^-$ cells. Scale bar=25 µm. E) and F) Blocking antibodies to Sdc4 prevent the mitogenic effect of Wnt7a on satellite stem cells (αSdc4&Wnt7a) when compared to an unspecific IgG (IgG&Wnt7a) after 42 hours of fiber culture. Inhibition of Sdc4 also slightly decreased numbers of Pax7$^+$/YFP$^-$ cells. Bars represent means±SEM. n=3. p value is **p<0.01. G) Quantification of satellite cell populations after 42 h of myofiber culture in the presence of PBS vehicle, Tenascin-C (TEN), PBS&Wnt7a or TEN&Wnt7a. TEN inhibition of FN binding to Sdc4 antagonizes the effect of Wnt7a on satellite stem cells. Bars represent means±SEM. n=3. p values is *p<0.05.

By 72 h of culture, FN&Wnt7a treatment resulted in 156% increase in numbers of satellite stem cells relative to COL&Wnt7a treatment (FIG. 10C). Strikingly, FN&Wnt7a treatment resulted in the formation of large homogeneous clusters of Pax7+/YFP− satellite stem cells after 72 h of myofiber culture (FIG. 10D). Again, neither FN nor COL alone had a significant effect on satellite cells after 72 hours of fiber culture (FIG. 16B). In addition, numbers of Pax7+/YFP+ cells were unchanged under all conditions at 42 hours and slightly increased by ~38% at 72 hours in the FN&Wnt7a condition (FIGS. 20A and 20B).

Figure 10G:
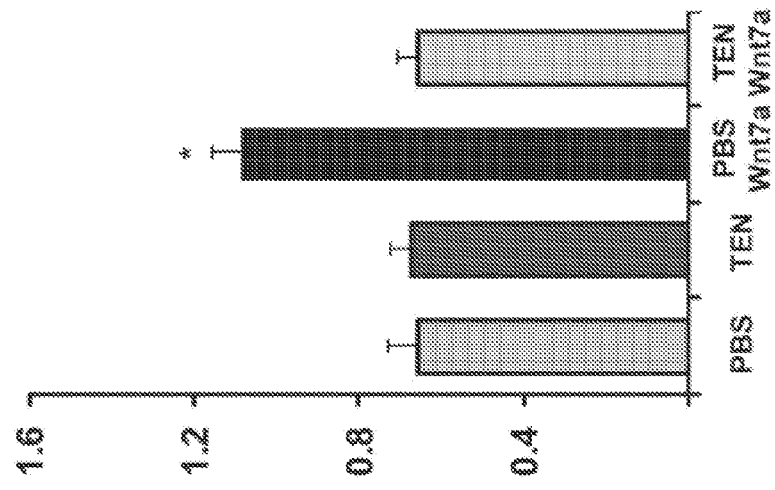
Figure 10F:
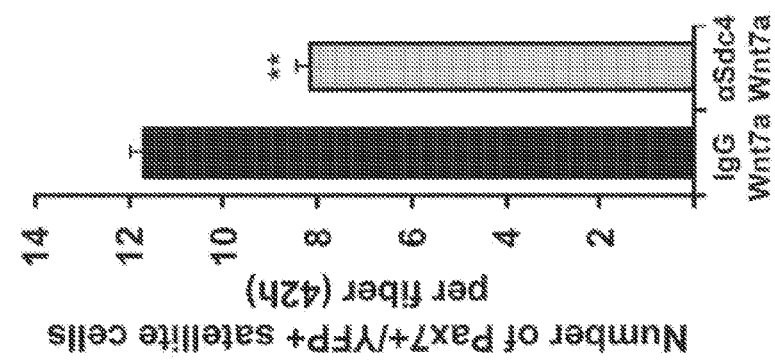
Figure 10E:
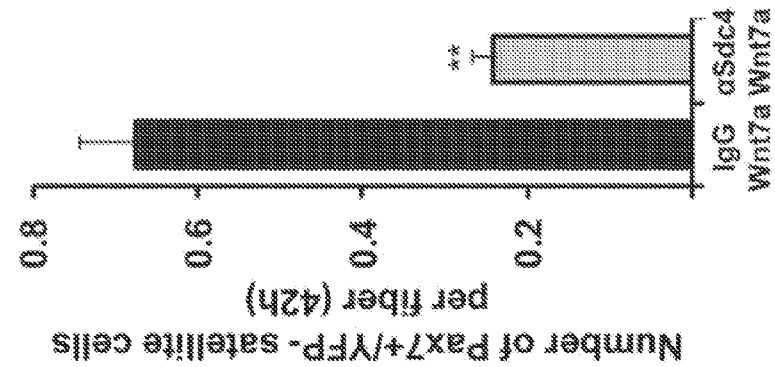

Unusually large clusters of Pax7+/YFP− satellite stem cells were found on FN&Wnt7a treated fibers after 72 hours of culture (FIG. 10D). To confirm that a functional Fzd7/Sdc4 receptor complex was required for Wnt7a mediated expansion of the Pax7+/YFP− satellite stem cell pool Sdc4 was blocked with an anti-Sdc4 antibody (Cornelison et al., 2004). When compared to an unspecific IgG in combination with Wnt7a (IgG&Wnt7a), Sdc4 antibody and Wnt7a (αSdc4&Wnt7a) led to a 30% decrease in the numbers of Pax7+/YFP+ satellite myogenic cells, and a 64% decrease in Pax7+/YFP− satellite stem cells after 42 h of myofiber culture (FIGS. 10E and 10F). Moreover, blocking of FN binding to Sdc4 with Tenascin-C (TEN) (Huang et al., 2001) selectively impaired the ability of Wnt7a to stimulate the expansion of the Pax7+/YFP− satellite stem cell pool on myofibers cultured for 42 h (FIG. 10G) without any observed effect on Pax7+/YFP+ satellite myogenic cells (FIG. 20C). However, the effect of αSdc4&Wnt7a was pronounced for Pax7+/YFP− satellite stem cells.

The data showed that the Fzd7/Sdc4 receptor complex exists in mammalian cells and that Wnt7a signaling through Fzd7 occurs through ligation of FN to its receptor Sdc4. In particular embodiments, the present invention contemplates, that other Sdc4 ligands, e.g., FGF, co-activate the Fzd7/Sdc4 receptor complex and further synergistically activate the PCP pathway in satellite stem cells.

Example 9

FN Plays a Role in the Maintenance of the Satellite Cell Pool

The foregoing examples indicate that Fzd7 and Sdc4 are co-receptors, and that Wnt7a signaling through Fzd7 requires ligation of FN to its receptor Sdc4. Therefore, activated satellite cells upregulate FN to remodel their niche and FN expression provides feedback to modulate Wnt7a-induced PCP signaling in satellite cells.

Figure 23A:
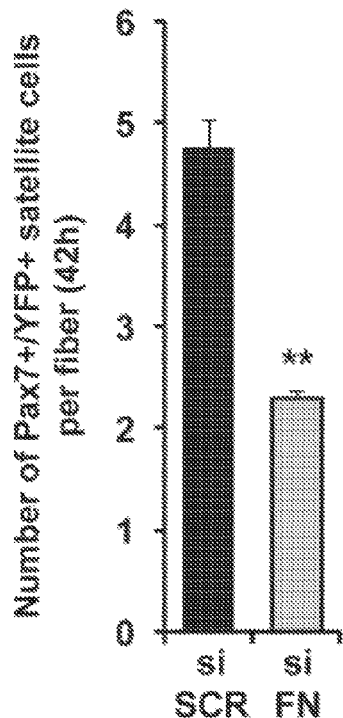
FIG. 23 shows that knock down of FN in satellite cells impairs their repopulation of muscle. A) FN was knocked down in satellite cells on isolated myofibers in pFN free culture medium for 42 h. siFN reduces the number of Pax7$^+$/YFP$^+$ cells per fiber when compared to the siSCR control. Bars represent means±SEM. n=3. p values are **p<0.01; *p<0.05. B) siFN reduced the number of symmetric Pax7$^+$/YFP$^+$ divisions. Bars represent means±SEM. n=3. p value is *p<0.05. C) Knockdown of FN severely reduced the number of Pax7$^+$/YFP$^-$ cells per fiber. Bars represent means±SEM. n=3. p value is *p<0.05. D) No symmetric Pax7$^+$/YFP$^-$ division was detected (n.d.=none detected) in the siFN condition when compared to siSCR. Bars represent means±SEM. n=3. E) Freshly FACS purified satellite cells from Pax7-zsGreen mice were transfected with siFN or siSCR and injected into regenerating muscle. Three weeks after transplantation, donor derived cells are observed as zsGreen$^+$/Pax7$^+$ cells (yellow arrowheads) in host tissue. Scale bar=50 μm. F) Knockdown of FN in transplanted satellite cells resulted in a 65% reduction in their number. Only Pax7$^+$/zsGreen$^+$ donor cells were included in the quantification. Resident Pax7$^+$/zsGreen$^-$ satellite cells displayed no significant change in their numbers (see FIG. 25B). Bars represent means±SEM. n=3. p value is *p<0.05. G) Whole-muscle knockdown of FN by intramuscular injection of a self-delivering siFN reduced the number of satellite cells by 59% at day ten. Bars represent means±SEM. n=3. p value is *p<0.05.

The cell-autonomous role of satellite cell-derived FN was examined. Satellite cells were prospectively isolated; an ex-vivo siRNA knockdown of FN was performed; the cells were transplanted back into muscle; and repopulation of the satellite cell niche was enumerated. Quiescent satellite cells were FACS purified from Pax7-zsGreen reporter mice (Bosnakovski et al., 2008) and transfected with a validated duplexed silencer select siRNA for FN (siFN) (Daley et al., 2009; Daley et al., 2011) or with a scrambled siRNA (siSCR) for three hours on ice. After washing, 15,000 transfected satellite cells were either injected into the TA of immunosupressed mice that had received a CTX injury two days previously, or cultured for three days for qPCR validation of knockdown efficiency. Three weeks after transplantation, mice were sacrificed and the engraftment of Pax7 and zsGreen double-positive (Pax7$^+$/zsGreen$^+$) cells was assessed by immunostaining of muscle sections (FIG. 23A).

Figure 23B:
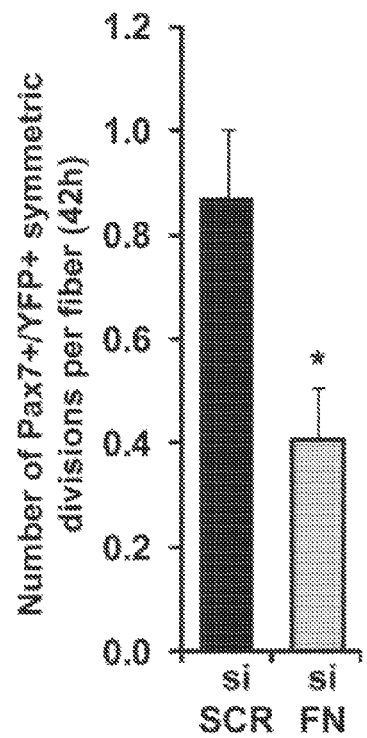
Figure 23C:
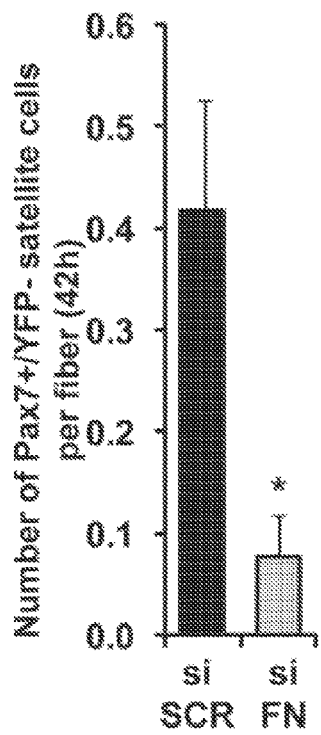
Figure 24A:
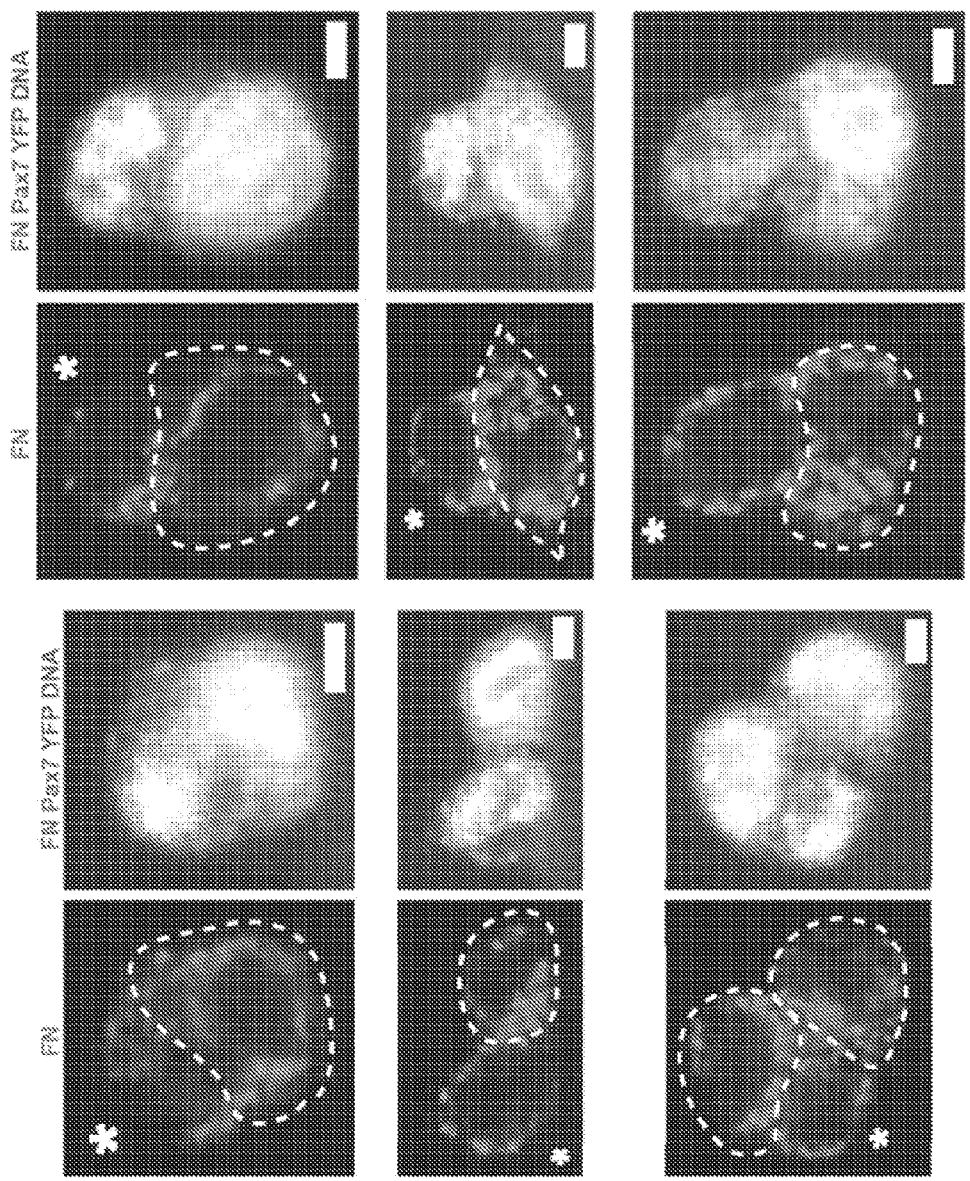
FIG. 24 shows FN expression in satellite cell subpopulations. A) Representative examples of asymmetric divisions that were densitometrically quantified for immunostaining grey values for FN. The YFP$^+$ cell is outlined and the YFP$^-$ cell is marked by an asterisk in the picture showing single FN staining for each division. Scale bar=5 μm. B) and C)

Ex-vivo siRNA knockdown of FN in prospectively isolated satellite cells resulted in a 65% reduction of their engraftment three weeks following injection (FIG. 23B). Transfection of siRNA reduced FN by 50% after three days in culture (FIG. 24A). In addition, resident satellite cells in the injected TA muscle displayed no significant change in their numbers (FIG. 24B). Direct injection of self-delivering FN siRNA into the TA muscles at three days after CTX injection resulted in a 59% reduction in satellite cell numbers relative to siSCR injected muscles when examined 10 days after injury (FIGS. 23C and 24C). Injection of siRNA into whole muscle reduced FN levels by 58% after 5 days (FIG. 24D). Taken together, these results demonstrate that cell-autonomous expression of FN by activated satellite cells within their niche plays a significant role in the homeostatic regulation of the satellite cell pool size during regenerative myogenesis.

Example 10

FN and Wnt7a Synergize In-Vivo

To elucidate whether increased FN levels were capable of boosting the satellite stem cell pool or modulating the satellite stem cell response to Wnt7a stimulation in-vivo, Wnt7a-HA and/or FN plasmids were electroporated into TA muscle fibers of Myf5-nLacZ mice and the number of satellite cells was quantified after seven days. Similar to Myf5-Cre-ROSA-YFP, the Myf5-nLacZ allele was used to detect satellite stem cells as Pax7$^+$/β-Gal$^-$. The nuclear localization of β-Gal allowed for superior staining for satellite stem cells on muscle cross sections.

Figure 11A:
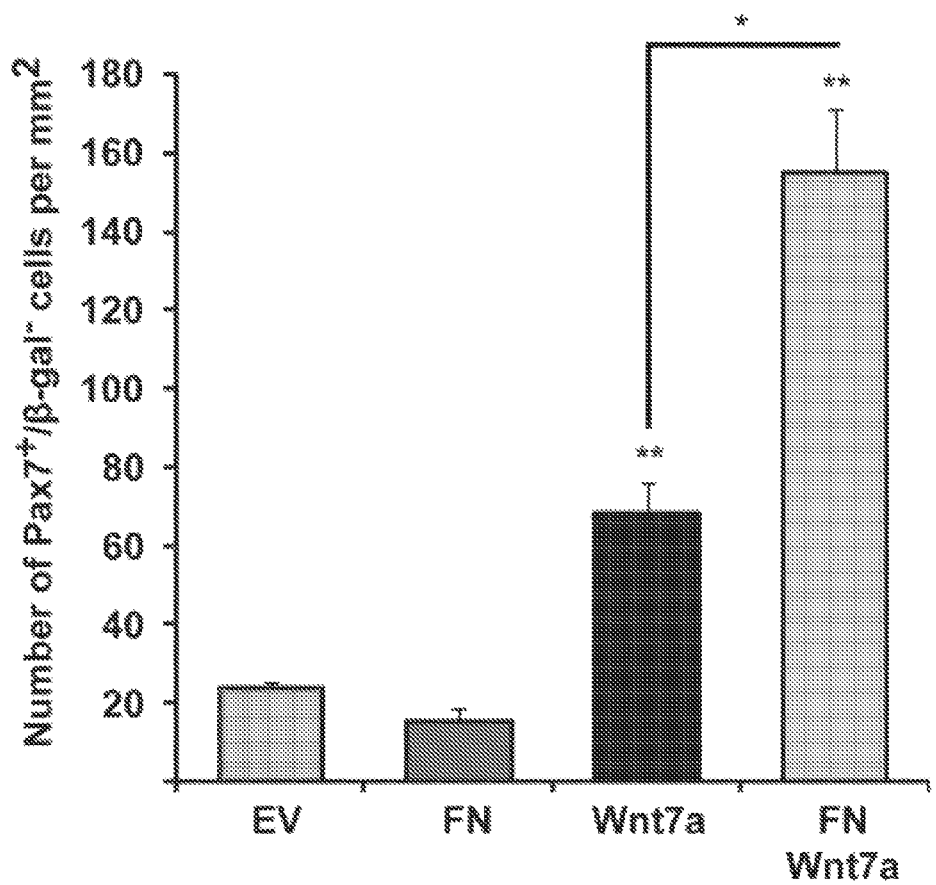
FIG. 11 shows that electroporation of Wnt7a with FN increases the amount of satellite stem cells in-situ after 7 days. A) Empty vector (EV), FN, Wnt7a, and FN&Wnt7a were electroporated into muscles of Myf5-LacZ mice. The electro-damage induced regeneration is accompanied by an increase in the amount of Pax7$^+$/β-gal$^-$ stem cells for Wnt7a and FN&Wnt7a when compared to empty vector. A significant increase in Pax7$^+$/β-gal$^-$ satellite stem cell numbers can be observed for FN&Wnt7a when compared to Wnt7a alone. Bars represent means±SEM. n=3. p values are *p<0.001; p<0.01; *p<0.05. B) Representative pictures illustrating the effect of Wnt7a and FN & Wnt7a. Arrows indicate Pax7$^+$/β-gal$^-$ satellite stem cells. Scale bar=50 µm.
Figure 11B:
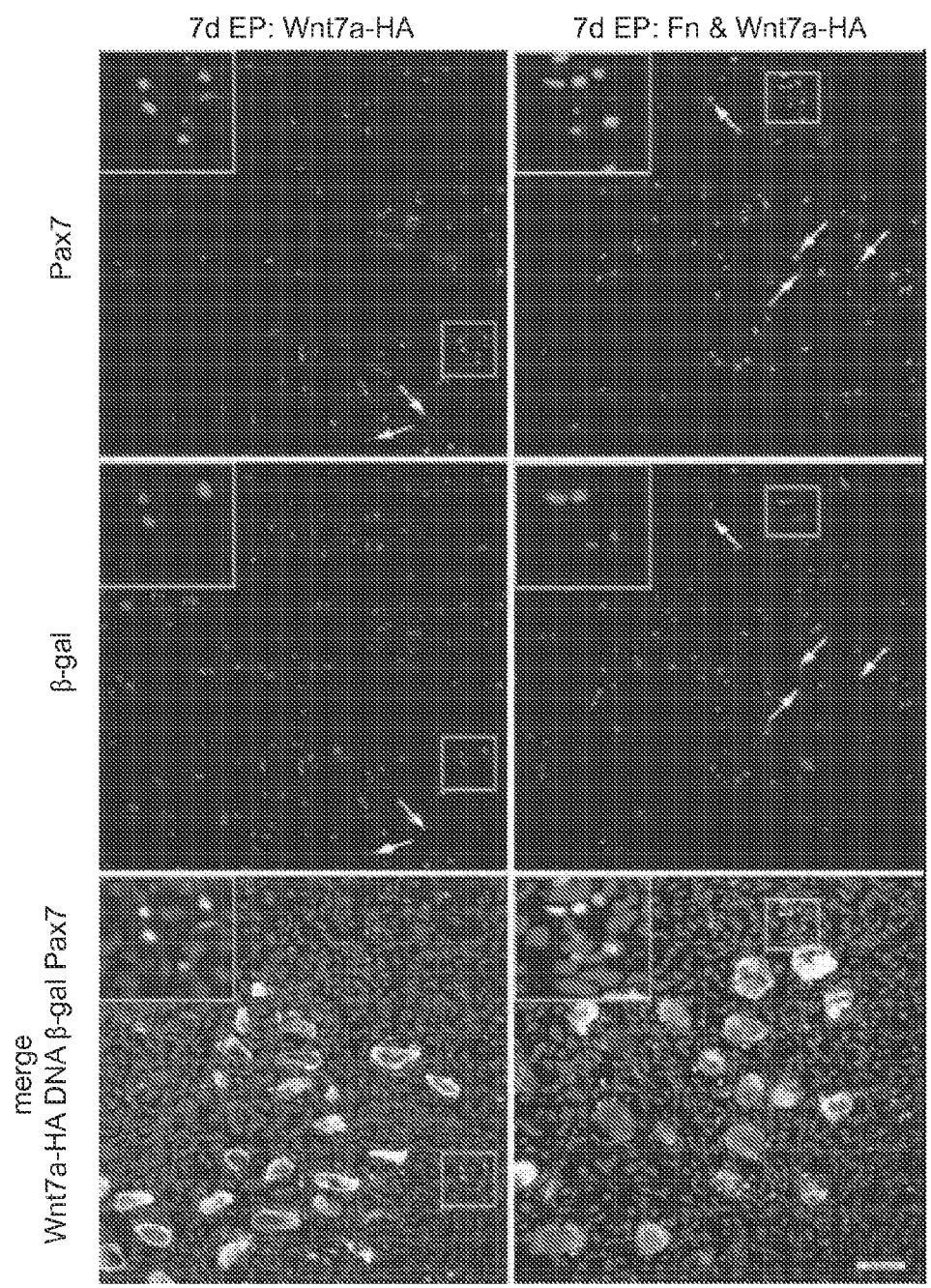

The electroporation (EP) caused significant electro-damage and most muscle fibers were centralized post EP. β-Gal antibody-staining revealed that CMV-FN plasmid alone did not significantly change numbers of Pax7$^+$/β-Gal-satellite cells (FIG. 11A). However, CMV-Wnt7a increased numbers Pax7$^+$/β-Gal-satellite cells by 289%. Importantly, the combination CMV-FN and CMV-Wnt7a plasmid lead to a 654% increase in the number of Pax7$^+$/β-Gal-satellite cells. Pax7$^+$/β-Gal-satellite cells were evenly distributed throughout the muscle cross-sections and we did not observe focal accumulation around Wn7a-HA expressing fibers (FIG. 11B).

FN activated the Fzd7/Sdc4 receptor complex in conjunction with Wnt7a leading to a synergistic expansion of the Myf5 negative satellite stem cell pool. This result indicated that Wnt7a and FN stimulate PCP signaling to drive the symmetric expansion of satellite stem cells during regenerative myogenesis. The present invention contemplates, in part, that a high tissue content of satellite stem cells facilitates the generation of committed daughter cells through asymmetric divisions. In a particular embodiment, the satellite stem cell pool is synergistically expanded by transient exposure to FN and Wnt7a.

Example 11

Decreasing FN Levels are Required for Lineage Progression and Differentiation

Figure 12A:
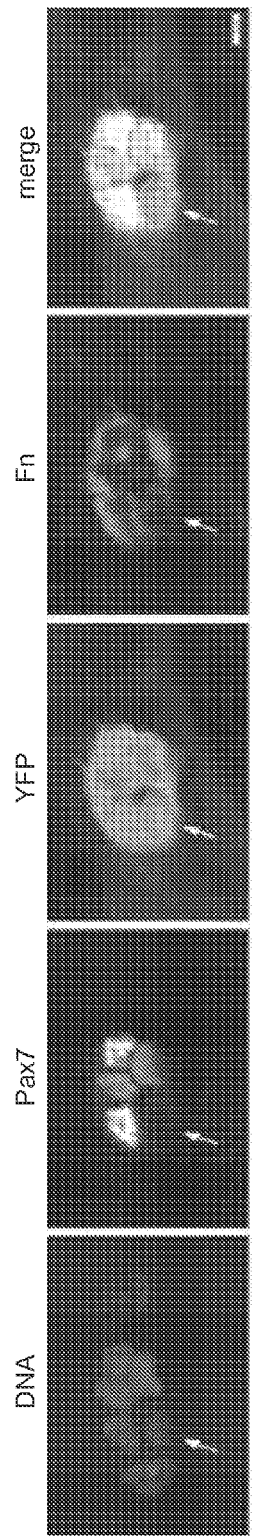
FIG. 12 shows that exposure of differentiating cells to FN impairs myogenesis. A) Differentiating YFP$^+$ cells which have downregulated Pax7 expression decrease FN expression (Arrow). Scale bar=5 µm. B) qPCR demonstrating that FN expression decreases during myotube formation. Bars represent means±SEM. n=3. p values are *p<0.001; p<0.01. C) Myoblasts were differentiated on either COL or on FN coated plates for 2 days. Impaired myotube formation and expression of Myosin heavy chain (MHC) can be observed for the cells on FN. Mononuclear MHC- cells are abundant in the presence of FN (Arrowheads). Scale bar=20 µm. D) Significantly fewer MHC+ cells were found on FN coated dishes after 2 days of differentiation. Bars represent means±SEM. n=3. p value is p<0.01. E) Cultured myoblasts express less Myf5 and MyoD after 2 days of differentiation on FN coated dishes when compared to COL coating. Bars represent means±SEM. n=3. p values are p<0.01; *p<0.05. F) siRNA knockdown of FN (siFN) from myoblasts before they were differentiated for 1 day facilitates myotube formation and increase MHC levels when compared to the scrambled siRNA control (siScr). Scale bar=20 µm. H) The fusion index (percentage of nuclei present in myotubes compared to the total number of nuclei) was quantified. Significantly increased myotube formation was observed when FN was knocked down. Bars represent means±SEM. n=3. p value is *p<0.05.
Figure 12C:
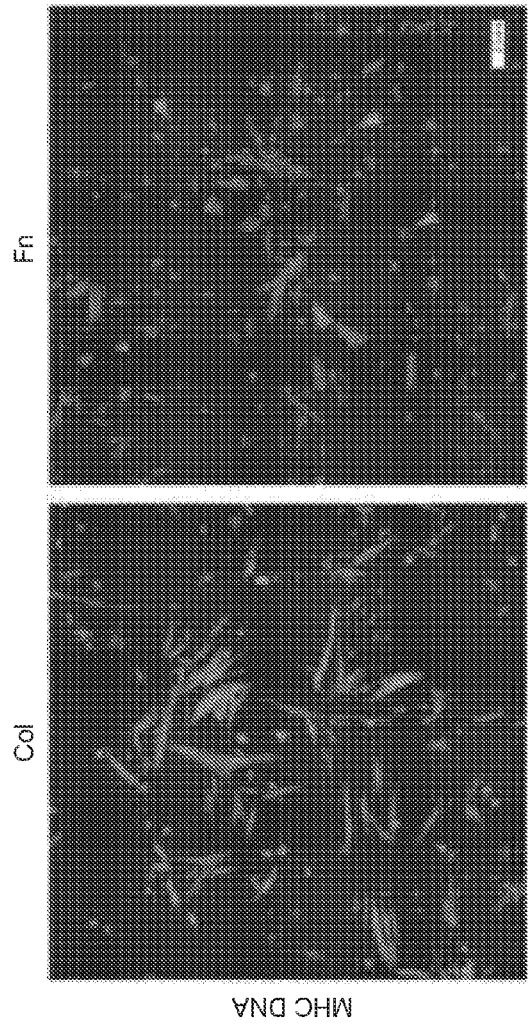
Figure 12B:
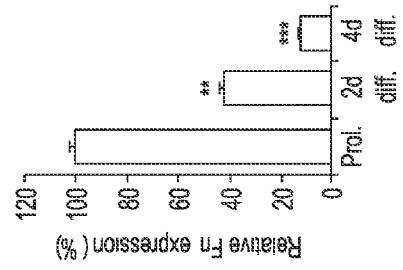

In 72 hour fiber cultures, a subset of YFP$^+$ satellite cells ceased to express Pax7 (Pax7$^-$/YFP$^+$). Downregulation of Pax7 was indicative of terminal differentiation. It was observed that Pax7$^-$/YFP$^+$ cells almost exclusively decreased FN protein levels (FIG. 12A). Moreover, qPCR confirmed that differentiating myoblasts dramatically downregulate FN expression (FIG. 12B).

Figure 12D:
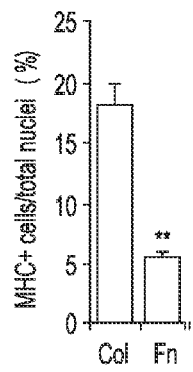

Satellite cell derived primary myoblasts were plated on FN or COL to determine the effect of sustained FN levels on differentiation. Myoblasts that were differentiated for 2 days on FN displayed impaired fusion and retained mononuclear cells (FIG. 12C). The fraction of MHC positive (MHC+) cells per total nuclei was strongly decreased on FN when compared to COL (FIG. 12D). Mononuclear MHC– cells were indicative of an anti-differentiation effect of FN.

Figure 12E:
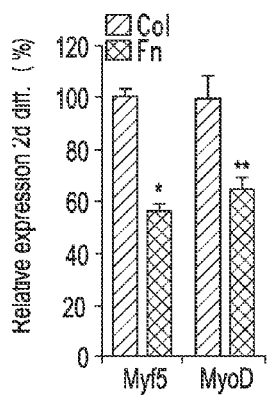
Figure 12G:
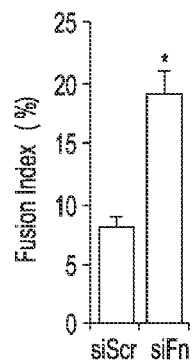
Figure 12F:
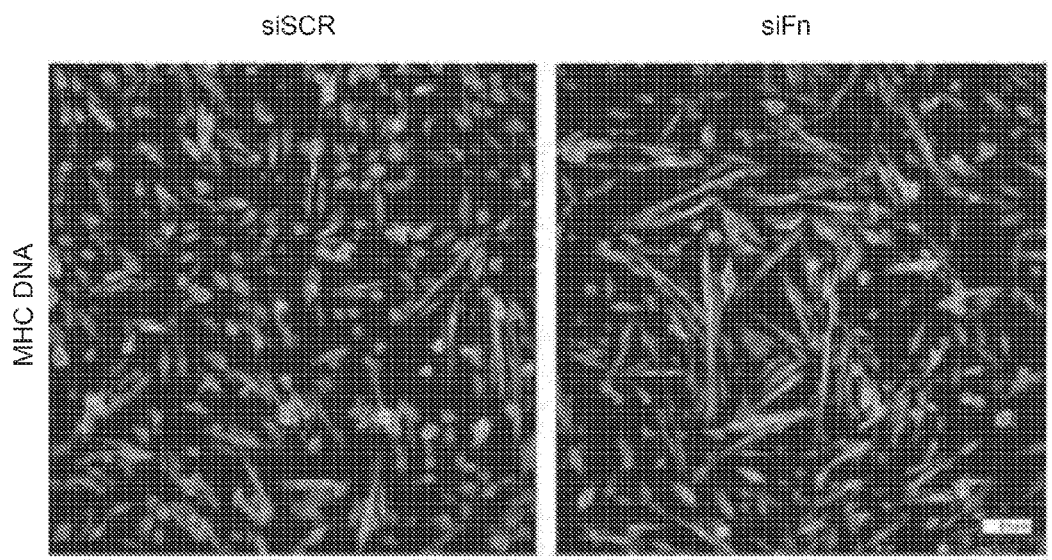

To test whether MRF levels are higher in cells that were differentiated on FN we determined the expression of Myf5 and MyoD. Myf5 and MyoD were expressed at significantly lower levels in cells differentiated on FN when compared to COL (FIG. 12E). We concluded that, in contrast to its beneficial effects for Pax7$^+$/YFP$^-$ satellite stem cells, FN had negative effects on terminal differentiation which were due to the conversion of myoblasts into a non-myogenic MHC– and MRF– cell type.

siRNA knockdown of FN (siFN) in primary myoblasts prior to differentiation, accelerated the formation of MHC+ myotubes and increased the fusion index when compared to a scrambled siRNA (siSCR) (FIGS. 12F&G), and confirmed these observations.

In advanced stages of regeneration, the majority of committed satellite cells downregulated FN expression which allowed them to differentiate and to become fusion competent. The data showed that differentiating primary myoblasts in the presence of FN become MHC– mononuclear cells.

Example 12

Sustained Levels of FN Force Satellite Cells into the Myofibroblast Lineage

Figure 13A:
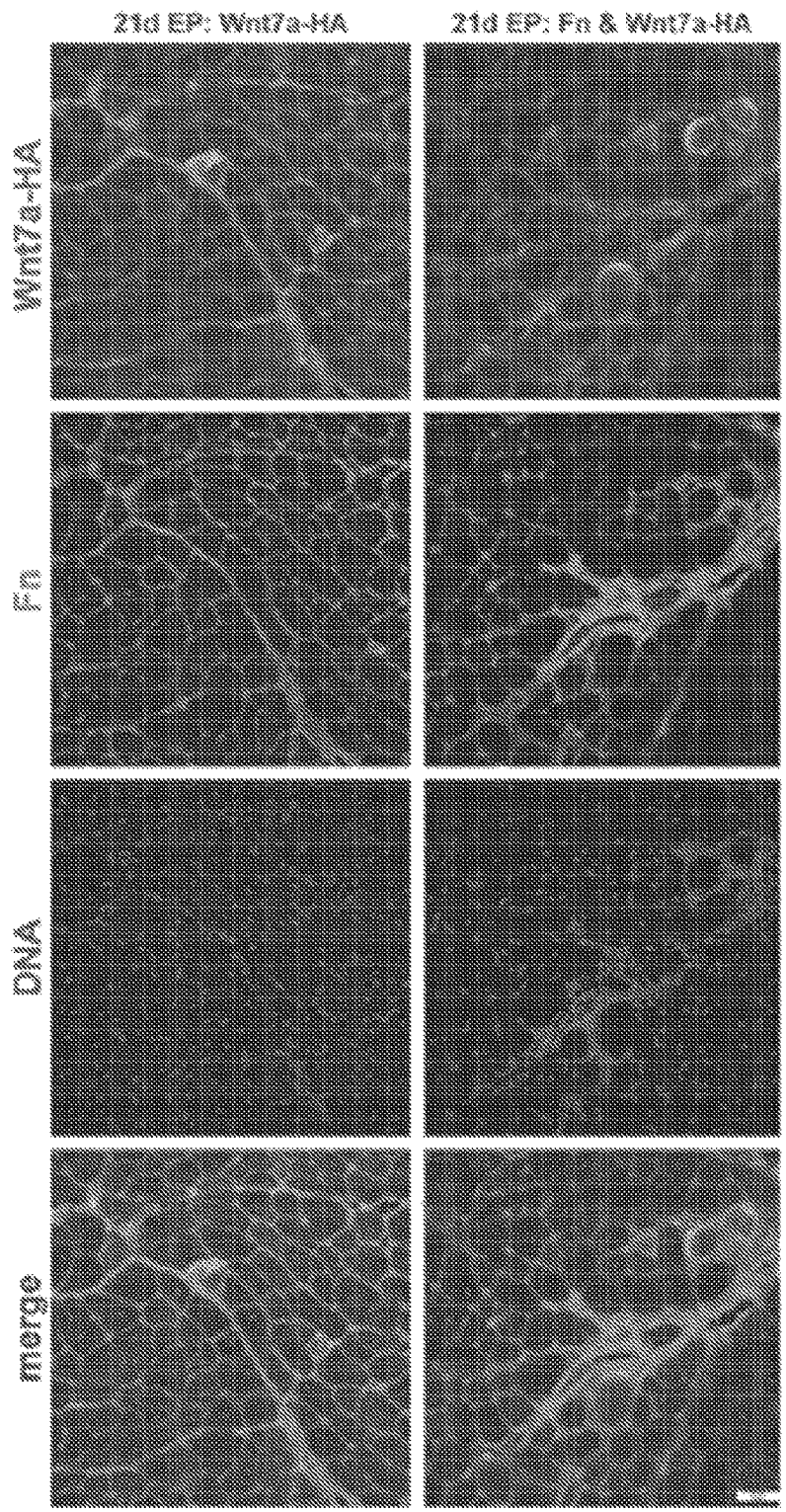
FIG. 13 shows that sustained exposure to FN in late stages of muscle regeneration converts satellite cells into myofibroblasts. A) After 21 days of electroporation FN&Wnt7a lead to an accumulation of mononuclear cells in the FN rich periphery of electroporated fibers when compared to Wnt7a alone. Scale bar=50 µm. B) Mononuclear cells in the periphery of FN&Wnt7a expressing fibers are not Pax7$^+$. Scale bar=20 µm. C) Mononuclear cells in the periphery of FN&Wnt7a expressing fibers stain for alpha smooth muscle actin (α-SMA), a myofibroblast marker. Scale bar=20 µm. D) For lineage tracing, satellite cells were irreversibly labeled in-vivo with tdTomato prior to EP of FN&Wnt7a. E) Cells which accumulate in the periphery of electroporated fibers are tdTomato positive and therefore satellite cell derived. Scale bar=20 µm.
Figure 13B:
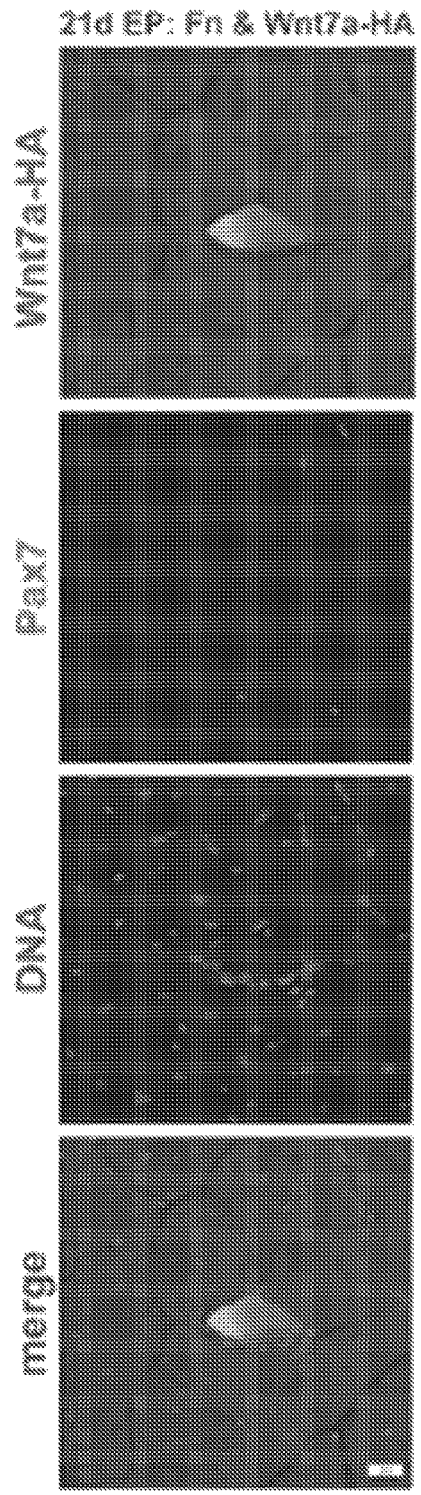
Figure 13C:
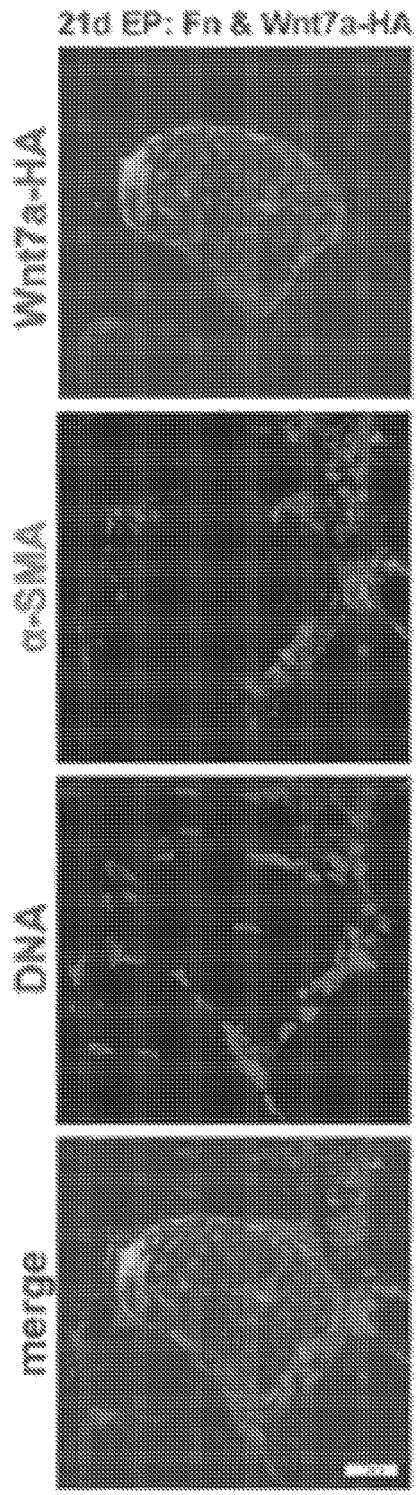
Figure 17:
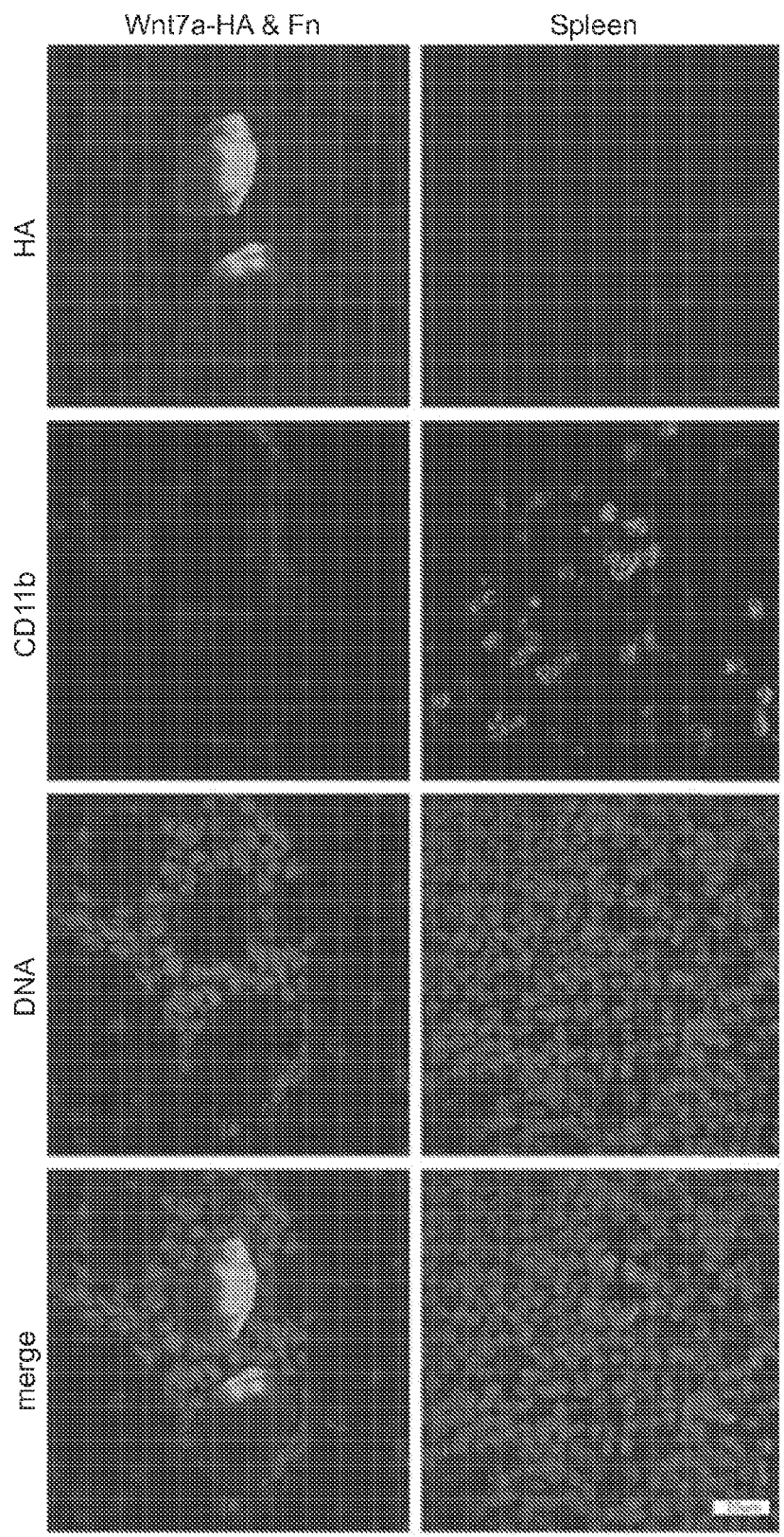
FIG. 17 shows that mononuclear cells which accumulate in ectopic FN rich areas 21 days after electroporation are not macrophages, granulocytes or killer cells. CD11b staining of sections from muscle that was electroporated with FN&Wnt7a-HA for 21 days or sections trough the spleen as a positive control. No CD11b reactivity can be observed in the periphery of the fibers expressing FN&Wnt7a-HA while strong staining is observed in the spleen. Scale bar=20 μm.

It was determined that sustained levels of FN have anti-myogenic effects in-vivo. After 21 days of EP with FN&Wnt7a-HA, a dramatic fibrosis was observed in the proximity of targeted fibers when compared to Wnt7a-HA alone (FIG. 13A). Mononuclear cells which were Pax7 negative and positive for the myofibroblast marker alpha smooth muscle actin (Pax7$^-$/α-SMA$^+$) accumulated in the FN rich fibrotic areas in the periphery of electroporated fibers (FIGS. 13B&C). None of these mononuclear cells stained positive for CD11b, excluding macrophages, granulocytes or killer cells (FIG. 17).

We used Pax7-Cre-ERT-ROSA-tdTomato mice to determine whether prolonged exposure to FN may force satellite cells into an alternative Pax7$^-$/α-SMA$^+$ lineage.

Tamoxifen injection of these mice leads to active Cre recombinase which irreversibly labels all Pax7 expressing satellite cells with the fluorescent protein tdTomato (FIG.

Figure 13D:
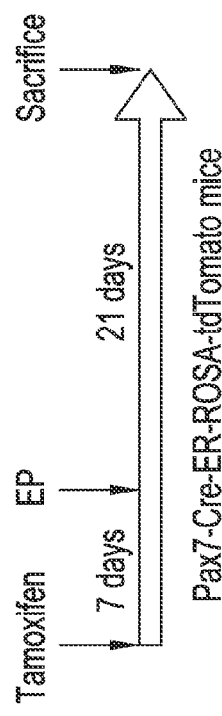

18A). In order to lineage trace satellite cells upon EP with FN&Wnt7a-HA we induced Pax7-Cre-ER-ROSA-tdTomato mice 1 week prior to EP with Tamoxifen and analyzed the mice 21 days after the plasmid transfer (FIG. 13D).

Figure 13E:
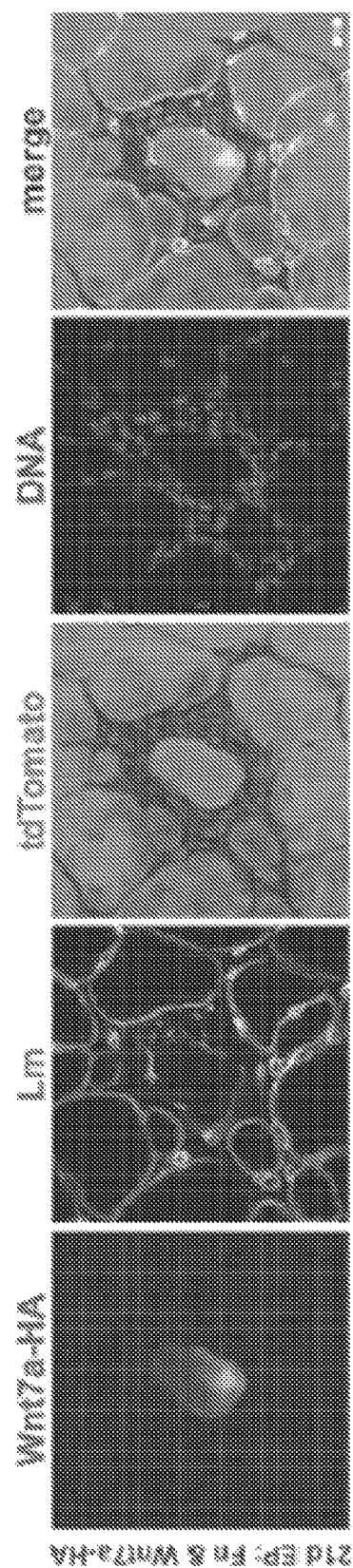
Figure 18B:
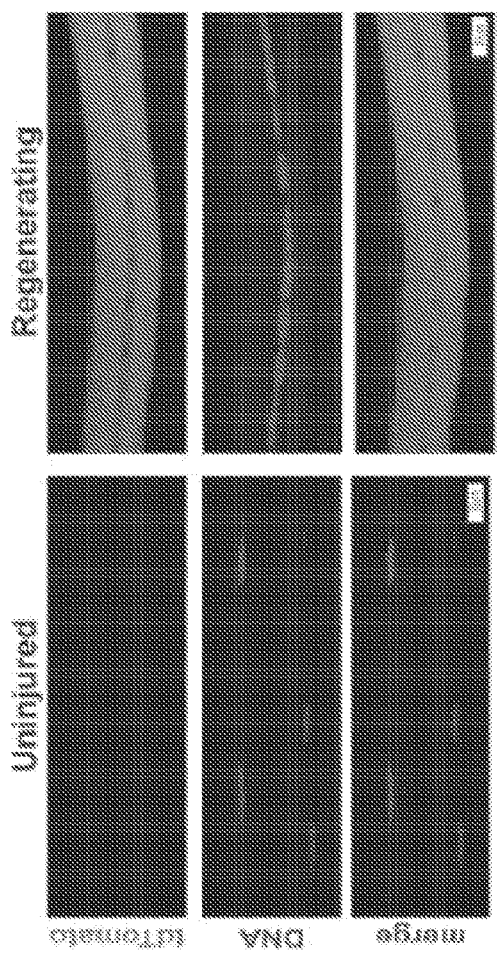
FIG. 18 shows that the Pax7-tdTomato lineage driver specifically labels Pax7 expressing satellite cells whose fusion with myofibers after muscle injury leads to tdTomato expression from myonuclei. A) Satellite cells on fibers that were isolated after tamoxifen induction from Pax7-Cre-ERT-ROSA-tdTomato mice express tdTomato. Scale bar=20 μm. B) In tamoxifen induced Pax7-Cre-ERTROSA-tdTomato mice myonuclei start to express tdTomato after injury. This is due to the fusion of differentiated labeled satellite cells. Scale bar=10 μm.
Figure 18A:
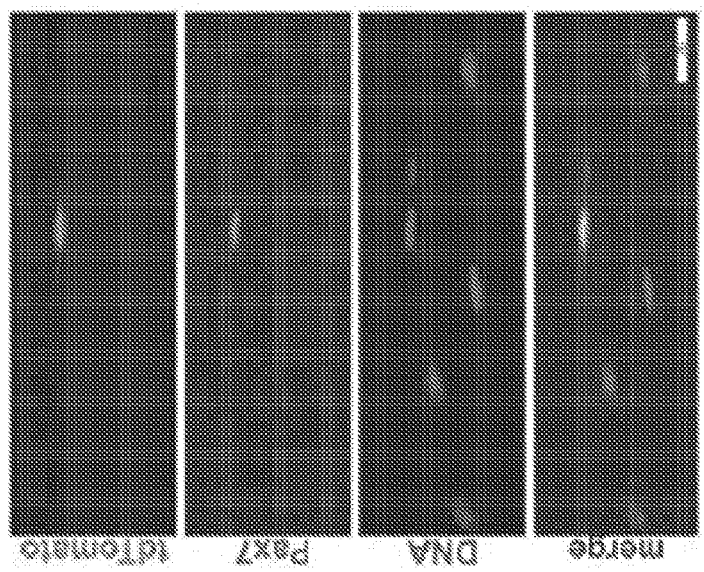

Electrodamage of the EP satellite cells having a recombined ROSA locus fused with myofibers induced regeneration and activation of satellite cells and lead to tdTomato expression from the new myonuclei (FIG. 18B). Therefore, in muscle cross sections most muscle fibers were brightly labeled with tdTomato after EP (FIG. 13E). In addition, most of the Pax7$^-$/α-SMA$^+$ cells that accumulated in fibrotic areas around FN&Wnt7a-HA expressing fibers were also positive for the Pax7-tdTomato lineage tracer. This data suggested that prolonged exposure of satellite cells to FN drives them into an alternative, non-myogenic myofibroblast lineage.

Pax7-tdTomato lineage tracing and the local accumulation of α-SMA positive cells in the fibrotic FN rich periphery of fibers after long-term EP, demonstrated that the sustained exposure of differentiating myogenic cells to FN prevents fusion and forces the cells into an alternative non-myogenic fibroblast lineage.

Example 13

Chronically High FN Levels Might Trigger Satellite Cell Pathology in Muscular Dystrophy Background Fibrosis is the formation of excess fibrous connective tissue, and is a common pathologic phenomenon in several forms of muscular dystrophy (Mann et al., 2011). Fibrosis and the accumulation of mononuclear inflammatory cells are a frequent problem in muscular dystrophy and anti-fibrotic drugs have been demonstrated to be beneficial for dystrophic muscle (Mann et al., 2011; Zhou and Lu, 2010). Many muscular dystrophies preferentially affect distinct muscle groups (Dalkilic and Kunkel, 2003). Moreover, it has been reported that in mdx mice, the mouse model for Duchenne muscular dystrophy, that certain muscle types contain unequal levels of hydroxyproline, a marker for fibrosis (Morrison et al., 2000). Intriguingly, the fibrotic phenotype of mdx mice is generally mild and the regenerative capacity of their muscles is almost unimpaired and superior to other muscular dystrophy mouse models such as Laminin-α2 deficient d$^{yw}$ mice (Dangain and Vrbova, 1984; Kuang et al., 1998; Torres and Duchen, 1987). In the mdx mouse sequential phases of de- and regeneration occur while degeneration in d$^{yw}$ mice is progressive.

Results

Figure 14A:
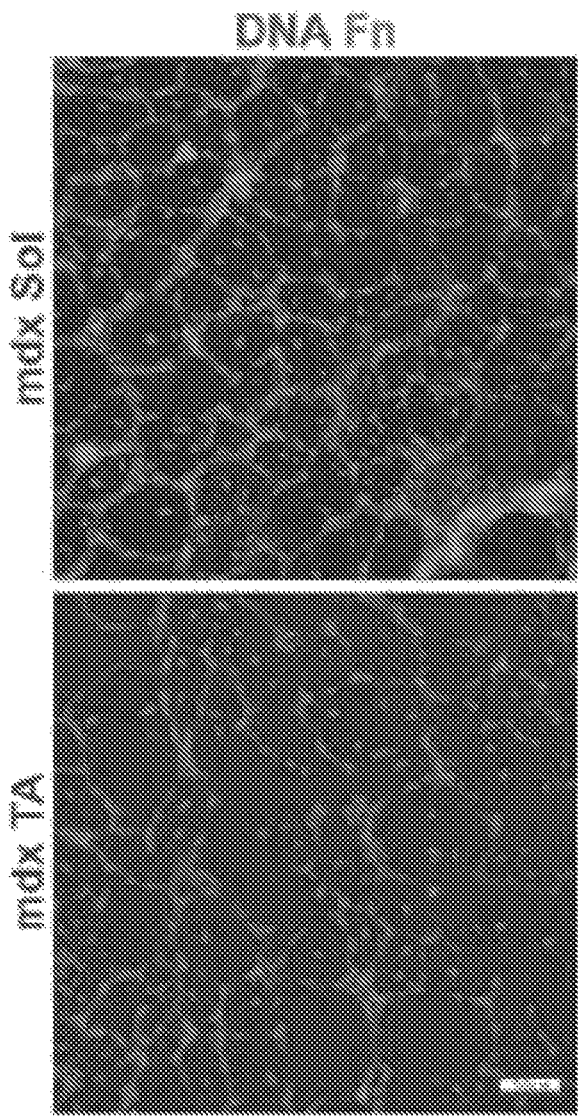
FIG. 14 shows that high FN levels in de- and regenerating mdx muscle is accompanied by low levels of committed satellite cells and abundant myofibroblasts. A) The fast TA and the slow Soleus (Sol) muscle of dystrophic mdx mice, were compared for their FN content by immunostaining Higher levels of FN are found in the Sol of mdx mice. Scale bar=50 µm. B) Western blot analysis comparing the absolute FN content of mdx TA and Sol muscles. Similar to the result shown under D, lower levels of FN are found in the TA muscle. α-actinin is shown as a loading control. C) qPCR from whole mdx TA or Sol muscles. Higher levels of FN in the Sol correlate with decreased MyoD expression. Data points represent means±SEM. n=4. p values are *p<0.001; p<0.01. D) Quantification showing that Pax7+/MyoD+ satellite cells are more abundant in sections from mdx TA when compared to Sol muscles. Data points represent means±SEM. n=4. p value is *p<0.05. E) Quantification showing increased numbers of Pax7−/α-SMA+/Vim+ myofibroblasts in mdx Sol muscles. Data points represent means±SEM. n=3. p value is *p<0.05.

Immunostaining for FN on cross sections of the slow Soleus (Sol) when compared to the mixed TA muscle was performed to determine whether FN content also varies between different muscles in the mdx mouse. Stronger immunostaining was observed for FN on cross sections of the slow Sol when compared to the mixed TA muscle (FIG. 14A). Due to the ongoing de- and regeneration of muscle fibers in mdx mice leading to sustained satellite cell activation, FN staining in both muscle types was not confined only to blood-vessels.

Figure 14B:
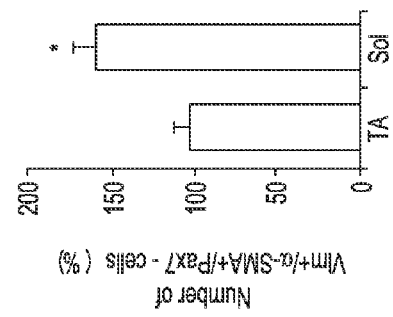
Figure 14C:
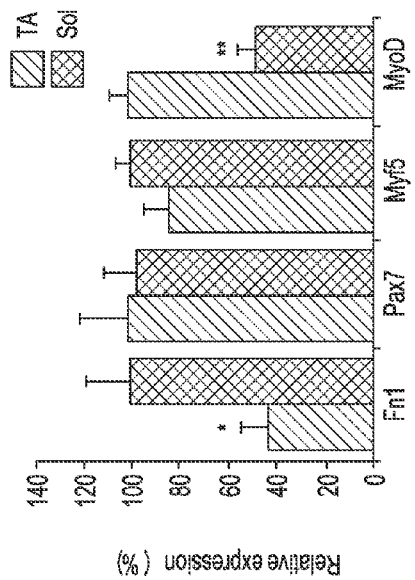
Figure 14D:
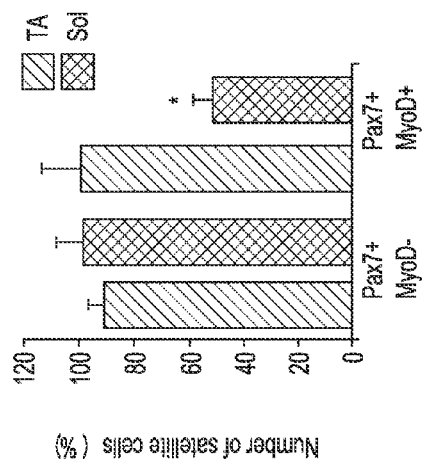

Western blot analysis and qPCR confirmed the differential FN content of Sol and TA (FIGS. 14B&C). In addition, it was found that the high FN content of the dystrophic mdx Sol had an effect on MRF expression when compared to the TA: lower MyoD transcript levels in the Sol were indicative of the antimyogenic FN effect (FIG. 14C). Further, lower numbers of Pax7$^+$/MyoD$^+$ satellite cells were found by immunostaining in mdx Sol cross sections when compared to TA (FIG. 14D). These results indicated that, similar to its effects in the in-vitro and EP paradigm, increased FN fibrosis in muscular dystrophy leads to negative effects on the differentiation of committed myogenic cells.

Figure 14E:
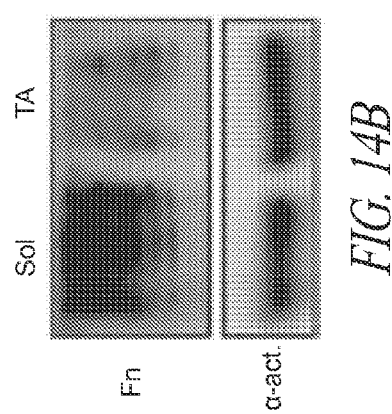

The amount of Pax7$^-$/α-SMA$^+$/Vimentin$^+$ (Pax7$^-$/α-SMA$^+$/Vim$^+$) in cross sections of mdx Sol and TA muscles was quantified to determine whether the increased FN content of the dystrophic muscles also triggered to a myofibroblast lineage deviation of satellite cells. Indeed, it was determined that the FN-rich Sol contained a higher number of Pax7$^-$/α-SMA$^+$/Vim$^+$ myofibroblasts (FIG. 14E).

The FN rich Sol muscle in mdx mice contained a lower number of MyoD+ satellite cells and more myofibroblasts than the less fibrotic TA muscle. These results indicated that, due to its high FN content, satellite cells in the mdx Sol have a lower potential for myogenic differentiation when compared to the TA.

These results suggested that linear degeneration of muscle leads to chronically high levels of FN-fibrosis which constantly impairs satellite cell function. However, in mdx mice phases with low myonecrosis allowed committed satellite cells to proliferate and differentiate under conditions of low tissue FN content. It could be therapeutically beneficial to pharmacologically treat fibrotic muscle pathology in intervals. Such treatment would simulate both physiological states of muscle regeneration, fibrotic conditions triggering satellite stem cell expansion, and lower levels of FN fostering lineage progression and the differentiation of myoblasts. Moreover, this therapeutic approach should theoretically reduce lineage switching of differentiating satellite cells into the myofibroblast state.

Example 14

Methods

Plasmid Electroporation pcDNA3.1 plasmids containing CMV-Wnt7a CT (lacks N-terminal domain), CMV-Wnt7a FL (a full-length Wnt7a), or CMV-Wnt7a NT (lacks C-terminal domain) or LacZ were transformed into OmniMax2 T1r competent cells (Invitrogen, Löhne, Germany). The DNA was extracted from 100 mL of an overnight bacterial culture using the MidiPrep Plasmid extraction kit (Invitrogen) DNA was dissolved in saline (0.9% NaCl). 17.5 µg of plasmid solution was injected into the right tibialis anterior (TA) muscle of 6 week old C57BL6 mice (Charles River Laboratories, Boston, Mass.), followed by five 20 ms rounds of 100V electrical impulse to optimize plasmid uptake by muscle fibers. Mice were sacrificed using $CO_2$ asphyxiation 6 days following electroporation and the TA muscle was excised and weighed. Muscles were divided in two, with one half frozen in a 2:1 solution of Tissue-Tek OCT (Optimal Cutting Temperature compound, Sakura Finetek, Torrance, Calif.): 30% sucrose using liquid nitrogen, and the other half was crushed with a pellet pastel and frozen in Protease Inhibitor cocktail (1 Complete Mini Protease Inhibitor Cocktail Tablet per 20 mL dd$H_2O$, Roche Scientific, Mannheim, Germany).

Cryosections and Immunohistochemistry

Examples 1-4

Frozen muscles were sectioned at 12 µm using a Leica CM 1850 Cryostat and mounted on Fisher brand slides (Waltham, Mass.). Cryosections were fixed with 4% PFA (paraformaldehyde). Sections were permeabilized with 0.1% Triton in PBS (Roche), and blocked in PBS containing 5% horse serum (Invitrogen) for 1 hr. Primary antibodies were applied overnight in the same blocking solution, followed by 1 hr incubation of fluorophore-conjugated secondary antibodies. Table 1 includes a complete list of the antibodies used.

TABLE 1

Antibodies

| Primary antibodies | Secondary antibodies |
|---|---|
| Anti-laminin rabbit IgG (Sigma L9393) | Alexa488 anti-rabbit IgG (Invitrogen) |
| Anti-HA mouse IgG1 (Sigma H9658) | Alexa568 anti-mouse IgG1 (Invitrogen) |
| Anti-α-Tubulin, mouse monoclonal IgG1 (DM1A) (Sigma T9026) | Goat anti-rabbit IgG (H + L)-HRP Conjugate (Bio-Rad, Hercules, CA) |
| Bis-benzimide-Hoechst 33342 (Sigma B2261) | Goat anti-mouse IgG (H + L)-HRP Conjugate (Bio-Rad, Hercules, CA) |
| | Goat pAb to chk IgY (HRP) (Abcam ab6877-1) |

Nuclei were counter-stained with Hoechst for 5 min. and coverslips (VWR International, Randor, Pa.) were mounted using Dako Fluorescent Mounting Medium (Glostrup, Denmark). Images of stained muscle sections were uploaded to ImageJ, which was used in measuring the average diameter of muscle fibers. The distance measured was the shortest, or ferret distance, which accounts for any variations in mounting.

Western Blotting

Examples 1-4

Muscle lysate protein concentrations were analyzed using Bradford Microassay and 50 μg of protein was loaded per lane on a 10% 1.5 mm SDS-Polyacrylamide gel and run at 115 mA. Samples were transferred to a PVDF (polyvinylidine fluoride) membrane (Millipore, Billerica, Mass.) for 1.5 hrs. Blocking and staining was performed using 5% skim milk powder in PBS-T (PBS-Tween 20, Roche) and primary and secondary antibody titers of 1/1000 (for a list of antibodies, see Table 1). Detection was done using Immobilon Western Chemiluminescent HRP Substrate (Millipore) on Kodak BioMax Film (Kodak, Rochester, N.Y.).

Plasmids

A 6xHis-TEV-3FLAG (HF) epitope was derived from pBRIT-TAP and added to the C-terminus of mouse Fzd7 (Invitrogen). EYFP derived from pEYFP-N1 (Clontech) was added to the C-terminus of mouse Sdc4 (Open Biosystems). Full length plasma fibronectin (Open Biosystems) was subcloned into pcDNA3. All expression constructs were either in the pEYFP-N1 or pcDNA3 backbone.

Cloning

Plasmids carrying the Coding Sequence (CDS) of Wnt7a variants were obtained. A C-terminal HA tag was added to the Wnt7a coding sequences through PCR amplification using the following primers:

(SEQ ID NO: 8)
5'ATATGGATCCACCATGAACCGGAAAGC 3',
and (SEQ ID NO: 9)
5'ATATCTCGAGTCAGGCGTAGTCAGGCACGTCGTATGGATACT
TGCACGTGTACATC 3'.

Protein truncation was carried out using the following set of primers:

| SEQ ID NO: | Primer | Sequence |
|---|---|---|
| 9 | Wnt7a SP sense | 5'ATATAAGCTTATGAACCGGAAAGCGC 3' |
| 10 | Wnt7a SP antisense | 5'ATATGGATCCAGCTACCACTGAGGAG 3' |
| 11 | Wnt7a NT sense | 5'ATATGGATCCCTGGGCGCAAGCATCA 3' |
| 12 | Wnt7a NT antisense | 5'ATATCTCGAGTCAGGCGTAGTCAGGCAC GTCGTATGGATACTTGGTGGTGCACGAG 3' |
| 13 | Wnt7a CT sense | 5'ATATGGATCCACGTGCTGGACCACACTGC C 3' |
| 14 | Wnt7a CT antisense | 5'ATATCTCGAGTCAGGCGTAGTCAGGCACGT CGTATGGATACTTGCACGTGTACATC 3' |
| 15 | Wnt7a FL sense | 5'ATATGGATCCCTGGGCGCAAGCATCA 3' |
| 16 | Wnt7a FL antisense | 5'ATATCTCGAGTCAGGCGTAGTCAGGCACGT CGTATGGATACTTGCACGTGTACATC 3' |

PCR amplification was done at denaturing, annealing and extension temperatures of 95° C., 65° C. and 72° C. respectively, and amplicons were introduced into pcDNA3.1 vector using BamHI and XhoI restriction endonucleases (New England Biolabs). Ligation mixtures were transformed in OmniMax2 T1r Competent Cells (Invitrogen), which were plated in Ampicillin-LB Agar plates overnight.

Immunostaining and Antibodies

Examples 5-13

Muscles frozen in liquid nitrogen-cooled isopentane were cut into 12 μm cross sections. Cross-sections were fixed with 4% PFA for 5 min, permeabilized with 1% Triton/PBS for 20 min, washed with 100 mM glycine/PBS for 10 min, blocked with 5% goat serum and 2% BSA in PBS for several hours, and incubated with specific primary antibody in blocking buffer overnight at 4° C. Samples were subsequently washed with PBS and stained with appropriate fluorescently labeled secondary antibodies for 1 hr at room temperature. After washing with PBS, samples were mounted with Permafluor (Fisher). For FN antibody staining 2% BSA in PBS without serum was used overnight at 4° C. To enrich for intracellular FN in asymmetric satellite cell doublets, 0.5% Triton was kept in all solutions during the staining procedure. The PLA (proximity ligation assay) was performed using the Duolink II Detection Reagents Red according to the instructions provided by the manufacturer (Olink). Primary antibodies were directly coupled to the PLA oligonucleotides using the Duolink II Probemaker (Olink). Antibodies are as follows: Rabbit anti-Fibronectin (Abcam, ab23750), rabbit anti-Laminin (Sigma, L9393), rabbit anti-HA (Millipore, 07-221), rabbit anti-zsGreen (Clontech, 632474), rabbit anti-MyoD (Santa Cruz, sc-304), Chicken anti-Sdc4 (Cornelison et al., 2004), chicken anti-GFP (Abcam, ab13970), chicken anti-βGal (Abcam, ab9361), rat anti-CD29 (BD biosciences, 550531), rat anti-Laminin B2 (Millipore, 05-206), rat anti-CD11b (eBioscience, 25-0112-82), mouse anti-Pax7 (DSHB), mouse anti-GFP (Roche, 11814460001), mouse anti-FLAG (Sigma, F3165), mouse anti-GAPDH (Ambion, AM4300), mouse anti-HA (Roche, 1583816), mouse anti-Myosin (DSHB), mouse anti-αSMA (Sigma, A2547).

qPCR and PCR for the Detection of FN Splice Variants

Total RNA was isolated (NucleoSpin RNA II, Macherey-Nagel). Reverse transcription was carried out using a mixture of oligodT and random hexamer primers (iScript cDNA Synthesis Kit, Bio-Rad). Sybr Green, real-time PCR analysis (iQ SYBR Supermix, Bio-Rad) was performed using Mx300P real time thermocycler (Stratagene). The following primers were used:

| SEQ ID NO: | Primer | Sequence |
|---|---|---|
| 17 | Pax7 sense | 5'TCTTACTGCCCACCCACCTA 3' |
| 18 | Pax7 antisense | 5'CACGTTTTTGGCCAGGTAAT 3' |
| 19 | Fn1 sense | 5'GGCCACACCTACAACCAGTA 3' |
| 20 | Fn1 antisense | 5'TCGTCTCTGTCAGCTTGCAC 3' |
| 21 | Itgα5 sense | 5'AATCCTCAAGACCAGCCTCA 3' |
| 22 | Itgα5 antisense | 5'TAGAGGAGCTGTTGGCCTTC 3' |
| 23 | Myf5 sense | 5'TGAGGGAACAGGTGGAGAAC 3' |
| 24 | Myf5 antisense | 5'CTGTTCTTTCGGGACCAGAC 3' |
| 25 | MyoD sense | 5'GGCTACGACACCGCCTACTA 3' |
| 26 | MyoD anti-sense | 5'GTGGAGATGCGCTCCACTAT 3' |
| 27 | Sdc4 sense | 5'AACCACATCCCTGAGAATGC 3' |
| 28 | Sdc4 anti-sense | 5'AGGAAAACGGCAAAGAGGAT 3' |
| 29 | β-actin sense | 5'CAGCTTCTTTGCAGCTCCTT 3' |
| 30 | β-actin anti-sense | 5'GCAGCGATATCGTCATCCA 3' |
| 31 | GAPDH sense | 5'ACCCAGAAGACTGTGGATG 3' |
| 32 | GAPDH anti-sense | 5'ACACATTGGGGGTAGGAACA 3' |
| 33 | Fn1 EIIIB sense | 5'CGAGATGGCCAGGAGAGA 3' |
| 34 | Fn1 EIIIB anti-sense | 5'AAGGTTGGTGAGGGTGATGG 3' |
| 35 | Fn1 EIIIA sense | 5'AAGGTTGGTGAGGGTGATGG 3' |
| 36 | Fn1 EIIIA anti-sense | 5'CCAGTTTCCATCAATTATAAACAGAA 3' |
| 37 | Fn1 IIICS sense | 5'CCCTGAAGAACAATCAGAAGAG 3' |
| 38 | Fn1 IIICS anti-sense | 5'TGAAATGACCACTGCCAAAG 3' |

Western Blotting and Immunoprecipitation

Examples 5-13

For co-immunoprecipitation (Co-IP) experiments and Rac1 activation assay satellite cell derived primary myoblasts were transfected with Lipofectamine 2000 according to the manufacturer's instructions. For Co-IP the cells were treated with disuccinimidyl suberate crosslinker prior to lysis (Pierce). Cell extracts were obtained by RIPA buffer lysis in the presence of protease inhibitor cocktail (Nacalai). GFP-Trap beads (Allele Biotechnology) or anti-flag M2 beads (Sigma) were used were used for Co-IP according to the manufacturer's recommendations. Whole muscle extracts for western blotting and grey value densitometry of western blots were performed as previously described (Bentzinger et al., 2008). Denaturing SDS-PAGE was performed using standard molecular biology techniques. Rac1 activation assay was performed according to the manufacturer's instructions (Pierce).

Tissue and Satellite Cell siRNA Knockdown

Figure 23D:
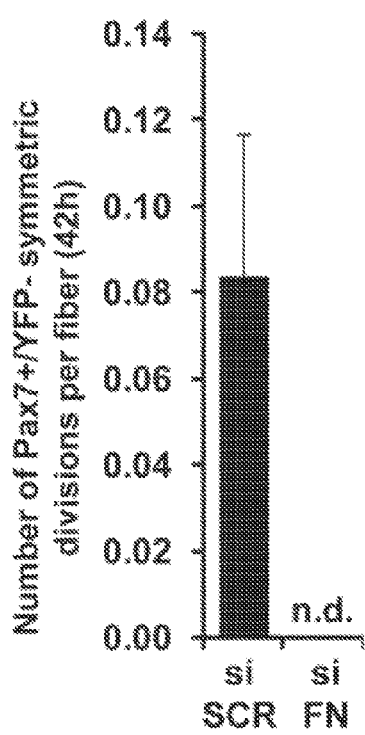
Figure 23E:
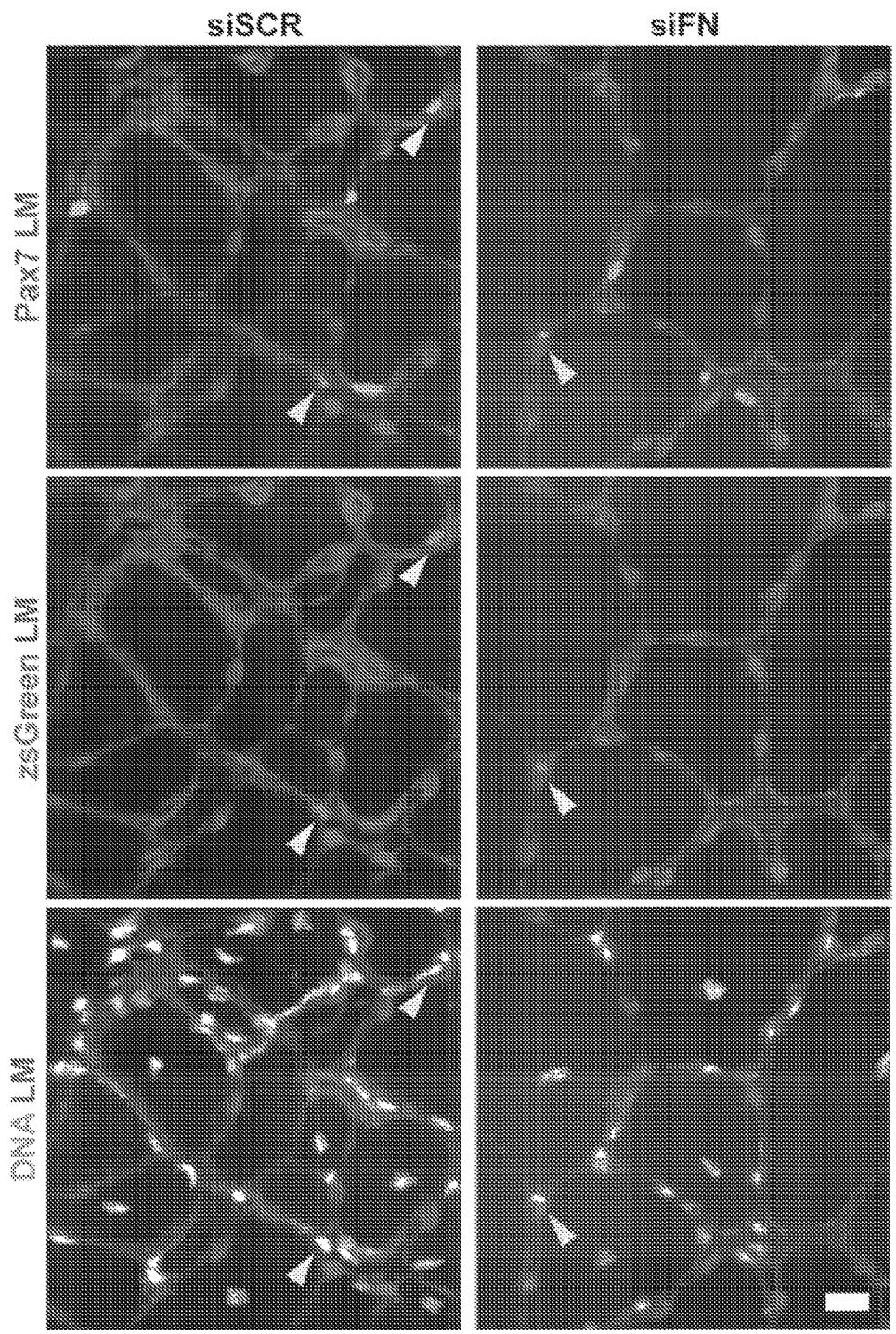
Figure 23F:
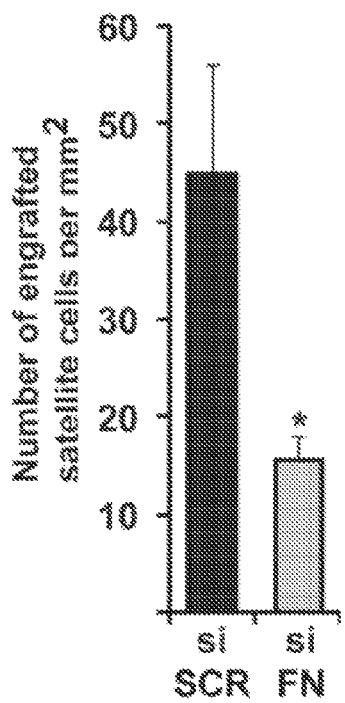
Figure 23G:
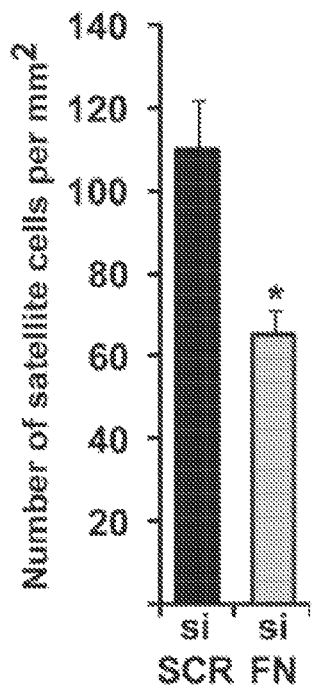

For FN knockdown in satellite cells and subsequent transplantation, cells were FACS purified from Pax7-zs-Green mice by gating for zsGreen and Hoechst (Bosnakovski et al., 2008). Directly after isolation, the cells were lipofected with a validated duplexed silencer select siRNA for FN (Daley et al., 2009; Daley et al., 2011) for three hours on ice. Silencer select FN siRNA was: Sense (5→3): CCGUUUUCAUCCAACAAGA(TT) (SEQ ID NO: 45) and anti-sense (3→5): UCUUGUUGGAUGAAAACGG (GT) (SEQ ID NO: 46). After siRNA transfection satellite cells were washed several times with FACS buffer. 15,000 cells for each condition were resuspended in 0.9% NaCl and transplanted into muscles of FK506 immunosupressed mice that had been injured two days before. Scd4 was knocked down in satellite cells in fiberculture as previously described (Le Grand et al., 2009). Silencer select Sdc4 siRNA was: Sense (5→3): GUUACGACUUGGGCAAGAA(TT) (SEQ ID NO: 47) and anti-sense (3→5): UUCUUGCCCAAGU-CGUAAC(TG) (SEQ ID NO: 48). siRNA to Fzd7 has been previously described (Le Grand et al., 2009). In all siRNA knockdown experiments, except for the in-vivo knockdown (FIGS. 23C, 23D and 23E), scrambled siRNA Silencer Select Negative Control No. 1 was used as a control (Ambion). For tissue knockdown the validated FN siRNA sequence was modified to the Accell self-delivering format (Dharmacon). 100 μg Accell siRNA was injected into muscles two days after CTX injury. FN Accell siRNA was: Sense (5→3): CCGUUUUCAUCCAACAAGA(dGdT) (SEQ ID NO: 49) and anti-sense (3→5): (dTdG) GGCAAAAGUAGGUUGUUCU(5'-P) (SEQ ID NO: 50). A similarly modified scrambled sequence was used as a negative control.

Mice and Animal Care 6-8 week old Myf5-Cre-ROSA-YFP mice were obtained by crossing Myf5-Cre mice with ROSA26-YFP reporter mice (Srinivas et al., 2001; Tallquist et al., 2000). zsGreen and Myf5-nLacZ mice were generated as described (Bosnakovski et al., 2008; Tajbakhsh et al., 1996). Pax7-Cre-ERTROSA-tdTomato were generated by crossing the Pax7-Cre-ERT allele with ROSAtdTomato mice (Madisen et al., 2010; Nishijo et al., 2009). To irreversibly label Pax7 expressing cells, Pax7-Cre-ERT-ROSA-tdTomato were intraperitoneally injected for 5 subsequent days with 200 μL Tamoxifen in corn oil (20 mg/mL). mdx mice were obtained from the Jackson Laboratory. All mice were maintained inside a barrier facility, and experiments were performed following the University of Ottawa regulations for animal care and handling.

Myofiber Isolation and Culture

Single myofibers were isolated from the EDL muscles as previously described (Rosenblatt et al., 1995). Isolated myofibers were cultured in suspension in horse serum coated dishes (Kuang et al., 2006). Fiber medium contained 20% FBS (Hyclone) and 1% chick embryo extract (CEE, Accurate Chemicals) and DMEM with 2% L-glutamine, 4.5% glucose, and 110 mg/ml sodium pyruvate. For Wnt stimulation, recombinant Wnt7a added to the fiber medium to a final concentration of 100 ng/ml (R&D Systems). To expose the fibers to increased FN or COL levels, human plasma fibronectin (BD biosciences) or rat tail collagen in PBS (VWR) were added to increase the concentration in the medium to 25 µg/ml. For inhibition of FN binding to Sdc4 in fibercultures, 5 µg/ml Tenascin-C (R&D Systems) was added to the fiber medium. For inhibition of Sdc4, 20 µg/ml chicken anti-Sdc4 (Cornelison et al., 2004) was added to the fiber medium.

Primary Myoblast Isolation and Culture

Pax7$^+$/YFP$^+$, Pax7$^+$/YFP$^-$ and total satellite cells were isolated from hind limb muscles and staining was performed as previously described (Kuang et al., 2006; Le Grand et al., 2009). Cells were separated on a MoFlo cytometer (Dako-Cytomation) equipped with three lasers. Dead cells and debris were excluded by Hoescht staining and by gating on forward and side scatter profiles. For myoblast culture, satellite cells were sorted and plated on COL or FN coated dishes (BD biosciences) in Ham's F10 medium supplemented with 20% FBS and 5 ng/ml of basic FGF (Millipore).

Affymetrix Microarray Analysis

For microarrays, cells were obtained from six week old BALB/c mice. Total RNA was isolated from freshly FACS isolated quiescent satellite cells that were pooled from nine mice, or in triplicates from established mouse primary myoblasts and differentiated myotubes using the RNeasy mini kit (Qiagen). The purity of RNA was analyzed by Bioanalyzer (Agilent Technologies, Santa Clara, Calif.). Samples with an RNI>9.0 were used for subsequent labeling and hybridization with Mouse Gene 1.0 ST Arrays (Affymetrix). Expression data was processed using Gene Expression Consol (Affymetrix).

Electroporation and Muscle Injury

40 µg of plasmid DNA in 0.9% NaCl was injected into the TA muscle of anesthetized mice through the skin. Similar amounts of individual plasmids were used for all conditions. For comparison of single plasmids with co-electroporated plasmids an empty stuffer plasmid was added to equalize the amount of DNA in each transfection. Immediately after injection, electric stimulation was applied to the TA by a pulse generator (ECM 830, BTX) of 100-150 volts for 6 pulses, with a fixed duration of 20 ms and an interval of 200 ms using 5 mm needle electrodes (BTX). For CTX-induced muscle regeneration, 25 ul of 10 µM cardiotoxin (Sigma) was directly injected into the TA muscle through the skin.

Statistical Analysis

Densitometry of grey values from western blots and FN staining in asymmetric doublets was performed with the Image-J software. Compiled data are expressed as mean±standard error of the mean (SEM). Compiled data were expressed as mean±SEM. Experiments were done with a minimum of three replicates. For statistical comparisons of two conditions, the Student's t-test was used. The level of significance is indicated as follows: * $p<0.001$,  $p<0.01$, * $p<0.05$.

ABBREVIATIONS USED

DMD: Duchenne Muscular Dystrophy
mdx: Duchenne Muscular Dystrophy mouse model
PCP: Planar Cell Polarity
CMV: cytomegalovirus
TA: Tibialis Anterior
HA: Hemagglutinin
β-Gal: β-Galactosidase
CDS: Coding Sequence
SP: signal peptide
NT: N-terminal domain (of Wnt7a)
CT: C-terminal domain (of Wnt7a)
FL: Full length Wnt7a
EP: electroporation In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition for increasing the symmetric expansion of stem cells comprising (a) a Wnt7a polypeptide fragment having the amino acid sequence set forth in SEQ ID NO: 5, (b) a Wnt7a polypeptide fragment having an N-terminal deletion of 210 to 219 amino acids in the amino acid sequence set forth in SEQ ID NO: 3, or (c) a polynucleotide encoding the polypeptide of (a) or (b).

2. The composition of claim 1, wherein the polynucleotide comprises an expression vector.

3. The composition of claim 1, further comprising a stem cell or a population of stem cells.

4. The composition of claim 3, wherein the stem cell or population of stem cells comprises an adult stem cell.

5. The composition of claim 4, wherein the adult stem cell is a satellite stem cell.

6. The composition of claim 1, further comprising one or more stem cell modulators.

7. The composition of claim 6, wherein the modulators comprise a FGF polypeptide, fibronectin polypeptide, or a polynucleotide encoding a FGF or fibronectin polypeptide.

8. The composition of claim 1, further comprising a physiologically acceptable carrier or diluent.

9. The composition of claim 1, wherein the compositions is formulated for injection.

10. The composition of claim 9, wherein the composition is formulated for one or more of intravenous injection, intramuscular injection, intracardiac injection, subcutaneous injection, or intraperitoneal injection.

11. A method for increasing the symmetric expansion of stem cells comprising contacting the stem cells with a composition comprising (a) a Wnt7a polypeptide fragment having the amino acid sequence set forth in SEQ ID NO: 5, (b) a Wnt7a polypeptide fragment having an N-terminal deletion of 210 to 219 amino acids in the amino acid sequence set forth in SEQ ID NO: 3, or (c) a polynucleotide encoding the polypeptide of (a) or (b).

12. The method of claim 11, wherein the polynucleotide comprises an expression vector.

13. The method of claim 11, wherein the stem cells are adult stem cells.

14. The method of claim 13, wherein the adult stem cells are satellite stem cells.

15. The method of claim 11, further comprising contacting the stem cells with one or more stem cell modulators.

16. The method of claim 15, wherein the modulators comprise a FGF polypeptide, a fibronectin polypeptide, or a polynucleotide encoding a fibroblast growth factor (FGF) or fibronectin polypeptide.

17. The method of claim 11, wherein the method is performed in vivo to a subject in need thereof who has, is suspected of having, or is at risk of having a disease or condition affecting muscle.

18. The method of claim 17, wherein the subject has a degenerative disease.

19. The method of claim 18, wherein the degenerative disease is a muscular dystrophy.

20. The method of claim 19, wherein the muscular dystrophy is selected from Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

21. A method for promoting muscle formation, regeneration, maintenance or repair in a subject comprising administering to the subject a composition comprising (a) a Wnt7a polypeptide fragment having the amino acid sequence set forth in SEQ ID NO: 5, (b) a Wnt7a polypeptide fragment having an N-terminal deletion of 210 to 219 amino acids in the amino acid sequence set forth in SEQ ID NO: 3, or (c) a polynucleotide encoding (a) or (b).

22. The method of claim 21, further comprising administering to the subject one or more stem cell modulators.

23. The method of claim 22, wherein the modulators comprise a FGF polypeptide, a fibronectin polypeptide, or a polynucleotide encoding a FGF or fibronectin polypeptide.

24. The method of claim 21, wherein the subject has, is suspected of having, or is at risk of having a disease or condition affecting muscle.

25. The method of claim 24, wherein the disease is a muscular dystrophy.

26. The method of claim 25, wherein the muscular dystrophy is selected from Duchenne muscular dystrophy (DMD), Becker muscular dystrophy (BMD), Emery-Dreifuss muscular dystrophy, Landouzy-Dejerine muscular dystrophy, facioscapulohumeral muscular dystrophy (FSH), Limb-Girdle muscular dystrophies, von Graefe-Fuchs muscular dystrophy, oculopharyngeal muscular dystrophy (OPMD), Myotonic dystrophy (Steinert's disease) and congenital muscular dystrophies.

\* \* \* \* \*

UNITED STATES PATENT AND TRADEMARK OFFICE
CERTIFICATE OF CORRECTION

PATENT NO. : 9,732,130 B2
APPLICATION NO. : 14/344309
DATED : August 15, 2017
INVENTOR(S) : Rudnicki et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 474 days.

Signed and Sealed this
Second Day of June, 2020

Andrei Iancu
*Director of the United States Patent and Trademark Office*